US012606832B2

(12) United States Patent
Kim et al.

(10) Patent No.: US 12,606,832 B2
(45) Date of Patent: *Apr. 21, 2026

(54) COMPOSITIONS FOR INDUCING MODIFICATIONS OF TARGET ENDOGENOUS NUCLEIC ACID SEQUENCES IN NUCLEUSES OF EUKARYOTIC CELLS

(71) Applicant: TOOLGEN INCORPORATED, Seoul (KR)

(72) Inventors: Jin-Soo Kim, Seoul (KR); Seung Woo Cho, Seoul (KR); Sojung Kim, Seoul (KR)

(73) Assignee: ToolGen Incorporated, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 19/023,934

(22) Filed: Jan. 16, 2025

(65) Prior Publication Data

US 2025/0327084 A1 Oct. 23, 2025

Related U.S. Application Data

(63) Continuation of application No. 18/932,745, filed on Oct. 31, 2024, which is a continuation of application No. 17/004,338, filed on Aug. 27, 2020, which is a continuation of application No. 14/685,568, filed on Apr. 13, 2015, now Pat. No. 10,851,380, which is a continuation of application No. PCT/KR2013/009488, filed on Oct. 23, 2013.

(60) Provisional application No. 61/837,481, filed on Jun. 20, 2013, provisional application No. 61/803,599, filed on Mar. 20, 2013, provisional application No. 61/717,324, filed on Oct. 23, 2012.

(51) Int. Cl.
| | |
|---|---|
| *C12N 9/22* | (2006.01) |
| *C12N 9/16* | (2006.01) |
| *C12N 15/10* | (2006.01) |
| *C12N 15/11* | (2006.01) |
| *C12N 15/52* | (2006.01) |
| *C12N 15/63* | (2006.01) |
| *C12N 15/82* | (2006.01) |
| *C12N 15/85* | (2006.01) |
| *C12N 15/90* | (2006.01) |

(52) U.S. Cl.
CPC .............. *C12N 15/52* (2013.01); *C12N 9/16* (2013.01); *C12N 9/22* (2013.01); *C12N 15/102* (2013.01); *C12N 15/111* (2013.01); *C12N 15/63* (2013.01); *C12N 15/8216* (2013.01); *C12N 15/85* (2013.01); *C12N 15/907* (2013.01); *C12Y 301/21* (2013.01); *C12N 2310/10* (2013.01); *C12N 2310/20* (2017.05); *C12N 2310/531* (2013.01)

(58) Field of Classification Search
None
See application file for complete search history.

(56) References Cited

U.S. PATENT DOCUMENTS

| | | | |
|---|---|---|---|
| 5,766,900 | A | 6/1998 | Shillito et al. |
| 5,767,367 | A | 6/1998 | Dudits et al. |
| 5,925,517 | A | 7/1999 | Tyagi et al. |
| 6,040,295 | A | 3/2000 | Rolland et al. |
| 8,697,359 | B1 | 4/2014 | Zhang |
| 8,771,495 | B2 | 7/2014 | Paneccasio et al. |
| 8,883,233 | B2 | 11/2014 | Gillessen |
| 8,889,559 | B2 | 11/2014 | Trapp et al. |
| 8,993,233 | B2 | 3/2015 | Zhang et al. |
| 8,999,641 | B2 | 4/2015 | Zhang et al. |
| 9,023,649 | B2 | 5/2015 | Mali et al. |
| 9,260,723 | B2 | 2/2016 | Mali et al. |
| 9,493,779 | B2 | 11/2016 | Ainley et al. |
| 9,637,739 | B2 | 5/2017 | Siksnys et al. |
| 10,851,380 | B2 | 12/2020 | Kim et al. |

(Continued)

FOREIGN PATENT DOCUMENTS

| | | |
|---|---|---|
| AU | 733057 B2 | 5/2001 |
| AU | 2011203213 A1 | 8/2011 |

(Continued)

OTHER PUBLICATIONS

Kim et al., Highly efficient RNA-guided genome editing in human cells via delivery of purified Cas9 ribonucleoproteins. Genome Research (2014), 24:1012-1019 (Year: 2014).*
Siu and Chen, Riboregulated toehold-gated gRNA for programmable CRISPR-Cas9 function. Nature Chemical Biology (2019), 15:217-220 (Year: 2019).*
Gaj et al., Targeted gene knockout by direct delivery of zinc-finger nuclease proteins. Nature Methods (2012), 9: 805-807 and Supplemental Material (Year: 2012).*
Chakrabarti et al., Transfer of Monoclonal Antibodies into Mammalian Cells by Electroporation. Journal of Biological Chemistry (1989), 263: 15494-15500 (Year: 1989).*

(Continued)

*Primary Examiner* — Catherine Konopka
(74) *Attorney, Agent, or Firm* — Gemini Law LLP

(57) ABSTRACT

The present disclosure relates to targeted genome editing in eukaryotic cells or organisms. More particularly, the present disclosure provides for compositions and methods that may induce modifications in target endogenous nucleic acid sequences in nucleuses of eukaryotic cells. For example, disclosed herein is a method of producing an engineered eukaryotic cell. In some embodiments, the method may comprise preparing a Cas9 protein, preparing a sgRNA, and preparing a cell-free buffer. The method may further comprise disposing the Cas9 protein and sgRNA in the cell-free buffer to provide for a transfection mixture and transfecting the transfection mixture into a eukaryotic cell, wherein a Cas9/sgRNA complex formed by the Cas9 protein and the sgRNA induces a modification of a target endogenous DNA sequence in the nucleus of the eukaryotic cell to provide for an engineered eukaryotic cell.

4 Claims, 61 Drawing Sheets

Specification includes a Sequence Listing.

(56) References Cited

U.S. PATENT DOCUMENTS

| | | |
|---|---|---|
| 2005/0220796 A1 | 10/2005 | Dynan et al. |
| 2009/0111119 A1 | 4/2009 | Doyon et al. |
| 2010/0001189 A1 | 1/2010 | Federici |
| 2010/0076057 A1 | 3/2010 | Sontheimer et al. |
| 2011/0223638 A1 | 9/2011 | Wiedenheft et al. |
| 2012/0058102 A1 | 3/2012 | Wilson et al. |
| 2014/0068797 A1* | 3/2014 | Doudna ............... C12N 15/746 |
| | | 435/375 |
| 2014/0090113 A1 | 3/2014 | Cogan et al. |
| 2014/0093913 A1 | 4/2014 | Cost et al. |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0189896 A1 | 7/2014 | Zhang et al. |
| 2014/0242664 A1 | 8/2014 | Zhang et al. |
| 2014/0273230 A1 | 9/2014 | Chen et al. |
| 2014/0310830 A1 | 10/2014 | Zhang et al. |
| 2014/0342456 A1 | 11/2014 | Mali et al. |
| 2014/0349405 A1 | 11/2014 | Sontheimer et al. |
| 2014/0357530 A1 | 12/2014 | Zhang et al. |
| 2015/0020223 A1 | 1/2015 | Zhang et al. |
| 2015/0031134 A1 | 1/2015 | Zhang et al. |
| 2015/0050699 A1 | 2/2015 | Siksnys et al. |
| 2015/0067921 A1 | 3/2015 | Cogan et al. |
| 2015/0067922 A1 | 3/2015 | Yang et al. |
| 2015/0079681 A1 | 3/2015 | Zhang |
| 2015/0166615 A1 | 6/2015 | Xia et al. |
| 2015/0203872 A1 | 7/2015 | Zhang |
| 2015/0225734 A1 | 8/2015 | Voytas et al. |
| 2015/0232882 A1 | 8/2015 | Zhang et al. |
| 2015/0247150 A1 | 9/2015 | Zhang et al. |
| 2015/0291965 A1 | 10/2015 | Zhang et al. |
| 2015/0344912 A1 | 12/2015 | Kim et al. |
| 2015/0351340 A1 | 12/2015 | Bundock et al. |
| 2015/0356239 A1 | 12/2015 | Zhang et al. |
| 2016/0017366 A1 | 1/2016 | Chen et al. |
| 2016/0032274 A1 | 2/2016 | Church et al. |
| 2016/0046961 A1 | 2/2016 | Jinek et al. |
| 2016/0153004 A1 | 6/2016 | Zhang et al. |
| 2016/0153005 A1 | 6/2016 | Zhang et al. |
| 2016/0153006 A1 | 6/2016 | Zhang et al. |
| 2016/0168594 A1 | 6/2016 | Zhang et al. |
| 2016/0175462 A1 | 6/2016 | Zhang et al. |
| 2016/0186213 A1 | 6/2016 | Zhang et al. |
| 2021/0047648 A1 | 2/2021 | Kim et al. |

FOREIGN PATENT DOCUMENTS

| | | |
|---|---|---|
| JP | 2005006578 A | 1/2005 |
| NZ | 228948 A | 6/1991 |
| WO | WO1998010084 A1 | 3/1998 |
| WO | WO2000055378 A1 | 9/2000 |
| WO | WO2002067966 A1 | 9/2002 |
| WO | WO2002067996 A2 | 9/2002 |
| WO | WO2005054494 A2 | 6/2005 |
| WO | WO2007024029 A1 | 3/2007 |
| WO | WO2007025195 A1 | 3/2007 |
| WO | WO2008108989 A2 | 9/2008 |
| WO | WO2009042164 A1 | 4/2009 |
| WO | WO2010001189 A1 | 1/2010 |
| WO | WO2010052341 A1 | 5/2010 |
| WO | WO2010076939 A1 | 7/2010 |
| WO | WO2011007193 A1 | 1/2011 |
| WO | WO2011056186 A1 | 5/2011 |
| WO | WO2011130346 A1 | 10/2011 |
| WO | WO2011146121 A1 | 11/2011 |
| WO | WO2012012738 A1 | 1/2012 |
| WO | WO2012138939 A1 | 10/2012 |
| WO | WO2013098244 A1 | 7/2013 |
| WO | WO2013188522 A2 | 12/2013 |
| WO | WO2014018423 A2 | 1/2014 |
| WO | WO2014022702 A2 | 2/2014 |
| WO | WO2014065596 A1 | 5/2014 |
| WO | WO-2014089290 A1 * | 6/2014 ........... C12N 15/102 |
| WO | WO2014093635 A1 | 6/2014 |
| WO | WO2014093694 A1 | 6/2014 |
| WO | WO2014093709 A1 | 6/2014 |
| WO | WO2014093718 A1 | 6/2014 |
| WO | WO2014099750 A2 | 6/2014 |
| WO | WO2014144155 A1 | 9/2014 |
| WO | WO2014197568 A2 | 12/2014 |
| WO | WO2014204725 A1 | 12/2014 |
| WO | WO2015026883 A1 | 2/2015 |

OTHER PUBLICATIONS

Eksioglu-Demiralp et al., A method for functional evaluation of caspase activation pathways in intact lymphoid cells using electroporation-mediated protein delivery and flow cytometric analysis. Journal of Immunological Methods (2003), 275: 41-56 (Year: 2003).*

Li et al., Electroporation of influenza virus ribonucleoprotein complexes for rescue of the nucleoprotein and matrix genes. Virus Research (1995), 37: 153-161 (Year: 1995).*

Angel, M. and Yanik, M. F., Innate Immune Suppression Enables Frequent Transfection with RNA Encoding Reprogramming Proteins. PLoS One. 2010, 5(7):e11756. (7 pages).

Anonymous, Product Information Thermo Scientific TurboFect Transfection Reagent Pub. No. MAN0013147 Rev. Date Aug. 24, 2018. Thermo Scientific, (2018) (2 pages).

Anonymous, PCT Third Party Observation dated Feb. 19, 2015, in relation to International Application No. PCT/KR2013/009488 filed on Oct. 23, 2013, pp. 1-5.

Anonymous, Third-Party Observation dated Jul. 18, 2014, in relation to International Application No. PCT/US2013/033106 filed Mar. 20, 2013 (7 pages).

Anonymous, Third-Party Observation dated Sep. 24, 2014, in relation to International Application No. PCT/US2013/032589 filed Mar. 15, 2013 (8 pages).

Anonymous, Third-Party Observations dated Jan. 17, 2019, in relation to European Patent Application No. 18158147.1 (Publication No. EP 3372679 A1) (302 pages).

Anonymous, Third-Party Submissions dated Dec. 22, 2014, in relation to U.S. Appl. No. 14/104,977, filed Dec. 12, 2013, pp. 1-56.

Anonymous, Third-Party Submission Under 37 C.F.R. §1.290 filed Apr. 6, 2016 in relation to U.S. Appl. No. 14/438,098.

Artimo, P., et al., ExPASy: SIB bioinformatics resource portal. Nucleic Acids Research. 2012, 40:W597-W603. (7 pages).

ATCC record ATCC 700294, 2019, "*Streptococcus pyogenes* Rosenbach (ATTC 700294)", retrieved from the internet on Apr. 18, 2019 at http://wwwlgcstandards-atcc.org/products/all/700294.aspx/geo_country=GB#history> (2 pages).

Barrangou, R., RNA-mediated programmable DNA cleavage. Nat Biotechnol. 2012, 30(9):836-838. (3 pages).

Bassett, A. R., et al., Highly Efficient Targeted Mutagenesis of *Drosophila* with the CRISPR/Cas9 System. Cell Reports. 2013, 4(1):220-228 and Supplementary Table.

Baum, A., et al., Preference of RIG-I for short viral RNA molecules in infected cells revealed by next-generation sequencing. PNAS. 2010, 107(37):16303-16308.

Bedell, V. M., et al., In vivo genome editing using a high-efficiency TALEN system. Nature. 2012, 491:114-118. (7 pages).

Bell, O., et al., Determinants and dynamics of genome accessibility. Nature Reviews Genetics. 2011, 12:554-564. (11 pages).

Bhaya, D., et al., CRISPR-Cas systems in bacteria and archaea: versatile small RNAs for adaptive defense and regulation. Annual Reviews of Genetics. 2011;45:273-297. (27 pages).

Bikard, D., et al., CRISPR Interference Can Prevent Natural Transformation and Virulence Acquisition during In Vivo Bacterial Infection. Cell Host & Microbe. 2012, 12(2):177-186.

Bikard, D., et al., Programmable repression and activation of bacterial gene expression using an engineered CRISPR-Cas system. Nucleic Acids Research. 2013, 41(15):7429-7437.

Boch, J. and Bonas, U., Xanthomonas AvrBs3 Family-Type III Effectors: Discovery and Function. Annual Review of Phytopathology. 2010, 48:419-436.

(56)                References Cited

OTHER PUBLICATIONS

Bogerd, H. P., et al., A Mammalian Herpesvirus uses Noncanonical Expression and Processing Mechanisms to Generate Viral MicroRNAs. Molecular Cell. 2010, 37(1):135-142.

Briggs, A.W., et al., Iterative capped assembly: rapid and scalable synthesis of repeat-module DNA such as TAL effectors from individual monomers. Nucleic Acids Research. 2012, 40(15):e117. (10 pages).

Brouns, S. J. J., A Swiss Army Knife of Immunity. Science. 2012, 337(6096):808-809.

Brzostek-Racine, S., et al., The DNA Damage Response Induces IFN. The Journal of Immunology. 2011, 187 (10):5336-5345.

Cain, C., CRISPR genome editing. SciBX Sci. Exch. 1-3, 2013, doi:10.1038/scibx.2013.77.

Carlson, D. F., et al., Targeting DNA with fingers and TALENs. Molecular Therapy-Nucleic Acids. 2012, 1:e3. (4 pages).

Carlson, E. D., et al., Cell-free protein synthesis: Applications come of age. Biotechnology Advances. 2012, 30 (5):1185-1194.

Carroll, D., A CRISPR Approach to Gene Targeting. Molecular Therapy. 2012, 20(9):1658-1660. (3 pages).

Carroll, D., Genome Engineering with Zinc-Finger Nucleases. Genetics. 2011, 188(4):773-782.

Carroll, D., Staying on target with CRISPR-Cas. Nat. Biotechnol. 2013, 31:807-809.

Cermak, T., et al., Efficient design and assembly of custom TALEN and other TAL effector-based constructs for DNA targeting. Nucleic Acids Research. 2011, 39(12):e82.

Chang, K., et al., RNAi in Cultured Mammalian Cells Using Synthetic siRNAs. Cold Spring Harb. Protoc. 2012, 9:957-961. (9 pages).

Chang, N., et al., Genome editing with RNA-guided Cas9 nuclease in Zebrafish embryos. Cell Res. 2013, 23 (4):465-472 and Supplementary Materials. (8 pages).

Chapdelaine, P., et al., Meganucleases can restore the reading frame of a mutated dystrophin. Gene Ther. 2010, 17:846-858. (13 pages).

Chen, B et al., Dynamic Imaging of Genomic Loci in Living Human Cells by an Optimized CRISPR/Cas system. Cell. 2013, 155(7):1479-1491.

Chen, F., et al., High-frequency genome editing using ssDNA oligonucleotides with zinc-finger nucleases. Nature Methods. 2011, 8(9):753-755 with Supplementary Information. (31 pages).

Chen, F., et al., 2012, Methods and Reagents for Modifying Genomes Using RNA-Guided Endonucleases. in relation to U.S. Appl. No. 61/734,256.

Cho, S. W., et al., Targeted genome engineering in human cells with Cas9 RNA-guided endonucleases. Nat Biotechnol. 2013, 31:230-232, and supplementary materials.

Cho, S. W., et al., Heritable gene knockout in Caenorhabditis elegans by direct injection of Cas9-sgRNA ribonucleoproteins. Genetics, 2013, 195(3):1177-1180. (5 pages).

Christian, M., et al., Targeting DNA Double-Strand Breaks with TAL Effector Nucleases. Genetics. 2010, 186 (2):757-761 and 2S1-8S1.

Chugh, A., et al., Cell-penetrating peptides: Nanocarrier for Macromolecule Delivery in Living Cells. IUBMB Life. 2010, 62(3):183-193. (11 pages).

Chylinski, K., et al., The tracrRNA and Cas9 families of type II CRISPR-Cas immunity systems. RNA Biology. 2013, 10(5):726-737.

Clark, K. J., et al., A TALE of Two Nucleases: Gene Targeting for the Masses. Zebrafish, 2011, 8(3):147-149.

Close, D., et al., Expression of Non-Native Genes in a Surrogate Host Organism. 2012. Retrieved from the Internet at <http://www.intechopen.com> (33 pages).

Close, D., et al., The evolution of the bacterial luciferase gene cassette (lux) as a real-time bioreporter. Sensors. 2012;12(1):732-752. (21 pages).

Cohen, J., et al., The Emerging Race to Cure HIV Infections. Science. 2011, 332(6031):784-789.

Collins, C. A., and Brown, E. J., Cytosol as battleground: ubiquitin as a weapon for both host and pathogen. Trends in Cell Biology. 2010, 20(4):205-213.

Cong, L., et al., Multiplex Genome Engineering Using CRISPR/Cas Systems. Science. 2013, 339(6121):819-823 and Supplementary Materials.

CNLS Mapper results of S. pyogenes Cas9. NLS mapper, URL: http://nls-mapper.iab.keio.ac.jp/cgi-bin/NLS_Mapper_ycgi (Apr. 25, 2016) (1 page).

Cradick, T. J., et al., CRISPR/Cas 9 systems targeting β-globin and CCR5 genes have substantial off-target activity. Nucleic Acids Research. 2013, 41(20):9584-9592.

Cristea, S., et al., Dissection of Splicing Regulation at an Endogenous Locus by Zinc-Finger Nuclease-Mediated Gene Editing. PLoS One. 2011, 6(2):e16961. (5 pages).

Davis, G. D., and Cui, X., Zinc Finger Nucleases for Genome Editing. Genetic Engineering & Biotechnology News. 2010, 30(13). (6 pages).

De Vries, R., Dna condensation in bacteria: Interplay between macromolecular crowding and nucleoid proteins. Biochimie. 2010, 92(12):1715-1721. (7 pages).

Declaration of Technical Expert Paul Simons, executed Dec. 22, 2015, in relation to U.S. Appl. No. 14/704,551 (77 pages).

Deltcheva, E., et al., Crispr Rna maturation by trans-encoded small RNA and host factor RNase III. Nature. 2011, 471(7340):602-607 and Supplementary Information (71 pages).

Deng, D., et al., Structural basis for sequence-specific recognition of DNA by TAL effectors. Science. 2012, 335 (6069):720-723.

Dicarlo, J. E., et al., Genome engineering in Saccharomyces cerevisiae using CRISPR-Cas systems. Nucleic Acids Research. 2013, 41(7):4336-4343.

Dickinson, D. J., et al., Engineering the Caenorhabditis elegans genome using Cas9-triggered homologous recombination. Nat. Methods. 2013, 10:1028-1034.

Ding, Q., et al., Enhanced efficiency of human pluripotent stem cell genome editing through replacing TALENs with CRISPRs. Cell Stem Cell. 2013, 12(4):393-394. (2 pages).

Doyon, J. B., et al., Rapid and efficient clathrin-mediated endocytosis revealed in genome-edited mammalian cells. Nature Cell Biology. 2011, 13(3):331-337. (31 pages).

Doyon, Y., et al., Enhancing zinc-finger-nuclease activity with improved obligate heterodimeric architectures. Nature Methods. 2011, 8:74-79. (38 pages).

Ebina, H., et al., Harnessing the CRISPR/Cas9 system to disrupt latent HIV-1 provirus. Sci Rep. 2013, 3:2510. (7 pages).

Edgar, R., and Qimron, U., The Escherichia coli CRISPR system protects from A lysogenization, lysogens, and prophage induction. J Bacteriol. 2010, 192(23):6291-6294.

Esvelt, K. M. et al., Orthogonal Cas9 proteins for RNA-guided gene regulation and editing. Nat. Methods. 2013, 10:1116-1121.

Fath, S., et al., Multiparameter RNA and Codon Optimization: A Standardized Tool to Assess and Enhance Autologous Mammalian Gene Expression. PLoS One. 2011, 6(3):e17596. (14 pages).

Feng, Z., et al., Efficient genome editing in plants using a CRISPR/Cas system. Cell Res. 2013, 23(10):1229-1232.

Fonfara, I., et al., Phylogeny of Cas9 determines functional exchangeability of dual-RNA and Cas9 among orthologous type II CRISPR-Cas systems. Nucleic Acids Research. 2014, 42(4):2577-2590. (14 pages).

Fortier, S., et al., Genome-Wide Interrogation of Mammalian Stem Cell Fate Determinants by Nested Chromosome Deletions. PLoS Genetics. 2010, 6(12):e1001241. (14 pages).

Francis, D. M. and Page, R., Strategies to Optimize Protein Expression in E. coli. Current Protocols in Protein Science. 2010, 61:5.24.1-5.24.29. (29 pages).

Friedland, A. E., et al., Heritable genome editing in C. elegans via a CRISPR-Cas 9 system. Nat. Methods. 2013, 10(8):741-743.

Fu, Y., et al., High-frequency off-target mutagenesis induced by CRISPR-Cas nucleases in human cells. Nat Biotechnol. 2013, 31(9):822-826.

Fujii, W., et al., Efficient generation of large-scale genome-modified mice using gRNA and CAS9 endonuclease. Nucleic Acids Research. 2013, 41(20):e187.

(56) References Cited

OTHER PUBLICATIONS

Gabriel, R., et al., An unbiased genome-wide analysis of zinc-finger nuclease specificity. Nat Biotechnol. 2011, 29 (9):816-823.

Gagnon, J. A., et al., Efficient Mutagenesis by Cas9 Protein-Mediated Oligonucleotide Insertion and Large-Scale Assessment of Single-Guide RNAs. PLoS One. 2014, 9(5):e98186. Supplementary Information (25 pages).

Gaj, T., et al., ZFN, TALEN, and CRISPR/Cas-based methods for genome engineering. Trends in Biotechnology. 2013, 31(7):397-405. (9 pages).

Gao, H., et al., Heritable targeting mutagenesis in maize using a designed endonuclease. The Plant Journal. 2010, 61(1):176-187. (13 pages).

Garneau, J. E., et al., The CRISPR/Cas bacterial immune system cleaves bacteriophage and plasmid DNA. Nature. 2010, 468:67-71.

Gasiunas, G., et al., Cas9-crRNA ribonucleoprotein complex mediates specific DNA cleavage for adaptive immunity in bacteria. PNAS. 2012, 109(39):E2579-E2586.

Genomic Cruise Missiles, Science, 2012;338: 1526-1527. (12 pages).

Gilbert, L. A. et al., CRISPR-Mediated Modular RNA-Guided Regulation of Transcription in Eukaryotes. Cell. 2013, 154(2):442-451. (10 pages).

Golic, K. G., RNA-Guided Nucleases: A New Era for Engineering the Genomes of Model and Nonmodel Organisms. Genetics. 2013, 195(2):303-308. (6 pages).

Gonzalez, B., et al., Modular system for the construction of zinc-finger libraries and proteins. Nat Protoc. 2010, 5(4):791-810.

Goren, M., et al., The bacterial CRISPR/Cas system as analog of the mammalian adaptive immune system. RNA Biology. 2012, 9(5):549-554.

Gottwein, E., et al., Viral microRNA targetome of KSHV-infected primary effusion lymphoma cell lines. Cell Host & Microbe. 2011, 10(5):515-526.

Gratz, S. J., et al., Genome engineering of *Drosophila* with the CRISPR RNA-guided Cas9 nuclease. Genetics, 2013, 194(4):1029-1035 and supplementary materials. (17 pages).

Groisman, E. A., et al., Bacterial Mg2+ Homeostasis, Transport, and Virulence. Annual Reviews of Genetics. 2013, 47:625-646. (22 pages).

Guschin, D. Y., et al., A Rapid and General Assay for Monitoring Endogenus Gene Modification. In: Mackay, J., Segal, D. (eds.) Engineeed Zinc Finger Proteins. Methods in Molecular Biology. 2010, vol. 649. Humana Press, Totowa, NJ.

Handel, E-M., et al., Versatile and Efficient Genome Editing in Human Cells by Combining Zinc-Finger Nucleases with Adeno-Associated Viral Vectors. Human Gene Therapy. 2011, 23(3):321-329. (9 pages).

Haurwitz, R. E., et al., Sequence- and structure-specific RNA processing by a CRISPR endonuclease. Science. 2010, 329(5997):1355-1358. (4 pages).

PCT International Search Report dated Jan. 27, 2014, in relation to International Application No. PCT/KR2013/009488 filed Oct. 23, 2013, pp. 1-5.

Hocine, S., et al., RNA processing and export. Cold Spring Harb Perspect Biol. 2010, 2:a000752.

Holt, N., et al., Zinc finger nuclease-mediated CCR5 knockout hematopoietic stem cell transplantation controls HIV-1 in vivo. Nat Biotechnol. 2010, 28(8):839-847. (26 pages).

Horvath, P., and Barrangou, R., RNA-guided genome editing a la carte. Cell Res. 2013, 23:733-734.

Horvath, P., and Barrangou, R., CRISPR/Cas, the immune system of bacteria and archaea. Science. 2010, 327(5962):167-170. (4 pages).

Hoshijima, K., et al., Highly efficient CRISPR-Cas9-based methods for generating deletion mutations and F0 embryos that lack gene function in zebrafish. Developmental Cell. 2019, 51(5):645-657.e4. (35 pages).

Hruscha, A., et al., Efficient CRISPR/Cas9 genome editing with low off-target effects in zebrafish. Development. 2013, 140(24):4982-4987. Supplementary Information (12 pages).

Hsu, P. D., et al., DNA targeting specificity of RNA-guided Cas9 nucleases. Nat Biotechnol. 2013, 31(9):827-832.

Hu, P, et al., Comparison of various nuclear localization signal-fused Cas9 proteins and Cas9 mRNA for genome editing in zebrafish. G3 Genes|Genomes|Genetics. 2018, 8(3):823-831. (9 pages).

Huang, P., et al., Heritable gene targeting in zebrafish using customized TALENs. Nature Biotechnology. 2011, 29(8):699-700. (2 pages).

Hwang, W. Y., et al., Efficient genome editing in zebrafish using a CRISPR-Cas system. Nat Biotechnol. 2013, 31:227-229 and Supplementary Materials.

Hwang, W. Y., et al., Heritable and Precise Zebrafish Genome Editing Using a CRISPR-Cas System. PLoS One. 2013, 8(7):e68708 and Supplementary Materials. (14 pages).

Jani, B. and Fuchs R., In Vitro Transcription and Capping of Gaussia Luciferase mRNA Followed by HeLa Cell Transfection. J. Vis. Exp. 2012, 61:3702. (9 pages).

Japanese Office Action dated Nov. 24, 2015 for Japanese Patent Application No. 2015-538033, pp. 1-10 (with English Translation).

Jensen, N. M., et al., An update on targeted gene repair in mammalian cells: methods and mechanisms. J. Biomed. Sci. 2011;18:10. (14 pages).

Jeyarajan, S., et al., 2010, Plasmid DNA delivery into MDA-MB-453 cells mediated by recombinant Her-NLS fusion protein. International Journal of Nanomedicine. 2010, 5:725-733. (9 pages).

Jiang, F., et al., 2011, Structural basis of RNA recognition and activation by innate immune receptor RIG-I. Nature. 2011, 479:423-429.

Jiang, W., et al., Demonstration of CRISPR/Cas9/sgRNA-mediated targeted gene modification in *Arabidopsis*, tobacco, sorghum and rice. Nucleic Acids Research. 2013, 41(20):e188.

Jiang, W., et al., RNA-guided editing of bacterial genomes using CRISPR-Cas systems. Nat. Biotechnol. 2013, 31:233-239.

Jiang, W., et al., CRISPR-assisted editing of bacterial genomes. Nat Biotechnol. 2013, 31(3):233-239.

Jinek, M., et al., A programmable dual-RNA-guided DNA endonuclease in adaptive bacterial immunity. Science. 2012, 337(6096):816-821 and Supplementary Materials. (7 pages).

Jinek, M., et al., Methods and Compositions for RNA-Directed Site-Specific DNA Modification. U.S. Appl. No. 61/652,086, filed May 25, 2012.

Jinek, M., et al., RNA-programmed genome editing in human cells. eLife. 2013, 2:e00471.

Jore, M. M., et al., Structural basis for CRISPR RNA-guided DNA recognition by Casade. Nat. Struct. Mol. Biol. 2011, 18(5):529-536. (9 pages).

Joung, J. K. and Sander J. D., TALENs: A widely applicable technology for targeted genome editing. Nat. Rev. Mol. Cell Biol. 2013, 14:49-55. (7 pages).

Kang, H. C. and Bae, Y. H., Co-delivery of small interfering RNA and plasmid DNA using a polymeric vector incorporating endosomolytic oligomeric sulfonamide. Biomaterials. 2011, 32(21):4914-4924. (11 pages).

Karginov, F. V. and Hannon, G. J., The CRISPR System: Small RNA-Guided Defense in Bacteria and Archaea. Molecular Cell. 2010, 37(1):7-19. (13 pages).

Karvelis, T., et al., crRNA and tracrRNA guide Cas9-mediated DNA interference in *Streptococcus thermophilus*. RNA Biology, 2013, 10(5):841-851.

Katic, I. and Grobhans, H., Targeted Heritable Mutation and Gene Conversion by Cas9-CRISPR in Caenorhabditis elegans. Genetics. 2013, 195(3):1173-1176. (4 pages).

Kim, E., et al., Precision genome engineering with programmable DNA-nicking enzymes. Genome Res. 2012, 22:1327-1333.

Kim, H., et al., Surrogate reporters for enrichment of cells with nuclease-induced mutations. Nat Methods. 2011, 8:941-943.

Kim, S., et al., Highly efficient RNA-guided genome editing in human cells via delivery of purified Cas9 ribonucleoproteins. Genome Res. 2014, 24:1012-1019. (9 pages).

Kim, S., et al., 2018, CRISPR RNAs trigger innate immune responses in human cells. Genome Res. 2018, 28:367-373. (8 pages).

(56) References Cited

OTHER PUBLICATIONS

Kim, T. K., and Eberwine, J. H., Mammalian cell transfection: the present and the future. Anal Bioanal Chem. 2010, 397:3173-3178. (6 pages).

Kolomeisky, A. B., Physics of protein—DNA interactions: mechanisms of facilitated target search. Phys. Chem. Chem. Phys. 2011, 13:2088-2095. (8 pages).

Kondo, S., et al., Highly Improved Gene Targeting by Germline-Specific Cas9 Expression in Drosophila. Genetics. 2013, 195(3):715-721.

Koo, T., et al., Measuring and Reducing Off-Target Activities of Programmable Nucleases Including CRISPR-Cas9. Molecules and Cells. 2015, 38(6):475-481. (7 pages).

Kouranova, E., et al., CRISPRs for optimal targeting: delivery of CRISPR components as DNA, RNA, and protein into cultured cells and single-cell embryos. Human Gene Therapy. 2016, 27(6):464-475. (12 pages).

Lambowitz, A. M. and Zimmerly, S., Group II Introns: Mobile Ribozymes that Invade DNA. Cold Spring Harb Perspect Biol. 2011, 3:a003616. (19 pages).

Lane, J., et al., Targeting RHoC by way of ribozyme trangene in human breast cancer cells and its impact on cancer invasion. World J Oncol. 2010, 1(1):7-13. (7 pages)Lane, J., et al., Targeting RHoC by way of ribozyme trangene in human breast cancer cells and its impact on cancer invasion. World J Oncol. 2010, 1(1):7-13. (7 pages).

Larson, D. R., et al., Real-time observation of transcription initiation and elongation on an endogenous yeast gene. Science. 2011, 332(6028):475-478.

Larsen, H. O., et al., Nonviral transfection of leukemic primary cells and cells lines by siRNA—a direct comparison between Nucleofection and Accell delivery. Experimental Hematology. 2011, 39:1081-1089. (9 pages).

Larson, M. H. et al., CRISPR interference (CRISPRi) for sequence-specific control of gene expression. Nat. Protoc. 2013, 8:2180-2196.

Ledford, H., Targeted gene editing enters clinic. Nature. 2011, 471:16. (1 page).

Lee, H. Y., et al., Targeted chromosomal deletions in human cells using zinc finger nucleases. Genome Res. 2010, 20:81-89.

Lee, H. J., et al., Targeted chromosomal duplications and inversions in the human genome using zinc finger nucleases. Genome Res, 2012, 22:539-548.

Lee, J-S., et al., RNA-guided genome editing in Drosophila with the purified Cas9 protein. G3 Genes|Genomes| Genetics. 2014, 4(7):1291-1295. (5 pages).

Notice of Allowance and Fees Due dated Feb. 4, 2015, U.S. Appl. No. 14/226,274, filed Mar. 26, 2014, pp. 1-22.

Li, D., et al., Heritable gene targeting in the mouse and rat using a CRISPR-Cas system. Nat Biotechnol. 2013, 31(8):681-683 and Supplementary Materials.

Li, J-F., et al., Multiplex and homologous recombination-mediated genome editing in Arabidopsis and Nicotiana benthamiana using guide RNA and Cas9. Nat Biotechnol. 2013, 31(8):688-691 and Supplemental Materials.

Li, T., et al., Modularly Assembled Designer TAL Effector Nucleases for Targeted Gene Knockout and Gene Replacement in Eukaryotes. Nucleic Acids Research, 2011, 39(14):6315-6325.

Li, T., et al., TAL nucleases (TALNs): hybrid protein composed of TAL effectors and FokI DNA-cleavage domain. Nucleic Acids Research. 2011, 39(1):359-372. (14 pages).

Li, W., et al., Simultaneous generation and germline transmission of multiple gene mutations in rat using CRISPR-Cas systems. Nat Biotechnol. 2013, 31(8):684-686 and Supplementary Materials.

Lieber, M. R., The Mechanism of Double-Strand DNA Break Repair by the Nonhomologous DNA End Joining Pathway. Annual Review of Biochemistry. 2010, 79:181-211. (34 pages).

Lino, C. A., et al., Delivering CRISPR: a review of the challenges and approaches. Drug Delivery. 2018, 25(1):1234-1257.

Liu, J., et al., Efficient and Specific Modifications of the Drosophila Genome by Means of an Easy TALEN Strategy. Journal of Genetics and Genomics. 2012, 39(5):209-215. (7 pages).

Liu, P-Q., et al., Generation of a triple-gene knockout mammalian cell line using engineered zinc-finger nucleases. Biotechnology and Bioengineering. 2010, 106(1):97-105.

Liu, Y., et al., Polyethylene glycol (PEG)-mediated transformation of the fused egfp-hph gene into Pleurotus ostreatus. African Journal of Biotechnology. 2012, 11(19):4345-4353. (9 pages).

Liu, Y-C., et al., Efficient Polyethylene Glycol (PEG) Mediated Transformation of the Moss Physcomitrella patens. J. Vis. Exp. 2011, 50:2560. (4 pages).

Lo, T-W., et al., Precise and Heritable Genome Editing in Evolutionarily Diverse Nematodes Using TALENs and CRISPR/Cas9 to Engineer Insertions and Deletions. Genetics. 2013, 195(2):331-348. (26 pages).

Lu, C. and Li, P., Preparation of Short RNA by In Vitro Transcription. In: Conn, G. (eds) Recombinant and In Vitro RNA Synthesis. Methods in Molecular Biology, 2013, vol. 941. Humana Totowa, NJ. (12 pages).

Ma, S. et al., Highly efficient and specific genome editing in silkworm using custom TALENs. PLoS One. 2012, 7(9):e45035. (7 pages).

Madrigal, P., and Pawel, K., Current bioinformatic approaches to identify DNase I hypersensitive sites and genomic footprints from DNase-seq data. Frontiers in Genetics. 2012, 3(230):1-3. (3 pages).

Maeder, M. L. et al., CRISPR RNA-guided activation of endogenous human genes. Nat. Methods. 2013, 10:977-979.

Magnani, L., et al., Pioneer factors: directing transcriptional regulators within the chromatin environment. Trends in Genetics. 2011, 27(11):465-474. (10 pages).

Mahfouz, M. M., et al., De novo-engineered transcription activator-like effector (TALE) hybrid nuclease with novel DNA binding specificity creates double-strand breaks. PNAS. 2011, 108(6):2623-2628.

Mak, A. N-S., et al., The Crystal Structure of TAL Effector PthXo1 Bound to Its DNA Target. Science. 2012, 335 (6069):716-719. (5 pages).

Makarova, K. S., et al., Evolution and classification of the CRISP-Cas systems. Nat Rev Microbiol. 2011, 9:467-477. (11 pages).

Mali, P., et al., Cas9 as a Versatile Tool for Engineering Biology. Nat Methods. 2013, 10(10):957-963.

Mali, P., et al., RNA-Guided Human Genome Engineering via Cas9. Science. 2013, 339(6121):823-826 and Supplementary Materials. (40 pages).

Mali, P., et al., CAS9 transcriptional activators for target specificity screening and paired nickases for cooperative genome engineering. Nat Biotechnol. 2013, 31:833-838.

Marchfelder, A., et al., Small RNAs for defence and regulation in archaea. Extremophiles. 2012, 16:685-696. (12 pages).

Maresca, M., et al., Obligate ligation-gated recombination (ObliGaRe): Custom-designed nuclease-mediated targeted integration through nonhomologous end joining. Genome Res. 2013, 23:539-546.

Marfori, M., et al., Molecular basis for specificity of nuclear import and prediction of nuclear localization. Biochimica et Biophysica Acta (BBA)—Molecular Cell Research. 2011, 1813(9):1562-1577. (16 pages).

Marraffini, L. A. and Sontheimer, E. J., Self versus non-self discrimination during CRISPR RNA-directed immunity. Nature. 2010, 463(7280):568-571. (13 pages).

Mashimo, T., et al., Generation of Knockout Rats with X-Linked Severe Combined Immunodeficiency (X-SCID) Using Zinc-Finger Nucleases. PLoS One 2010, 5(1):e8870. (7 pages).

Mazzara, G. P., et al., Maturation events leading to transfer RNA and ribosomal RNA. Cell Biology. 2012, 3:439-545.

Miao, J., et al., Targeted mutagenesis in rice using CRISPR-Cas system. Cell Res. 2013, 23(10):1233-1236.

Mika, J. T., and Poolman, B., Macromolecule diffusion and confinement in prokaryotic cells. Current Opinion in Biotechnology. 2011, 22(1):117-126. (10 pages).

Miller, J. C., et al., A Tale nuclease architecture for efficient genome editing. Nat Biotechnol. 2011, 29(2):143-148 and online methods.

(56) References Cited

OTHER PUBLICATIONS

Mougiakos, I., et al., Characterizing a thermostable Cas9 for bacterial genome editing and silencing. Nat Commun. 2017, 8:1647. (11 pages).

Mussolino, C., et al., A novel TALE nuclease scaffold enables high genome editing activity in combination with low toxicity. Nucleic Acids Research. 2011, 39(21):9283-9293.

Mussolino, C., and Cathomen, T., RNA guides genome engineering. Nat. Biotechnol. 2013, 31:208-209.

Mussolino, C., and Cathomen, T., TALE nucleases: tailored genome engineering made easy. Current Opinion in Biotechnology. 2012, 23(5):644-650. (7 pages).

Musunuru, K., Genome editing of human pluripotent stem cells to generate human cellular disease models. Dis Model Mech. 2013, 6(4):896-904. (17 pages).

Nakayama, T., et al., Simple and efficient CRISPR/Cas9-mediated targeted mutagenesis in Xenopus tropicalis. Genesis. 2013, 51(12):835-843. (15 pages).

Nature Biotechnology Journal webpage, vol. 30 issue 9, Sep. 10, 2012, available at https://www.nature.com/nbt/volumes/30/issues/9 (last accessed on Mar. 22, 2021), (15 pages).

NCBI record for NC-002737.2, 2019, "*Streptococcus pyogenes* M1 Gas, complete sequence", retrieved from the internet at <https://www.ncbi.nlm.nih.gov/nuccore/NC_002737.2> (1 page).

Nekrasov, V., et al., Targeted mutagenesis in the model plant Nicotiana benthamiana using Cas9 RNA-guided endonuclease. Nat Biotechnol. 2013;31(8):691-693 and Supplemental Materials.

Ng, Y. S., et al., Chemical transfection of dye-conjugated microRNA precursors for microRNA functional analysis of M2 macrophages. Journal of Cellular Biochemistry. 2012, 113(5):1714-1723. (10 pages).

Niinaka, Y., et al., Silencing of autocrine motility factor induces mesenchymalto-epithelial transition and suppression of osteosarcoma pulmonary metastasis. Cancer Res. 2010, 70(22):9483-9493. (11 pages).

Noland, C. L., et al., siRNA Repositioning for Guide Strand Selection by Human Dicer Complexes. Molecular Cell. 2011, 43(1):110-121. (12 pages).

Ogawa, A., Rational design of artificial riboswitches based on ligand-dependent modulation of internal ribosome entry in wheat germ extract and their applications as label-free biosensors. RNA. 2011, 17:478-488.

Pandika, M., 2014, "Jennifer Doudna, CRISPR Code Killer", www.ozy.com/rising-stars-and-provocateurs/jennifer-doudna-crispr-code-killer/4690, Jan. 7, 2014, pp. 1-6.

Pardo, R., et al., pARIS-htt: an optimised expression platform to study huntingtin reveals functional domains required for vesicular trafficking. Mol Brain. 2010, 3:17. (17 pages).

Pattanayak, V., et al., Revealing off-target cleavage specificities of zinc finger nucleases by in vitro selection. Nat Methods, 2011, 8(9):765-770.

Pattanayak, V., et al., High-throughput profiling of off-target DNA cleavage reveals RNA-programmed Cas9 nuclease specificity. Nat. Biotechnol. 2013, 31:839-843.

Pennisi, E., Encode Project Writes Eulogy for Junk DNA. Science. 2012, 337(6099):1159-1161. (2 pages).

Pennisi, E., The CRISPR Craze. Science. 2013, 341(6148):833-836.

Perez-Pinera, P., et al., RNA-guided gene activation by CRISPR-Cas9-based transcription factors. Nat Methods. 2013, 10(10):973-976.

Perez-Pinera, P., et al., Advances in Targeted Genome Editing. Current Opinion in Chemical Biology. 2012, 16(3-4):268-277. (1 page).

Perez-Rodriguez, R., Elucidating a novel mechanism of DNA silencing caused by envelope stress in *Escherichia coli*. Dissertation and Abstract first available to the public on Jun. 17, 2010 (156 pages).

Pillich, H., et al., Activation of the unfolded protein response by Listeria monocytogenes. Cellular Microbiology, 2012, 14(6):949-964.

Primo, M. N., et al., Lentiviral vectors for cutaneous RNA managing. Experimental Dermatology. 2012, 21(3):162-170.

Program and Conference Logistics provided to the attendees of the CRISPR 2012: 5th Annual CRISPR Research Meeting held at the University of California, Berkeley, CA (Jun. 2012). (5 pages).

PShooter™ Vector user guide, Invitrogen by Life Technologies, revision date Mar. 29, 2012 (36 pages).

Qi, L., et al., RNA Processing Enables Predictable Programming of Gene Expression. Nat Biotechnol. 2012, 30(10):1002-1006 and Supplementary Materials.

Qi, L. S., et al., Repurposing CRISPR as an RNA-Guided Platform for Sequence-Specific Control of Gene Expression. Cell. 2013, 152(5):1173-1183.

Ramirez, C. L., et al., Engineered zinc finger nickases induce homology-directed repair with reduced mutagenic effects. Nucleic Acid Research. 2012, 40(12):5560-5568. (9 pages).

Ran, F. A., et al., Double nicking by RNA-guided CRISPR cas9 for enhanced genome editing specificity. Cell, 2013, 154(6):1380-1389.

Ran, F. A., et al., Genome engineering using the CRISPR-Cas9 system. Nat. Protoc. 2013, 8:2281-2308.

Reyon, D., et al., FLASH assembly of TALENs for high-throughput genome editing. Nat Biotechnol. 2012, 30 (5):460-465. (8 pages).

Richter, H., et al., Exploiting CRISPR/Cas: Interference Mechanisms and Applications. International Journal of Molecular Sciences. 2013, 14(7):14518-14531. (14 pages).

Rios, X., et al., Stable Gene Targeting in Human Cells Using Single-Strand Oligonucleotides with Modified Bases. PLoS One. 2012, 7(5):e36697. (14 pages).

Sakurai, K., et al., Silencing of Gene Expression in Cultured Cells Using Small Interfering RNAs. Curr. Protoc. Cell Biol. 2010;47:27.1.1-27.1.28. (28 pages).

Sander, J. D., et al., Targeted gene disruption in somatic zebrafish cells using engineered TALENs. Nature Biotechnology. 2011, 29(8):697-698 with Supplementary Information. (27 pages).

Sanders, R., 2013, "Cheap and easy technique to snip DNA could revolutionize gene therapy," UC Berkeley News Center, Jan. 7, 2013, retrieved from the internet at <http://newscenter.berkeley.edu/2013/01/07/cheap-and-easy-technique-to-snip-dna-could-revolutionize-gene-therapy/> pp. 1-3 (3 pages).

Sanjana, N. E., et al., A Transcription Activator-Like Effector (TALE) Toolbox for Genome Engineering. Nat Protoc. 2012, 7(1):171-192. Supplementary Materials (28 pages).

Sapranauskas, R., et al., The *Streptococcus thermophilus* CRISPR/Cas system provides immunity in *Escherichia coli*. Nucleic Acids Research. 2011, 39(21):9275-9282 and Supplementary Materials. (15 pages).

Schmidt, A., et al., Sensing of viral nucleic acids by RIG-I: from translocation to translation. European Journal of Cell Biology. 2012, 91(1):78-85.

Second Declaration of Dr. Boch dated Apr. 26, 2019 as filed in Opposition to European Patent No. 2825654 (20 pages).

Segal, D., J., Genome Engineering: Bacteria herald a new era of gene editing. eLife. 2013, 2:e00563.

Shalem, O., et al., Genome-Scale CRISPR-Cas9 Knockout Screening in Human Cells. Science. 2013, 343(6166):84-87.

Shan, Q., et al., Targeted genome modification of crop plants using a CRISPR-Cas system. Nat Biotechnol. 2013, 31(8):686-688 and Supplementary Materials.

Shen, B., et al., Generation of gene-modified mice via Cas9/RNA-mediated gene targeting. Cell Res. 2013, 23:720-723.

Singapore Written Opinion dated Mar. 18, 2016 in relation to Singapore Patent Application No. 11201503059X.

Sinkunas, T., et al., Cas3 is a single-stranded DNA nuclease and ATP-dependent helicase in the CRISPR/Cas immune system. The EMBO Journal. 2011, 30:1335-1342. (8 pages).

Strecker, J., et al., Engineering of CRISPR-Cas12b for human genome editing. Nat Commun. 2019, 10(1):212.

Sternberg, S. H., et al., DNA interrogation by the CRISPR RNA-guided endonuclease Cas9. Biophysical Journal. 2014, 106(2):62-67. (17 pages).

Sternberg, S. H., et al., Mechanism of substrate selection by a highly specific CRISPR endoribonuclease. RNA 2012, 18:661-672. (12 pages).

(56)                    References Cited

OTHER PUBLICATIONS

*Streptococcus*—bacterial genus—Microbiology Dictionary, Hardy Diagnostics, available at https://catalog.hardydiagnostics.com/cp_prod/Content/hugo/Streptococcus.htm (last accessed Oct. 25, 2020), (4 pages).

Sun, C., et al., Functional reconstruction of human eukaryotic translation initiation factor 3 (eIF3). PNAS. 2011, 108(51):20473-20478. (6 pages).

Sung, Y. H., et al., Mouse genetics: Catalogue and scissors. BMB Rep. 2012, 45(12):686-692.

Sung, Y. H., et al., Highly efficient gene knockout in mice and zebrafish with RNA-guided endonucleases. Genome Res. 2014, 24:125-131. (7 pages).

Svitashev, S., et al., Genome editing in maize directed by CRISPR-Cas9 ribonucleoprotein complexes. Nature Communications. 2016, 7:13274. (7 pages).

Szczepankowska, A., Role of CRISPR/cas system in the development of bacteriophage resistance. Advances in Virus Research. 2012, 82:289-338. (50 pages).

Terns, M. P. and Terns, R. M., CRISPR-Based Adaptive Immune Systems. Current Opinion in Microbiology. 2011, 14(3):321-327. (13 pages).

Tesson, L., et al., Knockout rats generated by embryo microinjection of TALENs. Nat Biotechnol. 2011, 29(8):695-696 and Supplementary Materials. (15 pages).

Thurman, R. E., et al., The accessible chromatin landscape of the human genome. Nature. 2012, 489:75-82. (8 pages).

Tzur, Y. B., et al., Heritable Custom Genomic Modifications in Caenorhabditis elegans via a CRISPR-Cas9 System. Genetics. 2013, 195(3):1181-1185. (14 pages).

Urnov, F. D., et al., Genome editing with engineered zinc finger nucleases. Nat Rev Genet. 2010, 11(9):636-646.

Van Der Oost, J., New Tool for Genome Surgery. Science. 2013, 339(6121):768-770.

Vasu, K., et al., Endonuclease Active Site Plasticity Allows DNA Cleavage with Diverse Alkaline Earth and Transition Metal Ions. ACS Chemical Biology. 2011, 6(9):934-942. (9 pages).

Villion, M., and Moineau, S., The double-edged sword of CRISPR-Cas9 systems. Cell Res. 2013, 23:15-17. (4 pages).

Walsh, R. M., and Hochedlinger, K., A variant CRISPR-Cas9 system adds versatility to genome engineering. PNAS, 2013, 110(39):15514-15515.

Wang, H., et al., One-step generation of mice carrying mutations in multiple genes by CRISPR/Cas-mediated genome engineering. Cell. 2013, 153(4):910-918. (17 pages).

Wang, J., et al., Targeted gene addition to a predetermined site in the human genome using a ZFN-based nicking enzyme. Genome Res. 2012, 22(7):1316-1326. (11 pages).

Wang, T., et al., Genetic Screens in Human Cells Using the CRISPR/Cas9 System. Science. 2013, 343(6166):80-84.

Wee, L., et al., Argonaute divides its RNA Guide into domains with distinct functions and RNA-binding properties. Cell. 2012, 151(5):1055-1067. (23 pages).

Weeks, A., et al., Structural and Biochemical Studies of a Fluoroacetyl-CoA-Specific Thioesterase Reveal a Molecular Basis for Fluorine Selectivity. Biochemistry. 2010, 49(43):9269-9279 and Supplementary Materials. (21 pages).

Welch, M., et al., Chapter 3: Designing Genes for Successful Protein Expression. Eds: Voigt. C., Methods in Enzymology. Academic Press. 2011, 498:43-66. (24 pages).

Wente, S. R. and Rout, M. P., The Nuclear Pore Complex and Nuclear Transport. Cold Spring Harb Perspect Biol. 2010, 2:a000562. (21 pages).

Whisnant, A. W., et al., In depth analysis of the interaction of HIV-1 with cellular microRNA biogenesis and effector mechanisms. mBio. 2013, 4:10.1128/mbio.00193-13.

White, T. B. and Lambowitz, A. M., The Retrohoming of Linear Group II Intron RNAs in Drosophila melanogaster Occurs by Both DNA Ligase 4-Dependent and -Independent Mechanisms. PLoS Genetics. 2012, 8(2):e1002534. (16 pages).

Wiedenheft, B., et al., RNA-guided complex from a bacterial immune system enhances target recognition through seed sequence interactions. PNAS. 2011, 108(25):10092-10097. (7 pages).

Wiedenheft, B., et al., Structures of the RNA-guided surveillance complex from a bacterial immune system. Nature. 2011, 477:486-489. (5 pages).

Wiedenheft, B., et al., RNA-Guided Genetic Silencing Systems in Bacteria and Archaea. Nature. 2012, 482:331-338.

Wieland, M., et al., Engineering of ribozyme-based riboswitches for mammalian cells. Methods. 2012, 56(3):351-357. (7 pages).

Wilen, C. B., et al., Engineering HIV-Resistant Human CD4+ T Cells with CXCR4-Specific Zinc-Finger Nucleases. PLoS Pathogens. 2011, 7(4):e1002020. (15 pages).

Wilusz, J. E., et al., tRNAs marked with CCACCA are targeted for degradation. Science. 2011, 334(6057):817-821.

Woo, J. W., et al., DNA-free genome editing in plants with preassembled CRISPR-Cas9 ribonucleoproteins. Nature Biotechnology. 2015, 33:1162-1164. (4 pages).

Wood, A. J., et al., Targeted Genome Editing Across Species Using ZFNs and TALENs. Science. 2011, 333(6040):307 and Supplementary Materials. (27 pages).

Wu, S. et al., Establishment of a PEG-mediated protoplast transformation system based on DNA and CRISPR/Cas9 ribonucleoprotein complexes for banana. BMC Plant Biol. 2020, 20:425. (10 pages).

Wu, Z., et al., Effect of Genome Size on AAV Vector Packaging. Molecular Therapy, 2010, 18(1):80-86. (7 pages).

Xu, K., The Next Generation Biotechnology for Apple Improvement and Beyond: The CRISPR/Cas9 Story. New York Fruit Quarterly. 2013, 21(4):19-22. (4 pages).

Yamano, S., et al., Comparison of Transfection Efficiency of Nonviral Gene Transfer Reagents. Mol Biotechnol. 2010, 46:287-300. (14 pages).

Yang, H., et al., One-Step Generation of Mice Carrying Reporter and Conditional Alleles by CRISPR/Cas-Mediated Genome Engineering. Cell. 2013, 154(6):1370-1379 and Supplementary Materials.

Yarris, 2012, "Programmable DNA scissors found for bacterial immune system", downloaded from http://newscenter.lbl.gov/2012/06/28/programmabledna.scissors/ (4 pages).

Yi, Y., et al., Current Advances in Retroviral Gene Therapy. Current Gene Therapy. 2011, 11(3):218-228.

Yu, Z., et al., Highly Efficient Genome Modifications Mediated by CRISPR/Cas9 in Drosophila. Genetics. 2013, 195(1):289-291.

Zaret, K. S., and Carroll, J. S., Pioneer transcription factors: establishing competence for gene expression. Genes & Dev. 2011, 25:2227-2241.

Zhang, F., et al., Efficient construction of sequence-specific TAL effectors for modulating mammalian transcription. Nat Biotechnol. 2011, 29(2):149-153 and Supplementary Materials. (20 pages).

Zhang, Y., et al., Processing-Independent CRISPR RNAs Limit Natural Transformation in Neisseria meningitides. Molecular Cell. 2013, 50(4):488-503. (16 pages).

Zhang, Y. et al., A highly efficient rice green tissue protoplast system for transient gene expression and studying light/chloroplast-related processes. Plant Methods 2011, 7(1):30. (14 pages).

Zou, J., et al., Oxidase-deficient neutrophils from X-linked chronic granulomatous disease iPS cells: functional correction by zinc finger nuclease-mediated safe harbor targeting. Blood. 2011, 117(21):5561-5572. (13 pages).

Zuris, J. A., et al., Efficient Delivery of Genome-Editing Proteins In Vitro and In Vivo. Nat. Biotechnol. 2015, 33 (1):73-80. (26 pages).

Amaxa™ 4D-Nucleofector™ Protocol for K562 [ATCC®] For 4D-Nucleofector™ X Unit, Lonza (2010).

Bekard, I., et al. Electric Field Induced Changes in Protein Conformation. Soft Matter. 2014 10, 431-437.

Cong, L., et al. Multiplex genome engineering using CRISPR/Cas systems. Science. 2013, 339(6121):819-823.

Jacobi, A. M., et al. Simplified CRISPR Tools for Efficient Genome Editing and Streamlined Protocols for Their Delivery into Mammalian Cells and Mouse Zygotes. Methods. May 2017; 15:121-122:16-28.

Kanchiswamy, CN., et al. Fine-Tuning Next-Generation Genome Editing Tools, Trends Biotechnology Jul. 2016;34(7):562-574.

(56) References Cited

OTHER PUBLICATIONS

Kim, S., et al. Highly Efficient RNA-guided Genome Editing in Human Cells via Delivery of Purified Cas9 Ribonucleoproteins. Genome Research. Jun. 2014;24(6):1012-19 and Supplemental Materials.

Liang, X., et al. Rapid and Highly Efficient Mammalian Cell Engineering via Cas9 Protein Transfection. Journal of Biotechnology. Aug. 2015. 20:208:44-53 and Supplemental Materials.

Lin, S., et al. Enhanced homology-directed human genome engineering by controlled timing of CRISPR/Cas9 delivery, Elife Research Advance 2014; 3:e04766.

Mali, P., et al. RNA-guided human genome engineering via Cas9. Science. 2013, 339(6121):823-826).

Nucleofection® Protocol for K562 Cells—Transfection in Suspension, Lonza (2024).

Rodrigues, R., et al. Electric Field Effects on Proteins—Novel Perspectives on Food and Potential Health Implications. Food Research International 2020, 137:109709.

Zelphati, O., et al. Intracellular delivery of proteins with a new lipid-mediated delivery system. The Journal of Biological Chemistry. 2001, 276(37):35103-35110.

Zuris J. et al. Cationic lipid-mediated delivery of proteins enables efficient protein-based genome editing in vitro and in vivo. Nature Biotechnology. 2015, 33(1):73-80.

* cited by examiner

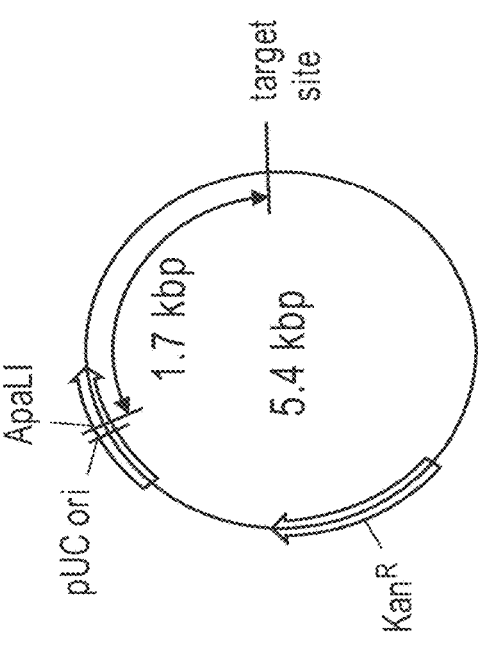
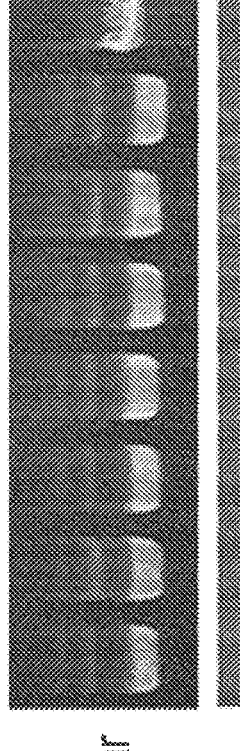
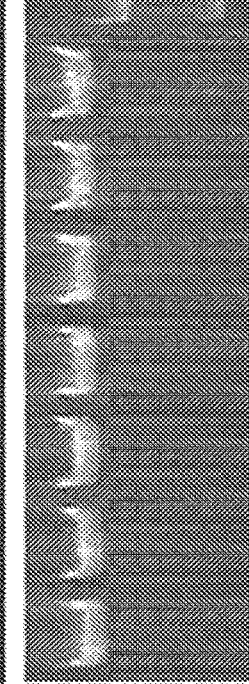
FIG. 1B

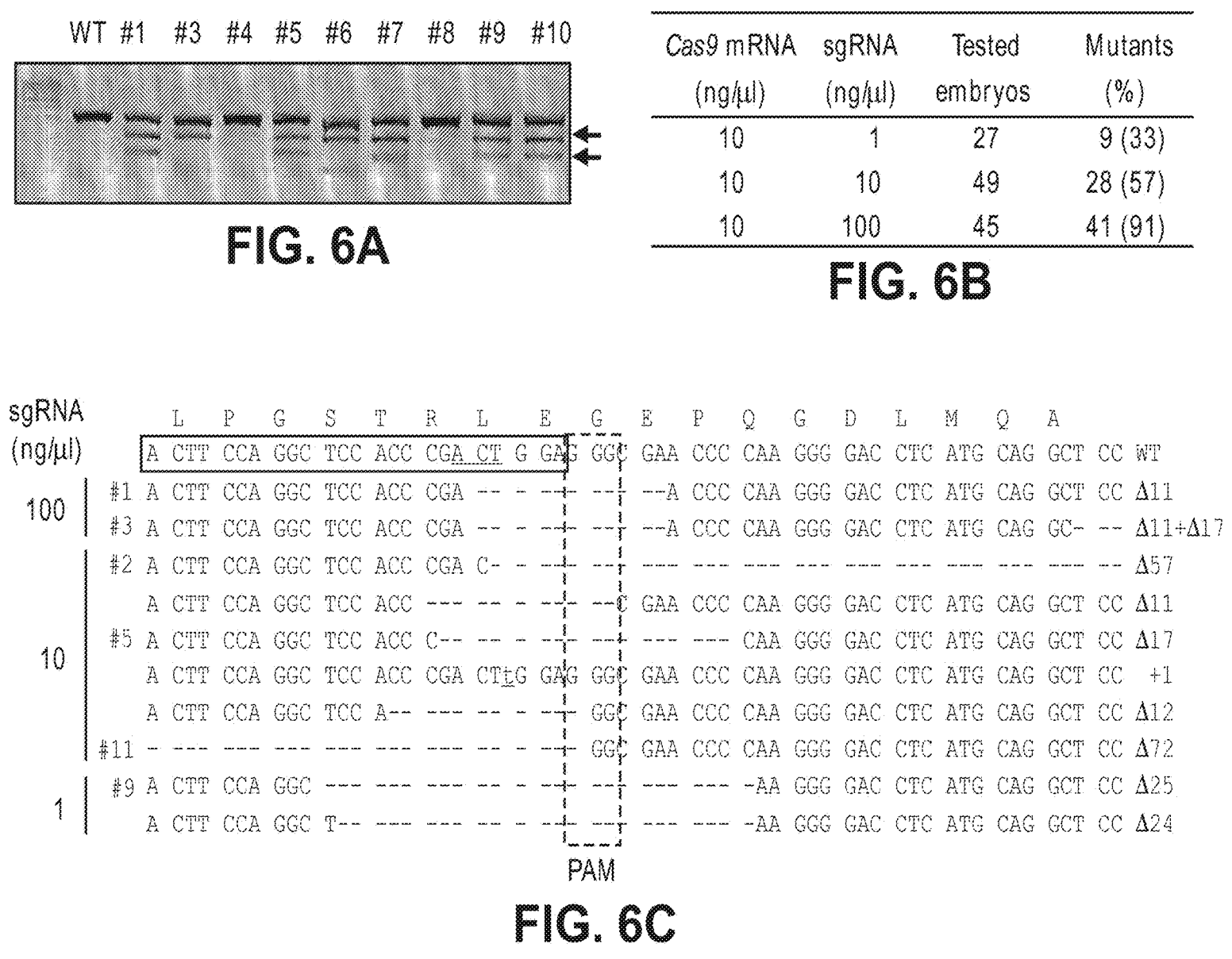

| Cas9 mRNA (ng/µl) | sgRNA (ng/µl) | Tested embryos | Mutants (%) |
|---|---|---|---|
| 10 | 1 | 27 | 9 (33) |
| 10 | 10 | 49 | 28 (57) |
| 10 | 100 | 45 | 41 (91) |

FIG. 6C

```
            L   P   G   S   T   R   L   E   G   E   P   Q   G   D   L   M   Q   A
     A    CTT CCA GGC TCC ACC CGA  CT  G GAG GAA CCC CAA GGG GAC CTC ATG CAG CAG GCT CC   WT sgRNA
(ng/µl)
100  #1  A CTT CCA GGC TCC ACC CGA  --  - --- --A CCC CAA GGG GAC CTC ATG CAG CAG GCT CC   Δ11
     #3  A CTT CCA GGC TCC ACC CGA  --  - --- --A CCC CAA GGG GAC CTC ATG CAG GC-  ---    Δ11+Δ17
     #2  A CTT CCA GGC TCC ACC CGA C--   - --- --- --- --- --- --- --- --- --- ---       Δ57

10   #5  A CTT CCA GGC TCC ACC ---  --  - --C GAA CCC CAA GGG GAC CTC ATG CAG CAG GCT CC   Δ11
     #11 A CTT CCA GGC TCC A--  ---  --  - GGT GAA CCC CAA GGG GAC CTC ATG CAG CAG GCT CC   Δ17
         A ---  ---  GGC TCC ACC CGA CT+G GAG GG+ --- CAA GGG GAC CTC ATG CAG CAG GCT CC   +1
         A ---  ---  ---  ---  ---  --- --- --- GG+ --- CAA GGG GAC CTC ATG CAG CAG GCT CC   Δ12

1    #9  A CTT CCA ---  ---  ---  --- --- --- --- -AA GGG GAC CTC ATG CAG CAG GCT CC        Δ72
     #9  A CTT CCA GGC T--  ---  --- --- --- --- -AA GGG GAC CTC ATG CAG CAG GCT CC        Δ25
                                                                                          Δ24
                                              └─── PAM ───┘
```

Pronucleous injection

| Cas9 protein (nM) | sgRNA (nM) | Tested embryos | Mutants (%) |
|---|---|---|---|
| 2 | 4 | 20 | 3 (15%) |
| 20 | 40 | 15 | 5 (33%) |
| 200 | 400 | 17 | 15 (88%) |

Intra-cytoplasmic injection

| Cas9 protein (nM) | sgRNA (nM) | Tested embryos | Mutants (%) |
|---|---|---|---|
| 2 | 4 | 18 | 1 (6%) |
| 20 | 40 | 19 | 6 (32%) |
| 200 | 400 | 14 | 10 (71%) |

| Sequence | Indels | Embryo no. |
|---|---|---|
| ACTTCCAGGCTCCACCCGACTGGAGGCGAACCCCAAGGGGGACCCTCATGCAG | WT | 2 |
| ACTTCCAGGCGGAACCCC--------AAGGGGGACCCTCATGCAG | Δ18 | 1 |
| ACTTCCAGGCTCCAC----------AAGGGGGACCCTCATGCAG | Δ20 | 1 |
| ACTTCCAGGCTCCACCC--------AAGGGGGACCCTCATGCCC | Δ19 | 1 |
| ACTTCCAGGCTCCACCC--------CAAGGGGGACCCTCATGCAG | Δ17 | 1 |
| ACTTCCAGGCTCCACCCGA-------ACCCCAAGGGGGACCCTCATGCAG | Δ11 | 3 |
| ACTTCCAGGCTCCACCCGAA--GGAGGGCGAACCCCAAGGGGGACCCTCATGCA | Δ3+1 | 1 |
| ACTTCCAGGCTCCACCCGACT--AGGGGCGAACCCCAAGGGGGACCCTCATGCAG | Δ2 | 1 |
| ACTTCCAGGCTCCACCCGACTGGGAGGCGAACCCCAAGGGGGACCCTCATGCA | +1 | 1 |
| ACTTCCAGGCTCCACCCGACTTGGAGGGCGAACCCCAAGGGGGACCCTCATGCA | +1 | 10 |
| ACTTCCAGGCTCCACCCGA------GGCGAACCCCAAGGGGGACCCTCATGCAG | Δ6 | 1 |
| ACTTCCAGGCTCCACCCGA------GGGCGAACCCCAAGGGGGACCCTCATGCAG | Δ5 | 2 |
| ACTTCCAGGCTCCACC---------------TCATGCAG | Δ28 | 1 |
| ------------------AGGGCGAACCCCAAGGGGGACCCTCATGCAG | Δ126 | 1 |
| Total | | 26 |

FIG. 7C

*CCR5*

```
                                    ▼
CAATCTATGACATCAATTATTATA-CATCGGAGCCCTGCCAAAAAATCAA        WT
CAATCTATGACATCAATTATTAT-----CGGAGCCCTGCCAAAAAATCAA        -4
CAATCTATGACATCAATTAT------CATCGGAGCCCTGCCAAAAAATCAA       -4
CAATCTATGACATCAATTAT---------CGGAGCCCTGCCAAAAAATCAA       -7
CAATCTATGACATCAATTATTAT--CATCGGAGCCCTGCCAAAAAATCAA        -1
CAATCTATGACATCAATTATTATAACATCGGAGCCCTGCCAAAAAATCAA        +1
CAATCTATGACAA-------------------GAGCCCTGCCAAAAAATCAA      -17,+1
```

FIG. 10C

*ABCC11*

| Cas9 protein | - | 15(4.5) | μg (μM) |
|---|---|---|---|
| sgRNA | - | 20(29) | μg (μM) |

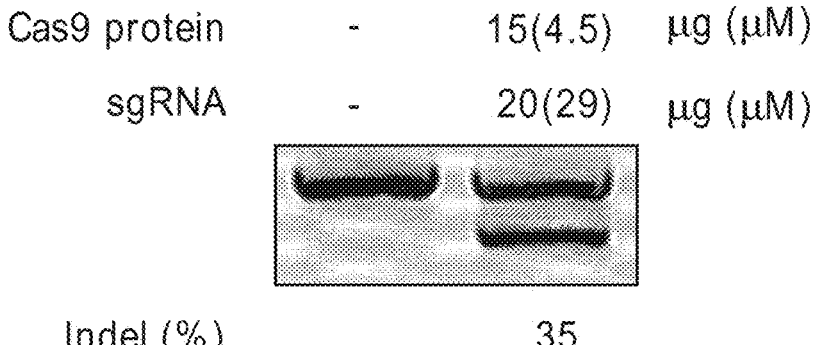

| Indel (%) | | 35 | |
|---|---|---|---|

FIG. 10D

*ABCC11*

```
                                ▼
TTCTCAAGGCAGCATCATACTTCCCCCACGGTGGGACAGCTGCCCTCCCTGG     WT
TTCTCAAGGCAGCATCATACTTCC-------CTGGGACAGCTGCCCTCCCTGG    -6
TTCTCAAGGCAGCATCATACTTC---CACGGTGGGACAGCTGCCCTCCCTGG     -3
TTCTCAAGGCAGC---------------------------TGCCCTCCCTGG     -29
TTCTCAAGGCAGCATCATACTT---------------------CCCTCCCTGG    -20
TTCTCAAGGCAGCATCATACTT----------------------CCCTCCCTGG   -20
TTCTC-------------------------------------------------   -256
```

FIG. 10E

Cas9-WT

Cas9-D10A

Cas9-D10A

AAVS1 Locus

S1    S2    S3    S4         S5         S6

AS1    AS2    AS3

Cas9-WT

Cas9-WT AS2 + L1 (~1050bp deletion)

Cas9-D10A AS2 + L1 (~1050bp deletion)

FIG. 20C

On-target
(*AAVS1* chr.19)

S3-3 Off-target
(*N/A* chr.1)

S3-1 Off-target
(*MRDS1* chr.6)

AS2 Off-1 sites
(*PLEKHG6* chr.12)

ON-F

OFF-F

ON-R

OFF-R

Plasmid target sequence

```
AATGACCACTACATCCT---CAAGGG    WT
AATGACCACTACATCCTT--CAAGGG    I1
AATGACCACTACATCCTTT-CAAGGG    I2
AATGACCACTACATCCTTTTCAAGGG    I3
AATGACCACTACATCCT----AAGGG    D1
AATGACCACTACATCCT-----AGGG    D2
AATGACCACTACATCCT------GGG    D3
```

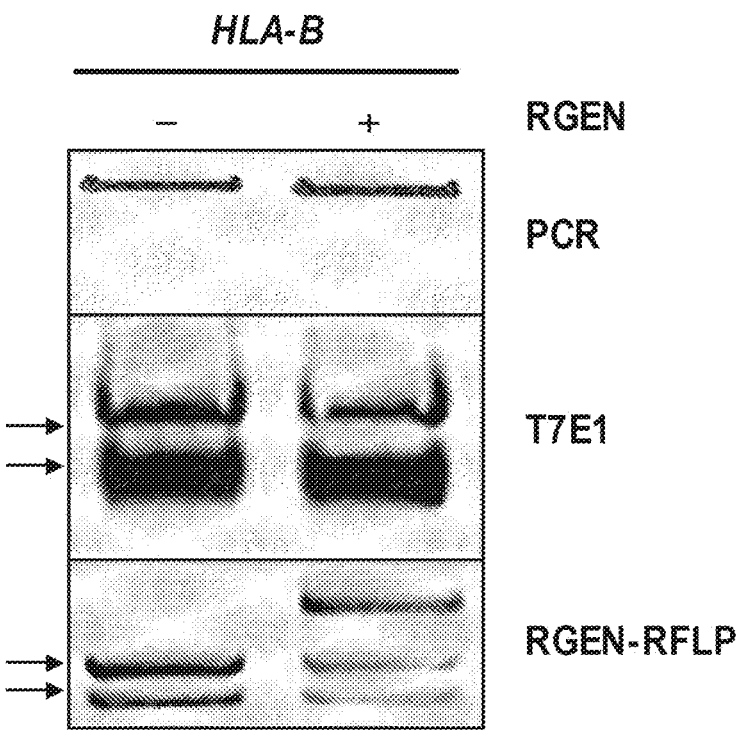
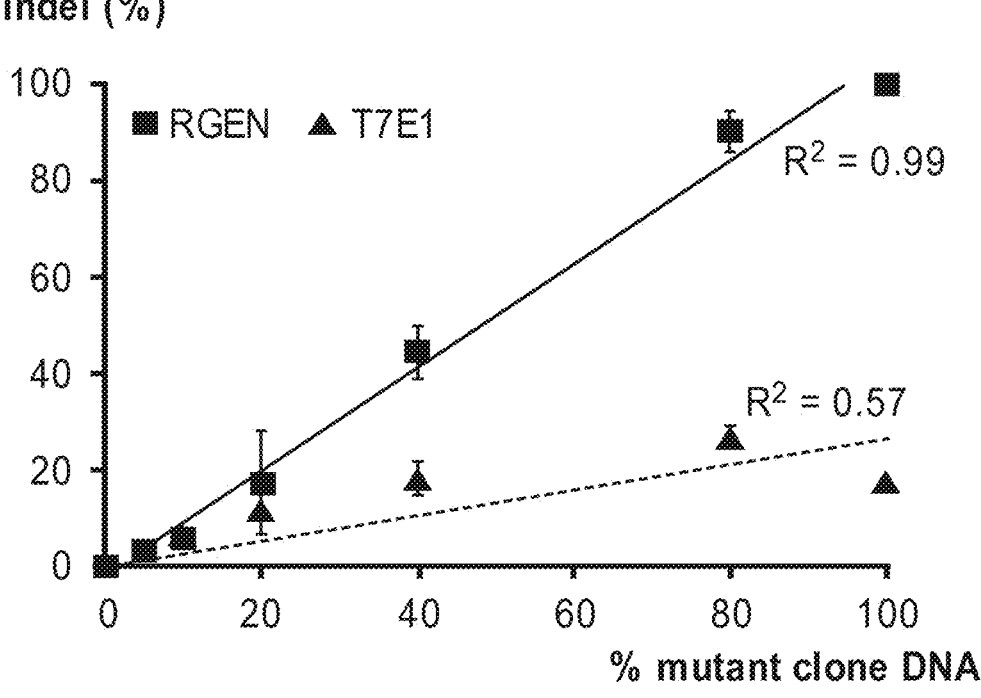
FIG. 25C

FIG. 26A

CCR5-ZFN

Target site-RGEN-RFLP

Forward primer

Reverse primer

GCTGGTGTCTGGGTTCTGTTGTCCCCAG[C]CCAGCCCCACCCCAGGTGTGTCCTGTCCATTCTCAGGCTG
GTCACATGGGTGGTCCTAGGTGTCCCATGA[GA]AGATGCAAAGCGCCTGAATTTTCTGACTCTTCCCATCA
GACCCCCAAAGACA[C]ATGTGACCCACCCC[A]TCTCTGACCATGAGGCCACCCTGAGGTGCTGGGCCC
TGG[C]TTCTACCCTG[C]GGAGATCACACTGACCTGGCGAGCGGGATGGCGACCAAACTCAGGACA[C]GA
GCTTGTGTGGAGACCAGCAGGAGATAGAACCTTCCAGAAGTGGGCAGCTGGGTG[CCTT]CTGGA
GAAGAGCAGAGAT[A]CACATGCCATGTACAGCCATGAGGGGCTGCCGAAGCCCCTCACCCTGAGATGGGGTA
AGGAGGGGGATGAGGGGTCATATC[G]TTCATATCTGTTCTCAGGGAAAGCAGGAGCCCTTC[TGGAGCCCT]
TCAGCAGGGTCAGGGCCCCCTCATCTTCCCTTCCTTTCCCAGAGC[A]TCTTCCCAGTCCACCATCCCCATC
GTGGGCATTGTTGCTGGCCTGGCTGTGTCCTAGCAGTTGTGGTCATCG

FIG. 28

HeLa

ACTACCACAGCTCCTTCTCTGAGTGG wild-type

HCT116

ACTACCACAGCTCCTTCTCTGAGTGG wild-type
ACTACCACAGCTCCT---CTGAGTGG c.133-135 del TCT

CCR5 WT
ccatacagtcagtatcaattctggaagaatttccagacattaaagatagtcatct

CCR5 WT target site

CCR5 Δ32
ccataca————————————ttaaagatagtcatct

CCR5 Δ32 on-target site

CCR5 Δ32 off-target site

Linearized plasmid uncut

WT    Δ32

RFLP with
CCR5 WT specific RNA

Dilution (Cas9 0.1ug/crRNA 25ng /tracrRNA 60ng)

Plasmid

−    1/81    1/27    1/9
on  off  on  off  on  off  on  off

On    agatgactatcttaatgtctag
Off    agatgactatcttaatgtatagg

*KRAS*

HeLa

GTAGTTGGAGCTGGTGGCGT<u>AGG</u> Wild-type

A549

GTAGTTGGAGCT⎡a⎤GTGGCGT<u>AGG</u> c.34G>A

HeLa      A549

**RFLP with
WT-specific RNA**

GTAGTTGGAGCTGGTGGCGT<u>AGG</u>

**RFLP with
Mutant-specific RNA**

GTAGTTGGAGCT⎡a⎤GTGGCGT<u>AGG</u>

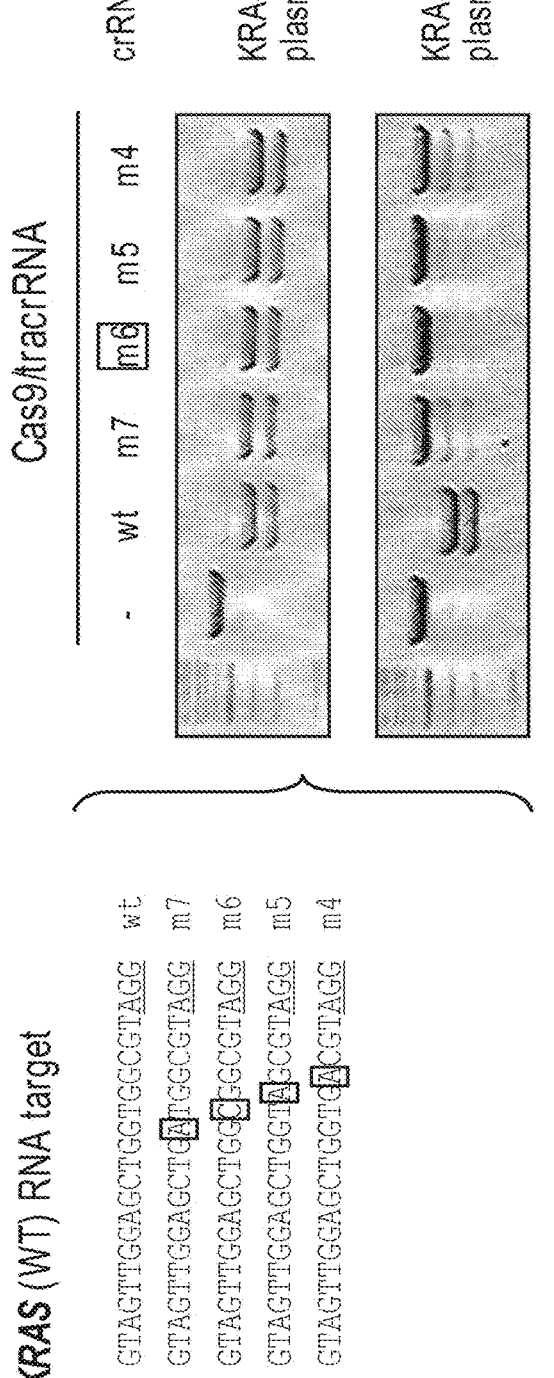
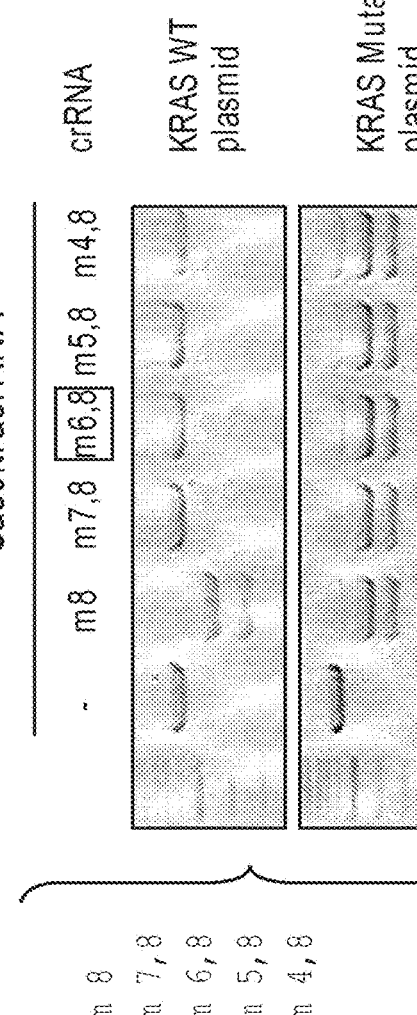
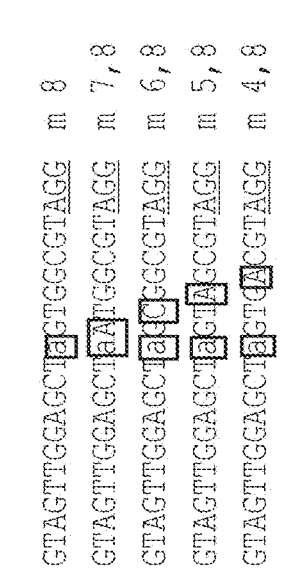
FIG. 31B

*PIK3CA*

HeLa

CAAATGAATGATGCACATCA<u>TGG</u>  Wild-type

HCT116

CAAATGAATGATGCACATCA<u>TGG</u>  Wild-type
CAAATGAATGATGCAC[g]TCA<u>TGG</u>  C.3140A>G

**RFLP with
WT-specific RNA**
CAAATGAATGATGCACATCA<u>TGG</u>

**RFLP with
Mutant-specific RNA**
CAAATGAATGATGCAC[g]TCA<u>TGG</u>

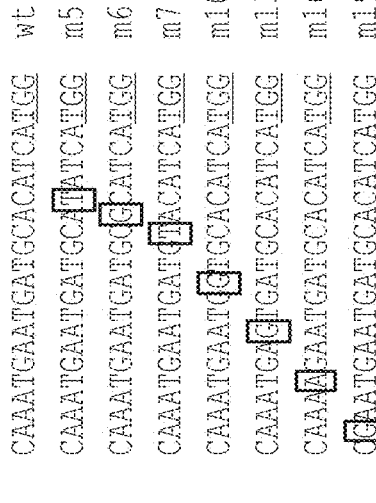
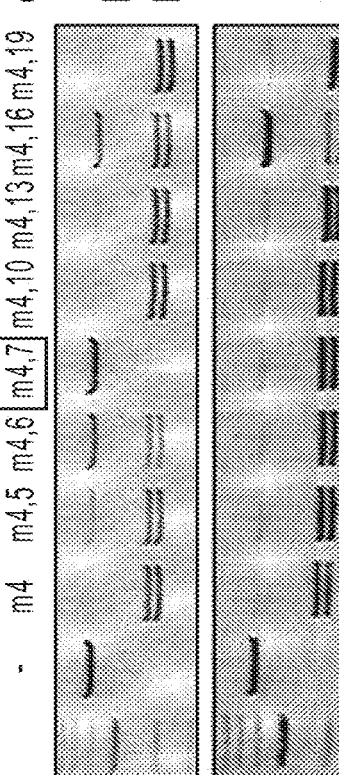
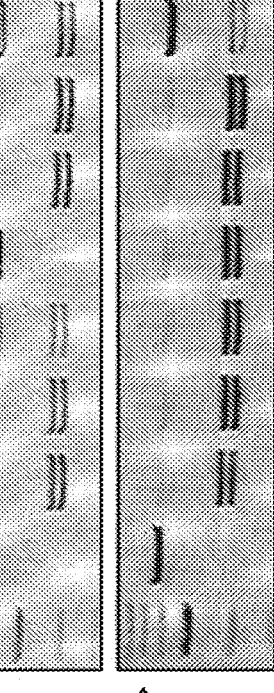
FIG. 32B

*IDH1*

HeLa
ATCATAGGTCGTCATGCTTATGG          Wild-type

HT1080
ATCATAGGTCGTCATGCTTATGG          Wild-typ
ATCATAGGT[C]GTCATGCTTATGG          c.394C>T

PCR

**RFLP with
WT-Specific RNA**
ATCATAGGTCGTC[C]TGCTTATGG

**RFLP with
Mutant-specific RNA**
ATCATAGGT[T]GTC[C]TGCTTATGG

FIG. 33A

*PIK3CA*

HeLa

CAAATGAATGATGCACATCATGG      Wild-type

HCT116

CAAATGAATGATGCACATCATGG      Wild-type

CAAATGAATGATGCAC[g]TCATGG      C.3140A>G

PCR

RFLP with
WT-Specific RNA

CAAATGAATGAT[CT]ACATCATGG

RFLP with
Mutant-specific RNA

CAAATGAATGAT[CT]AC[g]TCATGG

HeLa      HCT116

*NRAS*
HeLa
CTGGACAAGAAGAGTACAGTGCC     Wild-type
HT1080
CTGGACAAGAAGAGTACAGTGCC     Wild-type
CTGGA[a]AAGAAGAGTACAGTGCC     c.181C>A
HeLa     HT1080
PCR
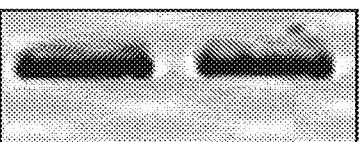
**RFLP with
WT-Specific RNA**
CTGGACAAGAAGAGTACAGTGCC
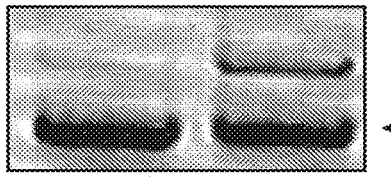
**RFLP with
Mutant-specific RNA**
CTGGA[a]AAGAAGAGTACAGTGCC
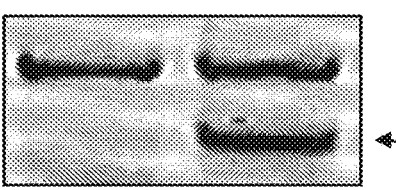
FIG. 33C

*BRAF*
HeLa
ACTCCATCGAGATTTCACTG<u>TAG</u> Wild-type
HT29
ACTCCATCGAGATTTCACTG<u>TAG</u> Wild-type
ACTCCATCGAGATTTC[t]CTG<u>TAG</u> (c.1799T>A)
HeLa    HT29
PCR
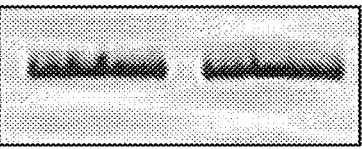
RFLP with WT-Specific RNA
ACTCCATCGAGATTTCACTG<u>TAG</u>
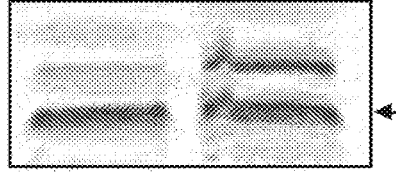
RFLP with Mutant-specific RNA
ACTCCATCGAGATTTC[t]CTG<u>TAG</u>
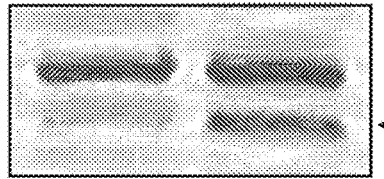
FIG. 33D

```
                          SEQUENCE LISTING

Sequence total quantity: 332
SEQ ID NO: 1              moltype = DNA  length = 4107
FEATURE                  Location/Qualifiers
misc_feature             1..4107
                         note = Description of Artificial Sequence: Synthetic
                          polynucleotide
misc_feature             1..4107
                         note = Cas9-coding sequence
source                   1..4107
                         mol_type = other DNA
                         organism = synthetic construct
SEQUENCE: 1
atggacaaga agtacagcat cggcctggac atcggtacca acagcgtggg ctgggccgtg  60
atcaccgacg agtacaaggt gcccagcaag aagttcaagg tgctgggcaa caccgaccgc 120
cacagcatca agaagaacct gatcggcgcc ctgctgttcg acagcggcga gaccgccgag 180
gccacccgcc tgaagcgcac cgcccgccgc cgctacaccc gccgcaagaa ccgcatctgc 240
tacctgcagg agatcttcag caacgagatg gccaaggtgg acgacagctt cttccaccgc 300
ctggaggaga gcttcctggt ggaggaggac aagaagcacg agcgccaccc catcttcggc 360
aacatcgtgg acgaggtggc ctaccacgag aagtacccca ccatctacca cctgcgcaag 420
aagctggtgg acagcaccga caaggccgac ctgcgcctga tctacctggc cctggcccac 480
atgatcaagt tccgcggcca cttcctgatc gagggcgacc tgaaccccga caacagcgac 540
```

```
gtggacaagc tgttcatcca gctggtgcag acctacaacc agctgttcga ggagaacccc    600
atcaacgcca gcggcgtgga cgccaaggcc atcctgagcg cccgcctgag caagagccgc    660
cgcctggaga acctgatcgc ccagctgccc ggcgagaaga agaacggcct gttcggcaac    720
ctgatcgccc tgagcctggg cctgaccccc aacttcaaga gcaacttcga cctggccgag    780
gacgccaagc tgcagctgag caaggacacc tacgacgacg acctgctggc cctgctggcc    840
cagatcggcg accagtacgc cgacctgttc ctggccgcca agaacctgag cgacgccatc    900
ctgctgagcg acatcctgcg cgtgaacacc gagatcacca aggcccccct gagcgccagc    960
atgatcaagc gctacgacga gcaccaccag gacctgaccc tgctgaaggc cctggtgcgc   1020
cagcagctgc ccgagaagta caaggagatc ttcttcgacc agagcaagaa cggctacgcc   1080
ggctacatcg acggcggcgc cagccaggag gagttctaca agttcatcaa gcccatcctg   1140
gagaagatgg acggcaccga ggagctgctg gtgaagctga accgcgagga cctgctgcgc   1200
aagcagcgca ccttcgacaa cggcagcatc ccccaccaga tccacctggg cgagctgcac   1260
gccatcctgc gccgccagga ggacttctac cccttcctga aggacaaccg cgagaagatc   1320
gagaagatcc tgaccttccg catccccctac tacgtgggcc cctggcccg cggcaacagc   1380
cgcttcgcct ggatgacccg caagagcgag gagaccatca cccccctggaa cttcgaggag   1440
gtggtcgaca agggcgccag cgcccagagc ttcatcgagc gcatgaccaa cttcgacaag   1500
aacctgccca acgagaaggt gctgcccaag cacagcctgc tgtacgagta cttcaccgtg   1560
tacaacgagc tgaccaaggt gaagtacgtg accgagggca tgcgcaagcc cgccttcctg   1620
agcggcgagc agaagaaggc catcgtggac ctgctgttca agaccaaccg caaggtgacc   1680
gtgaagcagc tgaaggagga ctacttcaag aagatcgagt gcttcgacag cgtggagatc   1740
agcggcgtgg aggaccgctt caacgccagc ctgggcacct accacgacct gctgaagatc   1800
atcaaggaca aggacttcct ggacaacgga gagaacgagg acatcctgga ggacatcgtg   1860
ctgaccctga ccctgttcga ggaccgcgag atgatcgagg agcgcctgaa gacctacgcc   1920
cacctgttcg acgacaaggt gatgaagcag ctgaagcgcc gccgctacac cggctggggc   1980
cgcctgagcc gcaagcttat caacggcatc cgcgacaagc agagcggcaa gaccatcctg   2040
gacttcctga gagcgacgg cttcgccaac cgcaacttca tgcagctgat ccacgacgac   2100
agcctgacct tcaaggagga catccagaag gcccaggtga gcggccaggg cgacagcctg   2160
cacgagcaca tcgccaacct ggccggcagc cccgccatca agaagggcat cctgcagacc   2220
gtgaaggtgg tggacgagct ggtgaaggtg atgggccgcc acaagcccga gaacatcgtg   2280
atcgagatgg cccgcgagaa ccagaccacc cagaaggcac agaagaacag ccgcgagcgc   2340
atgaagcgca tcgaggaggg catcaaggag ctgggcagcc agatcctgaa ggagcacccc   2400
gtggagaaca cccagctgca gaacgagaag ctgtacctgt actacctgca gaacggccgc   2460
gacatgtacg tggaccagga gctggacatc aaccgcctga gcgactacga cgtggaccac   2520
atcgtgcccc agagcttcct gaaggacgac agcatcgaca acaaggtgct gacccgcagc   2580
gacaagaacc gcggcaagag cgacaacgtg cccagcgagg aggtggtgaa gaagatgaag   2640
aactactggc gccagctgct gaacgccaag ctgatcaccc agcgcaagtt cgacaacctg   2700
accaaggccg agcgcggcgg cctgagcgag ctggacaagg ccggcttcat caagcgccag   2760
ctggtggaga cccgccagat caccaagcac gtggcccaga tcctggacag ccgcatgaac   2820
accaagtacg acgagaacga caagctgatc cgcgaggtga aggtgatcac cctgaagagc   2880
aagctggtga gcgacttccg caaggacttc cagttctaca aggtgcgcga gatcaacaac   2940
taccaccacg cccacgacgc ctacctgaac gccgtggtgg gcaccgccct gatcaagaag   3000
taccccaagc tggagagcga gttcgtgtac ggcgactaca aggtgtacga cgtgcgcaag   3060
atgatcgcca agagcgagca ggagatcggc aaggccaccg ccaagtactt cttctacgac   3120
aacatcatga acttcttcaa gaccgagatc accctggcca acggcgagat ccgcaagcgc   3180
cccctgatcg agaccaacgg cgagaccggc gagatcgtgt gggacaaggg ccgcgacttc   3240
gccaccgtgc gcaaggtgct gagcatgccc caggtgaaca tcgtgaagaa gaccgaggtg   3300
cagaccggcg gcttcagcaa ggagagcatc ctgcccaagc gcaacagcga caagctgatc   3360
gcccgcaaga aggactggga ccccaagaag tacggcggct cgacagccc caccgtggcc   3420
tacagccgc tggtggtggc caaggtggag aagggcaaga gcaagaagct gaagagcgtg   3480
aaggagctgc tgggcatcac catcatggag cgcagcagct cgagaagaa ccccatcgac   3540
ttcctggagg ccaaggggcta caaggaggtg aagaaggacc tgatcatcaa gctgcccaag   3600
tacagcctgt tcgagctgga gaacggccgc aagcgcatgc tggccagcgc cggcgagctg   3660
cagaagggca cgagctggc cctgcccagc aagtacgtga acttcctgta cctggccagc   3720
cactacgaga gctgaaggg cagccccgag gacaacgagc agaagcagct gttcgtggag   3780
cagcacaagc actacctgga cgagatcatc gagcagatca gcgagttcag caagcgcgtg   3840
atcctggccg acgccaacct ggacaaggtg ctgagcgcct acaacaagca ccgcgacaag   3900
cccatccgcg agcaggccga gaacatcatc cacctgttca cctgaccaa cctgggcgcc   3960
cccgccgcct tcaagtactt cgacaccacc atcgaccgca gcgctacac cagcaccaag   4020
gaggtgctgg acgccaccct gatccaccag agcatcaccg tgtctgtacga cacccgcatc   4080
gacctgagcc agctgggcgg cgactaa                                       4107
```

```
SEQ ID NO: 2            moltype = AA  length = 21
FEATURE                 Location/Qualifiers
REGION                  1..21
                        note = Description of Artificial Sequence: Synthetic peptide
REGION                  1..21
                        note = Peptide tag
source                  1..21
                        mol_type = protein
                        organism = synthetic construct
SEQUENCE: 2
GGSGPPKKKR KVYPYDVPDY A                                              21

SEQ ID NO: 3            moltype = DNA  length = 34
FEATURE                 Location/Qualifiers
misc_feature            1..34
                        note = Description of Artificial Sequence: Synthetic
                         oligonucleotide
misc_feature            1..34
```

```
                              note = F primer for CCR5
source                        1..34
                              mol_type = other DNA
                              organism = synthetic construct
SEQUENCE: 3
aattcatgac atcaattatt atacatcgga ggag                                   34

SEQ ID NO: 4                  moltype = DNA  length = 34
FEATURE                       Location/Qualifiers
misc_feature                  1..34
                              note = Description of Artificial Sequence: Synthetic
                               oligonucleotide
misc_feature                  1..34
                              note = R primer for CCR5
source                        1..34
                              mol_type = other DNA
                              organism = synthetic construct
SEQUENCE: 4
gatcctcctc cgatgtataa taattgatgt catg                                   34

SEQ ID NO: 5                  moltype = DNA  length = 20
FEATURE                       Location/Qualifiers
misc_feature                  1..20
                              note = Description of Artificial Sequence: Synthetic
                               oligonucleotide
misc_feature                  1..20
                              note = F1 primer for CCR5
source                        1..20
                              mol_type = other DNA
                              organism = synthetic construct
SEQUENCE: 5
ctccatggtg ctatagagca                                                   20

SEQ ID NO: 6                  moltype = DNA  length = 21
FEATURE                       Location/Qualifiers
misc_feature                  1..21
                              note = Description of Artificial Sequence: Synthetic
                               oligonucleotide
misc_feature                  1..21
                              note = F2 primer for CCR5
source                        1..21
                              mol_type = other DNA
                              organism = synthetic construct
SEQUENCE: 6
gagccaagct ctccatctag t                                                 21

SEQ ID NO: 7                  moltype = DNA  length = 20
FEATURE                       Location/Qualifiers
misc_feature                  1..20
                              note = Description of Artificial Sequence: Synthetic
                               oligonucleotide
misc_feature                  1..20
                              note = R primer for CCR5
source                        1..20
                              mol_type = other DNA
                              organism = synthetic construct
SEQUENCE: 7
gccctgtcaa gagttgacac                                                   20

SEQ ID NO: 8                  moltype = DNA  length = 20
FEATURE                       Location/Qualifiers
misc_feature                  1..20
                              note = Description of Artificial Sequence: Synthetic
                               oligonucleotide
misc_feature                  1..20
                              note = F1 primer for C4BPB
source                        1..20
                              mol_type = other DNA
                              organism = synthetic construct
SEQUENCE: 8
tatttggctg gttgaaaggg                                                   20

SEQ ID NO: 9                  moltype = DNA  length = 24
FEATURE                       Location/Qualifiers
misc_feature                  1..24
                              note = Description of Artificial Sequence: Synthetic
                               oligonucleotide
misc_feature                  1..24
                              note = R1 primer for C4BPB
```

-continued

```
source                  1..24
                        mol_type = other DNA
                        organism = synthetic construct
SEQUENCE: 9
aaagtcatga ataaacaca ccca                                        24

SEQ ID NO: 10          moltype = DNA   length = 24
FEATURE                Location/Qualifiers
misc_feature           1..24
                       note = Description of Artificial Sequence: Synthetic
                        oligonucleotide
misc_feature           1..24
                       note = F2 primer for C4BPB
source                 1..24
                       mol_type = other DNA
                       organism = synthetic construct
SEQUENCE: 10
ctgcattgat atggtagtac catg                                       24

SEQ ID NO: 11          moltype = DNA   length = 21
FEATURE                Location/Qualifiers
misc_feature           1..21
                       note = Description of Artificial Sequence: Synthetic
                        oligonucleotide
misc_feature           1..21
                       note = R2 primer for C4BPB
source                 1..21
                       mol_type = other DNA
                       organism = synthetic construct
SEQUENCE: 11
gctgttcatt gcaatggaat g                                          21

SEQ ID NO: 12          moltype = DNA   length = 20
FEATURE                Location/Qualifiers
misc_feature           1..20
                       note = Description of Artificial Sequence: Synthetic
                        oligonucleotide
misc_feature           1..20
                       note = F1 primer for ADCY5
source                 1..20
                       mol_type = other DNA
                       organism = synthetic construct
SEQUENCE: 12
gctcccacct tagtgctctg                                            20

SEQ ID NO: 13          moltype = DNA   length = 20
FEATURE                Location/Qualifiers
misc_feature           1..20
                       note = Description of Artificial Sequence: Synthetic
                        oligonucleotide
misc_feature           1..20
                       note = R1 primer for ADCY5
source                 1..20
                       mol_type = other DNA
                       organism = synthetic construct
SEQUENCE: 13
ggtggcagga acctgtatgt                                            20

SEQ ID NO: 14          moltype = DNA   length = 21
FEATURE                Location/Qualifiers
misc_feature           1..21
                       note = Description of Artificial Sequence: Synthetic
                        oligonucleotide
misc_feature           1..21
                       note = F2 primer for ADCY5
source                 1..21
                       mol_type = other DNA
                       organism = synthetic construct
SEQUENCE: 14
gtcattggcc agagatgtgg a                                          21

SEQ ID NO: 15          moltype = DNA   length = 20
FEATURE                Location/Qualifiers
misc_feature           1..20
                       note = Description of Artificial Sequence: Synthetic
                        oligonucleotide
misc_feature           1..20
                       note = R2 primer for ADCY5
source                 1..20
```

-continued

```
                         mol_type = other DNA
                         organism = synthetic construct
SEQUENCE: 15
gtcccatgac aggcgtgtat                                        20

SEQ ID NO: 16            moltype = DNA  length = 20
FEATURE                  Location/Qualifiers
misc_feature             1..20
                         note = Description of Artificial Sequence: Synthetic
                          oligonucleotide
misc_feature             1..20
                         note = F primer for KCNJ6
source                   1..20
                         mol_type = other DNA
                         organism = synthetic construct
SEQUENCE: 16
gcctggccaa gtttcagtta                                        20

SEQ ID NO: 17            moltype = DNA  length = 20
FEATURE                  Location/Qualifiers
misc_feature             1..20
                         note = Description of Artificial Sequence: Synthetic
                          oligonucleotide
misc_feature             1..20
                         note = R1 primer for KCNJ6
source                   1..20
                         mol_type = other DNA
                         organism = synthetic construct
SEQUENCE: 17
tggagccatt ggtttgcatc                                        20

SEQ ID NO: 18            moltype = DNA  length = 22
FEATURE                  Location/Qualifiers
misc_feature             1..22
                         note = Description of Artificial Sequence: Synthetic
                          oligonucleotide
misc_feature             1..22
                         note = R2 primer for KCNJ6
source                   1..22
                         mol_type = other DNA
                         organism = synthetic construct
SEQUENCE: 18
ccagaactaa gccgtttctg ac                                     22

SEQ ID NO: 19            moltype = DNA  length = 20
FEATURE                  Location/Qualifiers
misc_feature             1..20
                         note = Description of Artificial Sequence: Synthetic
                          oligonucleotide
misc_feature             1..20
                         note = F1 primer for CNTNAP2
source                   1..20
                         mol_type = other DNA
                         organism = synthetic construct
SEQUENCE: 19
atcaccgaca accagtttcc                                        20

SEQ ID NO: 20            moltype = DNA  length = 20
FEATURE                  Location/Qualifiers
misc_feature             1..20
                         note = Description of Artificial Sequence: Synthetic
                          oligonucleotide
misc_feature             1..20
                         note = F2 primer for CNTNAP2
source                   1..20
                         mol_type = other DNA
                         organism = synthetic construct
SEQUENCE: 20
tgcagtgcag actctttcca                                        20

SEQ ID NO: 21            moltype = DNA  length = 20
FEATURE                  Location/Qualifiers
misc_feature             1..20
                         note = Description of Artificial Sequence: Synthetic
                          oligonucleotide
misc_feature             1..20
                         note = R primer for CNTNAP2
source                   1..20
                         mol_type = other DNA
```

```
                          organism = synthetic construct
SEQUENCE: 21
aaggacacag ggcaactgaa                                        20

SEQ ID NO: 22             moltype = DNA  length = 20
FEATURE                   Location/Qualifiers
misc_feature              1..20
                          note = Description of Artificial Sequence: Synthetic
                           oligonucleotide
misc_feature              1..20
                          note = F1 primer for N/A Chr. 5
source                    1..20
                          mol_type = other DNA
                          organism = synthetic construct
SEQUENCE: 22
tgtggaacga gtggtgacag                                        20

SEQ ID NO: 23             moltype = DNA  length = 22
FEATURE                   Location/Qualifiers
misc_feature              1..22
                          note = Description of Artificial Sequence: Synthetic
                           oligonucleotide
misc_feature              1..22
                          note = R1 primer for N/A Chr. 5
source                    1..22
                          mol_type = other DNA
                          organism = synthetic construct
SEQUENCE: 23
gctggattag gaggcaggat tc                                     22

SEQ ID NO: 24             moltype = DNA  length = 22
FEATURE                   Location/Qualifiers
misc_feature              1..22
                          note = Description of Artificial Sequence: Synthetic
                           oligonucleotide
misc_feature              1..22
                          note = F2 primer for N/A Chr. 5
source                    1..22
                          mol_type = other DNA
                          organism = synthetic construct
SEQUENCE: 24
gtgctgagaa cgcttcatag ag                                     22

SEQ ID NO: 25             moltype = DNA  length = 23
FEATURE                   Location/Qualifiers
misc_feature              1..23
                          note = Description of Artificial Sequence: Synthetic
                           oligonucleotide
misc_feature              1..23
                          note = R2 primer for N/A Chr. 5
source                    1..23
                          mol_type = other DNA
                          organism = synthetic construct
SEQUENCE: 25
ggaccaaacc acattcttct cac                                    23

SEQ ID NO: 26             moltype = DNA  length = 20
FEATURE                   Location/Qualifiers
misc_feature              1..20
                          note = Description of Artificial Sequence: Synthetic
                           oligonucleotide
misc_feature              1..20
                          note = F primer for deletion
source                    1..20
                          mol_type = other DNA
                          organism = synthetic construct
SEQUENCE: 26
ccacatctcg ttctcggttt                                        20

SEQ ID NO: 27             moltype = DNA  length = 20
FEATURE                   Location/Qualifiers
misc_feature              1..20
                          note = Description of Artificial Sequence: Synthetic
                           oligonucleotide
misc_feature              1..20
                          note = R primer for deletion
source                    1..20
                          mol_type = other DNA
                          organism = synthetic construct
```

-continued

```
SEQUENCE: 27
tcacaagccc acagatattt                                               20

SEQ ID NO: 28            moltype = RNA   length = 105
FEATURE                  Location/Qualifiers
misc_feature             1..105
                         note = Description of Artificial Sequence: Synthetic
                         polynucleotide
misc_feature             1..105
                         note = sgRNA for CCR5
source                   1..105
                         mol_type = other RNA
                         organism = synthetic construct
SEQUENCE: 28
ggtgacatca attattatac atgtttttaga gctagaaata gcaagttaaa ataaggctag  60
tccgttatca acttgaaaaa gtggcaccga gtcggtgctt ttttt                  105

SEQ ID NO: 29            moltype = RNA   length = 44
FEATURE                  Location/Qualifiers
misc_feature             1..44
                         note = Description of Artificial Sequence: Synthetic
                         oligonucleotide
misc_feature             1..44
                         note = crRNA for CCR5
source                   1..44
                         mol_type = other RNA
                         organism = synthetic construct
SEQUENCE: 29
ggtgacatca attattatac atgtttttaga gctatgctgt tttg                   44

SEQ ID NO: 30            moltype = RNA   length = 86
FEATURE                  Location/Qualifiers
misc_feature             1..86
                         note = Description of Artificial Sequence: Synthetic
                         oligonucleotide
misc_feature             1..86
                         note = tracrRNA for CCR5
source                   1..86
                         mol_type = other RNA
                         organism = synthetic construct
SEQUENCE: 30
ggaaccattc aaaacagcat agcaagttaa aataaggcta gtccgttatc aacttgaaaa  60
agtggcaccg agtcggtgct tttttt                                       86

SEQ ID NO: 31            moltype = DNA   length = 86
FEATURE                  Location/Qualifiers
misc_feature             1..86
                         note = Description of Artificial Sequence: Synthetic
                         oligonucleotide
misc_feature             1..86
                         note = Foxn1 #1 sgRNA
source                   1..86
                         mol_type = other DNA
                         organism = synthetic construct
SEQUENCE: 31
gaaattaata cgactcacta taggcagtct gacgtcacac ttccgtttta gagctagaaa  60
tagcaagtta aaataaggct agtccg                                       86

SEQ ID NO: 32            moltype = DNA   length = 86
FEATURE                  Location/Qualifiers
misc_feature             1..86
                         note = Description of Artificial Sequence: Synthetic
                         oligonucleotide
misc_feature             1..86
                         note = Foxn1 #2 sgRNA
source                   1..86
                         mol_type = other DNA
                         organism = synthetic construct
SEQUENCE: 32
gaaattaata cgactcacta taggacttcc aggctccacc cgacgtttta gagctagaaa  60
tagcaagtta aaataaggct agtccg                                       86

SEQ ID NO: 33            moltype = DNA   length = 86
FEATURE                  Location/Qualifiers
misc_feature             1..86
                         note = Description of Artificial Sequence: Synthetic
                         oligonucleotide
misc_feature             1..86
                         note = Foxn1 #3 sgRNA
```

-continued

```
source                   1..86
                         mol_type = other DNA
                         organism = synthetic construct
SEQUENCE: 33
gaaattaata cgactcacta taggccaggc tccacccgac tggagtttta gagctagaaa   60
tagcaagtta aaataaggct agtccg                                        86

SEQ ID NO: 34            moltype = DNA   length = 86
FEATURE                  Location/Qualifiers
misc_feature             1..86
                         note = Description of Artificial Sequence: Synthetic
                          oligonucleotide
misc_feature             1..86
                         note = Foxn1 #4 sgRNA
source                   1..86
                         mol_type = other DNA
                         organism = synthetic construct
SEQUENCE: 34
gaaattaata cgactcacta taggactgga gggcgaaccc caaggtttta gagctagaaa   60
tagcaagtta aaataaggct agtccg                                        86

SEQ ID NO: 35            moltype = DNA   length = 86
FEATURE                  Location/Qualifiers
misc_feature             1..86
                         note = Description of Artificial Sequence: Synthetic
                          oligonucleotide
misc_feature             1..86
                         note = Foxn1 #5 sgRNA
source                   1..86
                         mol_type = other DNA
                         organism = synthetic construct
SEQUENCE: 35
gaaattaata cgactcacta taggacccca aggggacctc atgcgtttta gagctagaaa   60
tagcaagtta aaataaggct agtccg                                        86

SEQ ID NO: 36            moltype = DNA   length = 86
FEATURE                  Location/Qualifiers
misc_feature             1..86
                         note = Description of Artificial Sequence: Synthetic
                          oligonucleotide
misc_feature             1..86
                         note = Prkdc #1 sgRNA
source                   1..86
                         mol_type = other DNA
                         organism = synthetic construct
SEQUENCE: 36
gaaattaata cgactcacta taggttagtt ttttccagag acttgtttta gagctagaaa   60
tagcaagtta aaataaggct agtccg                                        86

SEQ ID NO: 37            moltype = DNA   length = 86
FEATURE                  Location/Qualifiers
misc_feature             1..86
                         note = Description of Artificial Sequence: Synthetic
                          oligonucleotide
misc_feature             1..86
                         note = Prkdc #2 sgRNA
source                   1..86
                         mol_type = other DNA
                         organism = synthetic construct
SEQUENCE: 37
gaaattaata cgactcacta taggttggtt tgcttgtgtt tatcgtttta gagctagaaa   60
tagcaagtta aaataaggct agtccg                                        86

SEQ ID NO: 38            moltype = DNA   length = 86
FEATURE                  Location/Qualifiers
misc_feature             1..86
                         note = Description of Artificial Sequence: Synthetic
                          oligonucleotide
misc_feature             1..86
                         note = Prkdc #3 sgRNA
source                   1..86
                         mol_type = other DNA
                         organism = synthetic construct
SEQUENCE: 38
gaaattaata cgactcacta taggcacaag caaaccaaag tctcgtttta gagctagaaa   60
tagcaagtta aaataaggct agtccg                                        86

SEQ ID NO: 39            moltype = DNA   length = 86
FEATURE                  Location/Qualifiers
```

-continued

```
misc_feature           1..86
                       note = Description of Artificial Sequence: Synthetic
                        oligonucleotide
misc_feature           1..86
                       note = Prkdc #4 sgRNA
source                 1..86
                       mol_type = other DNA
                       organism = synthetic construct
SEQUENCE: 39
gaaattaata cgactcacta taggcctcaa tgctaagcga cttcgtttta gagctagaaa  60
tagcaagtta aaataaggct agtccg                                       86

SEQ ID NO: 40          moltype = DNA  length = 29
FEATURE                Location/Qualifiers
misc_feature           1..29
                       note = Description of Artificial Sequence: Synthetic
                        oligonucleotide
misc_feature           1..29
                       note = F1 primer for Foxn1
source                 1..29
                       mol_type = other DNA
                       organism = synthetic construct
SEQUENCE: 40
gtctgtctat catctcttcc cttctctcc                                    29

SEQ ID NO: 41          moltype = DNA  length = 25
FEATURE                Location/Qualifiers
misc_feature           1..25
                       note = Description of Artificial Sequence: Synthetic
                        oligonucleotide
misc_feature           1..25
                       note = F2 primer for Foxn1
source                 1..25
                       mol_type = other DNA
                       organism = synthetic construct
SEQUENCE: 41
tccctaatcc gatggctagc tccag                                        25

SEQ ID NO: 42          moltype = DNA  length = 23
FEATURE                Location/Qualifiers
misc_feature           1..23
                       note = Description of Artificial Sequence: Synthetic
                        oligonucleotide
misc_feature           1..23
                       note = R1 primer for Foxn1
source                 1..23
                       mol_type = other DNA
                       organism = synthetic construct
SEQUENCE: 42
acgagcagct gaagttagca tgc                                          23

SEQ ID NO: 43          moltype = DNA  length = 32
FEATURE                Location/Qualifiers
misc_feature           1..32
                       note = Description of Artificial Sequence: Synthetic
                        oligonucleotide
misc_feature           1..32
                       note = R2 primer for Foxn1
source                 1..32
                       mol_type = other DNA
                       organism = synthetic construct
SEQUENCE: 43
ctactcaatg ctcttagagc taccaggctt gc                                32

SEQ ID NO: 44          moltype = DNA  length = 20
FEATURE                Location/Qualifiers
misc_feature           1..20
                       note = Description of Artificial Sequence: Synthetic
                        oligonucleotide
misc_feature           1..20
                       note = F primer for Prkdc
source                 1..20
                       mol_type = other DNA
                       organism = synthetic construct
SEQUENCE: 44
gactgttgtg gggagggccg                                              20

SEQ ID NO: 45          moltype = DNA  length = 24
FEATURE                Location/Qualifiers
```

-continued

```
misc_feature          1..24
                      note = Description of Artificial Sequence: Synthetic
                       oligonucleotide
misc_feature          1..24
                      note = F2 primer for Prkdc
source                1..24
                      mol_type = other DNA
                      organism = synthetic construct
SEQUENCE: 45
gggagggccg aaagtcttat tttg                                        24

SEQ ID NO: 46         moltype = DNA  length = 28
FEATURE               Location/Qualifiers
misc_feature          1..28
                      note = Description of Artificial Sequence: Synthetic
                       oligonucleotide
misc_feature          1..28
                      note = R1 primer for Prkdc
source                1..28
                      mol_type = other DNA
                      organism = synthetic construct
SEQUENCE: 46
cctgaagact gaagttggca gaagtgag                                    28

SEQ ID NO: 47         moltype = DNA  length = 27
FEATURE               Location/Qualifiers
misc_feature          1..27
                      note = Description of Artificial Sequence: Synthetic
                       oligonucleotide
misc_feature          1..27
                      note = R2 primer for Prkdc
source                1..27
                      mol_type = other DNA
                      organism = synthetic construct
SEQUENCE: 47
ctttagggct tcttctctac aatcacg                                     27

SEQ ID NO: 48         moltype = DNA  length = 38
FEATURE               Location/Qualifiers
misc_feature          1..38
                      note = Description of Artificial Sequence: Synthetic
                       oligonucleotide
misc_feature          1..38
                      note = F primer for Foxn1
source                1..38
                      mol_type = other DNA
                      organism = synthetic construct
SEQUENCE: 48
ctcggtgtgt agccctgacc tcggtgtgta gccctgac                         38

SEQ ID NO: 49         moltype = DNA  length = 21
FEATURE               Location/Qualifiers
misc_feature          1..21
                      note = Description of Artificial Sequence: Synthetic
                       oligonucleotide
misc_feature          1..21
                      note = R primer for Foxn1
source                1..21
                      mol_type = other DNA
                      organism = synthetic construct
SEQUENCE: 49
agactggcct ggaactcaca g                                           21

SEQ ID NO: 50         moltype = DNA  length = 23
FEATURE               Location/Qualifiers
misc_feature          1..23
                      note = Description of Artificial Sequence: Synthetic
                       oligonucleotide
misc_feature          1..23
                      note = F primer for Foxn1
source                1..23
                      mol_type = other DNA
                      organism = synthetic construct
SEQUENCE: 50
cactaaagcc tgtcaggaag ccg                                         23

SEQ ID NO: 51         moltype = DNA  length = 21
FEATURE               Location/Qualifiers
misc_feature          1..21
```

```
                           note = Description of Artificial Sequence: Synthetic
                             oligonucleotide
misc_feature              1..21
                           note = R primer for Foxn1
source                    1..21
                           mol_type = other DNA
                           organism = synthetic construct
SEQUENCE: 51
ctgtggagag cacacagcag c                                        21

SEQ ID NO: 52             moltype = DNA   length = 19
FEATURE                   Location/Qualifiers
misc_feature              1..19
                           note = Description of Artificial Sequence: Synthetic
                             oligonucleotide
misc_feature              1..19
                           note = F primer for Foxn1
source                    1..19
                           mol_type = other DNA
                           organism = synthetic construct
SEQUENCE: 52
gctgcgacct gagaccatg                                           19

SEQ ID NO: 53             moltype = DNA   length = 26
FEATURE                   Location/Qualifiers
misc_feature              1..26
                           note = Description of Artificial Sequence: Synthetic
                             oligonucleotide
misc_feature              1..26
                           note = R primer for Foxn1
source                    1..26
                           mol_type = other DNA
                           organism = synthetic construct
SEQUENCE: 53
cttcaatggc ttcctgctta ggctac                                   26

SEQ ID NO: 54             moltype = DNA   length = 23
FEATURE                   Location/Qualifiers
misc_feature              1..23
                           note = Description of Artificial Sequence: Synthetic
                             oligonucleotide
misc_feature              1..23
                           note = F primer for Foxn1
source                    1..23
                           mol_type = other DNA
                           organism = synthetic construct
SEQUENCE: 54
ggttcagatg aggccatcct ttc                                      23

SEQ ID NO: 55             moltype = DNA   length = 24
FEATURE                   Location/Qualifiers
misc_feature              1..24
                           note = Description of Artificial Sequence: Synthetic
                             oligonucleotide
misc_feature              1..24
                           note = R primer for Foxn1
source                    1..24
                           mol_type = other DNA
                           organism = synthetic construct
SEQUENCE: 55
cctgatctgc aggcttaacc cttg                                     24

SEQ ID NO: 56             moltype = DNA   length = 22
FEATURE                   Location/Qualifiers
misc_feature              1..22
                           note = Description of Artificial Sequence: Synthetic
                             oligonucleotide
misc_feature              1..22
                           note = F primer for Prkdc
source                    1..22
                           mol_type = other DNA
                           organism = synthetic construct
SEQUENCE: 56
ctcacctgca catcacatgt gg                                       22

SEQ ID NO: 57             moltype = DNA   length = 20
FEATURE                   Location/Qualifiers
misc_feature              1..20
                           note = Description of Artificial Sequence: Synthetic
```

-continued

```
                         oligonucleotide
misc_feature            1..20
                         note = R primer for Prkdc
source                  1..20
                         mol_type = other DNA
                         organism = synthetic construct
SEQUENCE: 57
ggcatccacc ctatggggtc                                        20

SEQ ID NO: 58           moltype = DNA  length = 25
FEATURE                 Location/Qualifiers
misc_feature            1..25
                         note = Description of Artificial Sequence: Synthetic
                         oligonucleotide
misc_feature            1..25
                         note = F primer for Prkdc
source                  1..25
                         mol_type = other DNA
                         organism = synthetic construct
SEQUENCE: 58
gccttgacct agagcttaaa gagcc                                  25

SEQ ID NO: 59           moltype = DNA  length = 25
FEATURE                 Location/Qualifiers
misc_feature            1..25
                         note = Description of Artificial Sequence: Synthetic
                         oligonucleotide
misc_feature            1..25
                         note = R primer for Prkdc
source                  1..25
                         mol_type = other DNA
                         organism = synthetic construct
SEQUENCE: 59
ggtcttgtta gcaggaagga cactg                                  25

SEQ ID NO: 60           moltype = DNA  length = 27
FEATURE                 Location/Qualifiers
misc_feature            1..27
                         note = Description of Artificial Sequence: Synthetic
                         oligonucleotide
misc_feature            1..27
                         note = F primer for Prkdc
source                  1..27
                         mol_type = other DNA
                         organism = synthetic construct
SEQUENCE: 60
aaaactctgc ttgatgggat atgtggg                                27

SEQ ID NO: 61           moltype = DNA  length = 26
FEATURE                 Location/Qualifiers
misc_feature            1..26
                         note = Description of Artificial Sequence: Synthetic
                         oligonucleotide
misc_feature            1..26
                         note = R primer for Prkdc
source                  1..26
                         mol_type = other DNA
                         organism = synthetic construct
SEQUENCE: 61
ctctcactgg ttatctgtgc tccttc                                 26

SEQ ID NO: 62           moltype = DNA  length = 23
FEATURE                 Location/Qualifiers
misc_feature            1..23
                         note = Description of Artificial Sequence: Synthetic
                         oligonucleotide
misc_feature            1..23
                         note = F primer for Prkdc
source                  1..23
                         mol_type = other DNA
                         organism = synthetic construct
SEQUENCE: 62
ggatcaatag gtggtggggg atg                                    23

SEQ ID NO: 63           moltype = DNA  length = 27
FEATURE                 Location/Qualifiers
misc_feature            1..27
                         note = Description of Artificial Sequence: Synthetic
                         oligonucleotide
```

-continued

```
misc_feature              1..27
                          note = R primer for Prkdc
source                    1..27
                          mol_type = other DNA
                          organism = synthetic construct
SEQUENCE: 63
gtgaatgaca caatgtgaca gcttcag                                      27

SEQ ID NO: 64             moltype = DNA  length = 28
FEATURE                   Location/Qualifiers
misc_feature              1..28
                          note = Description of Artificial Sequence: Synthetic
                           oligonucleotide
misc_feature              1..28
                          note = F primer for Prkdc
source                    1..28
                          mol_type = other DNA
                          organism = synthetic construct
SEQUENCE: 64
cacaagacag acctctcaac attcagtc                                     28

SEQ ID NO: 65             moltype = DNA  length = 32
FEATURE                   Location/Qualifiers
misc_feature              1..32
                          note = Description of Artificial Sequence: Synthetic
                           oligonucleotide
misc_feature              1..32
                          note = R primer for Prkdc
source                    1..32
                          mol_type = other DNA
                          organism = synthetic construct
SEQUENCE: 65
gtgcatgcat ataatccatt ctgattgctc tc                                32

SEQ ID NO: 66             moltype = DNA  length = 17
FEATURE                   Location/Qualifiers
misc_feature              1..17
                          note = Description of Artificial Sequence: Synthetic
                           oligonucleotide
misc_feature              1..17
                          note = F1 primer for Prkdc
source                    1..17
                          mol_type = other DNA
                          organism = synthetic construct
SEQUENCE: 66
gggaggcaga ggcaggt                                                 17

SEQ ID NO: 67             moltype = DNA  length = 23
FEATURE                   Location/Qualifiers
misc_feature              1..23
                          note = Description of Artificial Sequence: Synthetic
                           oligonucleotide
misc_feature              1..23
                          note = F2 primer for Prkdc
source                    1..23
                          mol_type = other DNA
                          organism = synthetic construct
SEQUENCE: 67
ggatctctgt gagtttgagg cca                                          23

SEQ ID NO: 68             moltype = DNA  length = 24
FEATURE                   Location/Qualifiers
misc_feature              1..24
                          note = Description of Artificial Sequence: Synthetic
                           oligonucleotide
misc_feature              1..24
                          note = R1 primer for Prkdc
source                    1..24
                          mol_type = other DNA
                          organism = synthetic construct
SEQUENCE: 68
gctccagaac tcactcttag gctc                                         24

SEQ ID NO: 69             moltype = DNA  length = 20
FEATURE                   Location/Qualifiers
misc_feature              1..20
                          note = Description of Artificial Sequence: Synthetic
                           oligonucleotide
misc_feature              1..20
```

-continued

```
                    note = Primer for Foxn1
source              1..20
                    mol_type = other DNA
                    organism = synthetic construct
SEQUENCE: 69
ctactccctc cgcagtctga                                               20

SEQ ID NO: 70       moltype = DNA   length = 20
FEATURE             Location/Qualifiers
misc_feature        1..20
                    note = Description of Artificial Sequence: Synthetic
                     oligonucleotide
misc_feature        1..20
                    note = Primer for Foxn1
source              1..20
                    mol_type = other DNA
                    organism = synthetic construct
SEQUENCE: 70
ccaggcctag gttccaggta                                               20

SEQ ID NO: 71       moltype = DNA   length = 20
FEATURE             Location/Qualifiers
misc_feature        1..20
                    note = Description of Artificial Sequence: Synthetic
                     oligonucleotide
misc_feature        1..20
                    note = Primer for Prkdc
source              1..20
                    mol_type = other DNA
                    organism = synthetic construct
SEQUENCE: 71
ccccagcatt gcagatttcc                                               20

SEQ ID NO: 72       moltype = DNA   length = 23
FEATURE             Location/Qualifiers
misc_feature        1..23
                    note = Description of Artificial Sequence: Synthetic
                     oligonucleotide
misc_feature        1..23
                    note = Primer for Prkdc
source              1..23
                    mol_type = other DNA
                    organism = synthetic construct
SEQUENCE: 72
agggcttctt ctctacaatc acg                                           23

SEQ ID NO: 73       moltype = DNA   length = 86
FEATURE             Location/Qualifiers
misc_feature        1..86
                    note = Description of Artificial Sequence: Synthetic
                     oligonucleotide
misc_feature        1..86
                    note = BRI1 target 1
source              1..86
                    mol_type = other DNA
                    organism = synthetic construct
SEQUENCE: 73
gaaattaata cgactcacta taggtttgaa agatggaagc gcgggtttta gagctagaaa  60
tagcaagtta aaataaggct agtccg                                       86

SEQ ID NO: 74       moltype = DNA   length = 86
FEATURE             Location/Qualifiers
misc_feature        1..86
                    note = Description of Artificial Sequence: Synthetic
                     oligonucleotide
misc_feature        1..86
                    note = BRI1 target 2
source              1..86
                    mol_type = other DNA
                    organism = synthetic construct
SEQUENCE: 74
gaaattaata cgactcacta taggtgaaac taaactggtc cacagtttta gagctagaaa  60
tagcaagtta aaataaggct agtccg                                       86

SEQ ID NO: 75       moltype = DNA   length = 64
FEATURE             Location/Qualifiers
misc_feature        1..64
                    note = Description of Artificial Sequence: Synthetic
                     oligonucleotide
```

```
misc_feature          1..64
                      note = Universal
source                1..64
                      mol_type = other DNA
                      organism = synthetic construct
SEQUENCE: 75
aaaaaaagcac cgactcggtg ccacttttc aagttgataa cggactagcc ttattttaac  60
ttgc                                                               64

SEQ ID NO: 76         moltype = DNA   length = 65
FEATURE               Location/Qualifiers
misc_feature          1..65
                      note = Description of Artificial Sequence: Synthetic
                       oligonucleotide
misc_feature          1..65
                      note = Templates for crRNA
misc_difference       25..44
                      note = modified_base - a, c, t, g, unknown or other
source                1..65
                      mol_type = other DNA
                      organism = synthetic construct
SEQUENCE: 76
gaaattaata cgactcacta taggnnnnnn nnnnnnnnnn nnnngtttta gagctatgct  60
gtttt                                                              65

SEQ ID NO: 77         moltype = DNA   length = 67
FEATURE               Location/Qualifiers
misc_feature          1..67
                      note = Description of Artificial Sequence: Synthetic
                       oligonucleotide
misc_feature          1..67
                      note = tracrRNA
source                1..67
                      mol_type = other DNA
                      organism = synthetic construct
SEQUENCE: 77
gaaattaata cgactcacta taggaaccat tcaaaacagc atagcaagtt aaaataaggc  60
tagtccg                                                            67

SEQ ID NO: 78         moltype = DNA   length = 69
FEATURE               Location/Qualifiers
misc_feature          1..69
                      note = Description of Artificial Sequence: Synthetic
                       oligonucleotide
misc_feature          1..69
                      note = tracrRNA
source                1..69
                      mol_type = other DNA
                      organism = synthetic construct
SEQUENCE: 78
aaaaaaagca ccgactcggt gccacttttt caagttgata acggactagc cttatttaa   60
cttgctatg                                                          69

SEQ ID NO: 79         moltype = DNA   length = 20
FEATURE               Location/Qualifiers
misc_feature          1..20
                      note = Description of Artificial Sequence: Synthetic
                       oligonucleotide
misc_feature          1..20
                      note = Primer
source                1..20
                      mol_type = other DNA
                      organism = synthetic construct
SEQUENCE: 79
ctccatggtg ctatagagca                                              20

SEQ ID NO: 80         moltype = DNA   length = 21
FEATURE               Location/Qualifiers
misc_feature          1..21
                      note = Description of Artificial Sequence: Synthetic
                       oligonucleotide
misc_feature          1..21
                      note = Primer
source                1..21
                      mol_type = other DNA
                      organism = synthetic construct
SEQUENCE: 80
gagccaagct ctccatctag t                                            21
```

```
SEQ ID NO: 81          moltype = DNA   length = 20
FEATURE                Location/Qualifiers
misc_feature           1..20
                       note = Description of Artificial Sequence: Synthetic
                       oligonucleotide
misc_feature           1..20
                       note = Primer
source                 1..20
                       mol_type = other DNA
                       organism = synthetic construct
SEQUENCE: 81
gccctgtcaa gagttgacac                                          20

SEQ ID NO: 82          moltype = DNA   length = 22
FEATURE                Location/Qualifiers
misc_feature           1..22
                       note = Description of Artificial Sequence: Synthetic
                       oligonucleotide
misc_feature           1..22
                       note = Primer
source                 1..22
                       mol_type = other DNA
                       organism = synthetic construct
SEQUENCE: 82
gcacagggtg gaacaagatg ga                                       22

SEQ ID NO: 83          moltype = DNA   length = 24
FEATURE                Location/Qualifiers
misc_feature           1..24
                       note = Description of Artificial Sequence: Synthetic
                       oligonucleotide
misc_feature           1..24
                       note = Primer
source                 1..24
                       mol_type = other DNA
                       organism = synthetic construct
SEQUENCE: 83
gccaggtacc tatcgattgt cagg                                     24

SEQ ID NO: 84          moltype = DNA   length = 21
FEATURE                Location/Qualifiers
misc_feature           1..21
                       note = Description of Artificial Sequence: Synthetic
                       oligonucleotide
misc_feature           1..21
                       note = Primer
source                 1..21
                       mol_type = other DNA
                       organism = synthetic construct
SEQUENCE: 84
gagccaagct ctccatctag t                                        21

SEQ ID NO: 85          moltype = DNA   length = 20
FEATURE                Location/Qualifiers
misc_feature           1..20
                       note = Description of Artificial Sequence: Synthetic
                       oligonucleotide
misc_feature           1..20
                       note = Primer
source                 1..20
                       mol_type = other DNA
                       organism = synthetic construct
SEQUENCE: 85
actctgactg ggtcaccagc                                          20

SEQ ID NO: 86          moltype = DNA   length = 20
FEATURE                Location/Qualifiers
misc_feature           1..20
                       note = Description of Artificial Sequence: Synthetic
                       oligonucleotide
misc_feature           1..20
                       note = Primer
source                 1..20
                       mol_type = other DNA
                       organism = synthetic construct
SEQUENCE: 86
tatttggctg gttgaaaggg                                          20

SEQ ID NO: 87          moltype = DNA   length = 24
```

-continued

```
FEATURE                Location/Qualifiers
misc_feature           1..24
                       note = Description of Artificial Sequence: Synthetic
                        oligonucleotide
misc_feature           1..24
                       note = Primer
source                 1..24
                       mol_type = other DNA
                       organism = synthetic construct
SEQUENCE: 87
aaagtcatga aataaacaca ccca                                         24

SEQ ID NO: 88          moltype = DNA  length = 24
FEATURE                Location/Qualifiers
misc_feature           1..24
                       note = Description of Artificial Sequence: Synthetic
                        oligonucleotide
misc_feature           1..24
                       note = Primer
source                 1..24
                       mol_type = other DNA
                       organism = synthetic construct
SEQUENCE: 88
ctgcattgat atggtagtac catg                                         24

SEQ ID NO: 89          moltype = DNA  length = 21
FEATURE                Location/Qualifiers
misc_feature           1..21
                       note = Description of Artificial Sequence: Synthetic
                        oligonucleotide
misc_feature           1..21
                       note = Primer
source                 1..21
                       mol_type = other DNA
                       organism = synthetic construct
SEQUENCE: 89
gctgttcatt gcaatggaat g                                            21

SEQ ID NO: 90          moltype = DNA  length = 22
FEATURE                Location/Qualifiers
misc_feature           1..22
                       note = Description of Artificial Sequence: Synthetic
                        oligonucleotide
misc_feature           1..22
                       note = Primer
source                 1..22
                       mol_type = other DNA
                       organism = synthetic construct
SEQUENCE: 90
atggagttgg acatggccat gg                                           22

SEQ ID NO: 91          moltype = DNA  length = 28
FEATURE                Location/Qualifiers
misc_feature           1..28
                       note = Description of Artificial Sequence: Synthetic
                        oligonucleotide
misc_feature           1..28
                       note = Primer
source                 1..28
                       mol_type = other DNA
                       organism = synthetic construct
SEQUENCE: 91
actcactatc cacagttcag catttacc                                     28

SEQ ID NO: 92          moltype = DNA  length = 23
FEATURE                Location/Qualifiers
misc_feature           1..23
                       note = Description of Artificial Sequence: Synthetic
                        oligonucleotide
misc_feature           1..23
                       note = Primer
source                 1..23
                       mol_type = other DNA
                       organism = synthetic construct
SEQUENCE: 92
tggagatagc tgtcagcaac ttt                                          23

SEQ ID NO: 93          moltype = DNA  length = 29
FEATURE                Location/Qualifiers
```

-continued

```
misc_feature          1..29
                      note = Description of Artificial Sequence: Synthetic
                       oligonucleotide
misc_feature          1..29
                      note = Primer
source                1..29
                      mol_type = other DNA
                      organism = synthetic construct
SEQUENCE: 93
caacaaagca aaggtaaagt tggtaatag                                              29

SEQ ID NO: 94         moltype = DNA  length = 25
FEATURE               Location/Qualifiers
misc_feature          1..25
                      note = Description of Artificial Sequence: Synthetic
                       oligonucleotide
misc_feature          1..25
                      note = Primer
source                1..25
                      mol_type = other DNA
                      organism = synthetic construct
SEQUENCE: 94
ggtttcagga gatgtgttac aaggc                                                  25

SEQ ID NO: 95         moltype = DNA  length = 27
FEATURE               Location/Qualifiers
misc_feature          1..27
                      note = Description of Artificial Sequence: Synthetic
                       oligonucleotide
misc_feature          1..27
                      note = Primer
source                1..27
                      mol_type = other DNA
                      organism = synthetic construct
SEQUENCE: 95
gattgtgcaa ttcctatgca atcggtc                                                27

SEQ ID NO: 96         moltype = DNA  length = 25
FEATURE               Location/Qualifiers
misc_feature          1..25
                      note = Description of Artificial Sequence: Synthetic
                       oligonucleotide
misc_feature          1..25
                      note = Primer
source                1..25
                      mol_type = other DNA
                      organism = synthetic construct
SEQUENCE: 96
cactgggtac ttaatctgta gcctc                                                  25

SEQ ID NO: 97         moltype = DNA  length = 23
FEATURE               Location/Qualifiers
misc_feature          1..23
                      note = Description of Artificial Sequence: Synthetic
                       oligonucleotide
misc_feature          1..23
                      note = Primer
source                1..23
                      mol_type = other DNA
                      organism = synthetic construct
SEQUENCE: 97
ggttccaagt cattcccagt agc                                                    23

SEQ ID NO: 98         moltype = DNA  length = 30
FEATURE               Location/Qualifiers
misc_feature          1..30
                      note = Description of Artificial Sequence: Synthetic
                       oligonucleotide
misc_feature          1..30
                      note = Primer
source                1..30
                      mol_type = other DNA
                      organism = synthetic construct
SEQUENCE: 98
catcactgca gttgtaggtt ataactatcc                                             30

SEQ ID NO: 99         moltype = DNA  length = 26
FEATURE               Location/Qualifiers
misc_feature          1..26
```

```
                              note = Description of Artificial Sequence: Synthetic
                                oligonucleotide
misc_feature                  1..26
                              note = Primer
source                        1..26
                              mol_type = other DNA
                              organism = synthetic construct
SEQUENCE: 99
ttgaaaacca cagatctggt tgaacc                                          26

SEQ ID NO: 100                moltype = DNA   length = 22
FEATURE                       Location/Qualifiers
misc_feature                  1..22
                              note = Description of Artificial Sequence: Synthetic
                                oligonucleotide
misc_feature                  1..22
                              note = Primer
source                        1..22
                              mol_type = other DNA
                              organism = synthetic construct
SEQUENCE: 100
ggagtgccaa gagaatatct gg                                              22

SEQ ID NO: 101                moltype = DNA   length = 32
FEATURE                       Location/Qualifiers
misc_feature                  1..32
                              note = Description of Artificial Sequence: Synthetic
                                oligonucleotide
misc_feature                  1..32
                              note = Primer
source                        1..32
                              mol_type = other DNA
                              organism = synthetic construct
SEQUENCE: 101
ctgaaactgg tttcaaaata ttcgttttaa gg                                  32

SEQ ID NO: 102                moltype = DNA   length = 22
FEATURE                       Location/Qualifiers
misc_feature                  1..22
                              note = Description of Artificial Sequence: Synthetic
                                oligonucleotide
misc_feature                  1..22
                              note = Primer
source                        1..22
                              mol_type = other DNA
                              organism = synthetic construct
SEQUENCE: 102
gctctgtatg ccctgtagta gg                                              22

SEQ ID NO: 103                moltype = DNA   length = 22
FEATURE                       Location/Qualifiers
misc_feature                  1..22
                              note = Description of Artificial Sequence: Synthetic
                                oligonucleotide
misc_feature                  1..22
                              note = Primer
source                        1..22
                              mol_type = other DNA
                              organism = synthetic construct
SEQUENCE: 103
tttgcatctg accttacctt tg                                              22

SEQ ID NO: 104                moltype = DNA   length = 23
FEATURE                       Location/Qualifiers
misc_feature                  1..23
                              note = Description of Artificial Sequence: Synthetic
                                oligonucleotide
misc_feature                  1..23
                              note = Target sequence of RGEN
source                        1..23
                              mol_type = other DNA
                              organism = synthetic construct
SEQUENCE: 104
aatgaccact acatcctcaa ggg                                             23

SEQ ID NO: 105                moltype = DNA   length = 23
FEATURE                       Location/Qualifiers
misc_feature                  1..23
                              note = Description of Artificial Sequence: Synthetic
```

```
                      oligonucleotide
misc_feature         1..23
                     note = Target sequence of RGEN
source               1..23
                     mol_type = other DNA
                     organism = synthetic construct
SEQUENCE: 105
agatgatgtc tcatcatcag agg                                           23

SEQ ID NO: 106        moltype = DNA  length = 4170
FEATURE               Location/Qualifiers
misc_feature         1..4170
                     note = Description of Artificial Sequence: Synthetic
                      polynucleotide
misc_feature         1..4170
                     note = Cas9-coding sequence in p3s-Cas9HC (humanized,
                      C-term tagging, human cell experiments)
source               1..4170
                     mol_type = other DNA
                     organism = synthetic construct
SEQUENCE: 106
atggacaaga agtacagcat cggcctggac atcggtacca acagcgtggg ctgggccgtg    60
atcaccgacg agtacaaggt gcccagcaag aagttcaagg tgctgggcaa caccgaccgc   120
cacagcatca agaagaacct gatcggcgcc ctgctgttcg acagcggcga gaccgccgag   180
gccacccgcc tgaagcgcac cgcccgccgc cgctacaccc gccgcaagaa ccgcatctgt   240
tacctgcagg agatcttcag caacgagatg gccaaggtgg acgacagctt cttccaccgc   300
ctggaggaga gcttcctggt ggaggaggac aagaagcacg agcgccaccc catcttcggc   360
aacatcgtgg acgaggtggc ctaccacgag aagtacccca ccatctacca cctgcgcaag   420
aagctggtgg acagcaccga caaggccgac ctgcgcctga tctacctggc cctggccac    480
atgatcaagt tccgcggcca cttcctgatc gagggcgacc tgaaccccga caacagcgac   540
gtggacaagc tgttcatcca gctggtgcag acctacaacc agctgttcga ggagaacccc   600
atcaacgcca gcggcgtgga cgccaaggcc atcctgagcg cccgcctgag caagagccgc   660
cgcctggaga acctgatcgc ccagctgccc ggcgagaaga gaaacggcct gttcggcaac   720
ctgatcgccc tgagcctggg cctgacccc aacttcaaga gcaacttcga cctggccgag   780
gacgccaagc tgcagctgag caaggacacc tacgacgacg acctggacaa cctgctggcc   840
cagatcggcg accagtacgc cgacctgttc ctggccgcca agaacctgag cgacgccatc   900
ctgctgagcg acatcctgcg cgtgaacacc gagatcacca aggccccct gagcgccagc   960
atgatcaagc gctacgacga gcaccaccag gacctgaccc tgctgaaggc cctggtgcgc  1020
cagcagctgc ccgagaagta caaggagatc ttcttcgacc agagcaagaa cggctacgcc  1080
ggctacatcg acggcggcgc cagccaggag gagttctaca agttcatcaa gcccatcctg  1140
gagaagatgg acggcaccga ggagctgctg gtgaagctga accgcgagga cctgctgcgc  1200
aagcagcgca ccttcgacaa cggcagcatc ccccaccaga tccacctggg cgagctgcac  1260
gccatcctgc gccgccagga ggacttctac cccttcctga aggacaaccg cgagaagatc  1320
gagaagatcc tgaccttccg catccccac tacgtgggcc ccctggcccg cggcaacagc  1380
cgcttcgcct ggatgacccg caagagcgag gagaccatca cccctggaa cttcgaggag  1440
gtggtggaca gggcgccag cgcccagagc ttcatcgagc gcatgaccaa cttcgacaag  1500
aacctgccca acgagaaggt gctgcccaag cacagcctgc tgtacgagta cttcaccgtg  1560
tacaacgagc tgaccaaggt gaagtacgtg accgagggca tgcgcaagcc cgccttcctg  1620
agcggcgagc agaagaaggc catcgtggac ctgctgttca agaccaaccg caaggtgacc  1680
gtgaagcagc tgaaggagga ctacttcaag aagatcgagt gcttcgacag cgtggagatc  1740
agcggcgtgg aggaccgctt caacgccagc ctgggcacct accacgacct gctgaagatc  1800
atcaaggaca aggacttcct ggacaacgag gagaacgagg acatcctgga ggacatcgtg  1860
ctgacctga ccctgttcga ggaccgcgag atgatcgagg agcgcctgaa gacctacgcc  1920
cacctgttcg acgacaaggt gatgaagcag ctgaagcgcc gccgctacac cggctggggc  1980
cgcctgagcc gcaagcttat caacggcatc cgcgacaagc agagcggcaa gaccatcctg  2040
gacttcctga gagcgacgg cttcgccaac cgcaacttca tgcagctgat ccacgacgac  2100
agcctgacct tcaaggagga catccagaag gcccaggtga cggcagggg cgacagcctg  2160
cacgagcaca tcgccaacct ggccggcagc cccgccatca gaagggcat cctgcagacc  2220
gtgaaggtgg tggacgagct ggtgaaggtg atgggccgcc acaagcccga gaacatcgtg  2280
atcgagatgg cccgcgagaa ccagaccacc cagaagggcc agaagaacag ccgcgagcgc  2340
atgaagcgca tcgaggaggg catcaaggag ctgggcagcc agatcctgaa ggagcacccc  2400
gtggagaaca cccagctgca gaacgagaag ctgtacctgt actacctgca gaacggccgc  2460
gacatgtacg tggaccagga gctggacatc aaccgcctga gcgactacga cgtggaccac  2520
atcgtgcccc agagcttcct gaaggacgac agcatcgaca acaaggtgct gacccgcagc  2580
gacaagaacc gcggcaagag cgacaacgtg cccagcgagg aggtggtgaa gaagatgaag  2640
aactactggc gccagctgct gaacgccaag ctgatcaccc agcgcaagtt cgacaacctg  2700
accaaggccg agcgcggcgg cctgagcgag ctggacaagg ccggcttcat caagcgccag  2760
ctggtggaga cccgccagat caccaagcac gtggcccaga tcctggacag ccgcatgaac  2820
accaagtacg acgagaacga caagctgatc cgcgaggtga aggtgatcac cctgaagagc  2880
aagctggtga gcgacttccg caaggacttc cagttctaca aggtgcgcga gatcaacaac  2940
taccaccacg cccacgacgc ctacctgaac gccgtggtgg gcaccgccct gatcaagaag  3000
tacccccaag tggagagcga gttcgtgtac ggcgactaca aggtgtacga cgtgcgcaag  3060
atgatcgcca gagcgagca ggagatcggc aaggccaccg ccaagtactt cttctacagc  3120
aacatcatga acttcttcaa gaccgagatc accctggcca acggcgagat ccgcaagcgc  3180
cccctgatcg agaccaacgg cgagaccggc gagatcgtgt gggacaaggg ccgcgacttc  3240
gccaccgtgc gcaaggtgct gagcatgccc caggtgaaca tcgtgaagaa gaccgaggtg  3300
cagaccggcg gcttcagcaa ggagagcatc ctgcccaagc gcaacagcga caagctgatc  3360
gcccgcaaga aggactggga cccccaagaag tacggcggct cgacagccc caccgtggcc  3420
tacagcgtgc tggtggtggc caaggtggag aagggcaaga gcaagaagct gaagagcgtg  3480
```

```
aaggagctgc tgggcatcac catcatggag cgcagcagct tcgagaagaa ccccatcgac   3540
ttcctggagg ccaagggcta caaggaggtg aagaaggacc tgatcatcaa gctgcccaag   3600
tacagcctgt tcgagctgga gaacggccgc aagcgcatgc tggccagcgc cggcgagctg   3660
cagaagggca acgagctggc cctgcccagc aagtacgtga acttcctgta cctggccagc   3720
cactacgaga agctgaaggg cagccccgag gacaaccagg agaagcagct gttcgtggag   3780
cagcacaagc actacctgga cgagatcatc gagcagatca gcgagttcag caagcgcgtg   3840
atcctggccg acgccaacct ggacaaggtg ctgagcgcct acaacaagca ccgcgacaag   3900
cccatccgcg agcaggccga aacatcatc cacctgttca ccctgaccaa cctgggcgcc   3960
cccgccgcct tcaagtactt cgacaccacc atcgaccgca agcgctacac cagcaccaag   4020
gaggtgctgg acgccaccct gatccaccag agcatcaccg gtctgtacga gacccgcatc   4080
gacctgagcc agctgggcgg cgacggcggc tccggacctc caaagaaaaa gagaaaagta   4140
taccccctacg acgtgcccga ctacgcctaa                                    4170

SEQ ID NO: 107          moltype = DNA  length = 4194
FEATURE                 Location/Qualifiers
misc_feature            1..4194
                        note = Description of Artificial Sequence: Synthetic
                        polynucleotide
misc_feature            1..4194
                        note = Cas9 coding sequence in p3s-Cas9HN (humanized codon,
                        N-term tagging (underlined), human cell experiments)
source                  1..4194
                        mol_type = other DNA
                        organism = synthetic construct SEQUENCE: 107
atggtgtacc cctacgacgt gcccgactac gccgaattgc ctccaaaaaa gaagagaaag   60
gtagggatcc gaattcccgg ggaaaaaccg gacaagaagt acagcatcgg cctggacatc   120
ggtaccaaca gcgtgggctg ggccgtgatc accgacgagt acaaggtgcc cagcaagaag   180
ttcaaggtgc tgggcaacac cgaccgccac agcatcaaga gaaacctgat cggcgccctg   240
ctgttcgaca gcggcgagac cgccgaggcc accgcctga agcgcaccgc ccgcgccaac   300
tacacccgcc gcaagaaccg catctgctac ctgcaggaga tcttcagcaa cgagatggcc   360
aaggtggacg acagcttctt ccaccgcctg gaggagagct tcctggtgga ggaggacaag   420
aagcacgagc gccaccccat cttcggcaac atcgtggacg aggtggccta ccacgagaag   480
taccccacca tctaccacct gcgcaagaag ctggtggaca ggcccgacaa ggcccaccta   540
cgcctgatct acctggccct ggcccacatg atcaagttcc gcggccactt cctgatcgag   600
ggcgacctga accccgacaa cagcgacgtg gacaagctgt tcatccagct ggtgcagacc   660
tacaaccagc tgttcgagga gaaccccatc aacgccagcg gcgtggacgc caaggccatc   720
ctgagcgccc gcctgagcaa gagccgccgc ctggagaacc tgatcgccca gctgcccggc   780
gagaagaaga acggcctgtt cggcaacctg atcgccctga gcctgggcct gacccccaac   840
ttcaagagca acttcgacct ggccgaggac gccaagctgc agctgagcaa ggacacctac   900
gacgacgacc tggacaacct gctggcccag atcggcgacc agtacgccga cctgttcctg   960
gccgccaaga acctgagcga cgccatcctg ctgagcgaca tcctgcgcgt gaacaccgag   1020
atcaccaagg cccccctgag cgccagcatg atcaagcgct acgacgagca ccaccaggac   1080
ctgaccctgc tgaaggccct ggtgcgccag cagctgcccg agaagtacaa ggagatcttc   1140
ttcgaccaga gcaagaacgg ctacgccggc tacatcgacg gcggcgccag ccaggaggag   1200
ttctacaagt tcatcaagcc catcctggag aagatggacg gcaccgagga gctgctggtg   1260
aagctgaacc gcgaggacct gctgcgcaag cagcgcacct tcgacaacgg cagcatcccc   1320
caccagatcc acctgggcga gctgcacgcc atcctgcgcc gccaggagga cttctacccc   1380
ttcctgaagg acaaccgcga gaagatcgag aagatcctga ccttccgcat ccctactac   1440
gtgggccccc tggcccgcgg caacagccgc ttcgcctgga tgacccgcaa gagcgaggag   1500
accatcaccc cctggaactt cgaggaggtg gtggacaagg gccagcgc cagagcttc   1560
atcgagcgca tgaccaactt cgacaagaac ctgcccaacg agaaggtgct gcccaagcac   1620
agcctgctgt acgagtactt caccgtgtac aacgagctga ccaaggtgaa gtacgtgacc   1680
gagggcatgc gcaagcccgc cttcctgagc ggcgagcaga gaaaggccat cgtggacctg   1740
ctgttcaaga ccaaccgcaa ggtgaccgtg aagcagctga aggaggacta cttcaagaag   1800
atcgagtgct cgacagcgt ggagatcagc ggcgtggagg accgcttcaa cgccagcctg   1860
ggcacctacc acgacctgct gaagatcatc aaggacaagg acttcctgga caacgaggag   1920
aacgaggaca tcctggagga catcgtgctg accctgaccc tgttcgagga ccgcgagatg   1980
atcgaggagc gcctgaagac ctacgcccac ctgttcgacg acaaggtgat gaagcagctg   2040
aagcgccgcc gctacaccgg ctggggccgc ctgagccgca agcttatcaa cggcatccgc   2100
gacaagcaga gcggcaagac catcctggac ttcctgaaga gcgacggctt cgccaaccgc   2160
aacttcatgc agctgatcca cgacgacagc ctgaccttca aggaggacat ccagaaggcc   2220
caggtgagcg gccagggcga cagcctgcac gagcacatcg ccaacctggc cggcagcccc   2280
gccatcaaga aggggcatcct gcagaccgtg aaggtggtga gacctggtg gaaggtgatg   2340
ggccgccaca gcccgagaa catcgtgatc gagatggccc gcgagaacca gaccacccag   2400
aagggccaga gaacagccg cgagcgcatg aagcgcatcg aggagggcat caaggagctg   2460
ggcagccaga tcctgaagga gcaccccgtg gagaacaccc agctgcagaa cgagaagctg   2520
tacctgtact acctgcagaa cggccgcgac atgtacgtgg accagggagct ggacatcaac   2580
cgcctgagcg actacgacgt ggaccacatc gtgccccaga gcttcctgaa ggacgacagc   2640
atcgacaaca aggtgctgac ccgcagcgac aagaaccgcg gcaagagcga caacgtgccc   2700
agcgaggagg tggtgaagaa gatgaagaac tactggcgcc agctgctgaa cgccaagctg   2760
atcacccagc gcaagttcga caacctgacc aaggccgagc gcggcggcct gagcgagctg   2820
gacaaggccg gcttcatcaa gcgccagctg gtggagaccc gccagatcac caagcacgtg   2880
gcccagatcc tggacagccg catgaacacc aagtacgacg agaacgacaa gctgatccgc   2940
gaggtgaagg tgatcaccct gaagagcaag ctggtgagcg acttccgcaa ggacttccag   3000
ttctacaagg tgcgcgagat caacaactac caccacgccc acgacgccta cctgaacgcc   3060
gtggtgggca ccgccctgat caagaagtac cccaagctgg agagcgagtt cgtgtacggc   3120
gactacaagg tgtacgacgt gcgcaagatg atcgccaaga gcgagcagga gatcggcaag   3180
gccaccgcca agtacttctt ctacagcaac atcatgaact tcttcaagac cgagatcacc   3240
```

-continued

```
ctggccaacg gcgagatccg caagcgcccc ctgatcgaga ccaacggcga gaccggcgag  3300
atcgtgtggg acaagggccg cgacttcgcc accgtgcgca aggtgctgag catgccccag  3360
gtgaacatcg tgaagaagac cgaggtgcag accggcggct tcagcaagga gagcatcctg  3420
cccaagcgca acagcgacaa gctgatcgcc cgcaagaagg actgggaccc caagaagtac  3480
ggcggcttcg acagccccac cgtggcctac agcgtgctgg tggtggccaa ggtggagaag  3540
ggcaagagca agaagctgaa gagcgtgaag gagctgctgg gcatcaccat catggagcgc  3600
agcagcttcg agaagaaccc catcgacttc ctggaggcca agggctacaa ggaggtgaag  3660
aaggacctga tcatcaagct gcccaagtac agcctgttcg agctggagaa cggccgcaag  3720
cgcatgctgg ccagcgccgg cgagctgcag aagggcaacg agctggccct gcccagcaag  3780
tacgtgaact tcctgtacct ggccagccac tacgagaagc tgaagggcag ccccgaggac  3840
aacgagcaga agcagctgtt cgtggagcag cacaagcact acctggacga gatcatcgag  3900
cagatcagcg agttcagcaa gcgcgtgatc ctggccgacg ccaacctgga caaggtgctg  3960
agcgcctaca acaagcaccg cgacaagccc atccgcgagc aggccgagaa catcatccac  4020
ctgttcaccc tgaccaacct gggcgccccc gccgccttca agtacttcga caccaccatc  4080
gaccgcaagc gctacaccag caccaaggag gtgctggacg ccaccctgat ccaccagagc  4140
atcaccggtc tgtacgagac ccgcatcgac ctgagccagc tgggcggcga ctaa  4194

SEQ ID NO: 108       moltype = DNA  length = 4107
FEATURE              Location/Qualifiers
misc_feature        1..4107
                    note = Description of Artificial Sequence: Synthetic
                     polynucleotide
misc_feature        1..4107
                    note = Cas9-coding sequence in Streptococcus pyogenes
source              1..4107
                    mol_type = other DNA
                    organism = synthetic construct
SEQUENCE: 108
atggataaga aatactcaat aggcttagat atcggcacaa atagcgtcgg atgggcggtg  60
atcactgatg aatataaggt tccgtctaaa aagttcaagg ttctgggaaa tacagaccgc  120
cacagtatca aaaaaaatct tataggggct ctttttattg acagtggaga gacagcggaa  180
gcgactcgtc tcaaacggac agctcgtaga aggtatacac gtcggaagaa tcgtatttgt  240
tatctacagg agatttttc aaatgagatg gcgaaagtag atgatagttt ctttcatcga  300
cttgaagagt cttttttggt ggaagaagac aagaagcatg aacgtcatcc tattttttgga  360
aatatagtag atgaagttgc ttatcatgag aaatatccaa ctatctatca tctgcgaaaa  420
aaattggtag attctactga taaagcggat ttgcgcttaa tctatttggc cttagcgcat  480
atgattaagt ttcgtggtca tttttttgatt gagggagatt aaatcctga taatagtgat  540
gtggacaaac tatttatcca gttggtacaa acctacaatc aattatttga agaaaaccct  600
attaacgcaa gtggagtaga tgctaaagcg attctttctg cacgattgag taaatcaaga  660
cgattagaaa atctcattgc tcagctcccc ggtgagaaga aaaatggctt atttgggaat  720
ctcattgctt tgtcattggg tttgacccct aattttaaat caaattttga tttggcagaa  780
gatgctaaat tacagctttc aaaagatact tacgatgatg atttagataa tttattggca  840
caaattggag atcaatatgc tgatttgttt ttggcagcta agaatttatc agatgctatt  900
ttactttcag atatcctaag agtaaatact gaaataacta aggctcccct atcagcttca  960
atgattaaac gctacgatga acatcatcaa gacttgactc ttttaaaagc tttagttcga  1020
caacaacttc cagaaaagta taaagaaatc tttttttgatc aatcaaaaaa cggatatgca  1080
ggttatattg atgggggagc tagccaagaa gaattttata aatttatcaa accaattttta  1140
gaaaaaatgg atggtactga ggaattattg gtgaaactaa atcgtaaga tttgctgcgc  1200
aagcaacgga cctttgacaa cggctctatt ccccatcaaa ttcacttggg tgagctgcat  1260
gctatttttga gaagacaaga gacttttat ccatttttaa aagacaatcg tgagaagatt  1320
gaaaaaatct tgacttttcg aattccttat tatgttgatc cattggccgg tggcaatagt  1380
cgttttgcat ggatgactcg gaagtctgaa gaaacaatta ccccatggaa ttttgaagaa  1440
gttgtcgata aaggtgcttc agctcaatca tttattgaac gcatgacaaa ctttgataaa  1500
aatcttccaa atgaaaaagt actaccaaaa catagtttttgc tttatgagta ttttacggtt  1560
tataacgaat tgacaaaggt caaatatgtt actgaaggaa tgcgaaaacc agcatttctt  1620
tcaggtgaac agaagaaagc cattgttgat ttactcttca aaacaaatcg aaaagtaacc  1680
gttaagcaat taaaagaaga ttatttcaaa aaaatagaat gttttgatag tgttgaaatt  1740
tcaggagtta agatagatt taatgcttca ttaggtacct accatgattt gctaaaaatt  1800
attaaagata aagatttttt ggataatgaa gaaaatgaag atatcttaga ggatattgtt  1860
ttaacattga ccttatttga agataggag atgattgagg aaagacttaa aacatatgct  1920
cacctctttg atgataaggt gatgaaacag cttaaacgtc gccgttatac tggttgggga  1980
cgtttgtctc gaaaattgat taatggtatt agggataagc aatctggcaa aacaatatta  2040
gattttttga aatcagatgg ttttgccaat cgcaatttta tgcagctgat ccatgatgat  2100
agtttgacat ttaaagaaga cattcaaaaa gcacaagtgt ctggacaagg cgatagtctta  2160
catgaacata ttgcaaattt agctggtagc cctgctatta aaaaaggtat tttacagact  2220
gtaaaagttg ttgatgaatt ggtcaaagta atggggcggc ataagccaga aaatatcgtt  2280
attgaaatgc acgtgaaaa tcagacaact caaaagggcc agaaaaattc gcgagagcgt  2340
atgaaacgaa tcgaagaagg tatcaaagaa ttaggaagtc agattcttaa agagcatcct  2400
gttgaaaata ctcaattgca aaatgaaaag ctctatctct attatctcca aaatggaaga  2460
gacatgtatg tggaccaaga attagatatt aatcgtttaa gtgattatga tgtcgatcac  2520
attgttccac aaagtttcct taaagacgat tcaatagaca ataaggtctt aacgcgttct  2580
gataaaaatc gtggtaaatc ggataacgtt ccaagtgaag aagtagtcaa aaagatgaaa  2640
aactattgga gacaacttct aaacgccaag ttaatcactc aacgtaagtt tgataattta  2700
acgaaagctg aacgtggagg tttgagtgaa cttgataaag ctgttttat caaacgccaa  2760
ttggttgaaa ctcgccaaat cactaagcat gtggcacaaa ttttggatag tcgcatgaat  2820
actaaatacg atgaaaatga taaacttatt cgagaggtta agtgattac cttaaaatct  2880
aaattagttt ctgacttccg aaaagatttc caattctata agtacgtga gattaacaat  2940
taccatcatg cccatgatgc gtatctaaat gccgtcgttg gaactgcttt gattaagaaa  3000
tatccaaaac ttgaatcgga gtttgtctat ggtgattata aagtttatga tgttcgtaaa  3060
```

```
atgattgcta agtctgagca agaaataggc aaagcaaccg caaaatattt cttttactct  3120
aatatcatga acttcttcaa aacagaaatt acacttgcaa atggagagat tcgcaaacgc  3180
cctctaatcg aaactaatgg ggaaactgga gaaattgtct gggataaagg gcgagatttt  3240
gccacagtgc gcaaagtatt gtccatgccc caagtcaata ttgtcaagaa aacagaagta  3300
cagacaggcg gattctccaa ggagtcaatt ttaccaaaaa gaaattcgga caagcttatt  3360
gctcgtaaaa aagactggga tccaaaaaaa tatggtggtt ttgatagtcc aacggtagct  3420
tattcagtcc tagtggttgc taaggtggaa aaagggaaat cgaagaagtt aaaatccgtt  3480
aaagagttac tagggatcac aattatggaa agaagttcct ttgaaaaaaa tccgattgac  3540
tttttagaag ctaaaggata taaggaagtt aaaaaagact taatcattaa actacctaaa  3600
tatagtcttt ttgagttaga aaacggtcgt aaacggdatgc tggctagtgc cggagaatta  3660
caaaaaggaa atgagctggc tctgccaagc aaatatgtga attttttata tttagctagt  3720
cattatgaaa agttgaaggg tagtccagaa gataacgaac aaaaacaatt gtttgtggag  3780
cagcataagc attatttaga tgagattatt gagcaaatca gtgaatttc taagcgtgtt  3840
attttagcag atgccaattt agataaaagt cttagtgcat ataacaaaca tagagacaaa  3900
ccaatacgtg aacaagcaga aaatattatt catttattta cgttgacgaa tcttggagct  3960
cccgctgctt ttaaatattt tgatacaaca attgatcgta aacgatatac gtctacaaaa  4020
gaagttttag atgccactct tatccatcaa tccatcactg tctttatga aacacgcatt  4080
gatttgagtc agctaggagg tgactaa                                      4107
```

```
SEQ ID NO: 109          moltype = AA   length = 1368
FEATURE                 Location/Qualifiers
REGION                  1..1368
                        note = Description of Artificial Sequence: Synthetic
                         polypeptide
REGION                  1..1368
                        note = Amino acid sequence of Cas9 from S.pyogenes
source                  1..1368
                        mol_type = protein
                        organism = synthetic construct
SEQUENCE: 109
MDKKYSIGLD IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVA 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGD             1368
```

```
SEQ ID NO: 110          moltype = DNA   length = 4221
FEATURE                 Location/Qualifiers
misc_feature            1..4221
                        note = Description of Artificial Sequence: Synthetic
                         polynucleotide
misc_feature            1..4221
                        note = Cas9-coding sequence in pET-Cas9N3T for the
                         production of recombinant Cas9 protein in E. coli
                         (humanized codon; hexa-His-tag and a nuclear localization
                         signal at the N terminus)
source                  1..4221
                        mol_type = other DNA
                        organism = synthetic construct
SEQUENCE: 110
atgggcagca gccatcatca tcatcatcat gtgtacccct acgacgtgcc cgactacgcc   60
gaattgcctc caaaaaagaa gagaaaggta gggatcgaga acctgtactt ccagggcgac  120
aagaagtaca gcatcggcct ggacatcggt accaacagcg tgggctgggc cgtgatcacc  180
gacgagtaca aggtgcccag caagaagttc aaggtgctgg caacaccga ccgccacagc  240
atcaagaaga acctgatcgg cgccctgctg ttcgacagcg gcgagaccgc cgaggccacc  300
cgcctgaagc gcaccgcccg ccgccgctac acccgccgga agaaccgcat ctgctacctg  360
caggagatct tcagcaacga gatggccaag gtggacgaca gcttcttcca ccgcctggag  420
gagagcttcc tggtggagga ggacaagaag cacgagcgcc accccatctt cggcaacatc  480
gtggacgagg tggcctacca cgagaagtac cccaccatct accacctgcg caagaagctg  540
gtggacagca ccgacaaggc cgacctgcgc ctgatctacc tggccctggc ccacatgatc  600
aagttccgcg gccacttcct gatcgagggc gacctgaacc ccgacaacag cgacgtggac  660
```

-continued

```
aagctgttca tccagctggt gcagacctac aaccagctgt tcgaggagaa ccccatcaac    720
gccagcggcg tggacgccaa ggccatcctg agcgcccgcc tgagcaagag ccgccgcctg    780
gagaacctga tcgcccagct gcccggcgag aagaagaacg gcctgttcgg caacctgatc    840
gccctgagcc tgggcctgac ccccaacttc aagagcaact cgacctggc cgaggacgcc     900
aagctgcagc tgagcaagga cacctacgac gacgacctga acaacctgct ggcccagatc    960
ggcgaccagt acgccgacct gttcctggcc gccaagaacc tgagcgacgc catcctgctg    1020
agcgacatcc tgcgcgtgaa caccgagatc accaaggccc ccctgagcgc cagcatgatc   1080
aagcgctacg acgagcacca ccaggacctg accctgctga aggccctggt gcgccagcag   1140
ctgcccgaga agtacaagga gatcttcttc gaccagagca agaacggcta cgccggctac   1200
atcgacggcg gcgccagcca ggaggagttc tacaagttca tcaagcccat cctggagaag   1260
atggacggca ccgaggagct gctggtgaag ctgaaccgcg aggacctgct gcgcaagcag   1320
cgcaccttcg acaacggcag catcccccac cagatccacc tgggcgagct gcacgccatc   1380
ctgcgccgcc aggaggactt ctaccccttc ctgaaggaca accgcgagaa gatcgagaag   1440
atcctgacct tccgcatccc ctactacgtg ggccccctgg cccggcgaca cagccgcttc   1500
gcctggatga cccgcaagag cgaggagacc atcaccccct ggaacttcga ggaggtggtg   1560
gacaagggcg ccagcgccca gagcttcatc gagcgcatga ccaacttcga caagaacctg   1620
cccaacgaga aggtgctgcc caagcacagc ctgctgtacg agtacttcac cgtgtacaac   1680
gagctgacca aggtgaagta cgtgaccgag ggcatgcgca gccccgcctt cctgagcggc   1740
gagcagaaga aggccatcgt ggacctgctg ttcaagacca accgcaaggt gaccgtgaag   1800
cagctgaagg aggactactt caagaagatc gagtgcttcg acagcgtgga gatcagcggc   1860
gtggaggacc gcttcaacgc cagcctgggc acctaccacg acctgctgaa gatcatcaag   1920
gacaaggact tcctggacaa cgaggagaac gaggacatcc tggaggacat cgtgctgacc   1980
ctgaccctgt tcgaggaccg cgagatgatc gaggagcgcc tgaagaccta cgcccacctg   2040
ttcgacgaca aggtgatgaa gcagctgaag cgccgccgct acaccggctg gggccgcctg   2100
agccgcaagc ttatcaacgg catccgcgac aagcagagcg gcaagaccat cctggacttc   2160
ctgaagagcg acggcttcgc caaccgcaac ttcatgcagc tgatccacga cgacagcctg   2220
accttcaagg aggacatcca gaaggcccag gtgagcggcc agggcgacag cctgcacgag   2280
cacatcgcca acctggccgg cagccccgcc atcaagaagg gcatcctgca gaccgtgaag   2340
gtggtggacg agctggtgaa ggtgatgggc cgccacaagc ccgagaacat cgtgatcgag   2400
atggcccgcg agaaccagac cacccagaag ggccagaaga acagccgcga gcgcatgaag   2460
cgcatcgagg agggcatcaa ggagctgggc agccagatcc tgaaggagca ccccgtggag   2520
aacacccagc tgcagaacga gaagctgtac ctgtactacc tgcagaacgg ccgcgacatg   2580
tacgtggacc aggagctgga catcaaccgc ctgagcgact acgacgtgga ccacatcgtg   2640
ccccagagct tcctgaagga cgacagcatc gacaacaagg tgctgacccg cagcgacaag   2700
aaccgcggca gagcgacaa cgtgcccagc gaggaggtgg tgaagaagat gaagaactac   2760
tggcgccagc tgctgaacgc caagctgatc acccagcgca gttcgacaa cctgaccaag   2820
gccgagcgcg gcggcctgag cgagctggac aaggccggct tcatcaagcg ccagctggtg   2880
gagacccgcc agatcaccaa gcacgtggcc cagatcctgg acagccgcat gaacaccaag   2940
tacgacgagg acgacaagct gatccgcgag gtgaaggtga tcaccctgaa gagcaagctg   3000
gtgagcgact ccgcaagga cttccagttc tacaaggtgc gcgagatcaa caactaccac   3060
cacgcccacg acgcctacct gaacgccgtg gtgggcaccg ccctgatcaa gaagtacccc   3120
aagctggaga gcgagttcgt gtacggcgac tacaaggtgt acgacgtgcg caagatgatc   3180
gccaagagcg agcaggagat cggcaaggcc accgccaagt acttcttcta cagcaacatc   3240
atgaacttct tcaagaccga gatcaccctg gccaacggcg agatccgcaa gcgcccctg   3300
atcgagacca acggcgagac cggcgagatc gtgtgggaca agggccgcga cttcgccacc   3360
gtgcgcaagg tgctgagcat gccccaggtg aacatcgtga gaagaccga ggtgcagacc   3420
ggcggcttca gcaaggagag catcctgccc aagcgcaaca gcgacaagct gatcgcccgc   3480
aagaaggact gggaccccaa gaagtacggc ggcttcgaca gccccaccgt ggcctacagc   3540
gtgctggtgg tggccaaggt ggagaagggc aagagcaaga gctgaagag cgtgaaggag   3600
ctgctgggca tcaccatcat ggagcgcagc agcttcgaga agaaccccat cgacttcctg   3660
gaggccaagg gctacaagga ggtgaagaag gacctgatca tcaagctgcc caagtacagc   3720
ctgttcgagc tggagaacgg ccgcaagcgc atgctggcca gcgccggcga gctgcagaag   3780
ggcaacagc tggccctgcc cagcaagtac gtgaacttcc tgtacctggc cagccactac   3840
gagaagctga agggcagccc cgaggacaac gagcagaagc agctgttcgt ggagcagcac   3900
aagcactacc tggacgagat catcgagcag atcagcgagt tcagcaaggc cgtgatcctg   3960
gccgacgcca acctggacaa ggtgctgagc gcctacaaca gcacccgcga caagcccatc   4020
cgcgagcagg ccgagaacat catccacctg ttcacccctga ccaacctggg cgcccccgcc   4080
gccttcaagt acttcgacac caccatcgac cgcaagcgct acaccagcac caaggaggtg   4140
ctggacgcca ccctgatcca ccagagcatc accggtctgt acgagacccg catcgacctg   4200
agccagctgg gcggcgacta a                                              4221
```

```
SEQ ID NO: 111          moltype = AA  length = 1406
FEATURE                 Location/Qualifiers
REGION                  1..1406
                        note = Description of Artificial Sequence: Synthetic
                         polypeptide
REGION                  1..1406
                        note = Amino acid sequence of Cas9 (pET-Cas9N3T)
source                  1..1406
                        mol_type = protein
                        organism = synthetic construct
SEQUENCE: 111
MGSSHHHHHH VYPYDVPDYA ELPPKKKRKV GIENLYFQGD KKYSIGLDIG TNSVGWAVIT   60
DEYKVPSKKF KVLGNTDRHS IKKNLIGALL FDSGETAEAT RLKRTARRRY TRRKNRICYL   120
QEIFSNEMAK VDDSFFHRLE ESFLVEEDKK HERHPIFGNI VDEVAYHEKY PTIYHLRKKL   180
VDSTDKADLR LIYLALAHMI KFRGHFLIEG DLNPDNSDVD KLFIQLVQTY NQLFEENPIN   240
ASGVDAKAIL SARLSKSRRL ENLIAQLPGE KKNGLFGNLI ALSLGLTPNF KSNFDLAEDA   300
KLQLSKDTYD DDLDNLLAQI GDQYADLFLA AKNLSDAILL SDILRVNTEI TKAPLSASMI   360
KRYDEHHQDL TLLKALVRQQ LPEKYKEIFF DQSKNGYAGY IDGGASQEEF YKFIKPILEK   420
```

```
MDGTEELLVK LNREDLLRKQ RTFDNGSIPH QIHLGELHAI LRRQEDFYPF LKDNREKIEK   480
ILTFRIPYYV GPLARGNSRF AWMTRKSEET ITPWNFEEVV DKGASAQSFI ERMTNFDKNL   540
PNEKVLPKHS LLYEYFTVYN ELTKVKYVTE GMRKPAFLSG EQKKAIVDLL FKTNRKVTVK   600
QLKEDYFKKI ECFDSVEISG VEDRFNASLG TYHDLLKIIK DKDFLDNEEN EDILEDIVLT   660
LTLFEDREMI EERLKTYAHL FDDKVMKQLK RRRYTGWGRL SRKLINGIRD KQSGKTILDF   720
LKSDGFANRN FMQLIHDDSL TFKEDIQKAQ VSGQGDSLHE HIANLAGSPA IKKGILQTVK   780
VVDELVKVMG RHKPENIVIE MARENQTTQK GQKNSRERMK RIEEGIKELG SQILKEHPVE   840
NTQLQNEKLY LYYLQNGRDM YVDQELDINR LSDYDVDHIV PQSFLKDDSI DNKVLTRSDK   900
NRGKSDNVPS EEVVKKMKNY WRQLLNAKLI TQRKFDNLTK AERGGLSELD KAGFIKRQLV   960
ETRQITKHVA QILDSRMNTK YDENDKLIRE VKVITLKSKL VSDFRKDFQF YKVREINNYH  1020
HAHDAYLNAV VGTALIKKYP KLESEFVYGD YKVYDVRKMI AKSEQEIGKA TAKYFFYSNI  1080
MNFFKTEITL ANGEIRKRPL IETNGETGEI VWDKGRDFAT VRKVLSMPQV NIVKKTEVQT  1140
GGFSKESILP KRNSDKLIAR KKDWDPKKYG GFDSPTVAYS VLVVAKVEKG KSKKLKSVKE  1200
LLGITIMERS SFEKNPIDFL EAKGYKEVKK DLIIKLPKYS LFELENGRKR MLASAGELQK  1260
GNELALPSKY VNFLYLASHY EKLKGSPEDN EQKQLFVEQH KHYLDEIIEQ ISEFSKRVIL  1320
ADANLDKVLS AYNKHRDKPI REQAENIIHL FTLTNLGAPA AFKYFDTTID RKRYTSTKEV  1380
LDATLIHQSI TGLYETRIDL SQLGGD                                      1406

SEQ ID NO: 112          moltype = DNA   length = 34
FEATURE                 Location/Qualifiers
source                  1..34
                        mol_type = unassigned DNA
                        organism = Homo sapiens
SEQUENCE: 112
caatctatga catcaattat tatacatcgg agcc                              34

SEQ ID NO: 113          moltype = RNA   length = 64
FEATURE                 Location/Qualifiers
misc_feature            1..64
                        note = Description of Artificial Sequence: Synthetic
                         oligonucleotide
source                  1..64
                        mol_type = other RNA
                        organism = synthetic construct
SEQUENCE: 113
ggtgacatca attattatac atgttttaga gctagaaata gcaagttaaa ataaggctag   60
tccg                                                               64

SEQ ID NO: 114          moltype = DNA   length = 49
FEATURE                 Location/Qualifiers
misc_feature            1..49
                        note = Description of Artificial Sequence: Synthetic
                         oligonucleotide
source                  1..49
                        mol_type = other DNA
                        organism = synthetic construct
SEQUENCE: 114
caatctatga catcaattat tatacatcgg agccctgcca aaaaatcaa              49

SEQ ID NO: 115          moltype = DNA   length = 50
FEATURE                 Location/Qualifiers
misc_feature            1..50
                        note = Description of Artificial Sequence: Synthetic
                         oligonucleotide
source                  1..50
                        mol_type = other DNA
                        organism = synthetic construct
SEQUENCE: 115
caatctatga catcaattat tataacatcg gagccctgcc aaaaaatcaa             50

SEQ ID NO: 116          moltype = DNA   length = 36
FEATURE                 Location/Qualifiers
misc_feature            1..36
                        note = Description of Artificial Sequence: Synthetic
                         oligonucleotide
source                  1..36
                        mol_type = other DNA
                        organism = synthetic construct
SEQUENCE: 116
caatctatga catcaattat tatgccaaaa aatcaa                            36

SEQ ID NO: 117          moltype = DNA   length = 35
FEATURE                 Location/Qualifiers
misc_feature            1..35
                        note = Description of Artificial Sequence: Synthetic
                         oligonucleotide
source                  1..35
                        mol_type = other DNA
                        organism = synthetic construct
```

```
SEQUENCE: 117
caatctatga catcggagcc ctgccaaaaa atcaa                                    35

SEQ ID NO: 118          moltype = DNA   length = 31
FEATURE                 Location/Qualifiers
misc_feature            1..31
                        note = Description of Artificial Sequence: Synthetic
                         oligonucleotide
source                  1..31
                        mol_type = other DNA
                        organism = synthetic construct
SEQUENCE: 118
caatctatga catgccctgc caaaaaatca a                                        31

SEQ ID NO: 119          moltype = DNA   length = 30
FEATURE                 Location/Qualifiers
misc_feature            1..30
                        note = Description of Artificial Sequence: Synthetic
                         oligonucleotide
source                  1..30
                        mol_type = other DNA
                        organism = synthetic construct
SEQUENCE: 119
caatctatga catcaattat tataaatcaa                                          30

SEQ ID NO: 120          moltype = DNA   length = 25
FEATURE                 Location/Qualifiers
misc_feature            1..25
                        note = Description of Artificial Sequence: Synthetic
                         oligonucleotide
source                  1..25
                        mol_type = other DNA
                        organism = synthetic construct
SEQUENCE: 120
caatctatga catccaaaaa atcaa                                               25

SEQ ID NO: 121          moltype = DNA   length = 19
FEATURE                 Location/Qualifiers
misc_feature            1..19
                        note = Description of Artificial Sequence: Synthetic
                         oligonucleotide
source                  1..19
                        mol_type = other DNA
                        organism = synthetic construct
SEQUENCE: 121
caatctatga caaaatcaa                                                      19

SEQ ID NO: 122          moltype = DNA   length = 46
FEATURE                 Location/Qualifiers
source                  1..46
                        mol_type = unassigned DNA
                        organism = Homo sapiens
SEQUENCE: 122
tatgtgcaat gaccactaca tcctcaaggg cagcaatcgg agccag                        46

SEQ ID NO: 123          moltype = DNA   length = 47
FEATURE                 Location/Qualifiers
misc_feature            1..47
                        note = Description of Artificial Sequence: Synthetic
                         oligonucleotide
source                  1..47
                        mol_type = other DNA
                        organism = synthetic construct
SEQUENCE: 123
tatgtgcaat gaccactaca tccttcaagg gcagcaatcg gagccag                       47

SEQ ID NO: 124          moltype = DNA   length = 48
FEATURE                 Location/Qualifiers
misc_feature            1..48
                        note = Description of Artificial Sequence: Synthetic
                         oligonucleotide
source                  1..48
                        mol_type = other DNA
                        organism = synthetic construct
SEQUENCE: 124
tatgtgcaat gaccactaca tcctctcaag gcagcaatc ggagccag                       48

SEQ ID NO: 125          moltype = DNA   length = 18
FEATURE                 Location/Qualifiers
```

-continued

```
misc_feature          1..18
                      note = Description of Artificial Sequence: Synthetic
                       oligonucleotide
source                1..18
                      mol_type = other DNA
                      organism = synthetic construct
SEQUENCE: 125
tatgtgcaat ggagccag                                            18

SEQ ID NO: 126        moltype = DNA   length = 13
FEATURE               Location/Qualifiers
misc_feature          1..13
                      note = Description of Artificial Sequence: Synthetic
                       oligonucleotide
source                1..13
                      mol_type = other DNA
                      organism = synthetic construct
SEQUENCE: 126
tatgtgcaat gac                                                 13

SEQ ID NO: 127        moltype = DNA   length = 23
FEATURE               Location/Qualifiers
source                1..23
                      mol_type = unassigned DNA
                      organism = Homo sapiens
SEQUENCE: 127
tgacatcaat tattatacat cgg                                      23

SEQ ID NO: 128        moltype = DNA   length = 23
FEATURE               Location/Qualifiers
source                1..23
                      mol_type = unassigned DNA
                      organism = Homo sapiens
SEQUENCE: 128
tgacatcaat tattatagat gga                                      23

SEQ ID NO: 129        moltype = DNA   length = 23
FEATURE               Location/Qualifiers
source                1..23
                      mol_type = unassigned DNA
                      organism = Homo sapiens
SEQUENCE: 129
tgacatcact tattatgcat ggg                                      23

SEQ ID NO: 130        moltype = DNA   length = 23
FEATURE               Location/Qualifiers
source                1..23
                      mol_type = unassigned DNA
                      organism = Homo sapiens
SEQUENCE: 130
tgacataaat tattctacat ggg                                      23

SEQ ID NO: 131        moltype = DNA   length = 23
FEATURE               Location/Qualifiers
source                1..23
                      mol_type = unassigned DNA
                      organism = Homo sapiens
SEQUENCE: 131
tgaaatcaat tatcatagat cgg                                      23

SEQ ID NO: 132        moltype = DNA   length = 23
FEATURE               Location/Qualifiers
source                1..23
                      mol_type = unassigned DNA
                      organism = Homo sapiens
SEQUENCE: 132
ccaggctcca cccgactgga ggg                                      23

SEQ ID NO: 133        moltype = RNA   length = 106
FEATURE               Location/Qualifiers
misc_feature          1..106
                      note = Description of Artificial Sequence: Synthetic
                       polynucleotide
source                1..106
                      mol_type = other RNA
                      organism = synthetic construct
SEQUENCE: 133
ggccaggctc cacccgactg gagttttaga gctagaaata gcaagttaaa ataaggctag  60
tccgttatca acttgaaaaa gtggcaccga gtcggtgctt tttttt             106
```

-continued

```
SEQ ID NO: 134          moltype = DNA   length = 53
FEATURE                 Location/Qualifiers
source                  1..53
                        mol_type = unassigned DNA
                        organism = Homo sapiens
SEQUENCE: 134
acttccaggc tccacccgac tggagggcga accccaaggg gacctcatgc agg       53

SEQ ID NO: 135          moltype = DNA   length = 13
FEATURE                 Location/Qualifiers
misc_feature            1..13
                        note = Description of Artificial Sequence: Synthetic
                        oligonucleotide
source                  1..13
                        mol_type = other DNA
                        organism = synthetic construct
SEQUENCE: 135
acttccaggc tcc                                                    13

SEQ ID NO: 136          moltype = DNA   length = 30
FEATURE                 Location/Qualifiers
misc_feature            1..30
                        note = Description of Artificial Sequence: Synthetic
                        oligonucleotide
source                  1..30
                        mol_type = other DNA
                        organism = synthetic construct
SEQUENCE: 136
acttccaggc tccacccgac ctcatgcagg                                  30

SEQ ID NO: 137          moltype = DNA   length = 36
FEATURE                 Location/Qualifiers
misc_feature            1..36
                        note = Description of Artificial Sequence: Synthetic
                        oligonucleotide
source                  1..36
                        mol_type = other DNA
                        organism = synthetic construct
SEQUENCE: 137
acttccaggc tccaccccaa ggggacctca tgcagg                           36

SEQ ID NO: 138          moltype = DNA   length = 54
FEATURE                 Location/Qualifiers
misc_feature            1..54
                        note = Description of Artificial Sequence: Synthetic
                        oligonucleotide
source                  1..54
                        mol_type = other DNA
                        organism = synthetic construct
SEQUENCE: 138
acttccaggc tccacccgac ttggagggcg aaccccaagg ggacctcatg cagg       54

SEQ ID NO: 139          moltype = DNA   length = 43
FEATURE                 Location/Qualifiers
misc_feature            1..43
                        note = Description of Artificial Sequence: Synthetic
                        oligonucleotide
source                  1..43
                        mol_type = other DNA
                        organism = synthetic construct
SEQUENCE: 139
acttccaggc tccacccgaa ccccaagggg acctcatgca ggg                   43

SEQ ID NO: 140          moltype = DNA   length = 47
FEATURE                 Location/Qualifiers
misc_feature            1..47
                        note = Description of Artificial Sequence: Synthetic
                        oligonucleotide
source                  1..47
                        mol_type = other DNA
                        organism = synthetic construct
SEQUENCE: 140
acttccaggc tccacccgac tcactatctt ctgggctcct ccatgtc               47

SEQ ID NO: 141          moltype = DNA   length = 45
FEATURE                 Location/Qualifiers
misc_feature            1..45
                        note = Description of Artificial Sequence: Synthetic
```

```
                          oligonucleotide
source                    1..45
                          mol_type = other DNA
                          organism = synthetic construct
SEQUENCE: 141
acttccaggc tccacccgac gaaccccaag gggacctcat gcagg                    45

SEQ ID NO: 142            moltype = AA  length = 18
FEATURE                   Location/Qualifiers
source                    1..18
                          mol_type = protein
                          organism = Homo sapiens
SEQUENCE: 142
LPGSTRLEGE PQGDLMQA                                                  18

SEQ ID NO: 143            moltype = DNA  length = 57
FEATURE                   Location/Qualifiers
source                    1..57
                          mol_type = unassigned DNA
                          organism = Homo sapiens
CDS                       2..55
SEQUENCE: 143
acttccaggc tccacccgac tggagggcga accccaaggg gacctcatgc aggctcc      57

SEQ ID NO: 144            moltype = DNA  length = 46
FEATURE                   Location/Qualifiers
misc_feature              1..46
                          note = Description of Artificial Sequence: Synthetic
                          oligonucleotide
source                    1..46
                          mol_type = other DNA
                          organism = synthetic construct
SEQUENCE: 144
acttccaggc tccacccgaa ccccaagggg acctcatgca ggctcc                  46

SEQ ID NO: 145            moltype = DNA  length = 43
FEATURE                   Location/Qualifiers
misc_feature              1..43
                          note = Description of Artificial Sequence: Synthetic
                          oligonucleotide
source                    1..43
                          mol_type = other DNA
                          organism = synthetic construct
SEQUENCE: 145
acttccaggc tccacccgaa ccccaagggg acctcatgca ggc                     43

SEQ ID NO: 146            moltype = DNA  length = 20
FEATURE                   Location/Qualifiers
misc_feature              1..20
                          note = Description of Artificial Sequence: Synthetic
                          oligonucleotide
source                    1..20
                          mol_type = other DNA
                          organism = synthetic construct
SEQUENCE: 146
acttccaggc tccacccgac                                               20

SEQ ID NO: 147            moltype = DNA  length = 40
FEATURE                   Location/Qualifiers
misc_feature              1..40
                          note = Description of Artificial Sequence: Synthetic
                          oligonucleotide
source                    1..40
                          mol_type = other DNA
                          organism = synthetic construct
SEQUENCE: 147
acttccaggc tccaccccaa ggggacctca tgcaggctcc                         40

SEQ ID NO: 148            moltype = DNA  length = 58
FEATURE                   Location/Qualifiers
misc_feature              1..58
                          note = Description of Artificial Sequence: Synthetic
                          oligonucleotide
source                    1..58
                          mol_type = other DNA
                          organism = synthetic construct
SEQUENCE: 148
acttccaggc tccacccgac ttggagggcg aaccccaagg ggacctcatg caggctcc     58
```

```
SEQ ID NO: 149          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 149
acttccaggc tccaggcgaa ccccaagggg acctcatgca ggctcc                    46

SEQ ID NO: 150          moltype = DNA   length = 32
FEATURE                 Location/Qualifiers
misc_feature            1..32
                        note = Description of Artificial Sequence: Synthetic
                        oligonucleotide
source                  1..32
                        mol_type = other DNA
                        organism = synthetic construct
SEQUENCE: 150
ggcgaacccc aagggacct catgcaggct cc                                    32

SEQ ID NO: 151          moltype = DNA   length = 32
FEATURE                 Location/Qualifiers
misc_feature            1..32
                        note = Description of Artificial Sequence: Synthetic
                        oligonucleotide
source                  1..32
                        mol_type = other DNA
                        organism = synthetic construct
SEQUENCE: 151
acttccaggc aagggacct catgcaggct cc                                    32

SEQ ID NO: 152          moltype = DNA   length = 33
FEATURE                 Location/Qualifiers
misc_feature            1..33
                        note = Description of Artificial Sequence: Synthetic
                        oligonucleotide
source                  1..33
                        mol_type = other DNA
                        organism = synthetic construct
SEQUENCE: 152
acttccaggc taaggggacc tcatgcaggc tcc                                  33

SEQ ID NO: 153          moltype = DNA   length = 52
FEATURE                 Location/Qualifiers
source                  1..52
                        mol_type = unassigned DNA
                        organism = Homo sapiens
SEQUENCE: 153
acttccaggc tccacccgac tggagggcga accccaaggg gacctcatgc ag            52

SEQ ID NO: 154          moltype = DNA   length = 34
FEATURE                 Location/Qualifiers
misc_feature            1..34
                        note = Description of Artificial Sequence: Synthetic
                        oligonucleotide
source                  1..34
                        mol_type = other DNA
                        organism = synthetic construct
SEQUENCE: 154
acttccaggc gaaccccaag gggacctcat gcag                                 34

SEQ ID NO: 155          moltype = DNA   length = 32
FEATURE                 Location/Qualifiers
misc_feature            1..32
                        note = Description of Artificial Sequence: Synthetic
                        oligonucleotide
source                  1..32
                        mol_type = other DNA
                        organism = synthetic construct
SEQUENCE: 155
acttccaggc tccacaaggg gacctcatgc ag                                   32

SEQ ID NO: 156          moltype = DNA   length = 34
FEATURE                 Location/Qualifiers
misc_feature            1..34
                        note = Description of Artificial Sequence: Synthetic
                        oligonucleotide
```

-continued

```
source                      1..34
                            mol_type = other DNA
                            organism = synthetic construct
SEQUENCE: 156
acttccaggc tccacccaag gggacctcat gccc                            34

SEQ ID NO: 157              moltype = DNA   length = 35
FEATURE                     Location/Qualifiers
misc_feature                1..35
                            note = Description of Artificial Sequence: Synthetic
                             oligonucleotide
source                      1..35
                            mol_type = other DNA
                            organism = synthetic construct
SEQUENCE: 157
acttccaggc tccaccccaa ggggacctca tgcag                           35

SEQ ID NO: 158              moltype = DNA   length = 41
FEATURE                     Location/Qualifiers
misc_feature                1..41
                            note = Description of Artificial Sequence: Synthetic
                             oligonucleotide
source                      1..41
                            mol_type = other DNA
                            organism = synthetic construct
SEQUENCE: 158
acttccaggc tccacccgaa ccccaagggg acctcatgca g                    41

SEQ ID NO: 159              moltype = DNA   length = 50
FEATURE                     Location/Qualifiers
misc_feature                1..50
                            note = Description of Artificial Sequence: Synthetic
                             oligonucleotide
source                      1..50
                            mol_type = other DNA
                            organism = synthetic construct
SEQUENCE: 159
acttccaggc tccacccgaa ggagggcgaa ccccaagggg acctcatgca          50

SEQ ID NO: 160              moltype = DNA   length = 50
FEATURE                     Location/Qualifiers
misc_feature                1..50
                            note = Description of Artificial Sequence: Synthetic
                             oligonucleotide
source                      1..50
                            mol_type = other DNA
                            organism = synthetic construct
SEQUENCE: 160
acttccaggc tccacccgac tagggcgaac cccaagggga cctcatgcag          50

SEQ ID NO: 161              moltype = DNA   length = 52
FEATURE                     Location/Qualifiers
misc_feature                1..52
                            note = Description of Artificial Sequence: Synthetic
                             oligonucleotide
source                      1..52
                            mol_type = other DNA
                            organism = synthetic construct
SEQUENCE: 161
acttccaggc tccacccgac tgggagggcg aaccccaagg ggacctcatg ca       52

SEQ ID NO: 162              moltype = DNA   length = 52
FEATURE                     Location/Qualifiers
misc_feature                1..52
                            note = Description of Artificial Sequence: Synthetic
                             oligonucleotide
source                      1..52
                            mol_type = other DNA
                            organism = synthetic construct
SEQUENCE: 162
acttccaggc tccacccgac ttggagggcg aaccccaagg ggacctcatg ca       52

SEQ ID NO: 163              moltype = DNA   length = 46
FEATURE                     Location/Qualifiers
misc_feature                1..46
                            note = Description of Artificial Sequence: Synthetic
                             oligonucleotide
source                      1..46
                            mol_type = other DNA
```

-continued

```
                         organism = synthetic construct
SEQUENCE: 163
acttccaggc tccacccgag gcgaacccca aggggacctc atgcag                46

SEQ ID NO: 164          moltype = DNA   length = 47
FEATURE                 Location/Qualifiers
misc_feature            1..47
                        note = Description of Artificial Sequence: Synthetic
                        oligonucleotide
source                  1..47
                        mol_type = other DNA
                        organism = synthetic construct
SEQUENCE: 164
acttccaggc tccacccgag ggcgaacccc aaggggacct catgcag               47

SEQ ID NO: 165          moltype = DNA   length = 24
FEATURE                 Location/Qualifiers
misc_feature            1..24
                        note = Description of Artificial Sequence: Synthetic
                        oligonucleotide
source                  1..24
                        mol_type = other DNA
                        organism = synthetic construct
SEQUENCE: 165
acttccaggc tccacctcat gcag                                        24

SEQ ID NO: 166          moltype = DNA   length = 29
FEATURE                 Location/Qualifiers
misc_feature            1..29
                        note = Description of Artificial Sequence: Synthetic
                        oligonucleotide
source                  1..29
                        mol_type = other DNA
                        organism = synthetic construct
SEQUENCE: 166
agggcgaacc ccaaggggac ctcatgcag                                   29

SEQ ID NO: 167          moltype = DNA   length = 45
FEATURE                 Location/Qualifiers
misc_feature            1..45
                        note = Description of Artificial Sequence: Synthetic
                        oligonucleotide
source                  1..45
                        mol_type = other DNA
                        organism = synthetic construct
SEQUENCE: 167
caatctatga catcaattat tatcggagcc ctgccaaaaa atcaa                 45

SEQ ID NO: 168          moltype = DNA   length = 45
FEATURE                 Location/Qualifiers
misc_feature            1..45
                        note = Description of Artificial Sequence: Synthetic
                        oligonucleotide
source                  1..45
                        mol_type = other DNA
                        organism = synthetic construct
SEQUENCE: 168
caatctatga catcaattat catcggagcc ctgccaaaaa atcaa                 45

SEQ ID NO: 169          moltype = DNA   length = 42
FEATURE                 Location/Qualifiers
misc_feature            1..42
                        note = Description of Artificial Sequence: Synthetic
                        oligonucleotide
source                  1..42
                        mol_type = other DNA
                        organism = synthetic construct
SEQUENCE: 169
caatctatga catcaattat cggagccctg ccaaaaaatc aa                    42

SEQ ID NO: 170          moltype = DNA   length = 48
FEATURE                 Location/Qualifiers
misc_feature            1..48
                        note = Description of Artificial Sequence: Synthetic
                        oligonucleotide
source                  1..48
                        mol_type = other DNA
                        organism = synthetic construct
SEQUENCE: 170
```

```
caatctatga catcaattat tatcatcgga gccctgccaa aaaatcaa              48

SEQ ID NO: 171           moltype = DNA   length = 33
FEATURE                  Location/Qualifiers
misc_feature             1..33
                         note = Description of Artificial Sequence: Synthetic
                          oligonucleotide
source                   1..33
                         mol_type = other DNA
                         organism = synthetic construct
SEQUENCE: 171
caatctatga caagagccct gccaaaaaat caa                             33

SEQ ID NO: 172           moltype = DNA   length = 52
FEATURE                  Location/Qualifiers
source                   1..52
                         mol_type = unassigned DNA
                         organism = Homo sapiens
SEQUENCE: 172
ttctcaaggc agcatcatac ttcccccacg gtgggacagc tgccctccct gg        52

SEQ ID NO: 173           moltype = DNA   length = 46
FEATURE                  Location/Qualifiers
misc_feature             1..46
                         note = Description of Artificial Sequence: Synthetic
                          oligonucleotide
source                   1..46
                         mol_type = other DNA
                         organism = synthetic construct
SEQUENCE: 173
ttctcaaggc agcatcatac ttccctggga cagctgccct ccctgg               46

SEQ ID NO: 174           moltype = DNA   length = 49
FEATURE                  Location/Qualifiers
misc_feature             1..49
                         note = Description of Artificial Sequence: Synthetic
                          oligonucleotide
source                   1..49
                         mol_type = other DNA
                         organism = synthetic construct
SEQUENCE: 174
ttctcaaggc agcatcatac ttccacggtg ggacagctgc cctccctgg            49

SEQ ID NO: 175           moltype = DNA   length = 25
FEATURE                  Location/Qualifiers
misc_feature             1..25
                         note = Description of Artificial Sequence: Synthetic
                          oligonucleotide
source                   1..25
                         mol_type = other DNA
                         organism = synthetic construct
SEQUENCE: 175
ttctcaaggc agctgccctc cctgg                                      25

SEQ ID NO: 176           moltype = DNA   length = 32
FEATURE                  Location/Qualifiers
misc_feature             1..32
                         note = Description of Artificial Sequence: Synthetic
                          oligonucleotide
source                   1..32
                         mol_type = other DNA
                         organism = synthetic construct
SEQUENCE: 176
ttctcaaggc agcatcatac ttccctccct gg                             32

SEQ ID NO: 177           moltype = DNA   length = 264
FEATURE                  Location/Qualifiers
misc_difference          38..227
                         note = modified_base - a, c, t, g, unknown or other
source                   1..264
                         mol_type = unassigned DNA
                         organism = Homo sapiens
SEQUENCE: 177
acaaagcgat tttgaaagat ggaagcgcgg tggctatnnn nnnnnnnnnn nnnnnnnnnn  60
nnnnnnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnnnnnnn  180
nnnnnnnnnn nnnnnnnnnn nnnnnnnnnn nnnnnnnnnn nnnnnnnggg gtgaaactaa  240
actggtccac acggcggaag attg                                      264
```

```
SEQ ID NO: 178          moltype = DNA   length = 257
FEATURE                 Location/Qualifiers
misc_feature            1..257
                        note = Description of Artificial Sequence: Synthetic
                        polynucleotide
misc_difference         38..227
                        note = modified_base - a, c, t, g, unknown or other
source                  1..257
                        mol_type = other DNA
                        organism = synthetic construct
SEQUENCE: 178
acaaagcgat tttgaaagat ggaagcgcgg tggctatnnn nnnnnnnnnn nnnnnnnnnn   60
nnnnnnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnnnnnnn  180
nnnnnnnnnn nnnnnnnnnn nnnnnnnnnn nnnnnnnnnn nnnnnnnggg gtgaaactaa  240
aacacggcgg aagattg                                                 257

SEQ ID NO: 179          moltype = DNA   length = 43
FEATURE                 Location/Qualifiers
misc_feature            1..43
                        note = Description of Artificial Sequence: Synthetic
                        oligonucleotide
source                  1..43
                        mol_type = other DNA
                        organism = synthetic construct
SEQUENCE: 179
acaaagcgat tttgaaagat ggaagcgaca cggcggaaga ttg                     43

SEQ ID NO: 180          moltype = DNA   length = 44
FEATURE                 Location/Qualifiers
misc_feature            1..44
                        note = Description of Artificial Sequence: Synthetic
                        oligonucleotide
source                  1..44
                        mol_type = other DNA
                        organism = synthetic construct
SEQUENCE: 180
acaaagcgat tttgaaagat ggaagcgcac acggcggaag attg                    44

SEQ ID NO: 181          moltype = DNA   length = 106
FEATURE                 Location/Qualifiers
misc_feature            1..106
                        note = Description of Artificial Sequence: Synthetic
                        polynucleotide
source                  1..106
                        mol_type = other DNA
                        organism = synthetic construct
SEQUENCE: 181
acaaagcgat tttgaaagat ggaagcgaaa tagcaagtta aaataaggct agtccgttat   60
caacttgaaa aagtggcacc gagtcggtgc acacggcgga agattg                 106

SEQ ID NO: 182          moltype = DNA   length = 23
FEATURE                 Location/Qualifiers
misc_feature            1..23
                        note = Description of Artificial Sequence: Synthetic
                        oligonucleotide
source                  1..23
                        mol_type = other DNA
                        organism = synthetic construct
SEQUENCE: 182
gggtgggggg agtttgctcc tgg                                           23

SEQ ID NO: 183          moltype = DNA   length = 23
FEATURE                 Location/Qualifiers
misc_feature            1..23
                        note = Description of Artificial Sequence: Synthetic
                        oligonucleotide
source                  1..23
                        mol_type = other DNA
                        organism = synthetic construct
SEQUENCE: 183
ggatggaggg agtttgctcc tgg                                           23

SEQ ID NO: 184          moltype = DNA   length = 23
FEATURE                 Location/Qualifiers
misc_feature            1..23
                        note = Description of Artificial Sequence: Synthetic
                        oligonucleotide
source                  1..23
```

```
                            mol_type = other DNA
                            organism = synthetic construct
SEQUENCE: 184
ggggaggggga agtttgctcc tgg                                                 23

SEQ ID NO: 185          moltype = DNA   length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 185
gacccctcc accccgcctc cgg                                                   23

SEQ ID NO: 186          moltype = DNA   length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 186
gaccccccc accccgcccc cgg                                                   23

SEQ ID NO: 187          moltype = DNA   length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 187
gccccacccc accccgcctc tgg                                                  23

SEQ ID NO: 188          moltype = DNA   length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 188
ctccccacccc accccgcctc agg                                                 23

SEQ ID NO: 189          moltype = DNA   length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 189
ggtgagtgag tgtgtgcgtg tgg                                                  23

SEQ ID NO: 190          moltype = DNA   length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 190
tgtgggtgag tgtgtgcgtg agg                                                  23

SEQ ID NO: 191          moltype = DNA   length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
```

-continued

```
SEQUENCE: 191
gagtccgagc agaagaagaa ggg                                            23

SEQ ID NO: 192              moltype = DNA   length = 23
FEATURE                     Location/Qualifiers
misc_feature                1..23
                            note = Description of Artificial Sequence: Synthetic
                             oligonucleotide
source                      1..23
                            mol_type = other DNA
                            organism = synthetic construct
SEQUENCE: 192
gagttagagc agaagaagaa agg                                            23

SEQ ID NO: 193              moltype = DNA   length = 23
FEATURE                     Location/Qualifiers
misc_feature                1..23
                            note = Description of Artificial Sequence: Synthetic
                             oligonucleotide
source                      1..23
                            mol_type = other DNA
                            organism = synthetic construct
SEQUENCE: 193
gaacctgagc tgctctgacg cgg                                            23

SEQ ID NO: 194              moltype = DNA   length = 23
FEATURE                     Location/Qualifiers
misc_feature                1..23
                            note = Description of Artificial Sequence: Synthetic
                             oligonucleotide
source                      1..23
                            mol_type = other DNA
                            organism = synthetic construct
SEQUENCE: 194
ttggcagggg gtgggaggga agg                                            23

SEQ ID NO: 195              moltype = DNA   length = 23
FEATURE                     Location/Qualifiers
misc_feature                1..23
                            note = Description of Artificial Sequence: Synthetic
                             oligonucleotide
source                      1..23
                            mol_type = other DNA
                            organism = synthetic construct
SEQUENCE: 195
gggagggaga gcttggcagg ggg                                            23

SEQ ID NO: 196              moltype = DNA   length = 23
FEATURE                     Location/Qualifiers
misc_feature                1..23
                            note = Description of Artificial Sequence: Synthetic
                             oligonucleotide
source                      1..23
                            mol_type = other DNA
                            organism = synthetic construct
SEQUENCE: 196
gatggagcca gagaggatcc tgg                                            23

SEQ ID NO: 197              moltype = DNA   length = 23
FEATURE                     Location/Qualifiers
misc_feature                1..23
                            note = Description of Artificial Sequence: Synthetic
                             oligonucleotide
source                      1..23
                            mol_type = other DNA
                            organism = synthetic construct
SEQUENCE: 197
cctgccaagc tctccctccc agg                                            23

SEQ ID NO: 198              moltype = DNA   length = 23
FEATURE                     Location/Qualifiers
misc_feature                1..23
                            note = Description of Artificial Sequence: Synthetic
                             oligonucleotide
source                      1..23
                            mol_type = other DNA
                            organism = synthetic construct
SEQUENCE: 198
ctccctccca ggatcctctc tgg                                            23
```

```
SEQ ID NO: 199            moltype = DNA   length = 23
FEATURE                   Location/Qualifiers
misc_feature              1..23
                          note = Description of Artificial Sequence: Synthetic
                          oligonucleotide
source                    1..23
                          mol_type = other DNA
                          organism = synthetic construct
SEQUENCE: 199
cctctaaggt ttgcttacga tgg                                               23

SEQ ID NO: 200            moltype = DNA   length = 23
FEATURE                   Location/Qualifiers
misc_feature              1..23
                          note = Description of Artificial Sequence: Synthetic
                          oligonucleotide
source                    1..23
                          mol_type = other DNA
                          organism = synthetic construct
SEQUENCE: 200
ggttctggca aggagagaga tgg                                               23

SEQ ID NO: 201            moltype = DNA   length = 23
FEATURE                   Location/Qualifiers
misc_feature              1..23
                          note = Description of Artificial Sequence: Synthetic
                          oligonucleotide
source                    1..23
                          mol_type = other DNA
                          organism = synthetic construct
SEQUENCE: 201
tctaacccccc acctcctgtt agg                                              23

SEQ ID NO: 202            moltype = DNA   length = 23
FEATURE                   Location/Qualifiers
misc_feature              1..23
                          note = Description of Artificial Sequence: Synthetic
                          oligonucleotide
source                    1..23
                          mol_type = other DNA
                          organism = synthetic construct
SEQUENCE: 202
ttggcagggg gtgggaggga tgg                                               23

SEQ ID NO: 203            moltype = DNA   length = 23
FEATURE                   Location/Qualifiers
misc_feature              1..23
                          note = Description of Artificial Sequence: Synthetic
                          oligonucleotide
source                    1..23
                          mol_type = other DNA
                          organism = synthetic construct
SEQUENCE: 203
ttggtagggg gtgggaggga tgg                                               23

SEQ ID NO: 204            moltype = DNA   length = 23
FEATURE                   Location/Qualifiers
misc_feature              1..23
                          note = Description of Artificial Sequence: Synthetic
                          oligonucleotide
source                    1..23
                          mol_type = other DNA
                          organism = synthetic construct
SEQUENCE: 204
gggaagggga gcttggcagg tgg                                               23

SEQ ID NO: 205            moltype = DNA   length = 23
FEATURE                   Location/Qualifiers
misc_feature              1..23
                          note = Description of Artificial Sequence: Synthetic
                          oligonucleotide
source                    1..23
                          mol_type = other DNA
                          organism = synthetic construct
SEQUENCE: 205
ggtagtgaga gcttggcagg tgg                                               23

SEQ ID NO: 206            moltype = DNA   length = 23
```

-continued

```
FEATURE             Location/Qualifiers
misc_feature        1..23
                    note = Description of Artificial Sequence: Synthetic
                     oligonucleotide
source              1..23
                    mol_type = other DNA
                    organism = synthetic construct
SEQUENCE: 206
ctccctccca ggatcctccc agg                                         23

SEQ ID NO: 207      moltype = DNA   length = 23
FEATURE             Location/Qualifiers
misc_feature        1..23
                    note = Description of Artificial Sequence: Synthetic
                     oligonucleotide
source              1..23
                    mol_type = other DNA
                    organism = synthetic construct
SEQUENCE: 207
gtccatggca ggatcctctc agg                                         23

SEQ ID NO: 208      moltype = DNA   length = 23
FEATURE             Location/Qualifiers
misc_feature        1..23
                    note = Description of Artificial Sequence: Synthetic
                     oligonucleotide
source              1..23
                    mol_type = other DNA
                    organism = synthetic construct
SEQUENCE: 208
ctcccccccca gtatcctctc agg                                        23

SEQ ID NO: 209      moltype = DNA   length = 108
FEATURE             Location/Qualifiers
source              1..108
                    mol_type = unassigned DNA
                    organism = Homo sapiens
SEQUENCE: 209
ccaatctatg acatcaatta ttatacatcg gagccctgcc aaaaaatcaa tgtgaagcaa  60
atcgcagccc gcctcctgcc tccgctctac tcactggtgt tcatcttt             108

SEQ ID NO: 210      moltype = DNA   length = 138
FEATURE             Location/Qualifiers
source              1..138
                    mol_type = unassigned DNA
                    organism = Homo sapiens
SEQUENCE: 210
ccaccctata attctgaacc tgcagaagaa tctgaacata aaaacaacaa ttacgaacca  60
aacctattta aaactccaca aaggaaacca tcttataatc agctggcttc aactccaata 120
atattcaaag agcaaggg                                              138

SEQ ID NO: 211      moltype = DNA   length = 49
FEATURE             Location/Qualifiers
source              1..49
                    mol_type = unassigned DNA
                    organism = Homo sapiens
SEQUENCE: 211
ggccgggaat caagagtcac ccagagacag tgaccaacca tccctgttt             49

SEQ ID NO: 212      moltype = DNA   length = 77
FEATURE             Location/Qualifiers
misc_feature        1..77
                    note = Description of Artificial Sequence: Synthetic
                     oligonucleotide
source              1..77
                    mol_type = other DNA
                    organism = synthetic construct
SEQUENCE: 212
ggccgggaat caagagtcac ccagtgacca accatccctg taagcaaacc ttagaggttc  60
tggcaaggag agagatg                                                77

SEQ ID NO: 213      moltype = DNA   length = 27
FEATURE             Location/Qualifiers
misc_feature        1..27
                    note = Description of Artificial Sequence: Synthetic
                     oligonucleotide
source              1..27
                    mol_type = other DNA
                    organism = synthetic construct
```

-continued

```
SEQUENCE: 213
ggccgggaat caagagtcac ccaggaa                                    27

SEQ ID NO: 214           moltype = DNA  length = 79
FEATURE                  Location/Qualifiers
misc_feature             1..79
                         note = Description of Artificial Sequence: Synthetic
                         oligonucleotide
source                   1..79
                         mol_type = other DNA
                         organism = synthetic construct
SEQUENCE: 214
ggccgggaat caagagtcac ccagacctct ctggctccat cgtaagcaaa ccttagaggt  60
tctggcaagg agagagatg                                             79

SEQ ID NO: 215           moltype = DNA  length = 28
FEATURE                  Location/Qualifiers
misc_feature             1..28
                         note = Description of Artificial Sequence: Synthetic
                         oligonucleotide
source                   1..28
                         mol_type = other DNA
                         organism = synthetic construct
SEQUENCE: 215
ggccgggaat caagagtcac cctaacag                                   28

SEQ ID NO: 216           moltype = DNA  length = 66
FEATURE                  Location/Qualifiers
misc_feature             1..66
                         note = Description of Artificial Sequence: Synthetic
                         oligonucleotide
source                   1..66
                         mol_type = other DNA
                         organism = synthetic construct
SEQUENCE: 216
ggccgggaat caagacgctg gctccatcgt aagcaaacct tagaggttct ggcaaggaga  60
gagatg                                                           66

SEQ ID NO: 217           moltype = DNA  length = 47
FEATURE                  Location/Qualifiers
misc_feature             1..47
                         note = Description of Artificial Sequence: Synthetic
                         oligonucleotide
source                   1..47
                         mol_type = other DNA
                         organism = synthetic construct
SEQUENCE: 217
ggctccatcg taagcaaacc ttagaggttc tggcaaggag agagatg               47

SEQ ID NO: 218           moltype = DNA  length = 78
FEATURE                  Location/Qualifiers
misc_feature             1..78
                         note = Description of Artificial Sequence: Synthetic
                         oligonucleotide
source                   1..78
                         mol_type = other DNA
                         organism = synthetic construct
SEQUENCE: 218
ggccgggaat caagagtcac ccagactctc tggctccatc gtaagcaaac cttagaggtt  60
ctggcaagga gagagatg                                              78

SEQ ID NO: 219           moltype = DNA  length = 80
FEATURE                  Location/Qualifiers
misc_feature             1..80
                         note = Description of Artificial Sequence: Synthetic
                         oligonucleotide
source                   1..80
                         mol_type = other DNA
                         organism = synthetic construct
SEQUENCE: 219
ggccgggaat caagagtcac ccagagacag tgaccaacca tcgtaagcaa accttagagg  60
ttctggcaag gagagagatg                                            80

SEQ ID NO: 220           moltype = DNA  length = 46
FEATURE                  Location/Qualifiers
misc_feature             1..46
                         note = Description of Artificial Sequence: Synthetic
                         oligonucleotide
source                   1..46
```

```
                          mol_type = other DNA
                          organism = synthetic construct
SEQUENCE: 220
ggtccatcgt aagcaaacct tagaggttct ggcaaggaga gagatg                 46

SEQ ID NO: 221            moltype = DNA   length = 69
FEATURE                   Location/Qualifiers
misc_feature              1..69
                          note = Description of Artificial Sequence: Synthetic
                           oligonucleotide
source                    1..69
                          mol_type = other DNA
                          organism = synthetic construct
SEQUENCE: 221
ggccgggaat caagagtcac ccatctccat cgtaagcaaa ccttagaggt tctggcaagg   60
agagagatg                                                          69

SEQ ID NO: 222            moltype = DNA   length = 76
FEATURE                   Location/Qualifiers
misc_feature              1..76
                          note = Description of Artificial Sequence: Synthetic
                           oligonucleotide
source                    1..76
                          mol_type = other DNA
                          organism = synthetic construct
SEQUENCE: 222
ggccgggaat caagagtcac ccagactctg gctccatcgt aagcaaacct tagaggttct   60
ggcaaggaga gagatg                                                  76

SEQ ID NO: 223            moltype = DNA   length = 50
FEATURE                   Location/Qualifiers
misc_feature              1..50
                          note = Description of Artificial Sequence: Synthetic
                           oligonucleotide
source                    1..50
                          mol_type = other DNA
                          organism = synthetic construct
SEQUENCE: 223
ggccgggaat caagagtcac ccagagacag tgaccaacca tcccatatca              50

SEQ ID NO: 224            moltype = DNA   length = 59
FEATURE                   Location/Qualifiers
misc_feature              1..59
                          note = Description of Artificial Sequence: Synthetic
                           oligonucleotide
source                    1..59
                          mol_type = other DNA
                          organism = synthetic construct
SEQUENCE: 224
ggccgggaat caagagtcat cgtaagcaaa ccttagaggt tctggcaagg agagagatg    59

SEQ ID NO: 225            moltype = DNA   length = 24
FEATURE                   Location/Qualifiers
misc_feature              1..24
                          note = Description of Artificial Sequence: Synthetic
                           oligonucleotide
source                    1..24
                          mol_type = other DNA
                          organism = synthetic construct
SEQUENCE: 225
aatgaccact acatccttca aggg                                         24

SEQ ID NO: 226            moltype = DNA   length = 25
FEATURE                   Location/Qualifiers
misc_feature              1..25
                          note = Description of Artificial Sequence: Synthetic
                           oligonucleotide
source                    1..25
                          mol_type = other DNA
                          organism = synthetic construct
SEQUENCE: 226
aatgaccact acatcctttc aaggg                                        25

SEQ ID NO: 227            moltype = DNA   length = 26
FEATURE                   Location/Qualifiers
misc_feature              1..26
                          note = Description of Artificial Sequence: Synthetic
                           oligonucleotide
source                    1..26
```

-continued

```
                          mol_type = other DNA
                          organism = synthetic construct
SEQUENCE: 227
aatgaccact acatcctttt caaggg                                  26

SEQ ID NO: 228          moltype = DNA   length = 22
FEATURE                 Location/Qualifiers
misc_feature            1..22
                          note = Description of Artificial Sequence: Synthetic
                           oligonucleotide
source                  1..22
                          mol_type = other DNA
                          organism = synthetic construct
SEQUENCE: 228
aatgaccact acatcctaag gg                                      22

SEQ ID NO: 229          moltype = DNA   length = 21
FEATURE                 Location/Qualifiers
misc_feature            1..21
                          note = Description of Artificial Sequence: Synthetic
                           oligonucleotide
source                  1..21
                          mol_type = other DNA
                          organism = synthetic construct
SEQUENCE: 229
aatgaccact acatcctagg g                                       21

SEQ ID NO: 230          moltype = DNA   length = 20
FEATURE                 Location/Qualifiers
misc_feature            1..20
                          note = Description of Artificial Sequence: Synthetic
                           oligonucleotide
source                  1..20
                          mol_type = other DNA
                          organism = synthetic construct
SEQUENCE: 230
aatgaccact acatcctggg                                         20

SEQ ID NO: 231          moltype = DNA   length = 42
FEATURE                 Location/Qualifiers
source                  1..42
                          mol_type = unassigned DNA
                          organism = Homo sapiens
SEQUENCE: 231
tatgtgcaat gaccactaca tcctcaaggg cagcaatcgg ag                42

SEQ ID NO: 232          moltype = DNA   length = 45
FEATURE                 Location/Qualifiers
misc_feature            1..45
                          note = Description of Artificial Sequence: Synthetic
                           oligonucleotide
source                  1..45
                          mol_type = other DNA
                          organism = synthetic construct
SEQUENCE: 232
tatgtgcaat gaccactaca tcctcctcaa gggcagcaat cggag             45

SEQ ID NO: 233          moltype = DNA   length = 30
FEATURE                 Location/Qualifiers
misc_feature            1..30
                          note = Description of Artificial Sequence: Synthetic
                           oligonucleotide
source                  1..30
                          mol_type = other DNA
                          organism = synthetic construct
SEQUENCE: 233
tatgtgcaat gaccactaca tcaatcggag                              30

SEQ ID NO: 234          moltype = DNA   length = 33
FEATURE                 Location/Qualifiers
misc_feature            1..33
                          note = Description of Artificial Sequence: Synthetic
                           oligonucleotide
source                  1..33
                          mol_type = other DNA
                          organism = synthetic construct
SEQUENCE: 234
tatgtgcaat gaccactaca tcagcaatcg gag                          33
```

-continued

```
SEQ ID NO: 235          moltype = DNA   length = 34
FEATURE                 Location/Qualifiers
misc_feature            1..34
                        note = Description of Artificial Sequence: Synthetic
                        oligonucleotide
source                  1..34
                        mol_type = other DNA
                        organism = synthetic construct
SEQUENCE: 235
tatgtgcaat gaccactaca tccagcaatc ggag                                  34

SEQ ID NO: 236          moltype = DNA   length = 10
FEATURE                 Location/Qualifiers
misc_feature            1..10
                        note = Description of Artificial Sequence: Synthetic
                        oligonucleotide
source                  1..10
                        mol_type = other DNA
                        organism = synthetic construct
SEQUENCE: 236
cagcaatcgg                                                             10

SEQ ID NO: 237          moltype = DNA   length = 41
FEATURE                 Location/Qualifiers
misc_feature            1..41
                        note = Description of Artificial Sequence: Synthetic
                        oligonucleotide
source                  1..41
                        mol_type = other DNA
                        organism = synthetic construct
SEQUENCE: 237
tatgtgcaat gaccactaca tccttcaagg gcagcaatcg g                          41

SEQ ID NO: 238          moltype = DNA   length = 41
FEATURE                 Location/Qualifiers
misc_feature            1..41
                        note = Description of Artificial Sequence: Synthetic
                        oligonucleotide
source                  1..41
                        mol_type = other DNA
                        organism = synthetic construct
SEQUENCE: 238
tatgtgcaat gaccactaca tcctccaagg gcagcaatcg g                          41

SEQ ID NO: 239          moltype = DNA   length = 41
FEATURE                 Location/Qualifiers
misc_feature            1..41
                        note = Description of Artificial Sequence: Synthetic
                        oligonucleotide
source                  1..41
                        mol_type = other DNA
                        organism = synthetic construct
SEQUENCE: 239
tatgtgcaat gaccactaca tcctbcaagg gcagcaatcg g                          41

SEQ ID NO: 240          moltype = DNA   length = 34
FEATURE                 Location/Qualifiers
misc_feature            1..34
                        note = Description of Artificial Sequence: Synthetic
                        oligonucleotide
source                  1..34
                        mol_type = other DNA
                        organism = synthetic construct
SEQUENCE: 240
tatgtgcaat gaccactaca ttggcagcaa tcgg                                  34

SEQ ID NO: 241          moltype = DNA   length = 21
FEATURE                 Location/Qualifiers
misc_feature            1..21
                        note = Description of Artificial Sequence: Synthetic
                        oligonucleotide
source                  1..21
                        mol_type = other DNA
                        organism = synthetic construct
SEQUENCE: 241
tatgtgcaat gaccactaca t                                                21

SEQ ID NO: 242          moltype = DNA   length = 53
FEATURE                 Location/Qualifiers
```

```
source                   1..53
                         mol_type = unassigned DNA
                         organism = Homo sapiens
SEQUENCE: 242
tcatacagat gatgtctcat catcagagga gcgagaaggt aaagtcaaaa tca          53

SEQ ID NO: 243           moltype = DNA   length = 32
FEATURE                  Location/Qualifiers
misc_feature             1..32
                         note = Description of Artificial Sequence: Synthetic
                          oligonucleotide
source                   1..32
                         mol_type = other DNA
                         organism = synthetic construct
SEQUENCE: 243
tcatacagat gatacaggta aagtcaaaat ca                                  32

SEQ ID NO: 244           moltype = DNA   length = 32
FEATURE                  Location/Qualifiers
misc_feature             1..32
                         note = Description of Artificial Sequence: Synthetic
                          oligonucleotide
source                   1..32
                         mol_type = other DNA
                         organism = synthetic construct
SEQUENCE: 244
tcatacaggt gatgaaggta aagtcaaaat ca                                  32

SEQ ID NO: 245           moltype = DNA   length = 50
FEATURE                  Location/Qualifiers
misc_feature             1..50
                         note = Description of Artificial Sequence: Synthetic
                          oligonucleotide
source                   1..50
                         mol_type = other DNA
                         organism = synthetic construct
SEQUENCE: 245
tcatacagat gatgtctcat catcagagcg agaaggtaaa gtcaaaatca               50

SEQ ID NO: 246           moltype = DNA   length = 48
FEATURE                  Location/Qualifiers
misc_feature             1..48
                         note = Description of Artificial Sequence: Synthetic
                          oligonucleotide
source                   1..48
                         mol_type = other DNA
                         organism = synthetic construct
SEQUENCE: 246
tcatacagat gatgtctcat catcagcgag aaggtaaagt caaaatca                 48

SEQ ID NO: 247           moltype = DNA   length = 52
FEATURE                  Location/Qualifiers
misc_feature             1..52
                         note = Description of Artificial Sequence: Synthetic
                          oligonucleotide
source                   1..52
                         mol_type = other DNA
                         organism = synthetic construct
SEQUENCE: 247
tcatacagat gatgtctcat catcagggag cgagaaggta aagtcaaaat ca            52

SEQ ID NO: 248           moltype = DNA   length = 41
FEATURE                  Location/Qualifiers
misc_feature             1..41
                         note = Description of Artificial Sequence: Synthetic
                          oligonucleotide
source                   1..41
                         mol_type = other DNA
                         organism = synthetic construct
SEQUENCE: 248
tcatacagat gatgtctcgc gagaaggtaa agtcaaaatc a                        41

SEQ ID NO: 249           moltype = DNA   length = 32
FEATURE                  Location/Qualifiers
misc_feature             1..32
                         note = Description of Artificial Sequence: Synthetic
                          oligonucleotide
source                   1..32
                         mol_type = other DNA
```

-continued

```
                        organism = synthetic construct
SEQUENCE: 249
tcatacagat gatgaaggta aagtcaaaat ca                              32

SEQ ID NO: 250          moltype = DNA  length = 29
FEATURE                 Location/Qualifiers
misc_feature            1..29
                        note = Description of Artificial Sequence: Synthetic
                        oligonucleotide
source                  1..29
                        mol_type = other DNA
                        organism = synthetic construct
SEQUENCE: 250
tcatacagat gaaggtaaag tcaaaatca                                  29

SEQ ID NO: 251          moltype = DNA  length = 42
FEATURE                 Location/Qualifiers
misc_feature            1..42
                        note = Description of Artificial Sequence: Synthetic
                        oligonucleotide
source                  1..42
                        mol_type = other DNA
                        organism = synthetic construct
SEQUENCE: 251
tcatacagat gatgtctaca gatgaaggta aagtcaaaat ca                   42

SEQ ID NO: 252          moltype = DNA  length = 51
FEATURE                 Location/Qualifiers
misc_feature            1..51
                        note = Description of Artificial Sequence: Synthetic
                        oligonucleotide
source                  1..51
                        mol_type = other DNA
                        organism = synthetic construct
SEQUENCE: 252
tcatacagat gatgtctcat catcaggagc gagaaggtaa agtcaaaatc a         51

SEQ ID NO: 253          moltype = DNA  length = 34
FEATURE                 Location/Qualifiers
misc_feature            1..34
                        note = Description of Artificial Sequence: Synthetic
                        oligonucleotide
source                  1..34
                        mol_type = other DNA
                        organism = synthetic construct
SEQUENCE: 253
gtcatcctca tcctgataaa ctgcaaaagg ctga                            34

SEQ ID NO: 254          moltype = DNA  length = 606
FEATURE                 Location/Qualifiers
source                  1..606
                        mol_type = unassigned DNA
                        organism = Homo sapiens
SEQUENCE: 254
gctggtgtct gggttctgtg ccccttcccc accccagccc accccaggtg tcctgtccat  60
tctcaggctg gtcacatggg tggtcctagg gtgtcccatg agagatgcaa agcgcctgaa  120
ttttctgact cttcccatca gaccccccaa agacacatgt gacccaccac cccatctctg  180
accatgaggc caccctgagg tgctgggccc tgggcttcta ccctgcggag atcacactga  240
cctggcagcg ggatggcgag gaccaaactc aggacaccga gcttgtggag accagaccag  300
caggagatag aaccttccag aagtgggcag ctgtggtggt gccttctgga gaagagcaga  360
gatacacatg ccatgtacag catgaggggc tgccgaagcc cctcaccctg agatggggta  420
aggaggggga tgaggggtca tatctgttca tatctgttct cagggaaagc aggagccctt  480
ctggagccct tcagcagggt cagggcccct catcttcccc tcctttccca gagccatctt  540
cccagtccac catcccccatc gtgggcattg ttgctggcct ggctgtccta gcagttgtgg  600
tcatcg                                                           606

SEQ ID NO: 255          moltype = DNA  length = 26
FEATURE                 Location/Qualifiers
source                  1..26
                        mol_type = unassigned DNA
                        organism = Homo sapiens
SEQUENCE: 255
actaccacag ctccttctct gagtgg                                     26

SEQ ID NO: 256          moltype = DNA  length = 23
FEATURE                 Location/Qualifiers
misc_feature            1..23
                        note = Description of Artificial Sequence: Synthetic
                        oligonucleotide
```

-continued

```
source              1..23
                    mol_type = other DNA
                    organism = synthetic construct
SEQUENCE: 256
actaccacag ctcctctgag tgg                                        23

SEQ ID NO: 257      moltype = DNA   length = 23
FEATURE             Location/Qualifiers
source              1..23
                    mol_type = unassigned DNA
                    organism = Homo sapiens
SEQUENCE: 257
gtagttggag ctggcggcgt agg                                        23

SEQ ID NO: 258      moltype = DNA   length = 23
FEATURE             Location/Qualifiers
misc_feature        1..23
                    note = Description of Artificial Sequence: Synthetic
                     oligonucleotide
source              1..23
                    mol_type = other DNA
                    organism = synthetic construct
SEQUENCE: 258
gtagttggag ctagcggcgt agg                                        23

SEQ ID NO: 259      moltype = DNA   length = 23
FEATURE             Location/Qualifiers
source              1..23
                    mol_type = unassigned DNA
                    organism = Homo sapiens
SEQUENCE: 259
gtagttggag ctggtggcgt agg                                        23

SEQ ID NO: 260      moltype = DNA   length = 23
FEATURE             Location/Qualifiers
misc_feature        1..23
                    note = Description of Artificial Sequence: Synthetic
                     oligonucleotide
source              1..23
                    mol_type = other DNA
                    organism = synthetic construct
SEQUENCE: 260
gtagttggag ctagtggcgt agg                                        23

SEQ ID NO: 261      moltype = DNA   length = 28
FEATURE             Location/Qualifiers
misc_feature        1..28
                    note = Description of Artificial Sequence: Synthetic
                     oligonucleotide
source              1..28
                    mol_type = other DNA
                    organism = synthetic construct
SEQUENCE: 261
ccatacatta aagatagtca tcttgggg                                   28

SEQ ID NO: 262      moltype = DNA   length = 60
FEATURE             Location/Qualifiers
source              1..60
                    mol_type = unassigned DNA
                    organism = Homo sapiens
SEQUENCE: 262
ccatacagtc agtatcaatt ctggaagaat ttccagacat taaagatagt catcttgggg  60

SEQ ID NO: 263      moltype = DNA   length = 55
FEATURE             Location/Qualifiers
source              1..55
                    mol_type = unassigned DNA
                    organism = Homo sapiens
SEQUENCE: 263
ccatacagtc agtatcaatt ctggaagaat ttccagacat taaagatagt catct        55

SEQ ID NO: 264      moltype = DNA   length = 23
FEATURE             Location/Qualifiers
misc_feature        1..23
                    note = Description of Artificial Sequence: Synthetic
                     oligonucleotide
source              1..23
                    mol_type = other DNA
                    organism = synthetic construct
```

-continued

```
SEQUENCE: 264
ccatacatta aagatagtca tct                                          23

SEQ ID NO: 265           moltype = DNA   length = 23
FEATURE                  Location/Qualifiers
source                   1..23
                         mol_type = unassigned DNA
                         organism = Homo sapiens
SEQUENCE: 265
agatgactat ctttaatgtc tgg                                          23

SEQ ID NO: 266           moltype = DNA   length = 23
FEATURE                  Location/Qualifiers
source                   1..23
                         mol_type = unassigned DNA
                         organism = Homo sapiens
SEQUENCE: 266
agatgactat ctttaatgta tgg                                          23

SEQ ID NO: 267           moltype = DNA   length = 23
FEATURE                  Location/Qualifiers
misc_feature             1..23
                         note = Description of Artificial Sequence: Synthetic
                          oligonucleotide
source                   1..23
                         mol_type = other DNA
                         organism = synthetic construct
SEQUENCE: 267
gtagttggag ctgatggcgt agg                                          23

SEQ ID NO: 268           moltype = DNA   length = 23
FEATURE                  Location/Qualifiers
misc_feature             1..23
                         note = Description of Artificial Sequence: Synthetic
                          oligonucleotide
source                   1..23
                         mol_type = other DNA
                         organism = synthetic construct
SEQUENCE: 268
gtagttggag ctggtagcgt agg                                          23

SEQ ID NO: 269           moltype = DNA   length = 23
FEATURE                  Location/Qualifiers
misc_feature             1..23
                         note = Description of Artificial Sequence: Synthetic
                          oligonucleotide
source                   1..23
                         mol_type = other DNA
                         organism = synthetic construct
SEQUENCE: 269
gtagttggag ctggtgacgt agg                                          23

SEQ ID NO: 270           moltype = DNA   length = 23
FEATURE                  Location/Qualifiers
misc_feature             1..23
                         note = Description of Artificial Sequence: Synthetic
                          oligonucleotide
source                   1..23
                         mol_type = other DNA
                         organism = synthetic construct
SEQUENCE: 270
gtagttggag ctaatggcgt agg                                          23

SEQ ID NO: 271           moltype = DNA   length = 23
FEATURE                  Location/Qualifiers
misc_feature             1..23
                         note = Description of Artificial Sequence: Synthetic
                          oligonucleotide
source                   1..23
                         mol_type = other DNA
                         organism = synthetic construct
SEQUENCE: 271
gtagttggag ctagtagcgt agg                                          23

SEQ ID NO: 272           moltype = DNA   length = 23
FEATURE                  Location/Qualifiers
misc_feature             1..23
                         note = Description of Artificial Sequence: Synthetic
                          oligonucleotide
```

-continued

```
source                 1..23
                       mol_type = other DNA
                       organism = synthetic construct
SEQUENCE: 272
gtagttggag ctagtgacgt agg                                            23

SEQ ID NO: 273         moltype = DNA   length = 23
FEATURE                Location/Qualifiers
source                 1..23
                       mol_type = unassigned DNA
                       organism = Homo sapiens
SEQUENCE: 273
caaatgaatg atgcacatca tgg                                            23

SEQ ID NO: 274         moltype = DNA   length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 274
caaatgaatg atgcacgtca tgg                                            23

SEQ ID NO: 275         moltype = DNA   length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 275
caaatgaatg atgcatatca tgg                                            23

SEQ ID NO: 276         moltype = DNA   length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 276
caaatgaatg atgcgcatca tgg                                            23

SEQ ID NO: 277         moltype = DNA   length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 277
caaatgaatg atgtacatca tgg                                            23

SEQ ID NO: 278         moltype = DNA   length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 278
caaatgaatg gtgcacatca tgg                                            23

SEQ ID NO: 279         moltype = DNA   length = 23
FEATURE                Location/Qualifiers
misc_feature           1..23
                       note = Description of Artificial Sequence: Synthetic
                        oligonucleotide
source                 1..23
                       mol_type = other DNA
                       organism = synthetic construct
SEQUENCE: 279
caaatgagtg atgcacatca tgg                                            23
```

-continued

```
SEQ ID NO: 280          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 280
caaaagaatg atgcacatca tgg                                                   23

SEQ ID NO: 281          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 281
cgaatgaatg atgcacatca tgg                                                   23

SEQ ID NO: 282          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 282
caaatgaatg atgcatgtca tgg                                                   23

SEQ ID NO: 283          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 283
caaatgaatg atgcgcgtca tgg                                                   23

SEQ ID NO: 284          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 284
caaatgaatg atgtacgtca tgg                                                   23

SEQ ID NO: 285          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 285
caaatgaatg gtgcacgtca tgg                                                   23

SEQ ID NO: 286          moltype = DNA  length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 286
caaatgagtg atgcacgtca tgg                                                   23

SEQ ID NO: 287          moltype = DNA  length = 23
```

-continued

```
FEATURE              Location/Qualifiers
misc_feature         1..23
                     note = Description of Artificial Sequence: Synthetic
                     oligonucleotide
source               1..23
                     mol_type = other DNA
                     organism = synthetic construct
SEQUENCE: 287
caaaagaatg atgcacgtca tgg                                                23

SEQ ID NO: 288       moltype = DNA   length = 23
FEATURE              Location/Qualifiers
misc_feature         1..23
                     note = Description of Artificial Sequence: Synthetic
                     oligonucleotide
source               1..23
                     mol_type = other DNA
                     organism = synthetic construct
SEQUENCE: 288
cgaatgaatg atgcacgtca tgg                                                23

SEQ ID NO: 289       moltype = DNA   length = 23
FEATURE              Location/Qualifiers
source               1..23
                     mol_type = unassigned DNA
                     organism = Homo sapiens
SEQUENCE: 289
atcataggtc gtcatgctta tgg                                                23

SEQ ID NO: 290       moltype = DNA   length = 23
FEATURE              Location/Qualifiers
misc_feature         1..23
                     note = Description of Artificial Sequence: Synthetic
                     oligonucleotide
source               1..23
                     mol_type = other DNA
                     organism = synthetic construct
SEQUENCE: 290
atcataggtt gtcatgctta tgg                                                23

SEQ ID NO: 291       moltype = DNA   length = 23
FEATURE              Location/Qualifiers
source               1..23
                     mol_type = unassigned DNA
                     organism = Homo sapiens
SEQUENCE: 291
atcataggtc gtcctgctta tgg                                                23

SEQ ID NO: 292       moltype = DNA   length = 23
FEATURE              Location/Qualifiers
misc_feature         1..23
                     note = Description of Artificial Sequence: Synthetic
                     oligonucleotide
source               1..23
                     mol_type = other DNA
                     organism = synthetic construct
SEQUENCE: 292
atcataggtt gtcctgctta tgg                                                23

SEQ ID NO: 293       moltype = DNA   length = 23
FEATURE              Location/Qualifiers
source               1..23
                     mol_type = unassigned DNA
                     organism = Homo sapiens
SEQUENCE: 293
ctggacaaga agagtacagt gcc                                                23

SEQ ID NO: 294       moltype = DNA   length = 23
FEATURE              Location/Qualifiers
misc_feature         1..23
                     note = Description of Artificial Sequence: Synthetic
                     oligonucleotide
source               1..23
                     mol_type = other DNA
                     organism = synthetic construct
SEQUENCE: 294
ctggaaaaga agagtacagt gcc                                                23

SEQ ID NO: 295       moltype = DNA   length = 23
```

-continued

```
FEATURE                 Location/Qualifiers
source                  1..23
                        mol_type = unassigned DNA
                        organism = Homo sapiens
SEQUENCE: 295
actccatcga gatttcactg tag                                        23

SEQ ID NO: 296          moltype = DNA   length = 23
FEATURE                 Location/Qualifiers
misc_feature            1..23
                        note = Description of Artificial Sequence: Synthetic
                         oligonucleotide
source                  1..23
                        mol_type = other DNA
                        organism = synthetic construct
SEQUENCE: 296
actccatcga gatttctctg tag                                        23

SEQ ID NO: 297          moltype = DNA   length = 34
FEATURE                 Location/Qualifiers
misc_feature            1..34
                        note = Description of Artificial Sequence: Synthetic
                         oligonucleotide
source                  1..34
                        mol_type = other DNA
                        organism = synthetic construct
SEQUENCE: 297
acttccaggc aaccccaagg ggacctcatg cagg                            34

SEQ ID NO: 298          moltype = DNA   length = 35
FEATURE                 Location/Qualifiers
misc_feature            1..35
                        note = Description of Artificial Sequence: Synthetic
                         oligonucleotide
source                  1..35
                        mol_type = other DNA
                        organism = synthetic construct
SEQUENCE: 298
acttccaggc gaaccccaag gggacctcat gcagg                           35

SEQ ID NO: 299          moltype = DNA   length = 13
FEATURE                 Location/Qualifiers
misc_feature            1..13
                        note = Description of Artificial Sequence: Synthetic
                         oligonucleotide
source                  1..13
                        mol_type = other DNA
                        organism = synthetic construct
SEQUENCE: 299
acttccaggc tcc                                                   13

SEQ ID NO: 300          moltype = DNA   length = 13
FEATURE                 Location/Qualifiers
misc_feature            1..13
                        note = Description of Artificial Sequence: Synthetic
                         oligonucleotide
source                  1..13
                        mol_type = other DNA
                        organism = synthetic construct
SEQUENCE: 300
acttccaggc tcc                                                   13

SEQ ID NO: 301          moltype = DNA   length = 32
FEATURE                 Location/Qualifiers
misc_feature            1..32
                        note = Description of Artificial Sequence: Synthetic
                         oligonucleotide
source                  1..32
                        mol_type = other DNA
                        organism = synthetic construct
SEQUENCE: 301
acttccaggc tcccaagggg acctcatgca gg                              32

SEQ ID NO: 302          moltype = DNA   length = 41
FEATURE                 Location/Qualifiers
misc_feature            1..41
                        note = Description of Artificial Sequence: Synthetic
                         oligonucleotide
source                  1..41
```

-continued

```
                        mol_type = other DNA
                        organism = synthetic construct
SEQUENCE: 302
acttccaggc tccttaggag gcgaacccca aggggacctc a                     41

SEQ ID NO: 303          moltype = DNA   length = 25
FEATURE                 Location/Qualifiers
misc_feature            1..25
                        note = Description of Artificial Sequence: Synthetic
                         oligonucleotide
source                  1..25
                        mol_type = other DNA
                        organism = synthetic construct
SEQUENCE: 303
acttccaggc tccacctcat gcagg                                       25

SEQ ID NO: 304          moltype = DNA   length = 32
FEATURE                 Location/Qualifiers
misc_feature            1..32
                        note = Description of Artificial Sequence: Synthetic
                         oligonucleotide
source                  1..32
                        mol_type = other DNA
                        organism = synthetic construct
SEQUENCE: 304
acttccaggc tccacccca agggacctca tg                                32

SEQ ID NO: 305          moltype = DNA   length = 35
FEATURE                 Location/Qualifiers
misc_feature            1..35
                        note = Description of Artificial Sequence: Synthetic
                         oligonucleotide
source                  1..35
                        mol_type = other DNA
                        organism = synthetic construct
SEQUENCE: 305
acttccaggc tccacccaag gggacctcat gcagg                            35

SEQ ID NO: 306          moltype = DNA   length = 36
FEATURE                 Location/Qualifiers
misc_feature            1..36
                        note = Description of Artificial Sequence: Synthetic
                         oligonucleotide
source                  1..36
                        mol_type = other DNA
                        organism = synthetic construct
SEQUENCE: 306
acttccaggc tccaccccaa ggggacctca tgcagg                           36

SEQ ID NO: 307          moltype = DNA   length = 38
FEATURE                 Location/Qualifiers
misc_feature            1..38
                        note = Description of Artificial Sequence: Synthetic
                         oligonucleotide
source                  1..38
                        mol_type = other DNA
                        organism = synthetic construct
SEQUENCE: 307
acttccaggc tccacccacc caaggggacc tcatgcag                         38

SEQ ID NO: 308          moltype = DNA   length = 38
FEATURE                 Location/Qualifiers
misc_feature            1..38
                        note = Description of Artificial Sequence: Synthetic
                         oligonucleotide
source                  1..38
                        mol_type = other DNA
                        organism = synthetic construct
SEQUENCE: 308
acttccaggc tccaccccac ccaaggggac tcatgca                          38

SEQ ID NO: 309          moltype = DNA   length = 40
FEATURE                 Location/Qualifiers
misc_feature            1..40
                        note = Description of Artificial Sequence: Synthetic
                         oligonucleotide
source                  1..40
                        mol_type = other DNA
                        organism = synthetic construct
```

-continued

```
SEQUENCE: 309
acttccaggc tccacccacc ccaaggggac ctcatgcagg                          40

SEQ ID NO: 310          moltype = DNA   length = 45
FEATURE                 Location/Qualifiers
misc_feature            1..45
                        note = Description of Artificial Sequence: Synthetic
                        oligonucleotide
source                  1..45
                        mol_type = other DNA
                        organism = synthetic construct
SEQUENCE: 310
acttccaggc tccacccggc gaaccccaag gggacctcat gcagg                    45

SEQ ID NO: 311          moltype = DNA   length = 34
FEATURE                 Location/Qualifiers
misc_feature            1..34
                        note = Description of Artificial Sequence: Synthetic
                        oligonucleotide
source                  1..34
                        mol_type = other DNA
                        organism = synthetic construct
SEQUENCE: 311
acttccaggc tccaccctgg ggacctcatg cagg                                34

SEQ ID NO: 312          moltype = DNA   length = 42
FEATURE                 Location/Qualifiers
misc_feature            1..42
                        note = Description of Artificial Sequence: Synthetic
                        oligonucleotide
source                  1..42
                        mol_type = other DNA
                        organism = synthetic construct
SEQUENCE: 312
acttccaggc tccacccgaa ccccaagggg acctcatgca gg                       42

SEQ ID NO: 313          moltype = DNA   length = 31
FEATURE                 Location/Qualifiers
misc_feature            1..31
                        note = Description of Artificial Sequence: Synthetic
                        oligonucleotide
source                  1..31
                        mol_type = other DNA
                        organism = synthetic construct
SEQUENCE: 313
acttccaggc tccacccgaa cctcatgcag g                                   31

SEQ ID NO: 314          moltype = DNA   length = 35
FEATURE                 Location/Qualifiers
misc_feature            1..35
                        note = Description of Artificial Sequence: Synthetic
                        oligonucleotide
source                  1..35
                        mol_type = other DNA
                        organism = synthetic construct
SEQUENCE: 314
acttccaggc tccacccgag gggacctcat gcagg                               35

SEQ ID NO: 315          moltype = DNA   length = 36
FEATURE                 Location/Qualifiers
misc_feature            1..36
                        note = Description of Artificial Sequence: Synthetic
                        oligonucleotide
source                  1..36
                        mol_type = other DNA
                        organism = synthetic construct
SEQUENCE: 315
acttccaggc tccaccccaa ggggacctca tgcagg                              36

SEQ ID NO: 316          moltype = DNA   length = 42
FEATURE                 Location/Qualifiers
misc_feature            1..42
                        note = Description of Artificial Sequence: Synthetic
                        oligonucleotide
source                  1..42
                        mol_type = other DNA
                        organism = synthetic construct
SEQUENCE: 316
acttccaggc tccacccgaa ccccaagggg acctcatgca gg                       42
```

-continued

```
SEQ ID NO: 317            moltype = DNA   length = 43
FEATURE                   Location/Qualifiers
misc_feature              1..43
                          note = Description of Artificial Sequence: Synthetic
                          oligonucleotide
source                    1..43
                          mol_type = other DNA
                          organism = synthetic construct
SEQUENCE: 317
acttccaggc tccacccgag accccaaggg gacctcatgc agg                          43

SEQ ID NO: 318            moltype = DNA   length = 48
FEATURE                   Location/Qualifiers
misc_feature              1..48
                          note = Description of Artificial Sequence: Synthetic
                          oligonucleotide
source                    1..48
                          mol_type = other DNA
                          organism = synthetic construct
SEQUENCE: 318
acttccaggc tccacccgag ggcgaacccc aaggggacct catgcagg                     48

SEQ ID NO: 319            moltype = DNA   length = 30
FEATURE                   Location/Qualifiers
misc_feature              1..30
                          note = Description of Artificial Sequence: Synthetic
                          oligonucleotide
source                    1..30
                          mol_type = other DNA
                          organism = synthetic construct
SEQUENCE: 319
acttccaggc tccacccgac ctcatgcagg                                         30

SEQ ID NO: 320            moltype = DNA   length = 42
FEATURE                   Location/Qualifiers
misc_feature              1..42
                          note = Description of Artificial Sequence: Synthetic
                          oligonucleotide
source                    1..42
                          mol_type = other DNA
                          organism = synthetic construct
SEQUENCE: 320
acttccaggc tccacccgac ccccaagggg acctcatgca gg                           42

SEQ ID NO: 321            moltype = DNA   length = 42
FEATURE                   Location/Qualifiers
misc_feature              1..42
                          note = Description of Artificial Sequence: Synthetic
                          oligonucleotide
source                    1..42
                          mol_type = other DNA
                          organism = synthetic construct
SEQUENCE: 321
acttccaggc tccacccgac gaagggcccc aaggggacct ca                           42

SEQ ID NO: 322            moltype = DNA   length = 45
FEATURE                   Location/Qualifiers
misc_feature              1..45
                          note = Description of Artificial Sequence: Synthetic
                          oligonucleotide
source                    1..45
                          mol_type = other DNA
                          organism = synthetic construct
SEQUENCE: 322
acttccaggc tccacccgac gaaccccaag gggacctcat gcagg                        45

SEQ ID NO: 323            moltype = DNA   length = 48
FEATURE                   Location/Qualifiers
misc_feature              1..48
                          note = Description of Artificial Sequence: Synthetic
                          oligonucleotide
source                    1..48
                          mol_type = other DNA
                          organism = synthetic construct
SEQUENCE: 323
acttccaggc tccacccgac ggcgaacccc aaggggacct catgcagg                     48

SEQ ID NO: 324            moltype = DNA   length = 51
```

-continued

```
FEATURE               Location/Qualifiers
misc_feature          1..51
                      note = Description of Artificial Sequence: Synthetic
                       oligonucleotide
source                1..51
                      mol_type = other DNA
                      organism = synthetic construct
SEQUENCE: 324
acttccaggc tccacccgac gtgcttgagg gcgaacccca aggggacctc a              51

SEQ ID NO: 325        moltype = DNA   length = 47
FEATURE               Location/Qualifiers
misc_feature          1..47
                      note = Description of Artificial Sequence: Synthetic
                       oligonucleotide
source                1..47
                      mol_type = other DNA
                      organism = synthetic construct
SEQUENCE: 325
acttccaggc tccacccgac tcactatctt ctgggctcct ccatgtc                  47

SEQ ID NO: 326        moltype = DNA   length = 49
FEATURE               Location/Qualifiers
misc_feature          1..49
                      note = Description of Artificial Sequence: Synthetic
                       oligonucleotide
source                1..49
                      mol_type = other DNA
                      organism = synthetic construct
SEQUENCE: 326
acttccaggc tccacccgac ttggcgaacc ccaaggggac ctcatgcag               49

SEQ ID NO: 327        moltype = DNA   length = 51
FEATURE               Location/Qualifiers
misc_feature          1..51
                      note = Description of Artificial Sequence: Synthetic
                       oligonucleotide
source                1..51
                      mol_type = other DNA
                      organism = synthetic construct
SEQUENCE: 327
acttccaggc tccacccgac ttgcagggcg aaccccaagg ggacctcatg c             51

SEQ ID NO: 328        moltype = DNA   length = 53
FEATURE               Location/Qualifiers
misc_feature          1..53
                      note = Description of Artificial Sequence: Synthetic
                       oligonucleotide
source                1..53
                      mol_type = other DNA
                      organism = synthetic construct
SEQUENCE: 328
acttccaggc tccacccgac ttggagggcg aaccccaagg ggacctcatg cag           53

SEQ ID NO: 329        moltype = DNA   length = 53
FEATURE               Location/Qualifiers
misc_feature          1..53
                      note = Description of Artificial Sequence: Synthetic
                       oligonucleotide
source                1..53
                      mol_type = other DNA
                      organism = synthetic construct
SEQUENCE: 329
acttccaggc tccacccgac tttggagggc gaaccccaag gggacctcat gca           53

SEQ ID NO: 330        moltype = DNA   length = 53
FEATURE               Location/Qualifiers
misc_feature          1..53
                      note = Description of Artificial Sequence: Synthetic
                       oligonucleotide
source                1..53
                      mol_type = other DNA
                      organism = synthetic construct
SEQUENCE: 330
acttccaggc tccacccgac tgttggaggg cgaaccccaa ggggacctca tgc           53

SEQ ID NO: 331        moltype = DNA   length = 502
FEATURE               Location/Qualifiers
misc_feature          1..502
```

-continued

```
                          note = Description of Artificial Sequence: Synthetic
                           oligonucleotide
misc_difference           26..480
                          note = misc_feature - a, c, t, g, unknown or other
source                    1..502
                          mol_type = other DNA
                          organism = synthetic construct
SEQUENCE: 331
acttccaggc tccacccgac tggagnnnnn nnnnnnnnnn nnnnnnnnnn nnnnnnnnnn  60
nnnnnnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnnnnnnn  180
nnnnnnnnnn nnnnnnnnnn nnnnnnnnnn nnnnnnnnnn nnnnnnnnnn nnnnnnnnnn  240
nnnnnnnnnn nnnnnnnnnn nnnnnnnnnn nnnnnnnnnn nnnnnnnnnn nnnnnnnnnn  300
nnnnnnnnnn nnnnnnnnnn nnnnnnnnnn nnnnnnnnnn nnnnnnnnnn nnnnnnnnnn  360
nnnnnnnnnn nnnnnnnnnn nnnnnnnnnn nnnnnnnnnn nnnnnnnnnn nnnnnnnnnn  420
nnnnnnnnnn nnnnnnnnnn nnnnnnnnnn nnnnnnnnnn nnnnnnnnnn nnnnnnnnnn  480
ggcgaacccc aaggggacct cc                                          502

SEQ ID NO: 332            moltype = DNA  length = 72
FEATURE                   Location/Qualifiers
source                    1..72
                          mol_type = unassigned DNA
                          organism = Homo sapiens
SEQUENCE: 332
agctctccct cccaggatcc tctctggctc catcgtaagc aaaccttaga ggttctggca  60
aggagagaga tg                                                      72
```

COMPOSITIONS FOR INDUCING MODIFICATIONS OF TARGET ENDOGENOUS NUCLEIC ACID SEQUENCES IN NUCLEUSES OF EUKARYOTIC CELLS

CROSS REFERENCE TO RELATED APPLICATIONS

The present application is a continuation application of U.S. application Ser. No. 18/932,745 filed Oct. 31, 2024, which is a continuation application of U.S. application Ser. No. 17/004,338 filed Aug. 27, 2020, which is a continuation application of U.S. application Ser. No. 14/685,568 filed Apr. 13, 2015, which is a continuation of PCT/KR2013/009488 filed Oct. 23, 2013, which claims priority to U.S. Provisional Application No. 61/837,481 filed on Jun. 20, 2013, U.S. Provisional Application No. 61/803,599 filed Mar. 20, 2013, and U.S. Provisional Application No. 61/717, 324 filed Oct. 23, 2012, the entire contents of each aforementioned application are incorporated herein by reference.

SEQUENCE LISTING

The instant application contains a Sequence Listing which has been submitted electronically in XML file format and is hereby incorporated by reference in its entirety. Said XML copy, created on Jan. 10, 2025, is named 00160 SL. xml and is 495,164 bytes in size.

TECHNICAL FIELD

The present invention relates to targeted genome editing in eukaryotic cells or organisms. More particularly, the present invention relates to a composition for cleaving a target DNA in eukaryotic cells or organisms comprising a guide RNA specific for the target DNA and Cas protein-encoding nucleic acid or Cas protein, and use thereof.

BACKGROUND ART

CRISPRs (Clustered Regularly Interspaced Short Palindromic Repeats) are loci containing multiple short direct repeats that are found in the genomes of approximately 40% of sequenced bacteria and 90% of sequenced archaea. CRISPR functions as a prokaryotic immune system, in that it confers resistance to exogenous genetic elements such as plasmids and phages. The CRISPR system provides a form of acquired immunity. Short segments of foreign DNA, called spacers, are incorporated into the genome between CRISPR repeats, and serve as a memory of past exposures. CRISPR spacers are then used to recognize and silence exogenous genetic elements in a manner analogous to RNAi in eukaryotic organisms.

Cas9, an essential protein component in the Type II CRISPR/Cas system, forms an active endonuclease when complexed with two RNAs termed CRISPR RNA (crRNA) and trans-activating crRNA (tracrRNA), thereby slicing foreign genetic elements in invading phages or plasmids to protect the host cells. crRNA is transcribed from the CRISPR element in the host genome, which was previously captured from such foreign invaders. Recently, Jinek et al. (1) demonstrated that a single-chain chimeric RNA produced by fusing an essential portion of crRNA and tracrRNA could replace the two RNAs in the Cas9/RNA complex to form a functional endonuclease.

CRISPR/Cas systems offer an advantage to zinc finger and transcription activator-like effector DNA-binding proteins, as the site specificity in nucleotide binding CRISPR-Cas proteins is governed by a RNA molecule instead of the DNA-binding protein, which can be more challenging to design and synthesize.

However, until now, a genome editing method using the RNA-guided endonuclease (RGEN) based on CRISPR/Cas system has not been developed.

Meanwhile, Restriction fragment length polymorphism (RFLP) is one of the oldest, most convenient, and least expensive methods of genotyping that is still used widely in molecular biology and genetics but is often limited by the lack of appropriate sites recognized by restriction endonucleases.

Engineered nuclease-induced mutations are detected by various methods, which include mismatch-sensitive T7 endonuclease I (T7E1) or Surveyor nuclease assays, RFLP, capillary electrophoresis of fluorescent PCR products, Dideoxy sequencing, and deep sequencing. The T7E1 and Surveyor assays are widely used but are cumbersome. Furthermore, these enzymes tend to underestimate mutation frequencies because mutant sequences can form homoduplexes with each other and cannot distinguish homozygous bi-allelic mutant clones from wildtype cells. RFLP is free of these limitations and therefore is a method of choice. Indeed, RFLP was one of the first methods to detect engineered nuclease-mediated mutations in cells and animals. Unfortunately, however, RFLP is limited by the availability of appropriate restriction sites. It is possible that no restriction sites are available at the target site of interest.

DISCLOSURE OF INVENTION

Technical Problem

Until now, a genome editing and genotyping method using the RNA-guided endonuclease (RGEN) based on CRISPR/Cas system has not been developed.

Under these circumstances, the present inventors have made many efforts to develop a genome editing method based on CRISPR/Cas system and finally established a programmable RNA-guided endonuclease that cleave DNA in a targeted manner in eukaryotic cells and organisms.

In addition, the present inventors have made many efforts to develop a novel method of using RNA-guided endonucleases (RGENs) in RFLP analysis. They have used RGENS to genotype recurrent mutations found in cancer and those induced in cells and organisms by engineered nucleases including RGENs themselves, thereby completing the present invention.

Solution to Problem

It is an object of the present invention to provide a composition for cleaving target DNA in eukaryotic cells or organisms comprising a guide RNA specific for target DNA or DNA that encodes the guide RNA, and Cas protein-encoding nucleic acid or Cas protein.

It is another object of the present invention to provide a composition for inducing targeted mutagenesis in eukaryotic cells or organisms, comprising a guide RNA specific for target DNA or DNA that encodes the guide RNA, and Cas protein-encoding nucleic acid or Cas protein.

It is still another object of the present invention to provide a kit for cleaving a target DNA in eukaryotic cells or organisms comprising a guide RNA specific for target DNA or DNA that encodes the guide RNA, and Cas protein-encoding nucleic acid or Cas protein.

It is still another object of the present invention to provide a kit for inducing targeted mutagenesis in eukaryotic cells or organisms comprising a guide RNA specific for target DNA or DNA that encodes the guide RNA, and Cas protein-encoding nucleic acid or Cas protein.

It is still another object of the present invention to provide a method for preparing a eukaryotic cell or organism comprising Cas protein and a guide RNA comprising a step of co-transfecting or serial-transfecting the eukaryotic cell or organism with a Cas protein-encoding nucleic acid or Cas protein, and a guide RNA or DNA that encodes the guide RNA.

It is still another object of the present invention to provide a eukaryotic cell or organism comprising a guide RNA specific for target DNA or DNA that encodes the guide RNA, and Cas protein-encoding nucleic acid or Cas protein.

It is still another object of the present invention to provide a method for cleaving a target DNA in eukaryotic cells or organisms comprising a step of transfecting the eukaryotic cells or organisms comprising a target DNA with a composition comprising a guide RNA specific for target DNA or DNA that encodes the guide RNA, and Cas protein-encoding nucleic acid or Cas protein.

It is still another object of the present invention to provide a method for inducing targeted mutagenesis in a eukaryotic cell or organism comprising a step of treating a eukaryotic cell or organism with a composition comprising a guide RNA specific for target DNA or DNA that encodes the guide RNA, and Cas protein-encoding nucleic acid or Cas protein.

It is still another object of the present invention to provide an embryo, a genome-modified animal, or genome-modified plant comprising a genome edited by a composition comprising a guide RNA specific for target DNA or DNA that encodes the guide RNA, and Cas protein-encoding nucleic acid or Cas protein.

It is still another object of the present invention to provide a method of preparing a genome-modified animal comprising a step of introducing the composition comprising a guide RNA specific for target DNA or DNA that encodes the guide RNA, and Cas protein-encoding nucleic acid or Cas protein into an embryo of an animal; and a step of transferring the embryo into a oviduct of pseudopregnant foster mother to produce a genome-modified animal.

It is still another object of the present invention to provide a composition for genotyping mutations or variations in an isolated biological sample, comprising a guide RNA specific for the target DNA sequence Cas protein.

It is still another object of the present invention to provide a method of using a RNA-guided endonuclease (RGEN) to genotype mutations induced by engineered nucleases in cells or naturally-occurring mutations or variations, wherein the RGEN comprises a guide RNA specific for target DNA and Cas protein.

It is still another object of the present invention to provide a kit for genotyping mutations induced by engineered nucleases in cells or naturally-occurring mutations or variations, comprising a RNA-guided endonuclease (RGEN), wherein the RGEN comprises a guide RNA specific for target DNA and Cas protein.

It is an object of the present invention to provide a composition for cleaving target DNA in eukaryotic cells or organisms comprising a guide RNA specific for target DNA or DNA that encodes the guide RNA, and Cas protein-encoding nucleic acid or Cas protein.

It is another object of the present invention to provide a composition for inducing targeted mutagenesis in eukaryotic cells or organisms, comprising a guide RNA specific for target DNA or DNA that encodes the guide RNA, and Cas protein-encoding nucleic acid or Cas protein.

It is still another object of the present invention to provide a kit for cleaving a target DNA in eukaryotic cells or organisms comprising a guide RNA specific for target DNA or DNA that encodes the guide RNA, and Cas protein-encoding nucleic acid or Cas protein.

It is still another object of the present invention to provide a kit for inducing targeted mutagenesis in eukaryotic cells or organisms comprising a guide RNA specific for target DNA or DNA that encodes the guide RNA, and Cas protein-encoding nucleic acid or Cas protein.

It is still another object of the present invention to provide a method for preparing a eukaryotic cell or organism comprising Cas protein and a guide RNA comprising a step of co-transfecting or serial-transfecting the eukaryotic cell or organism with a Cas protein-encoding nucleic acid or Cas protein, and a guide RNA or DNA that encodes the guide RNA.

It is still another object of the present invention to provide a eukaryotic cell or organism comprising a guide RNA specific for target DNA or DNA that encodes the guide RNA, and Cas protein-encoding nucleic acid or Cas protein.

It is still another object of the present invention to provide a method for cleaving a target DNA in eukaryotic cells or organisms comprising a step of transfecting the eukaryotic cells or organisms comprising a target DNA with a composition comprising a guide RNA specific for target DNA or DNA that encodes the guide RNA, and Cas protein-encoding nucleic acid or Cas protein.

It is still another object of the present invention to provide a method for inducing targeted mutagenesis in a eukaryotic cell or organism comprising a step of treating a eukaryotic cell or organism with a composition comprising a guide RNA specific for target DNA or DNA that encodes the guide RNA, and Cas protein-encoding nucleic acid or Cas protein.

It is still another object of the present invention to provide an embryo, a genome-modified animal, or genome-modified plant comprising a genome edited by a composition comprising a guide RNA specific for target DNA or DNA that encodes the guide RNA, and Cas protein-encoding nucleic acid or Cas protein.

It is still another object of the present invention to provide a method of preparing a genome-modified animal comprising a step of introducing the composition comprising a guide RNA specific for target DNA or DNA that encodes the guide RNA, and Cas protein-encoding nucleic acid or Cas protein into an embryo of an animal; and a step of transferring the embryo into a oviduct of pseudopregnant foster mother to produce a genome-modified animal.

It is still another object of the present invention to provide a composition for genotyping mutations or variations in an isolated biological sample, comprising a guide RNA specific for the target DNA sequence Cas protein.

It is still another object of the present invention to provide a composition for genotyping nucleic acid sequences in pathogenic microorganisms in an isolated biological sample, comprising a guide RNA specific for the target DNA sequence and Cas protein.

It is still another object of the present invention to provide a kit for genotyping mutations or variations in an isolated biological sample, comprising the composition, specifically comprising a RNA-guided endonuclease (RGEN), wherein the RGEN comprises a guide RNA specific for target DNA and Cas protein.

It is still another object of the present invention to provide a method of genotyping mutations or variations in an isolated biological sample, using the composition, specifically comprising a RNA-guided endonuclease (RGEN), wherein the RGEN comprises a guide RNA specific for target DNA and Cas protein.

Advantageous Effects of Invention

The present composition for cleaving a target DNA or inducing a targeted mutagenesis in eukaryotic cells or organisms, comprising a guide RNA specific for the target DNA and Cas protein-encoding nucleic acid or Cas protein, the kit comprising the composition, and the method for inducing targeted mutagenesis provide a new convenient genome editing tools. In addition, because custom RGENs can be designed to target any DNA sequence, almost any single nucleotide polymorphism or small insertion/deletion (indel) can be analyzed via RGEN-mediated RFLP, therefore, the composition and method of the present invention may be used in detection and cleaving naturally-occurring variations and mutations.

BRIEF DESCRIPTION OF DRAWINGS

FIGS. 1A and 1B show Cas9-catalyzed cleavage of plasmid DNA in vitro. FIG. 1A: Schematic representation of target DNA (SEQ ID NO: 112) and chimeric RNA sequences (SEQ ID NO: 113). Triangles indicate cleavage sites. The PAM sequence recognized by Cas9 is shown in bold. The sequences in the guide RNA (SEQ ID NO: 113) derived from crRNA and tracrRNA are shown in box and underlined, respectively. FIG. 1B: In vitro cleavage of plasmid DNA by Cas9. An intact circular plasmid or ApaLI-digested plasmid was incubated with Cas9 and guide RNA.

FIG. 2A: Schematic overview of cell-based assays using a RFP-GFP reporter. GFP is not expressed from this reporter because the GFP sequence is fused to the RFP sequence out-of-frame. The RFP-GFP fusion protein is expressed only when the target site between the two sequences is cleaved by a site-specific nuclease. FIG. 2B: Flow cytometry of cells transfected with Cas9. The percentage of cells that express the RFP-GFP fusion protein is indicated.

FIG. 3A: CCR5 locus. FIG. 3B: C4BPB locus. (Top) The T7E1 assay was used to detect RGEN-driven mutations. Arrows indicate the expected position of DNA bands cleaved by T7E1. Mutation frequencies (Indels (%)) were calculated by measuring the band intensities. (Bottom) DNA sequences of the wild-type (WT) CCR5 (SEQ ID NO: 114) and C4BPB (SEQ ID NO: 122) and mutant clones. DNA sequences of RGEN-induced mutations at the CCR5 locus: +1 (SEQ ID NO: 115), −13 (SEQ ID NO: 116), −14 (SEQ ID NO: 117), −18 (SEQ ID NO: 118), −19 (SEQ ID NO: 119), −24 (SEQ ID NO: 120), and −30 (SEQ ID NO: 121). DNA sequences of RGEN-induced mutations at the C4BPB locus: +1 (SEQ ID NO: 122), +2 (SEQ ID NO: 123), −30 (SEQ ID NO: 125), and −180 (SEQ ID NO: 126). The region of the target sequence complementary to the guide RNA is shown in box. The PAM sequence is shown in bold. Triangles indicate the cleavage site. Bases corresponding to microhomologies are underlined. The column on the right indicates the number of inserted or deleted bases.

FIG. 4A: On-target and potential off-target sequences. The human genome was searched in silico for potential off-target sites. Four sites were identified, ADCY5 (SEQ ID NO: 128), KCNJ6 (SEQ ID NO: 129), CNTNAP2 (SEQ ID NO: 130), and Chr. 5 N/A (SEQ ID NO: 131), each of which carries 3-base mismatches with the CCR5 on-target (SEQ ID NO: 127). Mismatched bases are underlined. FIG. 4B: The T7E1 assay was used to investigate whether these sites were mutated in cells transfected with the Cas9/RNA complex. No mutations were detected at these sites. N/A (not applicable), an intergenic site. FIG. 4C: Cas9 did not induce off-target-associated chromosomal deletions. The CCR5-specific RGEN and ZFN were expressed in human cells. PCR was used to detect the induction of the 15-kb chromosomal deletions in these cells.

FIG. 5A: A schematic diagram depicting target DNA (SEQ ID NO: 132) and a sgRNA specific to exon 2 of the mouse Foxn1 gene (SEQ ID NO: 133). PAM in exon 2 is shown in a box and the sequence in the sgRNA that is complementary to exon 2 is underlined. Triangles indicate cleavage sites.

FIG. 5B: Representative T7E1 assays demonstrating gene-targeting efficiencies of Cas9 mRNA plus Foxn1-specific sgRNA that were delivered via intra-cytoplasmic injection into one-cell stage mouse embryos. Numbers indicate independent founder mice generated from the highest dose. Arrows indicate bands cleaved by T7E1. FIG. 5C: DNA sequences of wild-type (WT) Foxn1 (SEQ ID NO: 134) and mutant alleles (SEQ ID NOs. 135-141) observed in three Foxn1 mutant founders identified in FIG. 5B. DNA sequences of mutant alleles in founder #108: −44 (SEQ ID NO: 135), −23 (SEQ ID NO: 136), −17 (SEQ ID NO: 137), and +1 (SEQ ID NO: 138). DNA sequences of mutant alleles in founder #111: +1 (SEQ ID NO: 138) and −11 (SEQ ID NO: 139). DNA sequences of mutant alleles in founder #114: −6 (SEQ ID NO: 140), −17 (SEQ ID NO: 137), and −8 (SEQ ID NO: 141). The number of occurrences is shown in parentheses. FIG. 5D: PCR genotyping of F1 progenies derived from crossing Foxn1 founder #108 and wild-type FVB/NTac. Note the segregation of the mutant alleles found in Foxn1 founder #108 in the progenies.

FIGS. 6A, 6B, and 6C show Foxn1 gene targeting in mouse embryos by intra-cytoplasmic injection of Cas9 mRNA and Foxn1-sgRNA. FIG. 6A: A representative result of a T7E1 assay monitoring the mutation rate after injecting the highest dose. Arrows indicate bands cleaved by T7E1. FIG. 6B: A summary of T7E1 assay results. Mutant fractions among in vitro cultivated embryos obtained after intra-cytoplasmic injection of the indicated RGEN doses are indicated. FIG. 6C: DNA sequences of wild-type (WT) Foxn1 (SEQ ID NO: 143) and Foxn1 mutant alleles (SEQ ID Nos. 144-152) identified from a subset of T7E1-positive mutant embryos. The DNA sequences of the mutant alleles are: A11 (SEQ ID NO: 144), A11+417 (SEQ ID NO: 145) 457 (SEQ ID NO: 146), 417 (SEQ ID NO: 147), +1 (SEQ ID NO: 148), A12 (SEQ ID NO: 149, 472 (SEQ ID NO: 150), 425 (SEQ ID NO: 151), A24 (SEQ ID NO: 152). The target sequence of the wild-type allele is denoted in box.

FIGS. 7A, 7B, and 7C show Foxn1 gene targeting in mouse embryos using the recombinant Cas9 protein: Foxn1-sgRNA complex. FIG. 7A and FIG. 7B are representative T7E1 assays results and their summaries. Embryos were cultivated in vitro after they underwent pronuclear (FIG. 7A) or intra-cytoplasmic injection (FIG. 7B). Underlined numbers indicate T7E1-positive mutant founder mice. FIG. 7C: DNA sequences of wild-type (WT) Foxn1 (SEQ ID NO: 153) and Foxn1 mutant alleles (SEQ ID NOS. 154-166) identified from the in vitro cultivated embryos that were obtained by the pronucleus injection of recombinant Cas9 protein: Foxn1-sgRNA complex at the highest dose. The target sequence of the wild-type allele is denoted in box. The DNA sequences of the mutant alleles are: 418 (SEQ ID NO: 154), A20 (SEQ ID NO: 155), A19 (SEQ ID NO: 156), A17 (SEQ ID NO: 157), A11 (SEQ ID NO: 158), A3+1 (SEQ ID NO: 159), A2 (SEQ ID NO: 160), +1, Embryo 1 (SEQ ID NO: 161), +1, Embryo 10 (SEQ ID NO: 162), 46 (SEQ ID NO: 163), A5 (SEQ ID NO: 164), 428 (SEQ ID NO: 165), and A126 (SEQ ID NO: 166).

FIG. 8A: wild type fPCR analysis. FIG. 8B: Foxn1 mutant founder #12 fPCR analysis. FIG. 8C: PCR genotyping of wild-type FVB/NTac, the founder mouse, and their F1 progenies.

FIG. 9A: fPCR analysis of wild-type, founder ♂25, and founder ♀15. Note that, due to the technical limitations of fPCR analysis, these results showed small differences from the precise sequences of the mutant alleles; e.g., from the sequence analysis, Δ269/Δ61/WT and Δ5+1/+7/+12/WT were identified in founders ♂25 and ♀15, respectively. FIG. 9B: Genotypes of the generated embryos.

FIGS. 10A, 10B, 10C, 10D, and 10E show Cas9 protein/sgRNA complex induced targeted mutation at CCR5 gene (FIGS. 10A-10C) and ABCC11 gene (FIGS. 10D-10E). FIG. 10A: Results of a T7E1 assay monitoring the mutation rate at CCR5 locus after introducing Cas9 protein and sgRNA or Cas9 protein and crRNA+tracrRNA into K562 cells. FIG. 10B: Results of a T7E1 assay using ⅕ scaled down doses of Cas9 protein and sgRNA. FIG. 10C: Wild-type (WT) CCR5 sequence (SEQ ID NO: 114) and Cas protein induced mutant sequences (SEQ ID NOs. 167-171 and 115) identified in CCR5 locus. The DNA sequences of the mutant sequences are: −4 (SEQ ID NO: 167), −4 (SEQ ID NO: 168), −7 (SEQ ID NO: 169), −1 (SEQ ID NO: 170), +1 (SEQ ID NO: 115), and −17, +1 (SEQ ID NO: 171). FIG. 10D: Results of a T7E1 assay monitoring the mutation rate at ABCC11 locus after introducing Cas9 protein and sgRNA into K562 cells. FIG. 10E: Wild-type (WT) ABCC11 sequence (SEQ ID NO: 172) and Cas9 protein induced mutant sequences (SEQ ID NOs. 173-176) identified in ABCC11 locus. The DNA sequences of the mutant sequences are: −6 (SEQ ID NO: 173), −3 (SEQ ID NO: 174), −29 (SEQ ID NO: 175), −20 (SEQ ID NO: 176), and −256 (TTCTC).

FIG. 14A: VEGFA site 1 on target sequence (SEQ ID NO: 182) and off target sequences, OT1-3 (SEQ ID NO: 183) and OT1-11 (SEQ ID NO: 184). VEGFA site 2 on target sequence (SEQ ID NO: 185) and off target sequences OT2-1 (SEQ ID NO: 186), OT2-9 (SEQ ID NO: 187) and OT2-24 (SEQ ID NO: 188). FIG. 14B: VEGFA site 3 on target sequence (SEQ ID NO: 189) and off target sequence OT3-18 (SEQ ID NO: 190) and EMX1 on target sequence (SEQ ID NO: 191) and off target sequence OT4-1 (SEQ ID NO: 192).

FIG. 15A: VEGFA site 1 on target sequence (SEQ ID NO: 182) and off target sequences OT1-3 (SEQ ID NO: 183 and OT1-11 (SEQ ID NO: 184). VEGFA site 2 on target sequence (SEQ ID NO: 185) and off target sequences OT2-1 (SEQ ID NO: 186), OT2-9 (SEQ ID NO: 187), and OT2-24 (SEQ ID NO: 188).

FIG. 15B: VEGFA site 3 on target sequence (SEQ ID NO: 189) and off target sequence OT3-18 (SEQ ID NO: 190) and EMX1 on target sequence (SEQ ID NO: 191) and off target sequence OT4-1 (SEQ ID NO: 192).

FIG. 16A: Schematic overview of the Cas9 nuclease and the paired Cas9 nickase. The PAM sequences and cleavage sites are shown in box. FIG. 16B: Target sites in the human AAVS1 locus. The position of each target site is shown in triangle. FIG. 16C: Schematic overview of DNA cleavage reactions. FAM dyes (shown in box) were linked to both 5' ends of the DNA substrate. FIG. 16D: DSBs and SSBs analyzed using fluorescent capillary electrophoresis. Fluorescently-labeled DNA substrates were incubated with Cas9 nucleases or nickases before electrophoresis.

FIG. 17A: On-target mutation frequencies associated with Cas9 nucleases (WT), nickases (D10A), and paired nickases at the following target sequences of the AAVS1 locus: S1 (SEQ ID NO: 193, S2 (SEQ ID NO: 194), S3 (SEQ ID NO: 195), S4 (SEQ ID NO: 196), S5 (SEQ ID NO: 197), S6 (SEQ ID NO: 198), AS1 (SEQ ID NO: 199), AS2 (SEQ ID NO: 200), and AS3 (SEQ ID NO: 201). Paired nickases that would produce 5' over-hangs or 3' overhangs are indicated. FIG. 17B: Analysis of off-target effects of Cas9 nucleases and paired nickases. A total of seven potential off-target sites (SEQ ID NOs. 202-208) for three sgRNAs were analyzed. The mutation frequency for the S2 on-target sequence (SEQ ID NO: 194) was compared to the off-target sequences, S2 Off-1 (SEQ ID NO: 202) and S2 Off-2 (SEQ ID NO: 203). The mutation frequency for the S3 on-target sequence (SEQ ID NO: 195) was compared to the off-target sequences, S3 Off-1 (SEQ ID NO: 204) and S3 Off-2 (SEQ ID NO: 205). The mutation frequency for the AS2 on-target sequence (SEQ ID NO: 198) was compared to the off-target sequences, AS2 Off-1 (SEQ ID NO: 206), AS2 Off-6 (SEQ ID NO: 207), and AS2 Off-9 (SEQ ID NO: 208).

18D) target sites were detected by the T7E1 assay. The repair of two nicks that would produce 5' overhangs led to the formation of indels much more frequently than did those producing 3' overhangs.

Figures 19A, 19B:
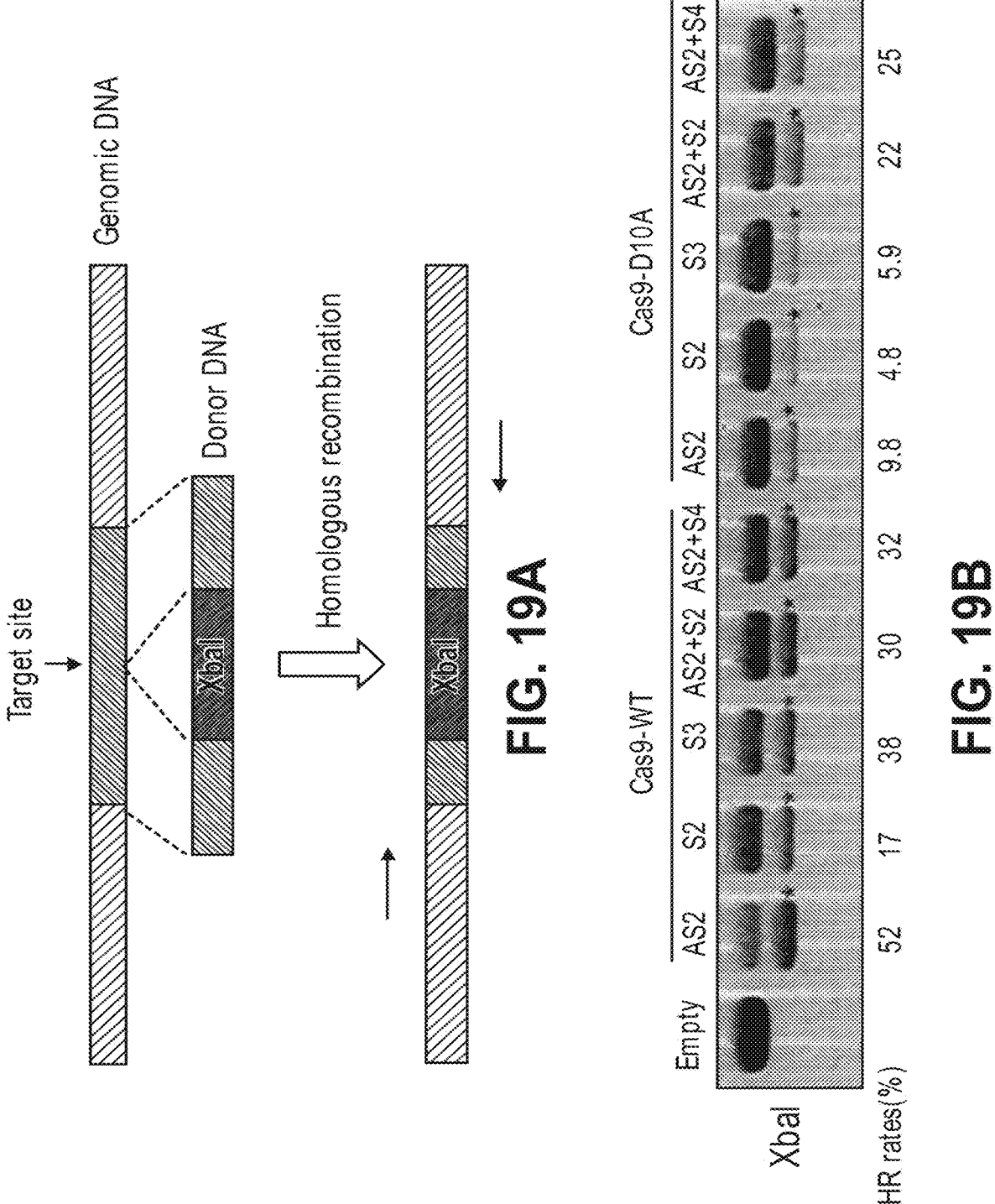

FIGS. 19A and 19B show that paired Cas9 nickases mediate homologous recombination. FIG. 19A: Strategy to detect homologous recombination. Donor DNA included an XbaI restriction enzyme site between two homology arms, whereas the endogenous target site lacked this site. A PCR assay was used to detect sequences that had undergone homologous recombination. To prevent amplification of contaminating donor DNA, primers specific to genomic DNA were used. FIG. 19B: Efficiency of homologous recombination. Only amplicons of a region in which homologous recombination had occurred could be digested with XbaI; the intensities of the cleavage bands were used to measure the efficiency of this method.

Figures 20A, 20B:
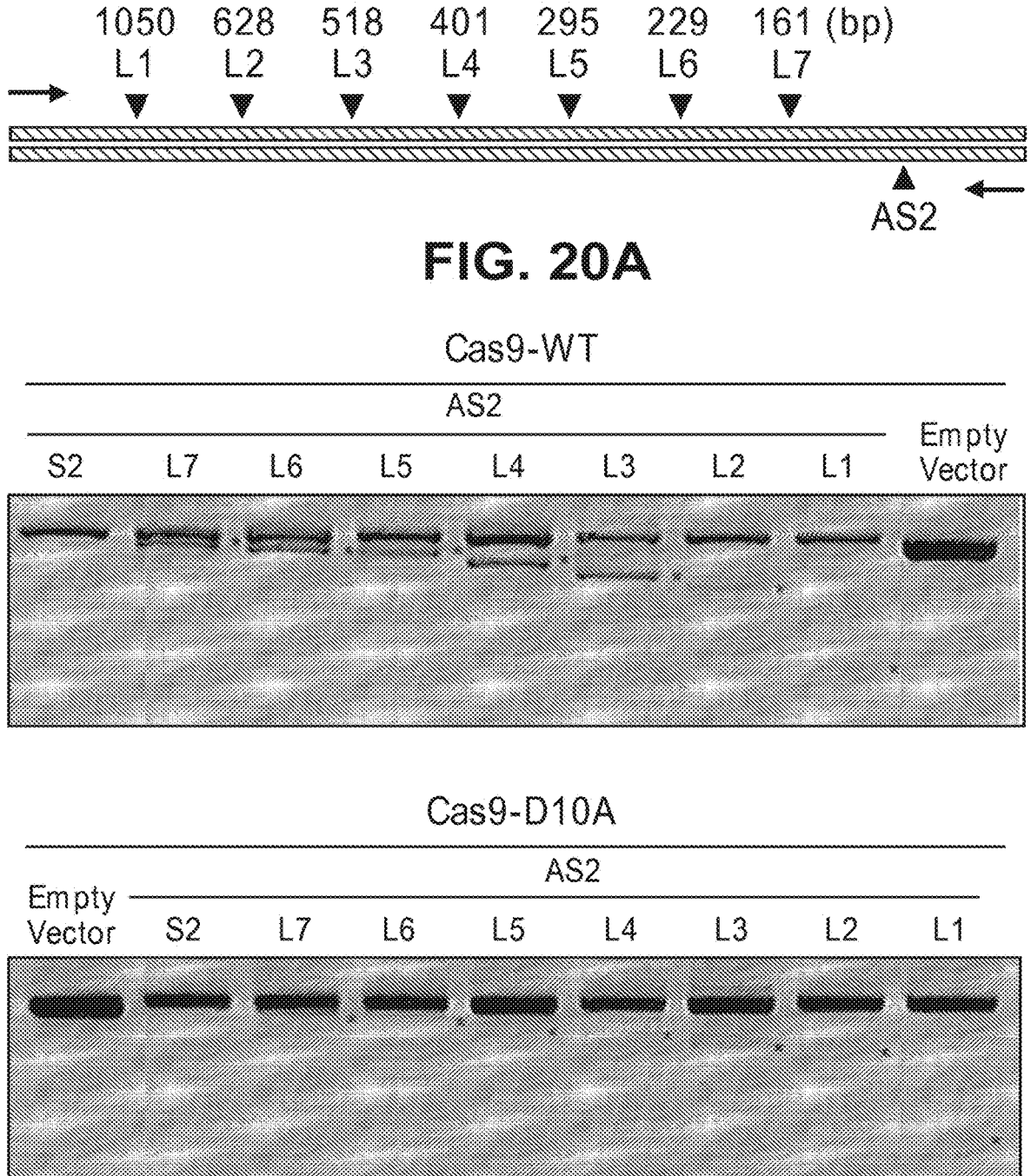

FIGS. 20A, 20B, 20C, and 20D show DNA splicing induced by paired Cas9 nickases. FIG. 20A: The target sites of paired nickases in the human AAVS1 locus. The distances between the AS2 site and each of the other sites are shown. Arrows indicate PCR primers. FIG. 20B: Genomic deletions detected using PCR. Asterisks indicate deletion-specific PCR products.

Figure 20C:
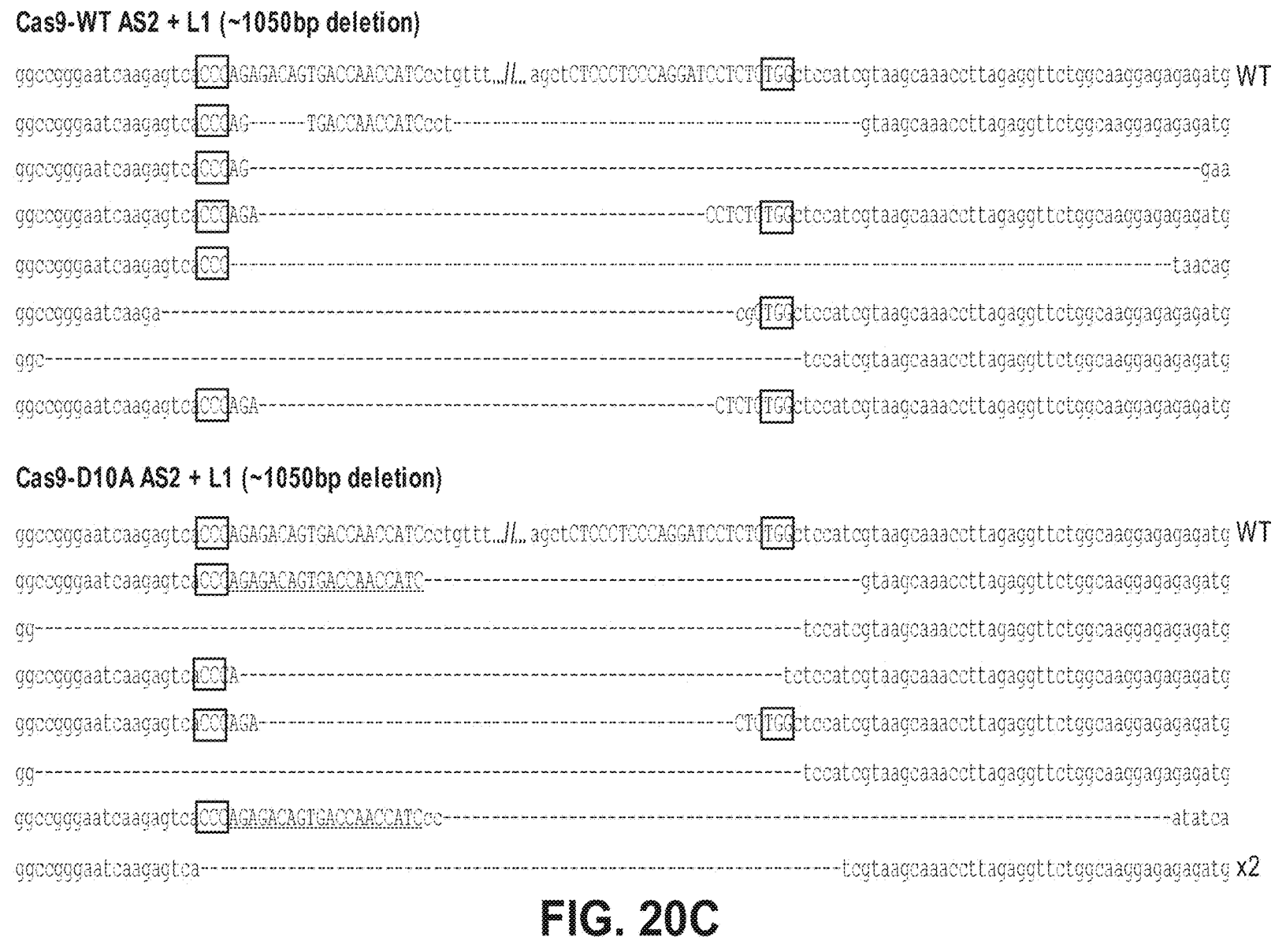
Figure 20D:
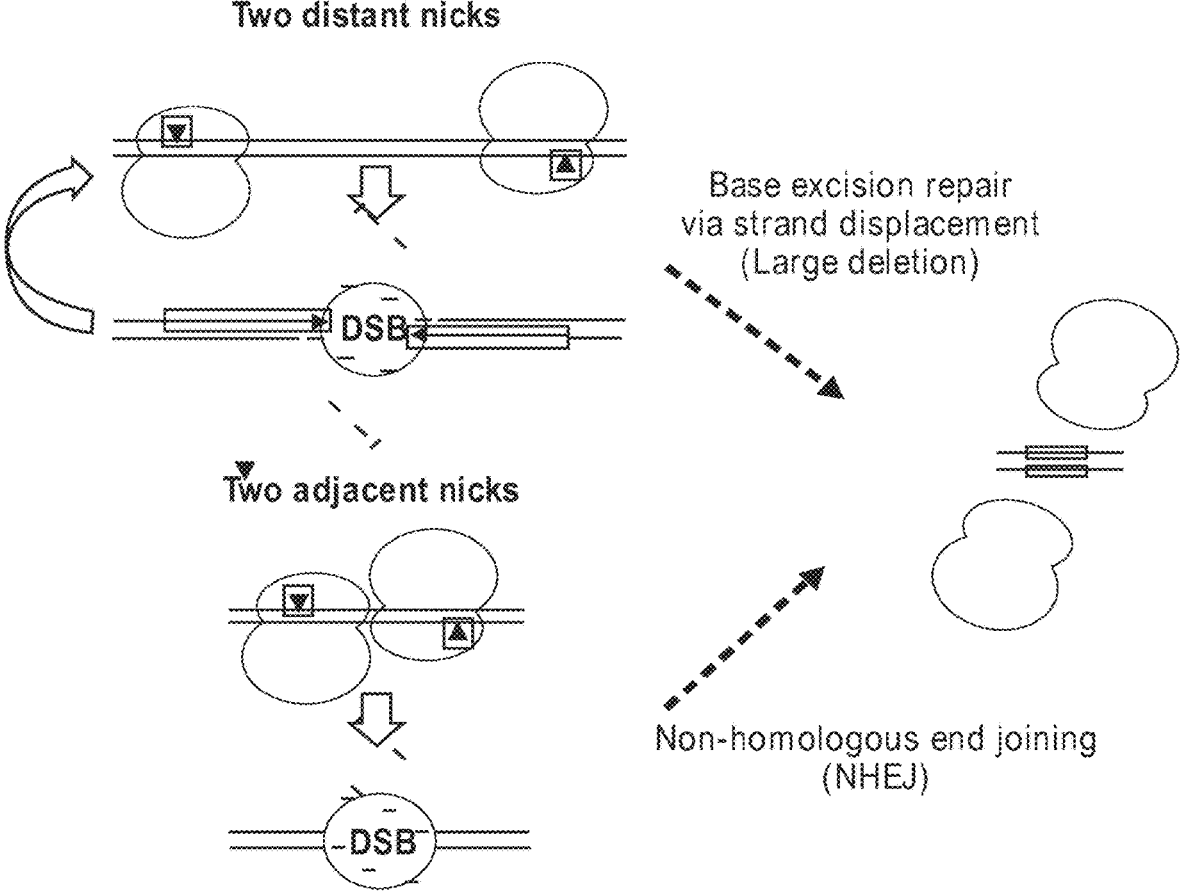

FIG. 20C: DNA sequences of wild-type (WT) (SEQ ID NO: 211 and 332) and the following deletion-specific PCR products (SEQ ID Nos. 212-218) obtained using AS2 sgRNAs or deletion-specific PCR products (SEQ ID NOs. 219-224) using L1 sgRNAs. Target site PAM sequences are shown in box and sgRNA-matching sequences are shown in capital letters. Intact sgRNA-matching sequences are underlined. FIG. 20D: A schematic model of paired Cas9 nickase-mediated chromosomal deletions. Newly-synthesized DNA strands are shown in box.

Figures 21A, 21B:
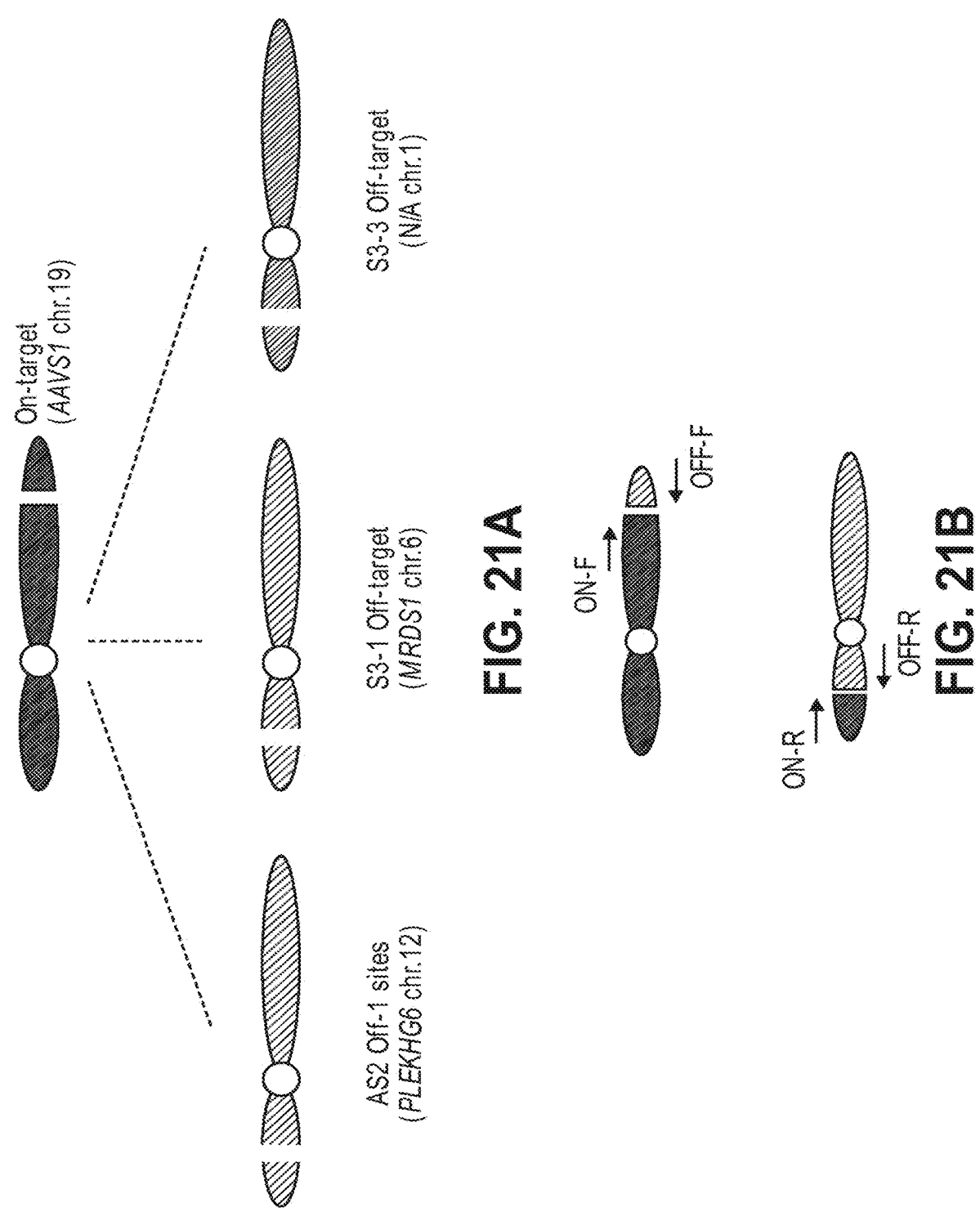
Figure 21C:
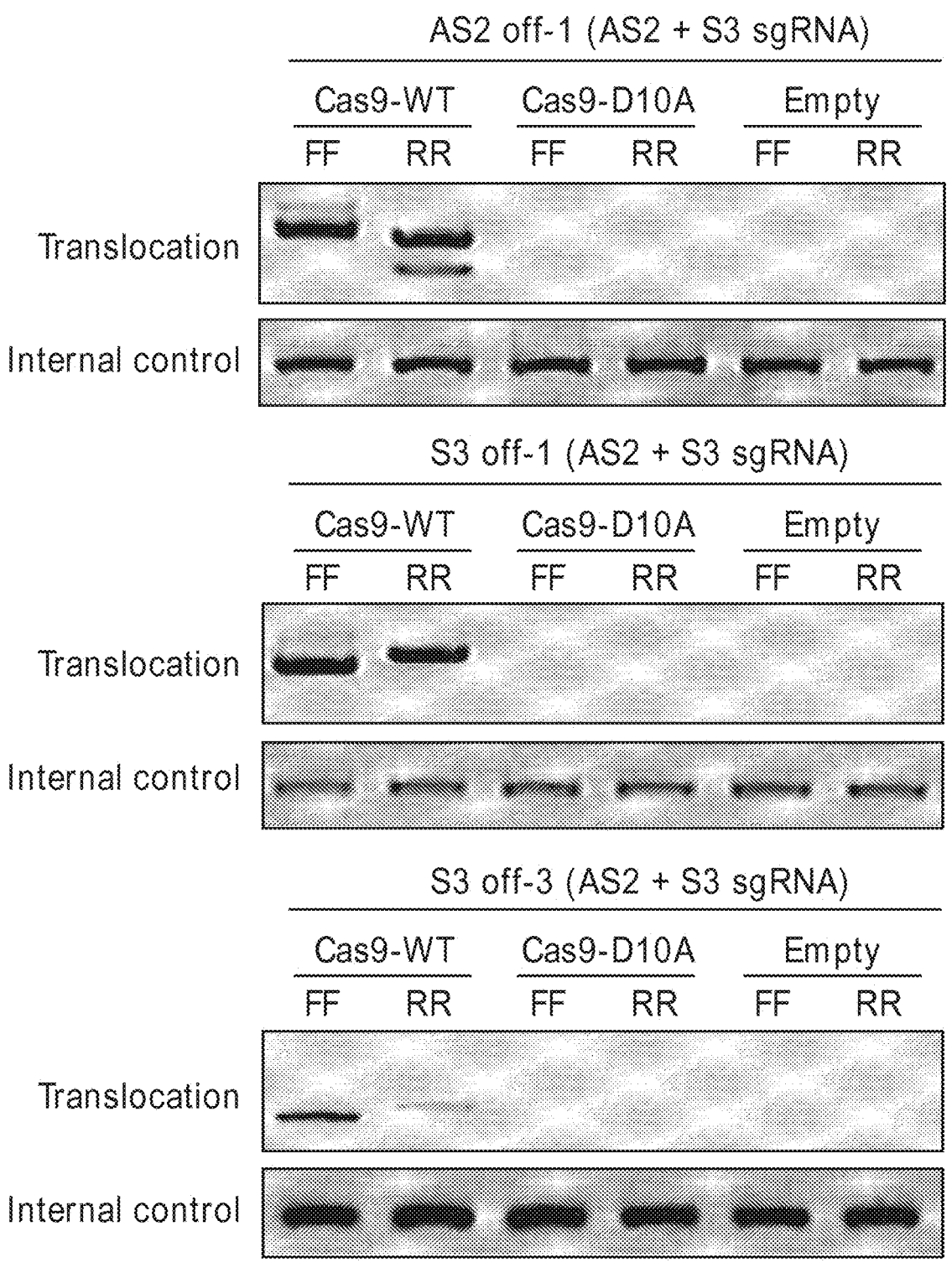

FIGS. 21A, 21B, and 21C show that paired Cas9 nickases do not induce translocations. FIG. 21A: Schematic overview of chromosomal translocations between the on-target and off-target sites. FIG. 21B: PCR amplification to detect chromosomal translocations. FIG. 21C: Translocations induced by Cas9 nucleases but not by the nickase pair.

Figure 22A:
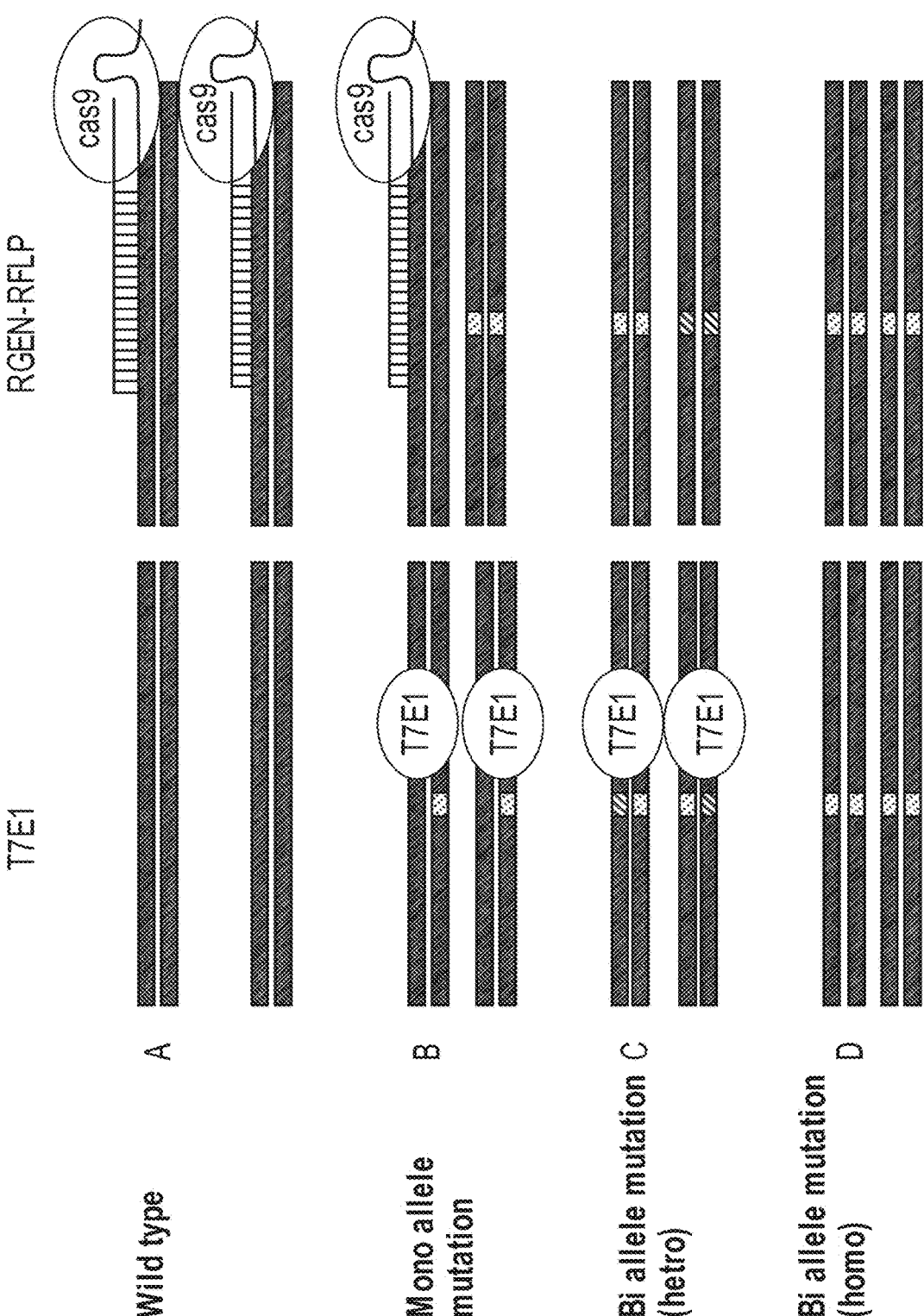
Figure 22B:
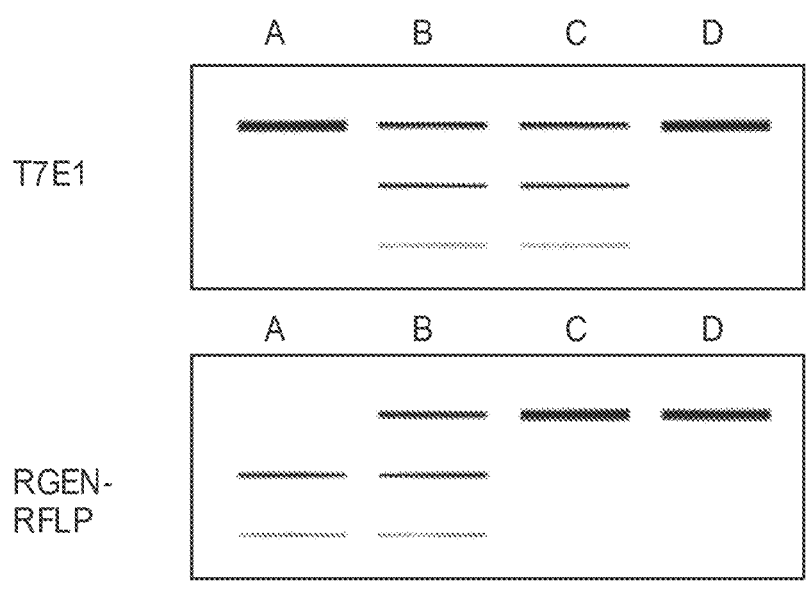

FIGS. 22A and 22B show a conceptual diagram of the T7E1 and RFLP assays. FIG. 22A: Comparison of assay cleavage reactions in four possible scenarios after engineered nuclease treatment in a diploid cell: (A) wild type, (B) a monoallelic mutation, (C) different biallelic mutations (hetero), and (D) identical biallelic mutations (homo). Black lines represent PCR products derived from each allele; dashed and dotted boxes indicate insertion/deletion mutations generated by NHEJ. FIG. 22B: Expected results of T7E1 and RGEN digestion resolved by electrophoresis.

Figure 23:
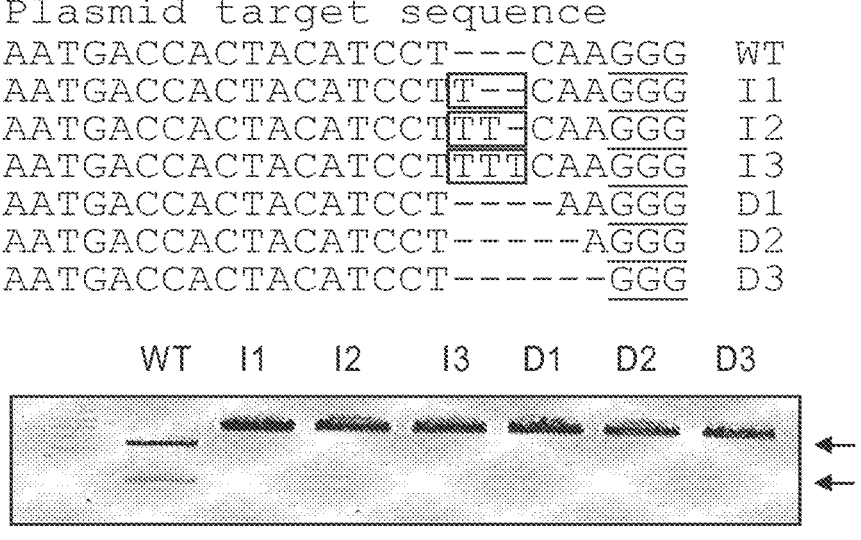

FIG. 23 shows in vitro cleavage assay of a linearized plasmid containing the C4BPB target site bearing indels. DNA sequences of individual plasmid substrates (upper panel): WT (SEQ ID NO: 104), 11 (SEQ ID NO: 225), 12 (SEQ ID NO: 226), 13 (SEQ ID NO: 227), D1 (SEQ ID NO: 228), D2 (SEQ ID NO: 229), and D3 (SEQ ID NO: 230). The PAM sequence is underlined. Inserted bases are shown in box. Arrows (bottom panel) indicate expected positions of DNA bands cleaved by the wild-type-specific RGEN after electrophoresis.

Figure 24A:
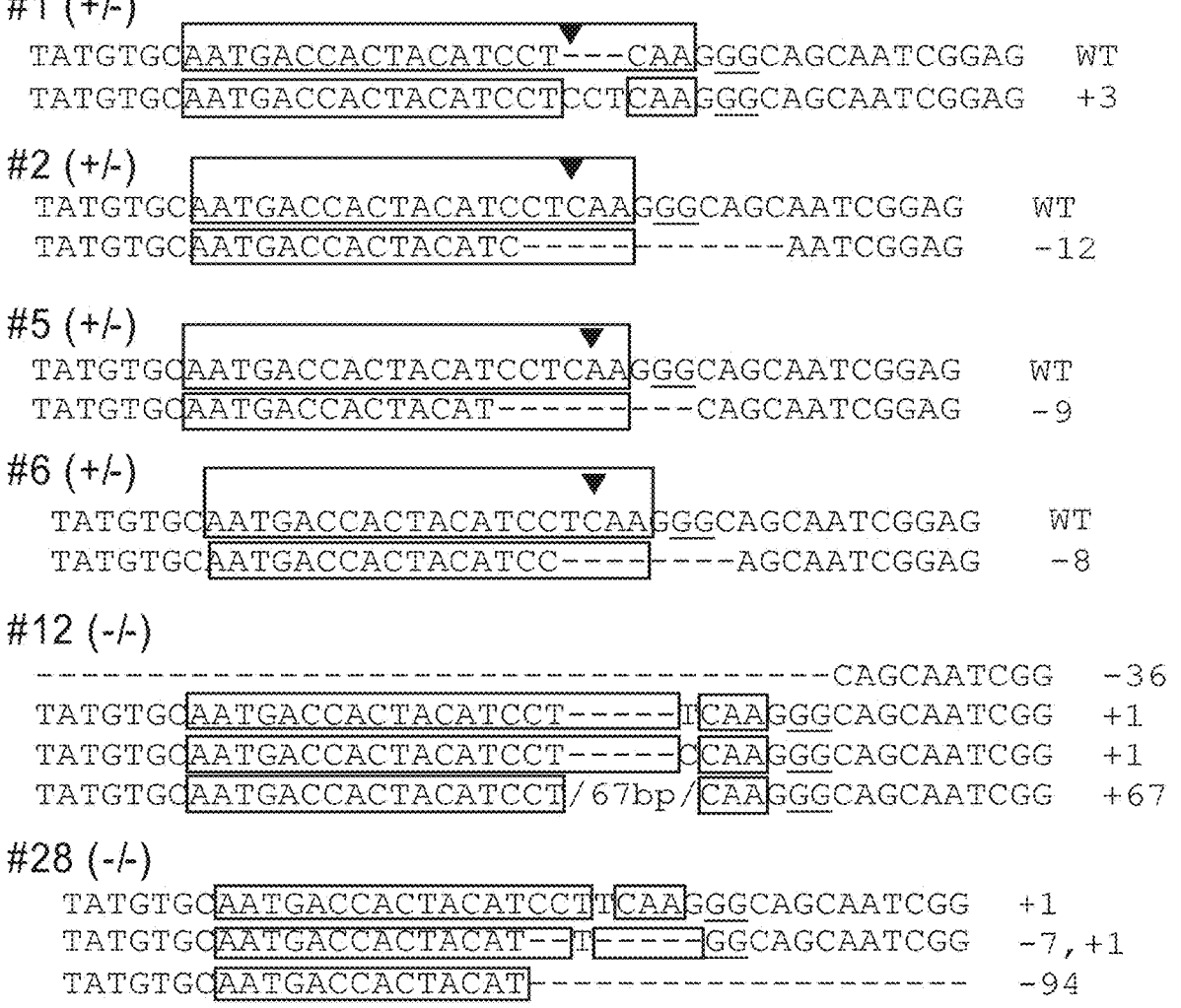
Figure 24B:
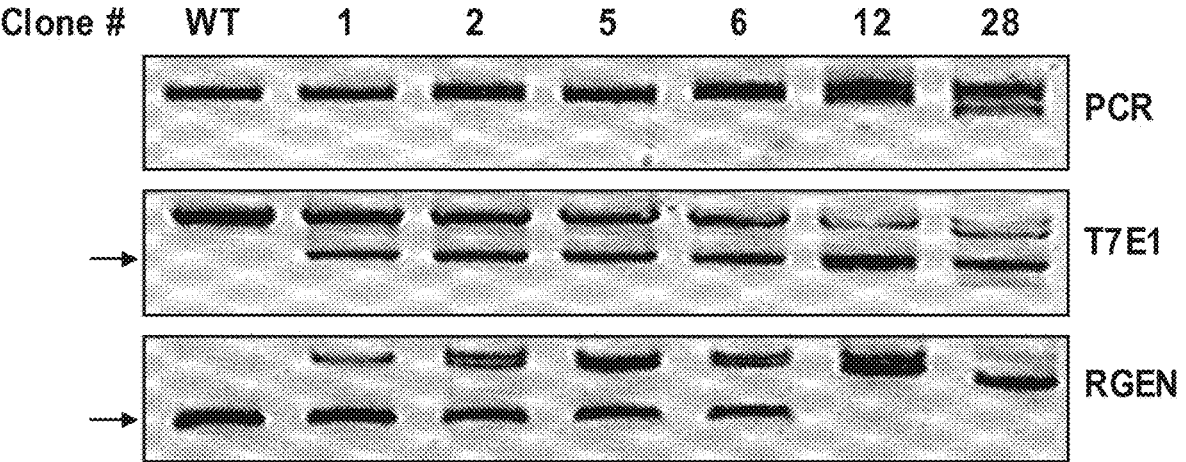

FIGS. 24A and 24B show genotyping of mutations induced by engineered nucleases in cells via RGEN-mediated RFLP. FIG. 24A: Genotype of C4BPB wild type (SEQ ID NO: 231) and the following mutant K562 cell clones: +3 (SEQ ID NO: 232), −12 (SEQ ID NO: 233), −9 (SEQ ID NO: 234), −8 (SEQ ID NO: 235), −36 (SEQ ID NO: 236), +1 (SEQ ID NO: 237), +1 (SEQ ID NO: 238), +67 (SEQ ID NO: 239), −7, +1 (SEQ ID NO: 240), −94 (SEQ ID NO: 241). FIG. 24B: Comparison of the mismatch-sensitive T7E1 assay with RGEN-mediated RFLP analysis. Black arrows indicate the cleavage product by treatment of T7E1 enzyme or RGENS.

Figures 25A, 25B:
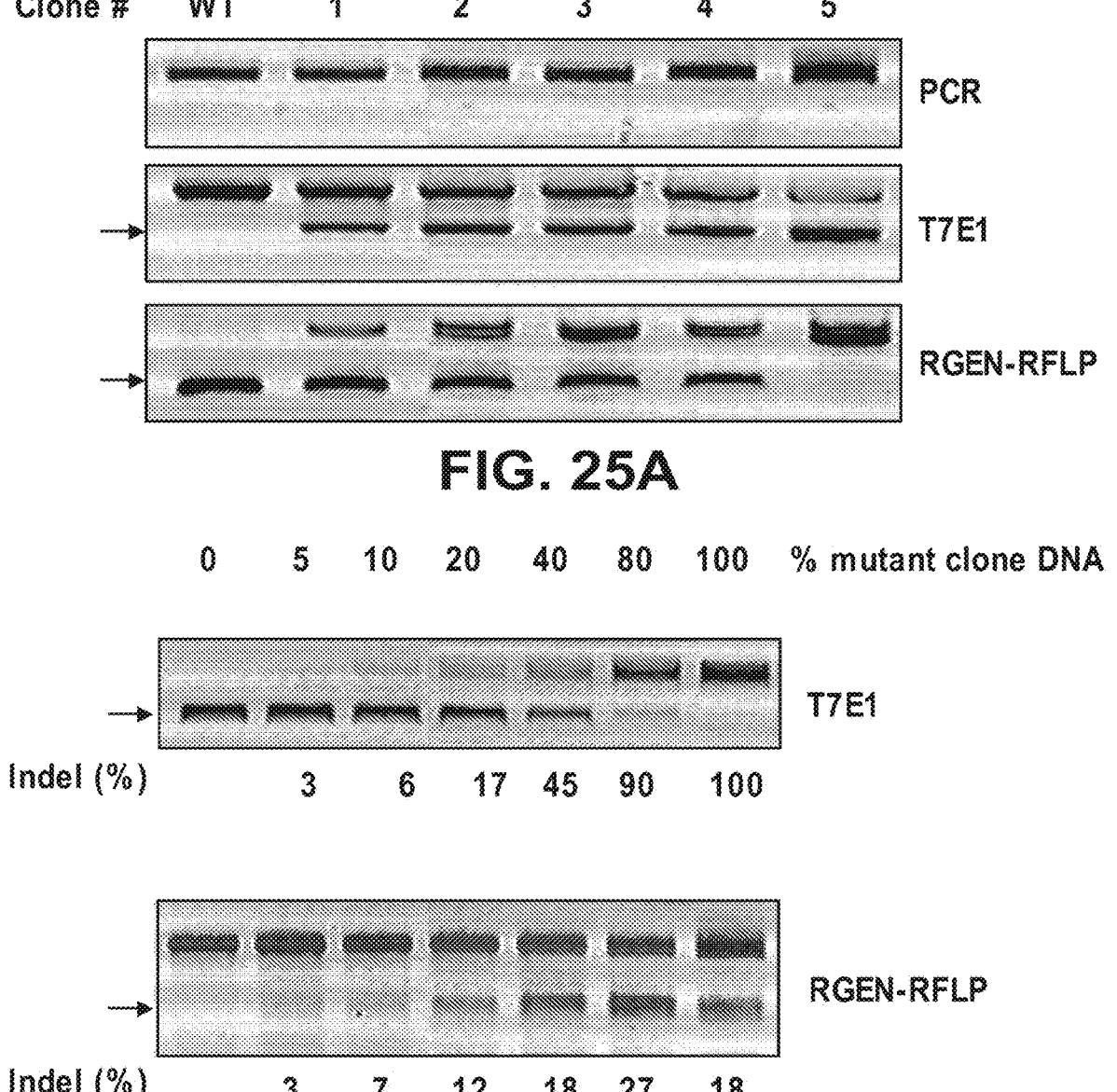

FIGS. 25A, 25B, and 25C show genotyping of RGEN-induced mutations via the RGEN-RFLP technique. FIG. 25A: Analysis of C4BPB-disrupted clones using RGEN-RFLP and T7E1 assays. Arrows indicate expected positions of DNA bands cleaved by RGEN or T7E1. FIG. 25B: Quantitative comparison of RGEN-RFLP analysis with T7E1 assays. Genomic DNA samples from wild-type and C4BPB-disrupted K562 cells were mixed in various ratios and subjected to PCR amplification. FIG. 25C: Genotyping of RGEN-induced mutations in the HLA-B gene in Hela cells with RFLP and T7E1 analyses.

Figure 26A:
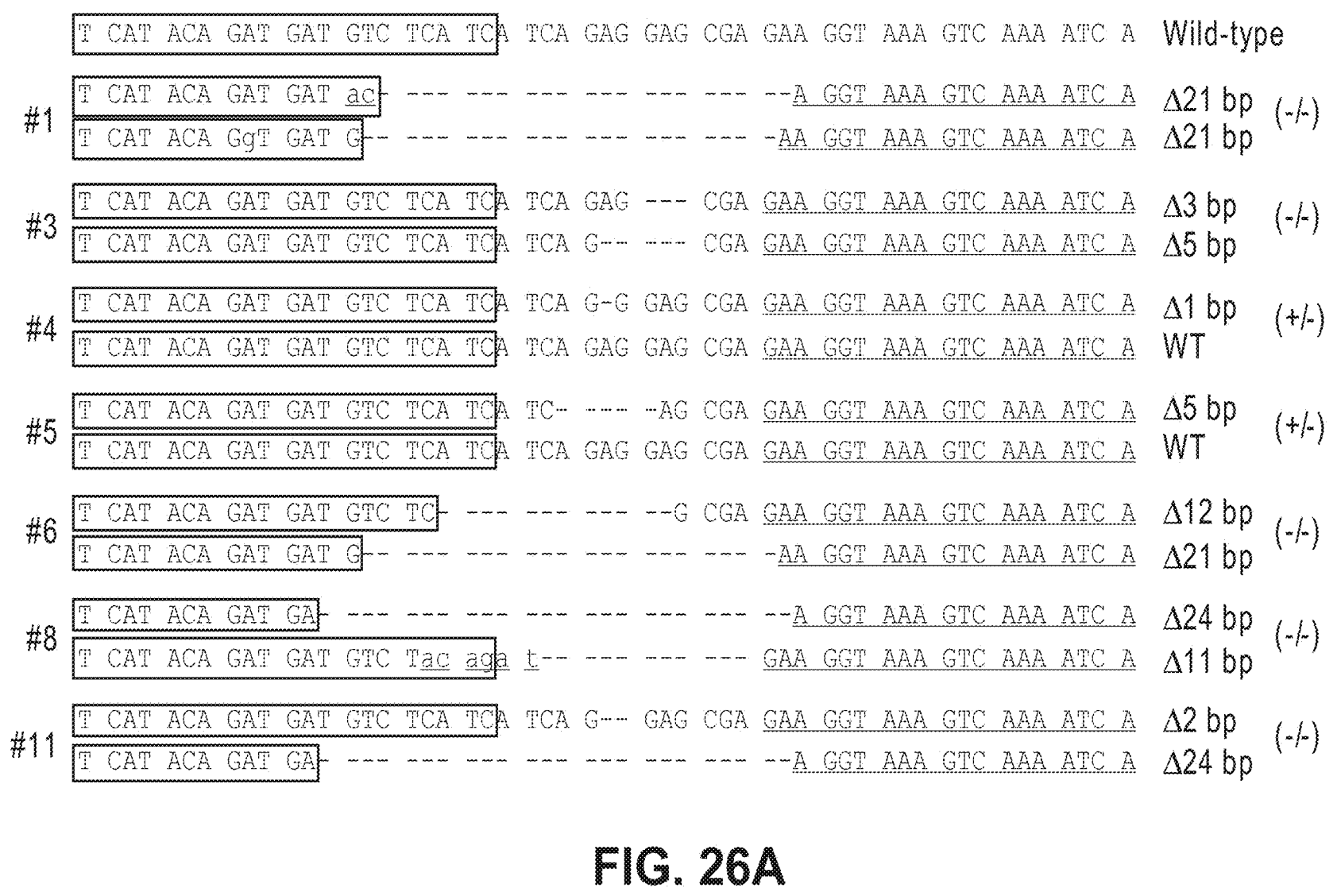
Figure 26B:
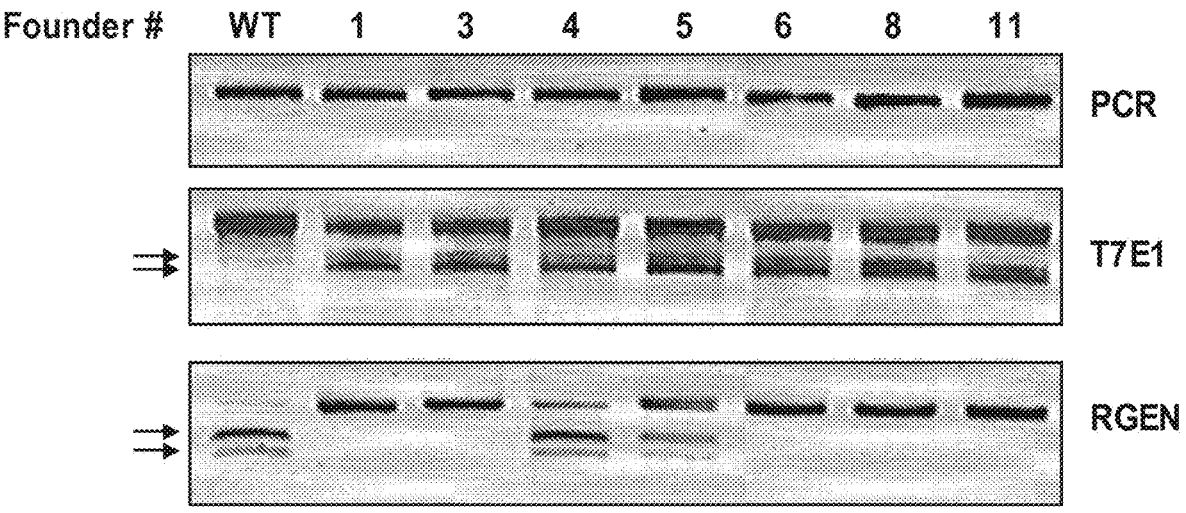

FIGS. 26A and 26B show genotyping of mutations induced by engineered nucleases in organisms via RGEN-mediated RFLP. FIG. 26A: Genotype of Pibf1 wild-type (WT) (SEQ ID NO: 242) and the following mutant founder mice: #1 (SEQ ID NO: 243 and SEQ ID NO: 244), #3 (SEQ ID NO: 245 and SEQ ID NO: 246), #4 (SEQ ID NO: 247 and SEQ ID NO: 242), #5 (SEQ ID NO: 246 and SEQ ID NO: 242), #6 (SEQ ID NO: 248 and SEQ ID NO: 249), #8 (SEQ ID NO: 250 and SEQ ID NO: 251), and #11 (SEQ ID NO: 252 and SEQ ID NO: 250). FIG. 26B: Comparison of the mismatch-sensitive T7E1 assay with RGEN-mediated RFLP analysis. Black arrows indicate the cleavage product by treatment of T7E1 enzyme or RGENS.

Figure 27:
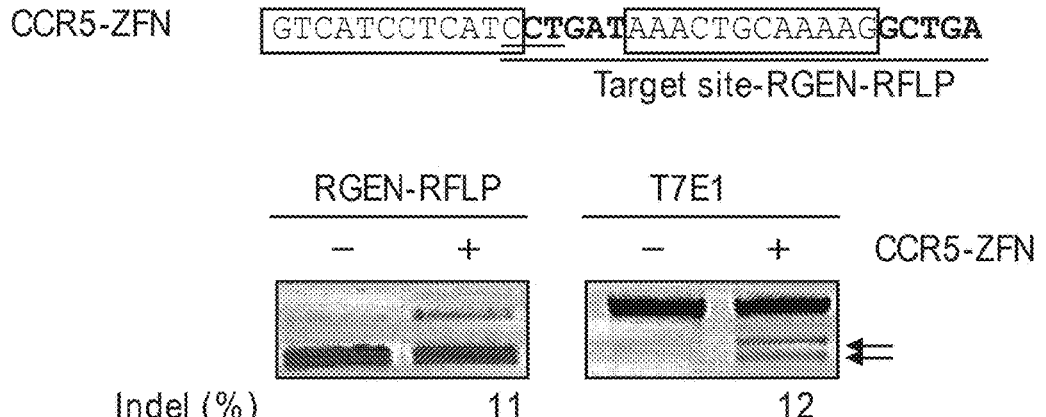

FIG. 27 shows RGEN-mediated genotyping of ZFN-induced mutations at a wild-type CCR5 sequence (SEQ ID NO: 253). The ZFN target site is shown in box. Black arrows indicate DNA bands cleaved by T7E1.

FIG. 28 shows polymorphic sites in a region of the human HLA-B gene (SEQ ID NO: 254). The sequence, which surrounds the RGEN target site, is that of a PCR amplicon from HeLa cells. Polymorphic positions are shown in box. The RGEN target site and the PAM sequence are shown in dashed and bolded box, respectively. Primer sequences are underlined.

Figure 29B:
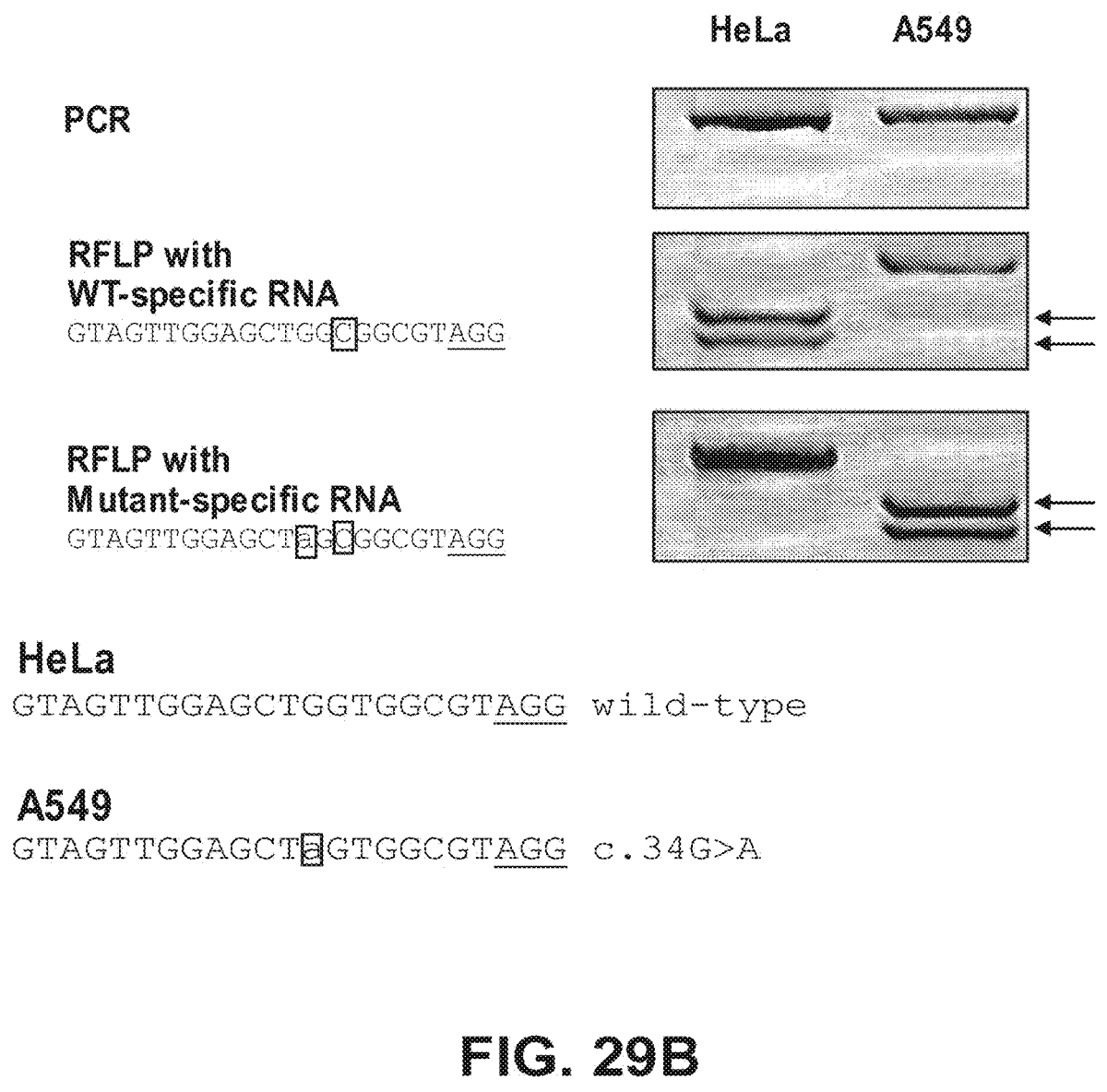

FIGS. 29A and 29B show genotyping of oncogenic mutations via RGEN-RFLP analysis. FIG. 29A: A recurrent mutation (c.133-135 deletion of TCT; SEQ ID NO: 256) in the human CTNNB1 gene in HCT116 cells was detected by RGENs. The wild-type CTNNB1 sequence is represented by SEQ ID NO: 255. Hela cells were used as a negative control. FIG. 29B: Genotyping of the KRAS substitution mutation (c.34 G>A) in the A549 cancer cell line with RGENs that contain mismatched guide RNA that are WT-specific (SEQ ID NO: 257) or mutant-specific (SEQ ID NO: 258). Mismatched nucleotides are shown in box. HeLa cells were used as a negative control. Arrows indicate DNA bands cleaved by RGENs. DNA sequences confirmed by Sanger sequencing are shown: wild-type (SEQ ID NO: 259) and c. 34G>A (SEQ ID NO: 260).

Figure 30A:
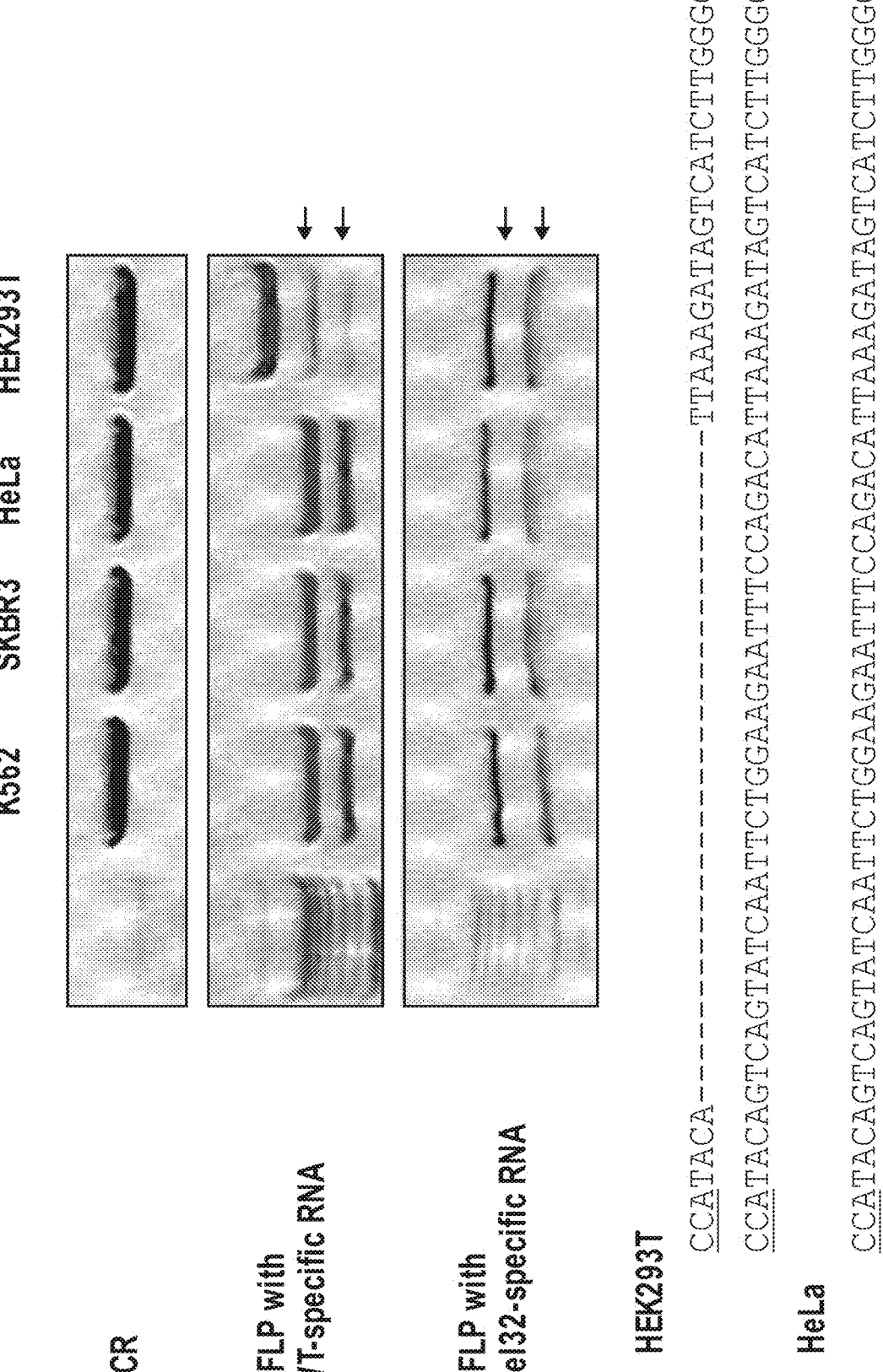
Figures 30B, 30C, 30D:
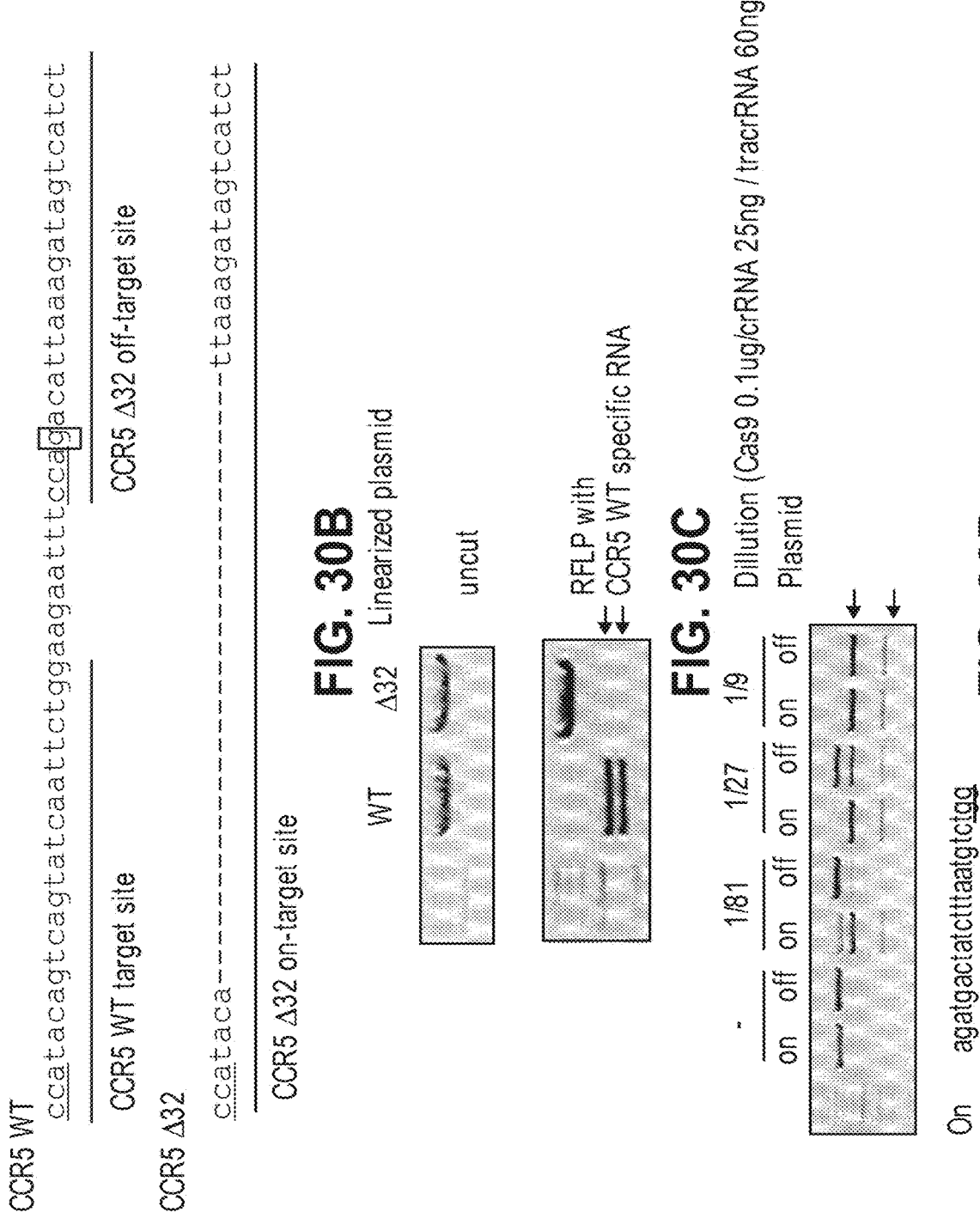

FIGS. 30A, 30B, 30C, and 30D show genotyping of the CCR5 delta32 allele in HEK293T cells via RGEN-RFLP analysis. FIG. 30A: RGEN-RFLP assays of cell lines. DNA sequences of the wild-type CCR5 locus (SEQ ID NO: 262) and delta 32 mutation (SEQ ID NO: 261) are shown. K562, SKBR3, and HeLa cells were used as wild-type controls. Arrows indicate DNA bands cleaved by RGENs. FIG. 30B: DNA sequence of wild-type (SEQ ID NO: 263) and delta32 CCR5 alleles (SEQ ID NO: 264). Both on-target and off-target sites of RGENs used in RFLP analysis are underlined. A single-nucleotide mismatch between the two sites is shown in box. The PAM sequence is underlined. FIG. 30C:

In vitro cleavage of plasmids harboring WT or del32 CCR5 alleles using the wild-type-specific RGEN. FIG. 30D Confirming the presence of an off-target site of the CCR5-delta32-specific RGEN at the CCR5 locus. In vitro cleavage assays of plasmids harboring either on-target (SEQ ID NO: 265) or off-target sequences (SEQ ID NO: 266) using various amounts of the del32-specific RGEN.

Figure 31A:
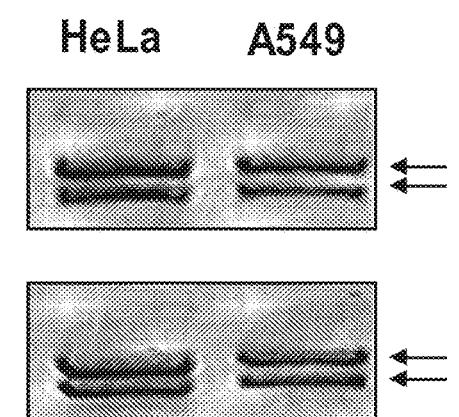

FIGS. 31A and 31B show genotyping of a KRAS point mutation (c.34 G>A). FIG. 31A: RGEN-RFLP analysis of the KRAS mutation (c.34 G>A) in cancer cell lines. PCR products from Hela cells (used as a wild-type control) or A549 cells, which are homozygous for the point mutation, were digested with RGENs with perfectly matched crRNA specific to the wild-type sequence (SEQ ID NO: 259) or the mutant sequence (SEQ ID NO: 260). KRAS genotypes in these cells were confirmed by Sanger sequencing. FIG. 31B: Plasmids harboring either the wild-type (SEQ ID NO: 259) or mutant KRAS sequences (SEQ ID NO: 260) were digested using RGENs with perfectly matched crRNAs or attenuated, one-base mismatched crRNAs: m7 (SEQ ID NO: 267), m6 (SEQ ID NO: 257), m5 (SEQ ID NO: 268), m4 (SEQ ID NO: 269), m8 (SEQ ID NO: 260), m7,8 (SEQ ID NO: 270), m6,8 (SEQ ID NO: 258), m5,8 (SEQ ID NO: 271), and m4,8 (SEQ ID NO: 272). Attenuated crRNAs that were chosen for genotyping are labeled in box above the gels.

Figure 32A:
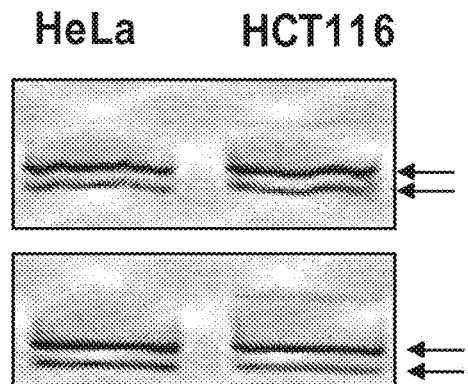

FIGS. 32A and 32B show genotyping of a PIK3CA point mutation (c.3140 A>G). FIG. 32A: RGEN-RFLP analysis of the PIK3CA mutation (c.3140 A>G) in cancer cell lines. PCR products from Hela cells (used as a wild-type control) or HCT116 cells that are heterozygous for the point mutation were digested with RGENs with perfectly matched crRNA specific to the wild-type sequence (SEQ ID NO: 273) or the mutant sequence (SEQ ID NO: 274). PIK3CA genotypes in these cells were confirmed by Sanger sequencing. FIG. 32B: Plasmids harboring either the wild-type PIK3CA sequence (SEQ ID NO: 273) or mutant PIK3CA sequence (SEQ ID NO: 274) were digested using RGENs with perfectly matched crRNAs or attenuated, one-base mismatched crRNAs: m5 (SEQ ID NO: 275), m6 (SEQ ID NO: 276), m7 (SEQ ID NO: 277), m10 (SEQ ID NO: 278), m13 (SEQ ID NO: 279), m16 (SEQ ID NO: 280), m19 (SEQ ID NO: 281), m4 (SEQ ID NO: 274), m4,5 (SEQ ID NO: 282), m4,6 (SEQ ID NO: 283), m4,7 (SEQ ID NO: 284), m4,10 (SEQ ID NO: 285), m4,13 (SEQ ID NO: 286), m4,16 (SEQ ID NO: 287), and m4,19 (SEQ ID NO: 288). Attenuated crRNAs that were chosen for genotyping are labeled in box above the gels.

Figure 33B:
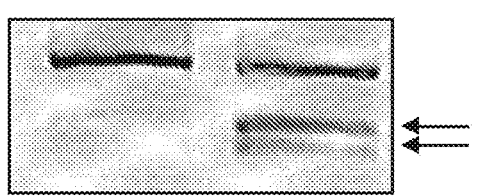

FIGS. 33A, 33B, 33C, and 33D show genotyping of recurrent point mutations in cancer cell lines. FIG. 33A: RGEN-RFLP assays to distinguish between a wild-type IDH gene sequence (SEQ ID NO: 289) and a recurrent oncogenic point mutation sequence in the IDH gene (c. 394c>T; SEQ ID NO: 290). RGENs with attenuated, one-base mismatched crRNAs, SEQ ID NO: 291 (WT-Specific RNA) and SEQ ID NO: 292 (Mutant-Specific RNA), distinguished the wild type and mutant IDH sequences. FIG. 33B: RGEN-RFLP assays to distinguish between a wild-type PIK3CA gene sequence (SEQ ID NO: 271) and a recurrent oncogenic point mutation sequence in the PIK3CA gene (c.3140A>G; SEQ ID NO: 273). RGENs with attenuated, one-base mismatched crRNAs, SEQ ID NO: 275 (WT-Specific RNA) and SEQ ID NO: 284 (Mutant-Specific RNA), distinguished the wild type and mutant PIK3CA sequences. FIG. 33C: RGEN-RFLP assays to distinguish between a wild-type NRAS gene sequence (SEQ ID NO: 293) and a recurrent oncogenic point mutation sequence in the NRAS gene (c.181C>A; SEQ ID NO: 294). RGENs with perfectly matched crRNAs, SEQ ID NO: 293 (WT-Specific RNA) and SEQ ID NO: 294 (Mutant-Specific RNA), distinguished the wild type and mutant NRAS sequences. FIG. 33D: RGEN-RFLP assays to distinguish between a wild-type BRAF gene sequence (SEQ ID NO: 295) and a recurrent oncogenic point mutation sequence in the BRAF gene (c.1799T>A; SEQ ID NO: 296). RGENs with perfectly matched crRNAs, SEQ ID NO: 295 (WT-Specific RNA) and SEQ ID NO: 296 (Mutant-Specific RNA), distinguished the wild type and mutant BRAF sequences. Genotypes of each cell line confirmed by Sanger sequencing are shown. Mismatched nucleotides are shown in box. Black arrows indicate DNA bands cleaved by RGENS.

BEST MODE FOR CARRYING OUT THE INVENTION

In accordance with one aspect of the invention, the present invention provides a composition for cleaving target DNA in eukaryotic cells or organisms comprising a guide RNA specific for target DNA or DNA that encodes the guide RNA, and Cas protein-encoding nucleic acid or Cas protein. In addition, the present invention provides a use of the composition for cleaving target DNA in eukaryotic cells or organisms comprising a guide RNA specific for target DNA or DNA that encodes the guide RNA, and Cas protein-encoding nucleic acid or Cas protein.

In the present invention, the composition is also referred to as a RNA-guided endonuclease (RGEN) composition.

ZFNs and TALENs enable targeted mutagenesis in mammalian cells, model organisms, plants, and livestock, but the mutation frequencies obtained with individual nucleases are widely different from each other. Furthermore, some ZFNs and TALENs fail to show any genome editing activities. DNA methylation may limit the binding of these engineered nucleases to target sites. In addition, it is technically challenging and time-consuming to make customized nucleases.

The present inventors have developed a new RNA-guided endonuclease composition based on Cas protein to overcome the disadvantages of ZFNs and TALENS.

Prior to the present invention, an endonuclease activity of Cas proteins has been known. However, it has not been known whether the endonuclease activity of Cas protein would function in an eukaryotic cell because of the complexity of the eukaryotic genome. Further, until now, a composition comprising Cas protein or Cas protein-encoding nucleic acid and a guide RNA specific for the target DNA to cleave a target DNA in eukaryotic cells or organisms has not been developed.

Compared to ZFNs and TALENs, the present RGEN composition based on Cas protein can be more readily customized because only the synthetic guide RNA component is replaced to make a new genome-editing nuclease. No sub-cloning steps are involved to make customized RNA guided endonucleases. Furthermore, the relatively small size of the Cas gene (for example, 4.2 kbp for Cas9) as compared to a pair of TALEN genes (~6 kbp) provides an advantage for this RNA-guided endonuclease composition in some applications such as virus-mediated gene delivery. Further, this RNA-guided endonuclease does not have off-target effects and thus does not induce unwanted mutations, deletion, inversions, and duplications. These features make the present RNA-guided endonuclease composition a scalable, versatile, and convenient tool for genome engineering in eukaryotic cells and organisms. In addition, RGEN can be designed to target any DNA sequence, almost any single nucleotide polymorphism or small insertion/deletion (indel)

can be analyzed via RGEN-mediated RFLP. The specificity of RGENS is determined by the RNA component that hybridizes with a target DNA sequence of up to 20 base pairs (bp) in length and by the Cas9 protein that recognizes the protospacer-adjacent motif (PAM). RGENS are readily reprogrammed by replacing the RNA component. Therefore, RGENs provide a platform to use simple and robust ROOFLP analysis for various sequence variations.

The target DNA may be an endogenous DNA, or artificial DNA, preferably, endogenous DNA.

As used herein, the term "Cas protein" refers to an essential protein component in the CRISPR/Cas system, forms an active endonuclease or nickase when complexed with two RNAs termed CRISPR RNA (crRNA) and trans-activating crRNA (tracrRNA).

The information on the gene and protein of Cas are available from GenBank of National Center for Biotechnology Information (NCBI), without limitation.

The CRISPR-associated (cas) genes encoding Cas proteins are often associated with CRISPR repeat-spacer arrays. More than forty different Cas protein families have been described. Of these protein families, Cas1 appears to be ubiquitous among different CRISPR/Cas systems. There are three types of CRISPR-Cas system. Among them, Type II CRISPR/Cas system involving Cas9 protein and crRNA and tracrRNA is representative and is well known. Particular combinations of cas genes and repeat structures have been used to define 8 CRISPR subtypes (Ecoli, Ypest, Nmeni, Dvulg, Tneap, Hmari, Apern, and Mtube).

The Cas protein may be linked to a protein transduction domain. The protein transduction domain may be poly-arginine or a TAT protein derived from HIV, but it is not limited thereto.

The present composition may comprise Cas component in the form of a protein or in the form of a nucleic acid encoding Cas protein.

In the present invention, Cas protein may be any Cas protein provided that it has an endonuclease or nickase activity when complexed with a guide RNA.

Preferably, Cas protein is Cas9 protein or variants thereof. The variant of the Cas9 protein may be a mutant form of Cas9 in which the catalytic aspartate residue is changed to any other amino acid. Preferably, the other amino acid may be an alanine, but it is not limited thereto.

Further, Cas protein may be the one isolated from an organism such as *Streptococcus* sp., preferably *Streptococcus pyogenes* or a recombinant protein, but it is not limited thereto.

The Cas protein derived from *Streptococcus pyogenes* may recognize NGG trinucleotide. The Cas protein may comprise an amino acid sequence of SEQ ID NO: 109, but it is not limited thereto.

The term "recombinant" when used with reference, e.g., to a cell, nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, a recombinant Cas protein may be generated by reconstituting Cas protein-encoding sequence using the human codon table.

As for the present invention, Cas protein-encoding nucleic acid may be a form of vector, such as plasmid comprising Cas-encoding sequence under a promoter such as CMV or CAG. When Cas protein is Cas9, Cas9 encoding sequence may be derived from *Streptococcus* sp., and preferably derived from *Streptococcus pyogenes*. For example, Cas9 encoding nucleic acid may comprise the nucleotide sequence of SEQ ID. NO: 1. Moreover, Cas9 encoding nucleic acid may comprise the nucleotide sequence having homology of at least 50% to the sequence of SEQ ID NO: 1, preferably at least 60, 70, 80, 90, 95, 97, 98, or 99% to the SEQ ID NO:1, but it is not limited thereto. Cas9 encoding nucleic acid may comprise the nucleotide sequence of SEQ ID NOs. 108, 110, 106, or 107.

As used herein, the term "guide RNA" refers to a RNA which is specific for the target DNA and can form a complex with Cas protein and bring Cas protein to the target DNA.

In the present invention, the guide RNA may consist of two RNA, i.e., CRISPR RNA (crRNA) and transactivating crRNA (tracrRNA) or be a single-chain RNA (sgRNA) produced by fusion of an essential portion of crRNA and tracrRNA.

The guide RNA may be a dualRNA comprising a crRNA and a tracrRNA.

If the guide RNA comprises the essential portion of crRNA and tracrRNA and a portion complementary to a target, any guide RNA may be used in the present invention.

The crRNA may hybridize with a target DNA.

The RGEN may consist of Cas protein, and dualRNA (invariable tracrRNA and target-specific crRNA), or Cas protein and sgRNA (fusion of an essential portion of invariable tracrRNA and target-specific crRNA), and may be readily reprogrammed by replacing crRNA.

The guide RNA further comprises one or more additional nucleotides at the 5' end of the single-chain guide RNA or the crRNA of the dualRNA.

Preferably, the guide RNA further comprises 2-additional guanine nucleotides at the 5' end of the single-chain guide RNA or the crRNA of the dualRNA.

The guide RNA may be transferred into a cell or an organism in the form of RNA or DNA that encodes the guide RNA. The guide RNA may be in the form of an isolated RNA, RNA incorporated into a viral vector, or is encoded in a vector. Preferably, the vector may be a viral vector, plasmid vector, or *agrobacterium* vector, but it is not limited thereto.

A DNA that encodes the guide RNA may be a vector comprising a sequence coding for the guide RNA. For example, the guide RNA may be transferred into a cell or organism by transfecting the cell or organism with the isolated guide RNA or plasmid DNA comprising a sequence coding for the guide RNA and a promoter.

Alternatively, the guide RNA may be transferred into a cell or organism using virus-mediated gene delivery.

When the guide RNA is transfected in the form of an isolated RNA into a cell or organism, the guide RNA may be prepared by in vitro transcription using any in vitro transcription system known in the art. The guide RNA is preferably transferred to a cell in the form of isolated RNA rather than in the form of plasmid comprising encoding sequence for a guide RNA. As used herein, the term "isolated RNA" may be interchangeable to "naked RNA". This is cost- and time-saving because it does not require a step of cloning. However, the use of plasmid DNA or virus-mediated gene delivery for transfection of the guide RNA is not excluded.

The present RGEN composition comprising Cas protein or Cas protein-encoding nucleic acid and a guide RNA can specifically cleave a target DNA due to a specificity of the guide RNA for a target and an endonuclease or nickase activity of Cas protein.

As used herein, the term "cleavage" refers to the breakage of the covalent backbone of a nucleotide molecule.

In the present invention, a guide RNA may be prepared to be specific for any target which is to be cleaved. Therefore, the present RGEN composition can cleave any target DNA by manipulating or genotyping the target-specific portion of the guide RNA.

The guide RNA and the Cas protein may function as a pair. As used herein, the term "paired Cas nickase" may refer to the guide RNA and the Cas protein functioning as a pair. The pair comprises two guide RNAs. The guide RNA and Cas protein may function as a pair, and induce two nicks on different DNA strand. The two nicks may be separated by at least 100 bps, but are not limited thereto.

In the Example, the present inventors confirmed that paired Cas nickase allow targeted mutagenesis and large deletions of up to 1-kbp chromosomal segments in human cells. Importantly, paired nickases did not induce indels at off-target sites at which their corresponding nucleases induce mutations. Furthermore, unlike nucleases, paired nickases did not promote unwanted translocations associated with off-target DNA cleavages. In principle, paired nickases double the specificity of Cas9-mediated mutagenesis and will broaden the utility of RNA-guided enzymes in applications that require precise genome editing such as gene and cell therapy.

In the present invention, the composition may be used in the genotyping of a genome in the eukaryotic cells or organisms in vitro.

In one specific embodiment, the guide RNA may comprise the nucleotide sequence of Seq ID. No. 1, wherein the portion of nucleotide position 3~ 22 is a target-specific portion and thus, the sequence of this portion may be changed depending on a target.

As used herein, a eukaryotic cell or organism may be yeast, fungus, protozoa, plant, higher plant, and insect, or amphibian cells, or mammalian cells such as CHO, HeLa, HEK293, and COS-1, for example, cultured cells (in vitro), graft cells and primary cell culture (in vitro and ex vivo), and in vivo cells, and also mammalian cells including human, which are commonly used in the art, without limitation.

In one specific embodiment, it was found that Cas9 protein/single-chain guide RNA could generate site-specific DNA double-strand breaks in vitro and in mammalian cells, whose spontaneous repair induced targeted genome mutations at high frequencies.

Moreover, it was found that gene-knockout mice could be induced by the injection of Cas9 protein/guide RNA complexes or Cas9 mRNA/guide RNA into one-cell stage embryo and germ-line transmittable mutations could be generated by Cas9/guide RNA system.

Using Cas protein rather than a nucleic acid encoding Cas protein to induce a targeted mutagenesis is advantageous because exogeneous DNA is not introduced into an organism. Thus, the composition comprising Cas protein and a guide RNA may be used to develop therapeutics or value-added crops, livestock, poultry, fish, pets, etc.

In accordance with another aspect of the invention, the present invention provides a composition for inducing targeted mutagenesis in eukaryotic cells or organisms, comprising a guide RNA specific for target DNA or DNA that encodes the guide RNA, and Cas protein-encoding nucleic acid or Cas protein. In addition, the present invention provides a use of the composition for inducing targeted mutagenesis in eukaryotic cells or organisms, comprising a guide RNA specific for target DNA or DNA that encodes the guide RNA, and Cas protein-encoding nucleic acid or Cas protein.

A guide RNA, Cas protein-encoding nucleic acid or Cas protein are as described in the above.

In accordance with another aspect of the invention, the present invention provides a kit for cleaving a target DNA or inducing targeted mutagenesis in eukaryotic cells or organisms comprising a guide RNA specific for target DNA or DNA that encodes the guide RNA, and Cas protein-encoding nucleic acid or Cas protein.

A guide RNA, Cas protein-encoding nucleic acid or Cas protein are as described in the above.

The kit may comprise a guide RNA and Cas protein-encoding nucleic acid or Cas protein as separate components or as one composition.

The present kit may comprise some additional components necessary for transferring the guide RNA and Cas component to a cell or an organism. For example, the kit may comprise an injection buffer such as DEPC-treated injection buffer, and materials necessary for analysis of mutation of a target DNA, but are not limited thereto.

In accordance with another aspect, the present invention provides a method for preparing a eukaryotic cell or organism comprising Cas protein and a guide RNA comprising a step of co-transfecting or serial-transfecting the eukaryotic cell or organism with a Cas protein-encoding nucleic acid or Cas protein, and a guide RNA or DNA that encodes the guide RNA.

A guide RNA, Cas protein-encoding nucleic acid or Cas protein are as described in the above.

In the present invention, a Cas protein-encoding nucleic acid or Cas protein and a guide RNA or DNA that encodes the guide RNA may be transferred into a cell by various methods known in the art, such as microinjection, electroporation, DEAE-dextran treatment, lipofection, nanoparticle-mediated transfection, protein transduction domain mediated transduction, virus-mediated gene delivery, and PEG-mediated transfection in protoplast, and so on, but are not limited thereto. Also, a Cas protein encoding nucleic acid or Cas protein and a guide RNA may be transferred into an organism by various method known in the art to administer a gene or a protein such as injection. A Cas protein-encoding nucleic acid or Cas protein may be transferred into a cell in the form of complex with a guide RNA, or separately. Cas protein fused to a protein transduction domain such as Tat can also be delivered efficiently into cells.

Preferably, the eukaryotic cell or organism is co-transfected or serial-transfected with a Cas9 protein and a guide RNA.

The serial-transfection may be performed by transfection with Cas protein-encoding nucleic acid first, followed by second transfection with naked guide RNA. Preferably, the second transfection is after 3, 6, 12, 18, 24 hours, but it is not limited thereto.

In accordance with another aspect, the present invention provides a eukaryotic cell or organism comprising a guide RNA specific for target DNA or DNA that encodes the guide RNA, and Cas protein-encoding nucleic acid or Cas protein.

The eukaryotic cells or organisms may be prepared by transferring the composition comprising a guide RNA specific for target DNA or DNA that encodes the guide RNA, and Cas protein-encoding nucleic acid or Cas protein into the cell or organism.

The eukaryotic cell may be yeast, fungus, protozoa, higher plant, and insect, or amphibian cells, or mammalian cells such as CHO, HeLa, HEK293, and COS-1, for example, cultured cells (in vitro), graft cells and primary cell culture (in vitro and ex vivo), and in vivo cells, and also mammalian cells including human, which are commonly used in the art, without limitation. Further the organism may be yeast, fungus, protozoa, plant, higher plant, insect, amphibian, or mammal.

In accordance with another aspect of the invention, the present invention provides a method for cleaving a target DNA or inducing targeted mutagenesis in eukaryotic cells or organisms, comprising a step of treating a cell or organism comprising a target DNA with a composition comprising a guide RNA specific for target DNA or DNA that encodes the guide RNA, and Cas protein-encoding nucleic acid or Cas protein.

The step of treating a cell or organism with the composition may be performed by transferring the present composition comprising a guide RNA specific for target DNA or DNA that encodes the guide RNA, and Cas protein-encoding nucleic acid or Cas protein into the cell or organism.

As described in the above, such transfer may be performed by microinjection, transfection, electroporation, and so on.

In accordance with another aspect of the invention, the present invention provides an embryo comprising a genome edited by the present RGEN composition comprising a guide RNA specific for target DNA or DNA that encodes the guide RNA, and Cas protein-encoding nucleic acid or Cas protein.

Any embryo can be used in the present invention, and for the present invention, the embryo may be an embryo of a mouse. The embryo may be produced by injecting PMSG (Pregnant Mare Serum Gonadotropin) and hCG (human Chorionic Gonadotropin) into a female mouse of 4 to 7 weeks and the super-ovulated female mouse may be mated to males, and the fertilized embryos may be collected from oviducts.

The present RGEN composition introduced into an embryo can cleave a target DNA complementary to the guide RNA by the action of Cas protein and cause a mutation in the target DNA. Thus, the embryo into which the present RGEN composition has been introduced has an edited genome.

In one specific embodiment, it was found that the present RGEN composition could cause a mutation in a mouse embryo and the mutation could be transmitted to offspring.

A method for introducing the RGEN composition into the embryo may be any method known in the art, such as microinjection, stem cell insertion, retrovirus insertion, and so on. Preferably, a microinjection technique can be used.

In accordance with another aspect, the present invention provides a genome-modified animal obtained by transferring the embryo comprising a genome edited by the present RGEN composition into the oviducts of an animal.

In the present invention, the term "genome-modified animal" refers to an animal of which genome has been modified in the stage of embryo by the present RGEN composition and the type of the animal is not limited.

The genome-modified animal has mutations caused by a targeted mutagenesis based on the present RGEN composition. The mutations may be any one of deletion, insertion, translocation, inversion. The site of mutation depends on the sequence of guide RNA of the RGEN composition.

The genome-modified animal having a mutation of a gene may be used to determine the function of the gene.

In accordance with another aspect of the invention, the present invention provides a method of preparing a genome-modified animal comprising a step of introducing the present RGEN composition comprising a guide RNA specific for the target DNA or DNA that encodes the guide RNA and Cas protein-encoding nucleic acid or Cas protein into an embryo of an animal; and a step of transferring the embryo into a oviduct of pseudopregnant foster mother to produce a genome-modified animal.

The step of introducing the present RGEN composition may be accomplished by any method known in the art such as microinjection, stem cell insertion, retroviral insertion, and so on.

In accordance with another aspect of the invention, the present invention provides a plant regenerated form the genome-modified protoplasts prepared by the method for eukaryotic cells comprising the RGEN composition.

In accordance with another aspect of the invention, the present invention provides a composition for genotyping mutations or variations in an isolated biological sample, comprising a guide RNA specific for the target DNA sequence Cas protein. In addition, the present invention provides a composition for genotyping nucleic acid sequences in pathogenic microorganisms in an isolated biological sample, comprising a guide RNA specific for the target DNA sequence and Cas protein.

A guide RNA, Cas protein-encoding nucleic acid or Cas protein are as described in the above.

As used herein the term "genotyping" refers to the "Restriction fragment length polymorphism (RFLP) assay".

RFLP may be used in 1) the detection of indel in cells or organisms induced by the engineered nucleases, 2) the genotyping naturally-occurring mutations or variations in cells or organisms, or 3) the genotyping the DNA of infected pathogenic microorganisms including virus or bacteria, etc.

The mutations or variation may be induced by engineered nucleases in cells.

The engineered nuclease may be a Zinc Finger Nuclease (ZFNs), Transcription Activator-Like Effector Nucleases (TALENs), or RGENs, but it is not limited thereto.

As used herein the term "biological sample" includes samples for analysis, such as tissues, cells, whole blood, serum, plasma, saliva, sputum, cerebrospinal fluid or urine, but is not limited thereto.

The mutations or variation may be a naturally-occurring mutations or variations.

The mutations or variations are induced by the pathogenic microorganisms. Namely, the mutations or variations occur due to the infection of pathogenic microorganisms, when the pathogenic microorganisms are detected, the biological sample is identified as infected.

The pathogenic microorganisms may be virus or bacteria, but are not limited thereto.

Engineered nuclease-induced mutations are detected by various methods, which include mismatch-sensitive Surveyor or T7 endonuclease I (T7E1) assays, RFLP analysis, fluorescent PCR, DNA melting analysis, and Sanger and deep sequencing. The T7E1 and Surveyor assays are widely used but often underestimate mutation frequencies because the assays detect heteroduplexes (formed by the hybridization of mutant and wild-type sequences or two different mutant sequences); they fail to detect homoduplexes formed by the hybridization of two identical mutant sequences. Thus, these assays cannot distinguish homozygous biallelic mutant clones from wild-type cells nor heterozygous biallelic mutants from heterozygous monoallelic mutants (FIG. 22). In addition, sequence polymorphisms near the nuclease target site can produce confounding results because the enzymes can cleave heteroduplexes formed by hybridization of these different wild-type alleles. RFLP analysis is free of these limitations and therefore is a method of choice. Indeed, RFLP analysis was one of the first methods used to detect engineered nuclease-mediated mutations. Unfortunately, however, it is limited by the availability of appropriate restriction sites.

In accordance with another aspect of the invention, the present invention provides a kit for genotyping mutations or variations in an isolated biological sample, comprising the composition for genotyping mutations or variations in an isolated biological sample. In addition, the present invention provides a kit for genotyping nucleic acid sequences in pathogenic microorganisms in an isolated biological sample, comprising a guide RNA specific for the target DNA sequence and Cas protein.

A guide RNA, Cas protein-encoding nucleic acid or Cas protein are as described in the above.

In accordance with another aspect of the invention, the present invention provides a method of genotyping mutations or variations in an isolated biological sample, using the composition for genotyping mutations or variations in an isolated biological sample. In addition, the present invention provides a method of genotyping nucleic acid sequences in pathogenic microorganisms in an isolated biological sample, comprising a guide RNA specific for the target DNA sequence and Cas protein.

A guide RNA, Cas protein-encoding nucleic acid or Cas protein are as described in the above.

MODE FOR THE INVENTION

Hereinafter, the present invention will be described in more detail with reference to Examples. However, these Examples are for illustrative purposes only, and the invention is not intended to be limited by these Examples.

Example 1: Genome Editing Assay 1-1. DNA Cleavage Activity of Cas9 Protein

Firstly, the DNA cleavage activity of Cas9 derived from *Streptococcus pyogenes* in the presence or absence of a chimeric guide RNA in vitro was tested.

Figure 1A:
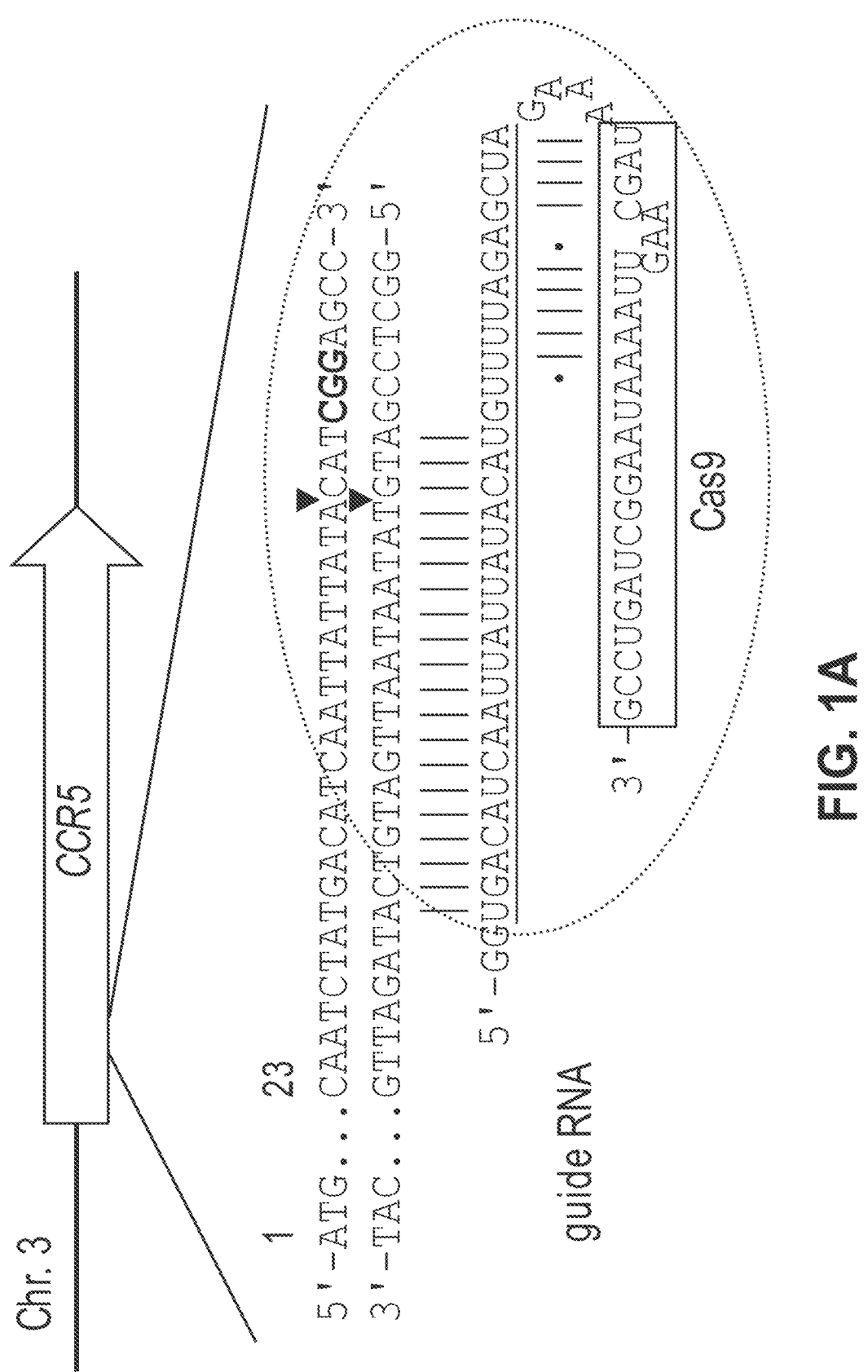

To this end, recombinant Cas9 protein that was expressed in and purified from *E. coli* was used to cleave a predigested or circular plasmid DNA that contained the 23-base pair (bp) human CCR5 target sequence. A Cas9 target sequence consists of a 20-bp DNA sequence complementary to crRNA or a chimeric guide RNA and the trinucleotide (5'-NGG-3') protospacer adjacent motif (PAM) recognized by Cas9 itself (FIG. 1A).

Specifically, the Cas9-coding sequence (4,104 bp), derived from *Streptococcus pyogenes* strain M1 GAS (NC_002737.1), was reconstituted using the human codon usage table and synthesized using oligonucleotides. First, 1-kb DNA segments were assembled using overlapping ~35-mer oligonucleotides and Phusion™ polymerase (New England Biolabs) and cloned into T-vector (SolGent). A full-length Cas9 sequence was assembled using four 1-kbp DNA segments by overlap PCR. The Cas9-encoding DNA segment was subcloned into p3s, which was derived from pcDNA3.1 (Invitrogen). In this vector, a peptide tag (NH2-GGSGPPKKKRKVYPYDVPDYA-COOH, SEQ ID NO: 2) containing the HA epitope and a nuclear localization signal (NLS) was added to the C-terminus of Cas9. Expression and nuclear localization of the Cas9 protein in HEK 293T cells were confirmed by western blotting using anti-HA antibody (Santa Cruz).

Then, the Cas9 cassette was subcloned into pET28-b (+) and transformed into BL21 (DE3). The expression of Cas9 was induced using 0.5 mM IPTG for 4 h at 25° C. The Cas9 protein containing the His6-tag at the C terminus was purified using Ni-NTA agarose resin (Qiagen) and dialyzed against 20 mM HEPES (pH 7.5), 150 mM KCl, 1 mM DTT, and 10% glycerol (1). Purified Cas9 (50 nM) was incubated with super-coiled or pre-digested plasmid DNA (300 ng) and chimeric RNA (50 nM) in a reaction volume of 20 μl in NEB buffer 3 for 1 h at 37° C. Digested DNA was analyzed by electrophoresis using 0.8% agarose gels.

Cas9 cleaved the plasmid DNA efficiently at the expected position only in the presence of the synthetic RNA and did not cleave a control plasmid that lacked the target sequence (FIG. 1B).

1-2. DNA Cleavage by Cas9/Guide RNA Complex in Human Cells

A RFP-GFP reporter was used to investigate whether the Cas9/guide RNA complex can cleave the target sequence incorporated between the RFP and GFP sequences in mammalian cells.

Figure 2A:
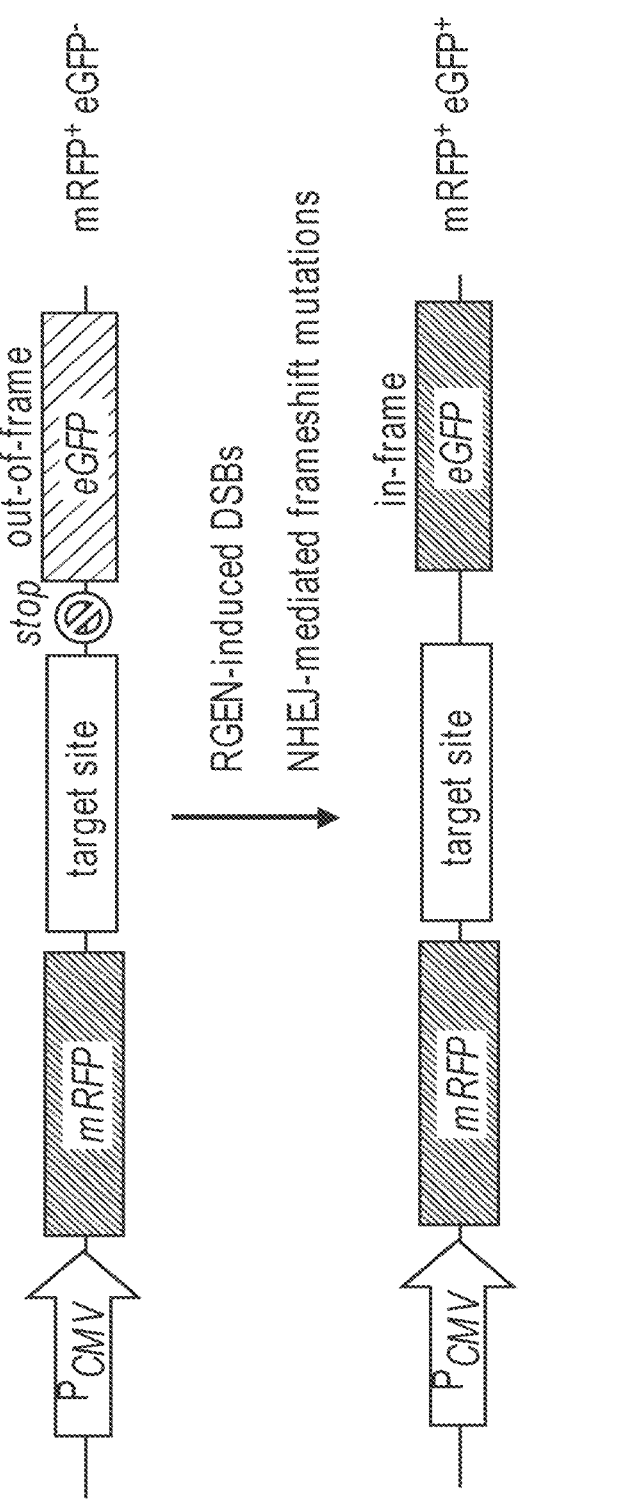
FIGS. 2A and 2B show Cas9-induced mutagenesis at an episomal target site.
Figure 2B:
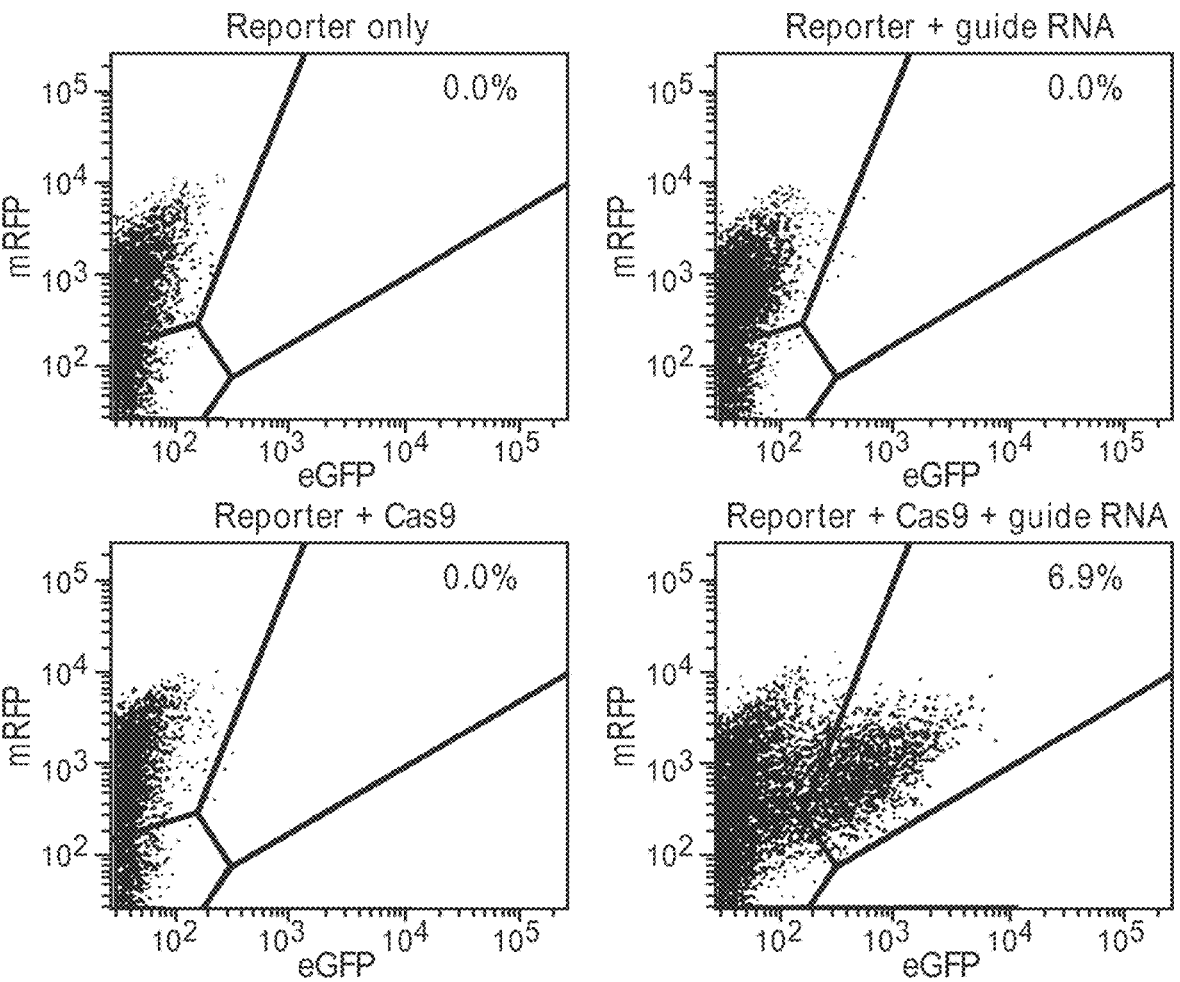

In this reporter, the GFP sequence is fused to the RFP sequence out-of-frame (2). The active GFP is expressed only when the target sequence is cleaved by site-specific nucleases, which causes frameshifting small insertions or deletions (indels) around the target sequence via error-prone non-homologous end-joining (NHEJ) repair of the double-strand break (DSB) (FIG. 2).

The RFP-GFP reporter plasmids used in this study were constructed as described previously (2). Oligonucleotides corresponding to target sites (Table 1) were synthesized (Macrogen) and annealed. The annealed oligonucleotides were ligated into a reporter vector digested with EcoRI and BamHI.

HEK 293T cells were co-transfected with Cas9-encoding plasmid (0.8 μg) and the RFP-GFP reporter plasmid (0.2 μg) in a 24-well plate using Lipofectamine™ 2000 (Invitrogen).

Meanwhile, the in vitro transcribed chimeric RNA had been prepared as follows. RNA was in vitro transcribed through run-off reactions using the MEGAshortscript™ T7 kit (Ambion) according to the manufacturer's manual. Templates for RNA in vitro transcription were generated by annealing two complementary single strand DNAs or by PCR amplification (Table 1). Transcribed RNA was resolved on a 8% denaturing urea-PAGE gel. The gel slice containing RNA was cut out and transferred to probe elution buffer. RNA was recovered in nuclease-free water followed by phenol: chloroform extraction, chloroform extraction, and ethanol precipitation. Purified RNAs were quantified by spectrometry.

At 12 h post transfection, chimeric RNA (1 μg) prepared by in vitro transcription was transfected using Lipofectamine 2000.

At 3d post-transfection, transfected cells were subjected to flow cytometry and cells expressing both RFP and GFP were counted.

It was found that GFP-expressing cells were obtained only when the cells were transfected first with the Cas9 plasmid and then with the guide RNA 12 h later (FIG. 2), demonstrating that RGENs could recognize and cleave the target DNA sequence in cultured human cells. Thus GFP-expressing cells were obtained by serial-transfection of the Cas9 plasmid and the guide RNA rather than co-transfection.

TABLE 1

| Gene | | sequence (5' to 3') | SEQ ID NO. |
|------|---|---------------------|------------|
| Oligonucleotides used for the construction of the reporter plasmid | | | |
| CCR5 | F | AATTCATGACATCAATTATTATACATCGGAGGAG | 3 |
| | R | GATCCTCCTCCGATGTATAATAATTGATGTCATG | 4 |
| Primers used in the T7E1 assay | | | |
| CCR5 | F1 | CTCCATGGTGCTATAGAGCA | 5 |
| | F2 | GAGCCAAGCTCTCCATCTAGT | 6 |
| | R | GCCCTGTCAAGAGTTGACAC | 7 |
| C4BPB | F1 | TATTTGGCTGGTTGAAAGGG | 8 |
| | R1 | AAAGTCATGAAATAAACACACCCA | 9 |
| | F2 | CTGCATTGATATGGTAGTACCATG | 10 |
| | R2 | GCTGTTCATTGCAATGGAATG | 11 |
| Primers used for the amplification of off-target sites | | | |
| ADCY5 | F1 | GCTCCCACCTTAGTGCTCTG | 12 |
| | R1 | GGTGGCAGGAACCTGTATGT | 13 |
| | F2 | GTCATTGGCCAGAGATGTGGA | 14 |
| | R2 | GTCCCATGACAGGCGTGTAT | 15 |
| KCNJ6 | F | GCCTGGCCAAGTTTCAGTTA | 16 |
| | R1 | TGGAGCCATTGGTTTGCATC | 17 |
| | R2 | CCAGAACTAAGCCGTTTCTGAC | 18 |
| CNTNAP2 | F1 | ATCACCGACAACCAGTTTCC | 19 |
| | F2 | TGCAGTGCAGACTCTTTCCA | 20 |
| | R | AAGGACACAGGGCAACTGAA | 21 |
| N/A Chr. 5 | F1 | TGTGGAACGAGTGGTGACAG | 22 |
| | R1 | GCTGGATTAGGAGGCAGGATTC | 23 |
| | F2 | GTGCTGAGAACGCTTCATAGAG | 24 |
| | R2 | GGACCAAAGGACATTCTTCTCAC | 25 |
| Primers used for the detection of chromosomal deletions | | | |
| Deletion | F | CCACATCTCGTTCTCGGTTT | 26 |
| | R | TCACAAGCCCACAGATATTT | 27 |

1-3. Targeted Disruption of Endogenous Genes in Mammalian Cells by RGEN

To test whether RGENs could be used for targeted disruption of endogenous genes in mammalian cells, genomic DNA isolated from transfected cells using T7 endonuclease I (T7E1), a mismatch-sensitive endonuclease that specifically recognizes and cleaves heteroduplexes formed by the hybridization of wild-type and mutant DNA sequences was analyzed (3).

To introduce DSBs in mammalian cells using RGENs, $2 \times 10^6$ K562 cells were transfected with 20 μg of Cas9-encoding plasmid using the 4D-Nucleofector™, SF Cell Line 4D-Nucleofector® X Kit, Program FF-120 (Lonza) according to the manufacturer's protocol. For this experiment, K562 (ATCC, CCL-243) cells were grown in RPMI-1640 with 10% FBS and the penicillin/streptomycin mix (100 U/ml and 100 μg/ml, respectively).

After 24 h, 10-40 μg of in vitro transcribed chimeric RNA was nucleofected into $1 \times 10^6$ K562 cells. The in vitro transcribed chimeric RNA had been prepared as described in the Example 1-2.

Cells were collected two days after RNA transfection and genomic DNA was isolated. The region including the target site was PCR-amplified using the primers described in Table 1. The amplicons were subjected to the T7E1 assay as described previously (3). For sequencing analysis, PCR products corresponding to genomic modifications were purified and cloned into the T-Blunt vector using the T-Blunt PCR Cloning Kit (SolGent). Cloned products were sequenced using the M13 primer.

Figure 3A:
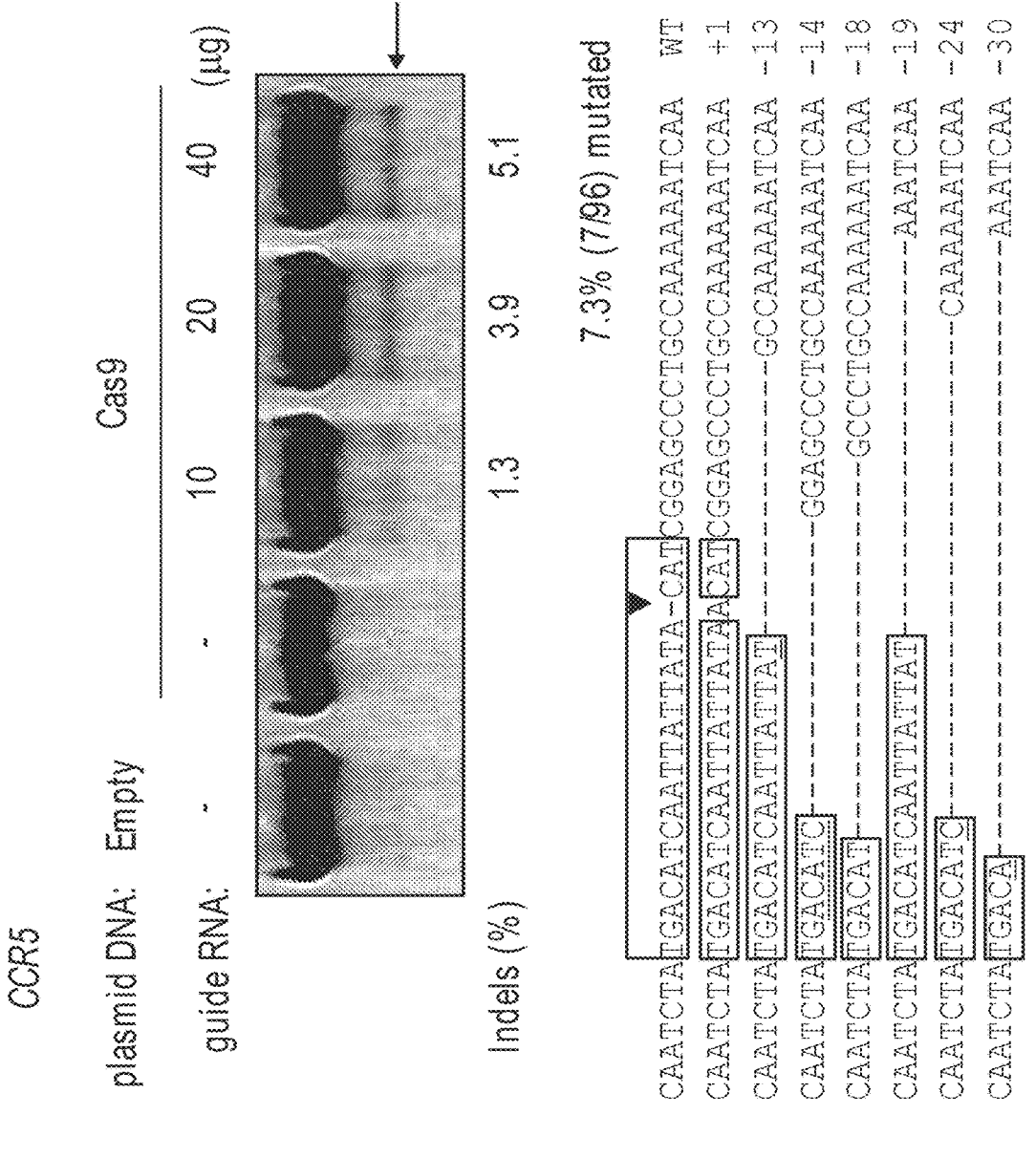
FIGS. 3A and 3B show RGEN-driven mutations at endogenous chromosomal sites.

It was found that mutations were induced only when the cells were transfected serially with Cas9-encoding plasmid and then with guide RNA (FIG. 3). Mutation frequencies (Indels (%) in FIG. 3A) estimated from the relative DNA band intensities were RNA-dosage dependent, ranging from 1.3% to 5.1%. DNA sequencing analysis of the PCR amplicons corroborated the induction of RGEN-mediated mutations at the endogenous sites. Indels and microhomologies, characteristic of error-prone NHEJ, were observed at the target site. The mutation frequency measured by direct sequencing was 7.3% (=7 mutant clones/96 clones), on par with those obtained with zinc finger nucleases (ZFNs) or transcription-activator-like effector nucleases (TALENS).

Serial-transfection of Cas9 plasmid and guide RNA was required to induce mutations in cells. But when plasmids that encode guide RNA, serial transfection was unnecessary and cells were co-transfected with Cas9 plasmid and guide RNA-encoding plasmid.

In the meantime, both ZFNs and TALENs have been successfully developed to disrupt the human CCR5 gene (3-6), which encodes a G-protein-coupled chemokine receptor, an essential co-receptor of HIV infection. A CCR5-specific ZEN is now under clinical investigation in the US for the treatment of AIDS (7). These ZFNs and TALENs, however, have off-target effects, inducing both local mutations at sites whose sequences are homologous to the on-target sequence (6,8-10) and genome rearrangements that arise from the repair of two concurrent DSBs induced at on-target and off-target sites (11-12). The most striking off-target sites associated with these CCR5-specific engineered nucleases reside in the CCR2 locus, a close homolog of CCR5, located 15-kbp upstream of CCR5. To avoid off-target mutations in the CCR2 gene and unwanted deletions, inversions, and duplications of the 15-kbp chromosomal segment between the CCR5 on-target and CCR2 off-target sites, the present inventors intentionally chose the target site of our CCR5-specific RGEN to recognize a region within the CCR5 sequence that has no apparent homology with the CCR2 sequence.

Figures 4A, 4B:
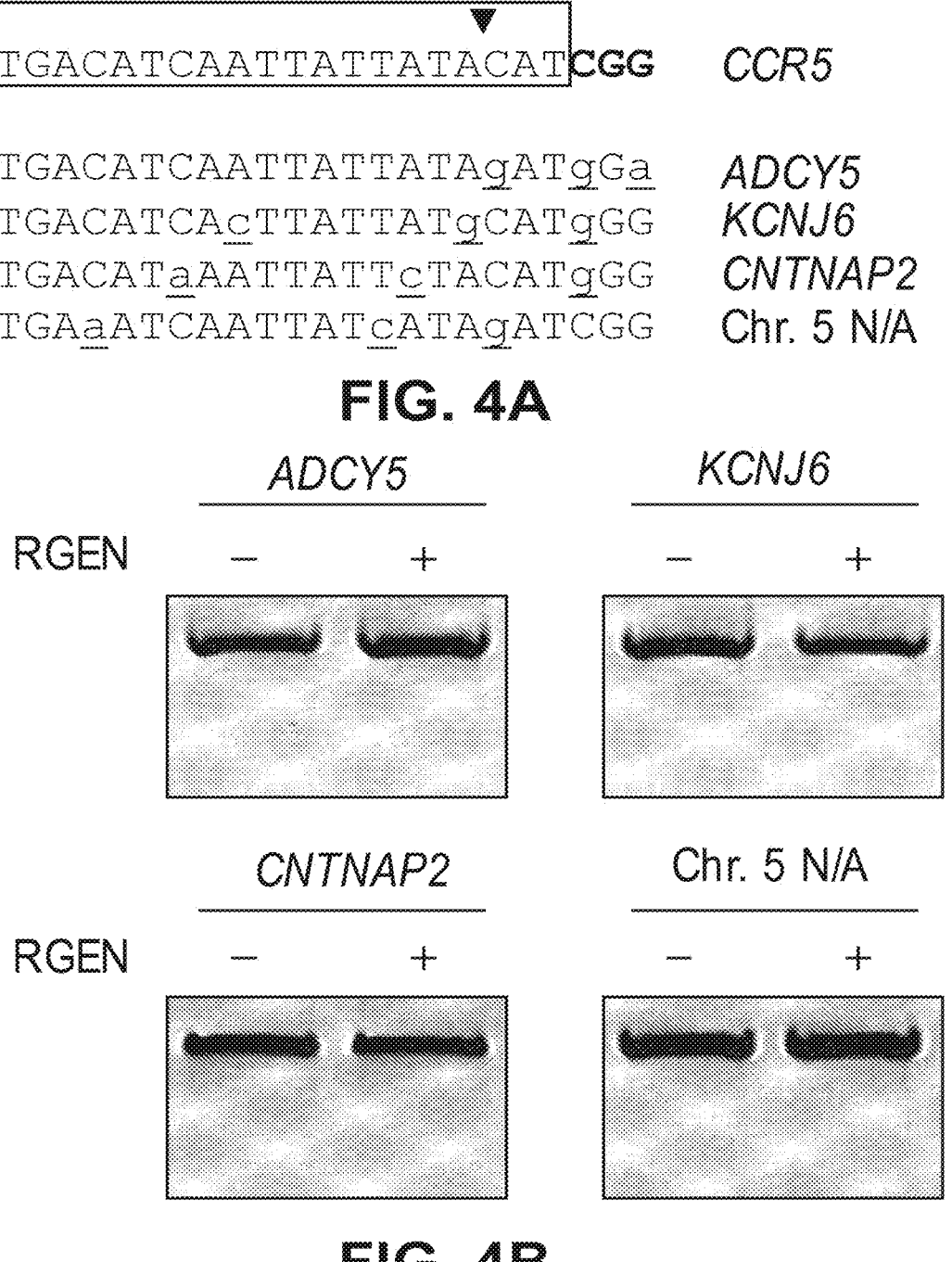
FIGS. 4A, 4B, and 4C show that RGEN-driven off-target mutations are undetectable.
Figure 4C:
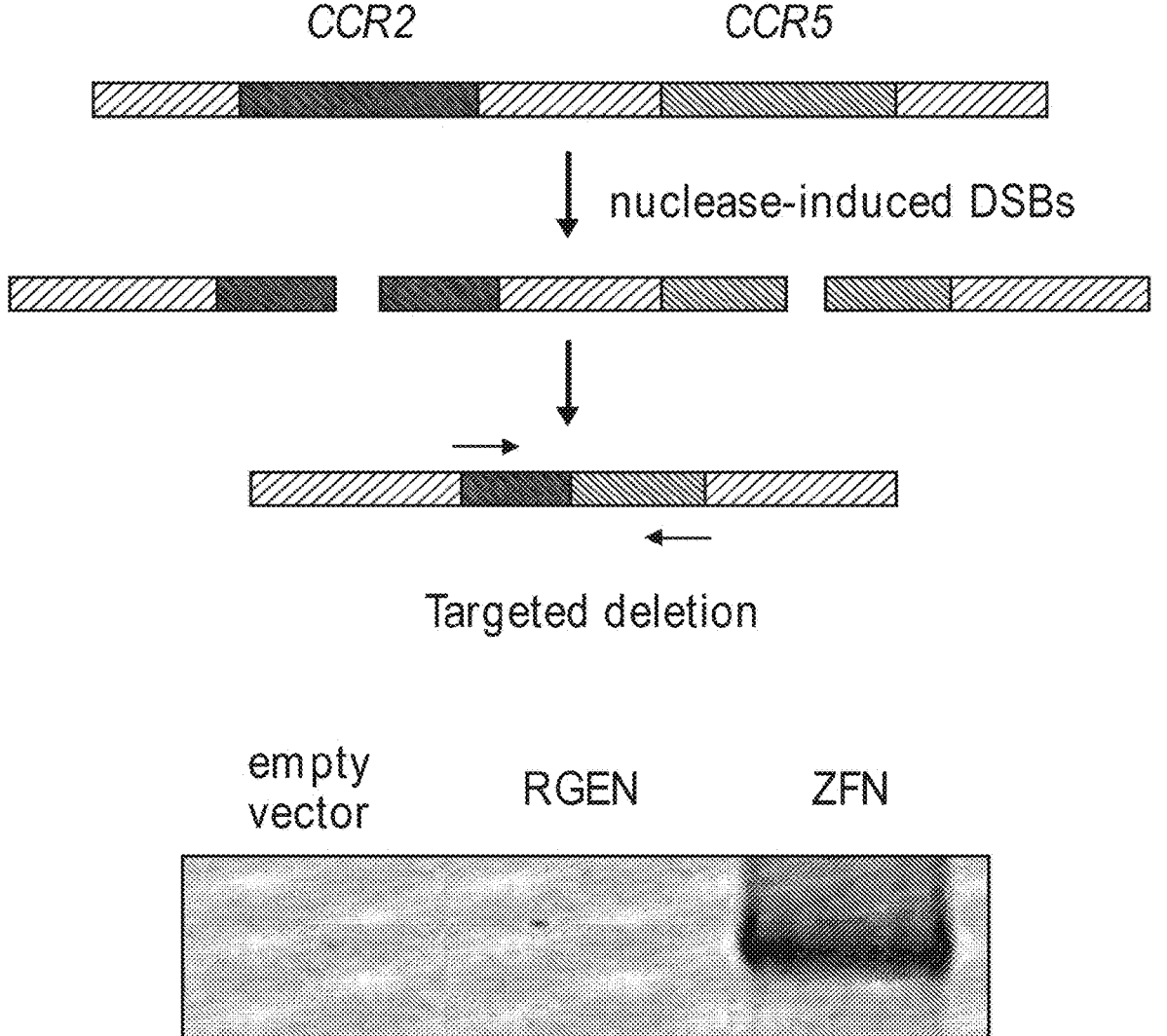

The present inventors investigated whether the CCR5-specific RGEN had off-target effects. To this end, we searched for potential off-target sites in the human genome by identifying sites that are most homologous to the intended 23-bp target sequence. As expected, no such sites were found in the CCR2 gene. Instead, four sites, each of which carries 3-base mismatches with the on-target site, were found (FIG. 4A). The T7E1 assays showed that mutations were not detected at these sites (assay sensitivity, ~0.5%), demonstrating exquisite specificities of RGENS (FIG. 4B). Furthermore, PCR was used to detect the induction of chromosomal deletions in cells separately transfected with plasmids encoding the ZEN and RGEN specific to CCR5. Whereas the ZEN induced deletions, the RGEN did not (FIG. 4C).

Figure 3B:
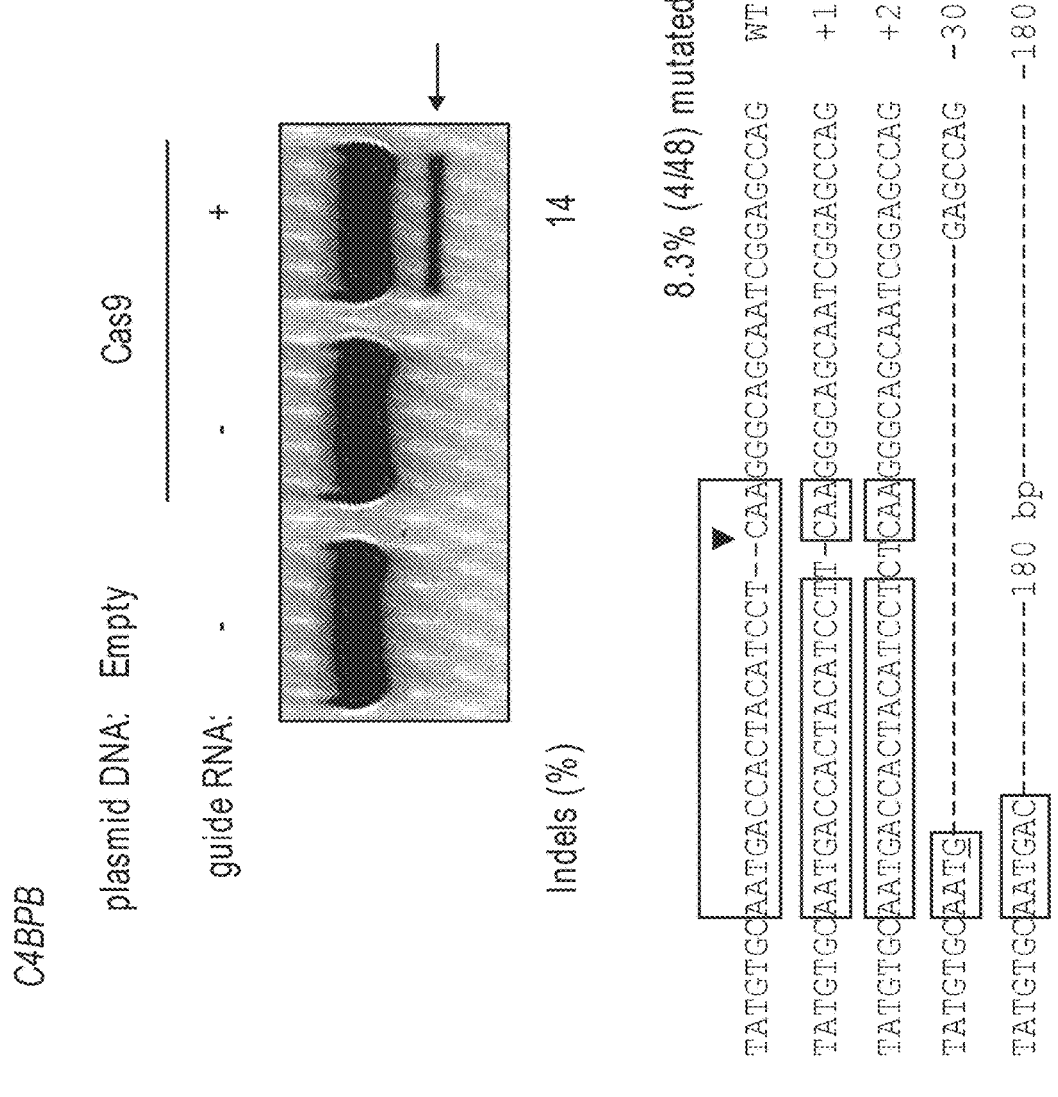

Next, RGENs was reprogrammed by replacing the CCR5-specific guide RNA with a newly-synthesized RNA designed to target the human C4BPB gene, which encodes the beta chain of C4b-binding protein, a transcription factor. This RGEN induced mutations at the chromosomal target site in K562 cells at high frequencies (FIG. 3B). Mutation frequencies measured by the T7E1 assay and by direct sequencing were 14% and 8.3% (=4 mutant clones/48 clones), respectively. Out of four mutant sequences, two clones contained a single-base or two-base insertion precisely at the cleavage site, a pattern that was also observed at the CCR5 target site. These results indicate that RGENs cleave chromosomal target DNA at expected positions in cells.

Example 2: Proteinaceous RGEN-Mediated Genome Editing

Figure 10A:
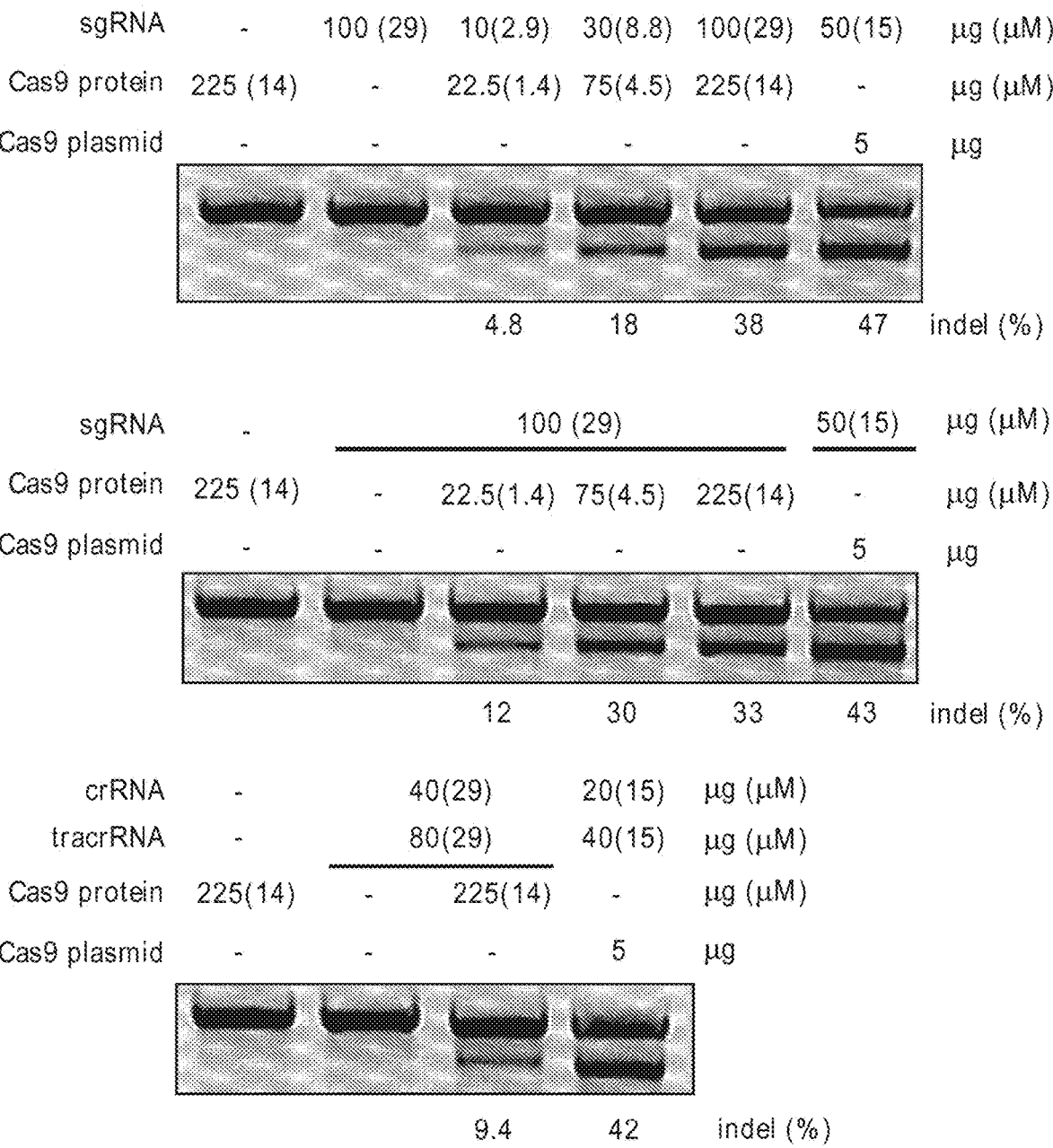
Figure 10B:
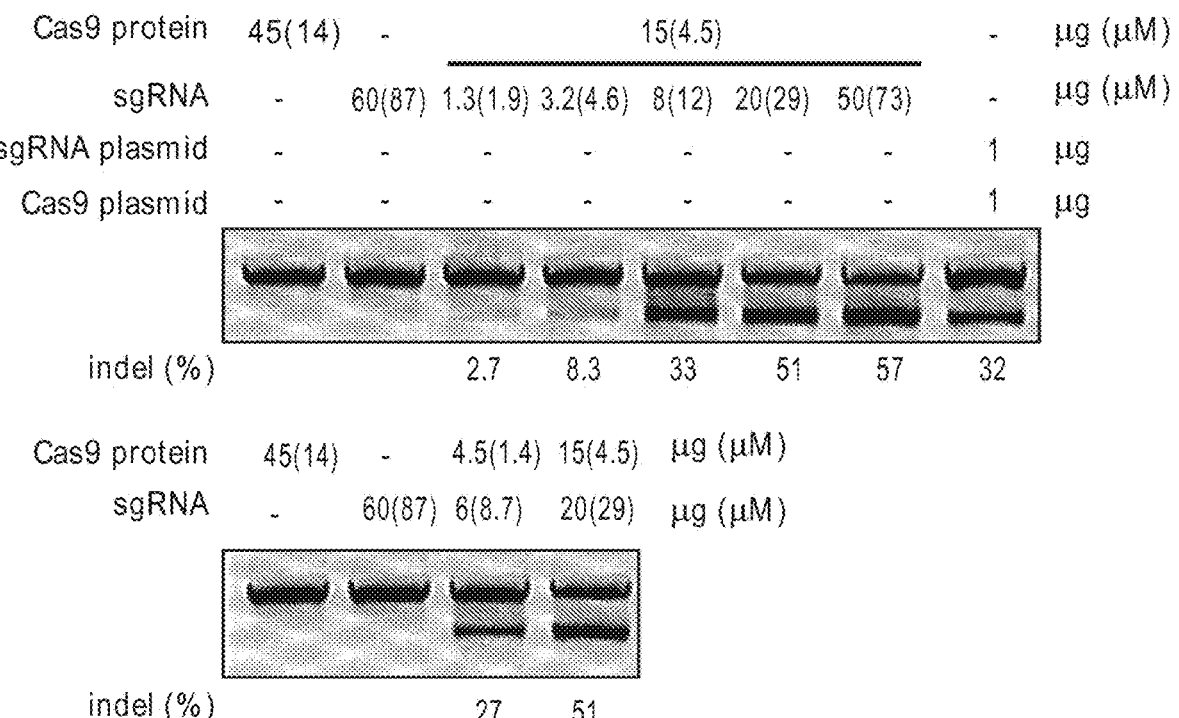

RGENs can be delivered into cells in many different forms. RGENs consist of Cas9 protein, crRNA, and tracrRNA. The two RNAs can be fused to form a single-chain guide RNA (sgRNA). A plasmid that encodes Cas9 under a promoter such as CMV or CAG can be transfected into cells. crRNA, tracrRNA, or sgRNA can also be expressed in cells using plasmids that encode these RNAs. Use of plasmids, however, often results in integration of the whole or part of the plasmids in the host genome. The As shown in FIG. 10, Cas9 protein/sgRNA complex induced targeted mutation at the CCR5 locus at frequencies that ranged from 4.8 to 38% in a sgRNA or Cas9 protein dose-dependent manner, on par with the frequency obtained with Cas9 plasmid transfection (45%). Cas9 protein/crRNA/tracrRNA complex was able to induce mutations at a frequency of 9.4%. Cas9 protein alone failed to induce mutations. When $2 \times 10^5$ cells were transfected with $\frac{1}{5}$ scale-downed doses of Cas9 protein and sgRNA, mutation frequencies at the CCR5 locus ranged from 2.7 to 57% in a dose-dependent manner, greater than that obtained with co-transfection of Cas9 plasmid and sgRNA plasmid (32%).

We also tested Cas9 protein/sgRNA complex that targets the ABCC11 gene and found that this complex induced indels at a frequency of 35%, demonstrating general utility of this method.

TABLE 2

Sequences of guide RNA

| Target | RNA type | RNA sequence 5' to 3') | Length | SEQ ID NO |
|--------|----------|------------------------|--------|-----------|
| CCR5 | sgRNA | GGUGACAUCAAUUAUUAUACAUGUUUUAGAGCUAG AAAUAGCAAGUUAAAAUAAGGCUAGUCCGUUAUCA ACUUGAAAAAGUGGCACCGAGUCGGUGCUUUUUUU | 104 bp | 28 |
| | crRNA | GGUGACAUCAAUUAUUAUACAUGUUUUAGAGCUAU GCUGUUUUG | 44 bp | 29 |
| | tracrRNA | GGAACCAUUCAAAACAGCAUAGCAAGUUAAAAUAA GGCUAGUCCGUUAUCAACUUGAAAAAGUGGCACCG AGUCGGUGCUUUUUUU | 86 bp | 30 | bacterial sequences incorporated in plasmid DNA can cause unwanted immune response in vivo. Cells transfected with plasmid for cell therapy or animals and plants derived from DNA-transfected cells must go through a costly and lengthy regulation procedure before market approval in most developed countries. Furthermore, plasmid DNA can persist in cells for several days post-transfection, aggravating off-target effects of RGENS.

Here, we used recombinant Cas9 protein complexed with in vitro transcribed guide RNA to induce targeted disruption of endogenous genes in human cells. Recombinant Cas9 protein fused with the hexa-histidine tag was expressed in and purified from *E. coli* using standard Ni ion affinity chromatography and gel filtration. Purified recombinant Cas9 protein was concentrated in storage buffer (20 mM HEPES pH 7.5, 150 mM KCl, 1 mM DTT, and 10% glycerol). Cas9 protein/sgRNA complex was introduced directly into K562 cells by nucleofection: $1 \times 10^6$ K562 cells were transfected with 22.5-225 (1.4-14 μM) of Cas9 protein mixed with 100 μg (29 μM) of in vitro transcribed sgRNA (or crRNA 40 μg and tracrRNA 80 μg) in 100 μl solution using the 4D-Nucleofector, SF Cell Line 4D-Nucleofector X Kit, Program FF-120 (Lonza) according to the manufacturer's protocol. After nucleofection, cells were placed in growth media in 6-well plates and incubated for 48 hr. When $2 \times 10^5$ K562 cells were transfected with $\frac{1}{5}$ scale-downed protocol, 4.5-45 μg of Cas9 protein mixed with 6-60 μg of in vitro transcribed sgRNA (or crRNA 8 μg and tracrRNA 16 μg) were used and nucleofected in 20 μl solution. Nucleofected cells were then placed in growth media in 48-well plates. After 48 hr, cells were collected and genomic DNA was isolated. The genomic DNA region spanning the target site was PCR-amplified and subjected to the T7E1 assay.

Example 3: RNA-Guided Genome Editing in Mice

To examine the gene-targeting potential of RGENs in pronuclear (PN)-stage mouse embryos, the forkhead box N1 (Foxn1) gene, which is important for thymus development and keratinocyte differentiation (Nehls et al., 1996), and the protein kinase, DNA activated, catalytic polypeptide (Prkdc) gene, which encodes an enzyme critical for DNA DSB repair and recombination (Taccioli et al., 1998) were used.

Figure 5A:
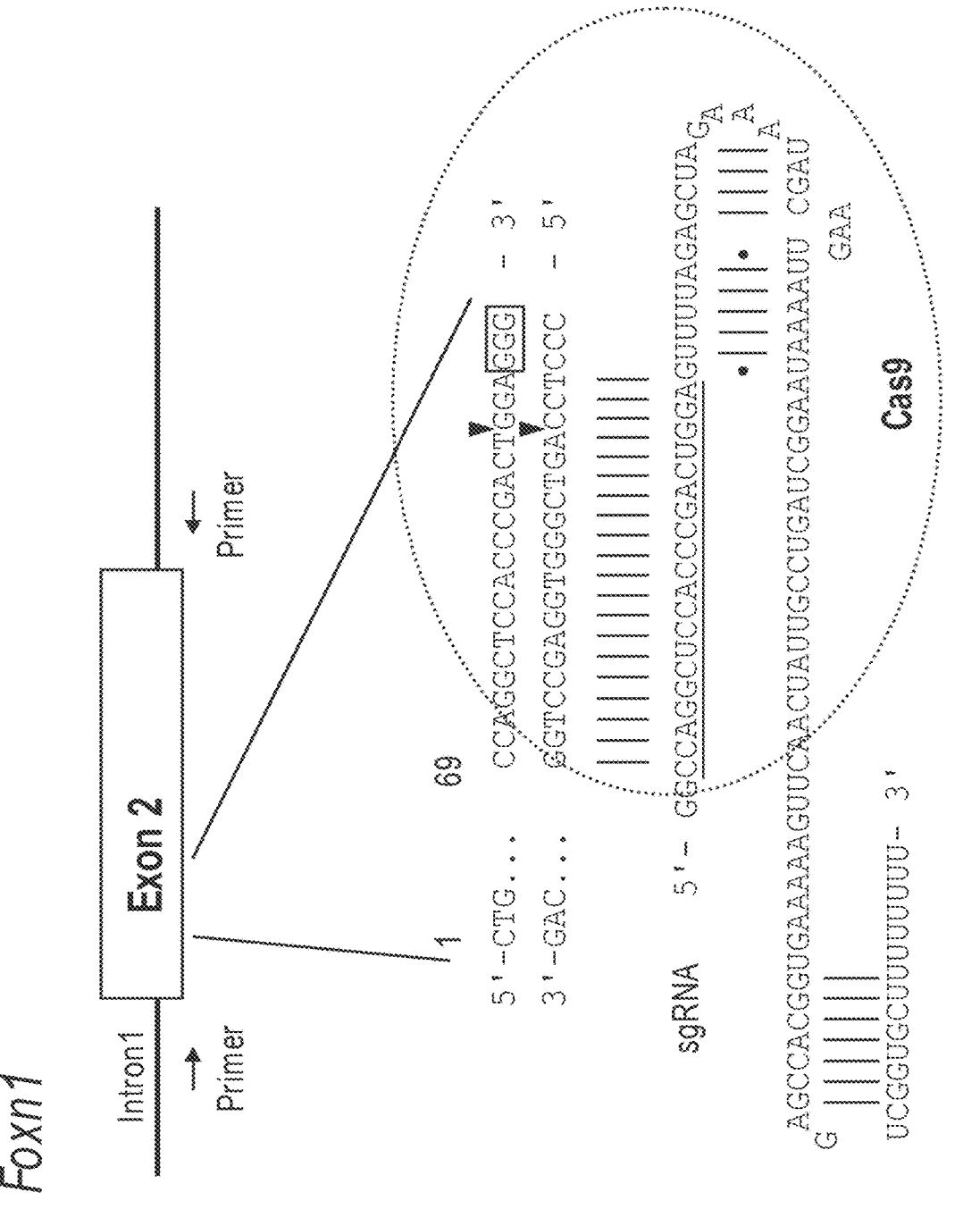
FIGS. 5A, 5B, 5C, and 5D show RGEN-induced Foxn1 gene targeting in mice.

To evaluate the genome-editing activity of the Foxn1-RGEN, we injected Cas9 mRNA (10-ng/μl solution) with various doses of the sgRNA (FIG. 5*a*) into the cytoplasm of PN-stage mouse embryos, and conducted T7 endonuclease I (T7E1) assays (Kim et al. 2009) using genomic DNAs obtained from in vitro cultivated embryos (FIG. 6*a*).

Alternatively, we directly injected the RGEN in the form of recombinant Cas9 protein (0.3 to 30 ng/μl) complexed with the two-fold molar excess of Foxn1-specific sgRNA (0.14 to 14 ng/μl) into the cytoplasm or pronucleus of one-cell mouse embryos, and analyzed mutations in the Foxn1 gene using in vitro cultivated embryos (FIG. 7).

Specifically, Cas9 mRNA and sgRNAs were synthesized in vitro from linear DNA templates using the mMESSAGE mMACHINE T7 Ultra kit (Ambion) and MEGAshortscript T7 kit (Ambion), respectively, according to the manufacturers' instructions, and were diluted with appropriate amounts of diethyl pyrocarbonate (DEPC, Sigma)-treated injection buffer (0.25 mM EDTA, 10 mM Tris, pH 7.4). Templates for sgRNA synthesis were generated using oligonucleotides listed in Table 3. Recombinant Cas9 protein was obtained from ToolGen, Inc.

TABLE 3

| RNA Name | Direc-tion | Sequence (5' to 3') | SEQ ID NO |
|---|---|---|---|
| Foxn1 #1 sgRNA | F | GAAATTAATACGACTCACTATAGG*CAGTCTGACG* *TCACACTTCCGTTTTAGAGCTAGAAATAGCAAGT* TAAAATAAGGCTAGTCCG | 31 |
| Foxn1 #2 sgRNA | F | GAAATTAATACGACTCACTATAGG*ACTTCCAGGC* *TCCACCCGACGTTTTAGAGCTAGAAATAGCAAGT* TAAAATAAGGCTAGTCCG | 32 |
| Foxn1 #3 sgRNA | F | GAAATTAATACGACTCACTATAGG*CCAGGCTCCA* *CCCGACTGGAGTTTTAGAGCTAGAAATAGCAAGT* TAAAATAAGGCTAGTCCG | 33 |
| Foxn1 #4 sgRNA | F | GAAATTAATACGACTCACTATAGG*ACTGGAGGGC* *GAACCCCAAGGTTTTAGAGCTAGAAATAGCAAGT* TAAAATAAGGCTAGTCCG | 34 |
| Foxn1 #5 sgRNA | F | GAAATTAATACGACTCACTATAGG*ACCCCAAGGG* *GACCTCATGCGTTTTAGAGCTAGAAATAGCAAGT* TAAAATAAGGCTAGTCCG | 35 |
| Prkdc #1 sgRNA | F | GAAATTAATACGACTCACTATAGG*TTAGTTTTTT* *CCAGAGACTTGTTTTAGAGCTAGAAATAGCAAGT* TAAAATAAGGCTAGTCCG | 36 |
| Prkdc #2 sgRNA | F | GAAATTAATACGACTCACTATAGG*TTGGTTTGCT* *TGTGTTTATCGTTTTAGAGCTAGAAATAGCAAGT* TAAAATAAGGCTAGTCCG | 37 |
| Prkdc #3 sgRNA | F | GAAATTAATACGACTCACTATAGG*CACAAGCAAA* *CCAAAGTCTCGTTTTAGAGCTAGAAATAGCAAGT* TAAAATAAGGCTAGTCCG | 38 |
| Prkdc #4 sgRNA | F | GAAATTAATACGACTCACTATAGG*CCTCAATGCT* *AAGCGACTTCGTTTTAGAGCTAGAAATAGCAAGT* TAAAATAAGGCTAGTCCG | 39 |

All animal experiments were performed in accordance with the Korean Food and Drug Administration (KFDA) guidelines. Protocols were reviewed and approved by the Institutional Animal Care and Use Committees (IACUC) of the Laboratory Animal Research Center at Yonsei University (Permit Number: 2013-0099). All mice were maintained in the specific pathogen-free facility of the Yonsei Laboratory Animal Research Center. FVB/NTac (Taconic) and ICR mouse strains were used as embryo donors and foster mothers, respectively. Female FVB/NTac mice (7-8 weeks old) were super-ovulated by intra-peritoneal injections of 5 IU pregnant mare serum gonadotropin (PMSG, Sigma) and 5 IU human chorionic gonadotropin (hCG, Sigma) at 48-hour intervals. The super-ovulated female mice were mated to FVB/NTac stud males, and fertilized embryos were collected from oviducts.

Cas9 mRNA and sgRNAs in M2 medium (Sigma) were injected into the cytoplasm of fertilized eggs with well-recognized pronuclei using a Piezo-driven micromanipulator (Prime Tech).

In the case of injection of recombinant Cas9 protein, the recombinant Cas9 protein: Foxn1-sgRNA complex was diluted with DEPC-treated injection buffer (0.25 mM EDTA, 10 mM Tris, pH 7.4) and injected into male pronuclei using a TransferMan NK2 micromanipulator and a Femto-Jet® microinjector (Eppendorf).

The manipulated embryos were transferred into the oviducts of pseudopregnant foster mothers to produce live animals, or were cultivated in vitro for further analyses.

To screen F0 mice and in vitro cultivated mouse embryos with RGEN-induced mutations, T7E1 assays were performed as previously described using genomic DNA samples from tail biopsies and lysates of whole embryos (Cho et al., 2013).

Briefly, the genomic region encompassing the RGEN target site was PCR-amplified, melted, and re-annealed to form heteroduplex DNA, which was treated with T7 endo-nuclease 1 (New England Biolabs), and then analyzed by agarose gel electrophoresis. Potential off-target sites were identified by searching with bowtie 0.12.9 and were also similarly monitored by T7E1 assays. The primer pairs used in these assays were listed in Tables 4 and 5.

TABLE 4

Primers used in the T7E1 assay

| Gene | Direc-tion | Sequence (5' to 3') | SEQ ID NO |
|---|---|---|---|
| Foxn1 | F1 | GTCTGTCTATCATCTCTTCCCTTCTCTCC | 40 |
| | F2 | TCCCTAATCCGATGGCTAGCTCCAG | 41 |
| | R1 | ACGAGCAGCTGAAGTTAGCATGC | 42 |
| | R2 | CTACTCAATGCTCTTAGAGCTACCAGGCTTGC | 43 |
| Prkdc | F | GACTGTTGTGGGGAGGGCCG | 44 |
| | F2 | GGGAGGGCCGAAAGTCTTATTTTG | 45 |
| | R1 | CCTGAAGACTGAAGTTGGCAGAAGTGAG | 46 |
| | R2 | CTTTAGGGCTTCTTCTCTACAATCACG | 47 |

TABLE 5

Primers used for amplification of off-target sites

| Gene | Nota-tion | Direc-tion | Sequence (5' to 3') | SEQ ID NO |
|---|---|---|---|---|
| Foxn1 | off 1 | F | CTCGGTGTGTAGCCCTGAC | 48 |
| | | R | AGACTGGCCTGGAACTCACAG | 49 |
| | off 2 | F | CACTAAAGCCTGTCAGGAAGCCG | 50 |
| | | R | CTGTGGAGAGCACACAGCAGC | 51 |
| | off 3 | F | GCTGCGACCTGAGACCATG | 52 |
| | | R | CTTCAATGGCTTCCTGCTTAGGCTAC | 53 |
| | off 4 | F | GGTTCAGATGAGGCCATCCTTTC | 54 |
| | | R | CCTGATCTGCAGGCTTAACCCTTG | 55 |
| Prkdc | off 1 | F | CTCACCTGCACATCACATGTGG | 56 |
| | | R | GGCATCCACCCTATGGGGTC | 57 |
| | off 2 | F | GCCTTGACCTAGAGCTTAAAGAGCC | 58 |
| | | R | GGTCTTGTTAGCAGGAAGGACACTG | 59 |
| | off 3 | F | AAAACTCTGCTTGATGGGATATGTGG | 60 |
| | | R | CTCTCACTGGTTATCTGTGCTCCTTC | 61 |
| | off 4 | F | GGATCAATAGGTGGTGGGGGATG | 62 |
| | | R | GTGAATGACACAATGTGACAGCTTCAG | 63 |
| | off 5 | F | CACAAGACAGACCTCTCAACATTCAGTC | 64 |
| | | R | GTGCATGCATATAATCCATTCTGATTGCTCTC | 65 |
| | off 6 | F1 | GGGAGGCAGAGGCAGGT | 66 |
| | | F2 | GGATCTCTGTGAGTTTGAGGCCA | 67 |
| | | R1 | GCTCCAGAACTCACTCTTAGGCTC | 68 |

Mutant founders identified by the T7E1 assay were further analyzed by fPCR. Appropriate regions of genomic DNA were sequenced as described previously (Sung et al., 2013). For routine PCR genotyping of F1 progenies, the following primer pairs were used for both wild-type and mutant alleles: 5'-CTACTCCCTCCGCAGTCTGA-3' (SEQ ID NO: 69) and 5'-CCAGGCCTAGGTTCCAGGTA-3' (SEQ ID NO: 70) for the Foxn1 gene, 5'-CCCCAGCAT-TGCAGATTTCC-3' (SEQ ID NO: 71) and 5'-AGGGCTTCTTCTCTACAATCACG-3' (SEQ ID NO: 72) for Prkdc gene.

In the case of injection of Cas9 mRNA, mutant fractions (the number of mutant embryos/the number of total embryos) were dose-dependent, ranging from 33% (1 ng/μl sgRNA) to 91% (100 ng/μl) (FIG. 6b). Sequence analysis confirmed mutations in the Foxn1 gene; most mutations were small deletions (FIG. 6c), reminiscent of those induced by ZFNs and TALENS (Kim et al., 2013).

Figure 7A:
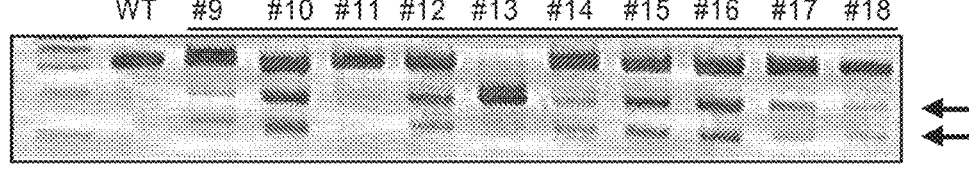
Figure 7B:
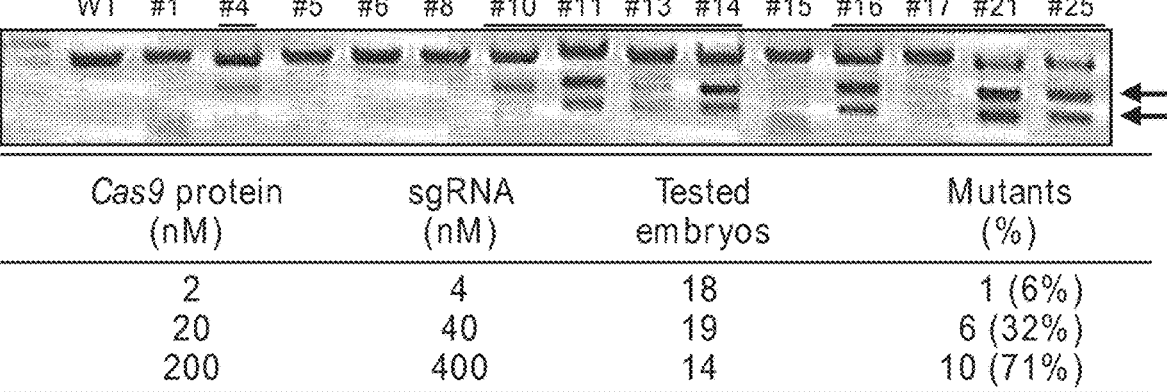

In the case of injection of Cas9 protein, these injection doses and methods minimally affected the survival and development of mouse embryos in vitro: over 70% of RGEN-injected embryos hatched out normally in both experiments. Again, mutant fractions obtained with Cas9 protein injection were dose-dependent, and reached up to 88% at the highest dose via pronucleus injection and to 71% via intra-cytoplasmic injection (FIGS. 7a and 7b). Similar to the mutation patterns induced by Cas9 mRNA plus sgRNA (FIG. 6c), those induced by the Cas9 protein-sgRNA complex were mostly small deletions (FIG. 7c). These results clearly demonstrate that RGENs have high gene-targeting activity in mouse embryos.

Encouraged by the high mutant frequencies and low cytotoxicity induced by RGENs, we produced live animals by transferring the mouse embryos into the oviducts of pseudo-pregnant foster mothers.

Notably, the birth rates were very high, ranging from 58% to 738, and were not affected by the increasing doses of Foxn1-sgRNA (Table 6).

TABLE 6

| | RGEN-mediated gene-targeting in FVB/NTaC mice | | | | | |
|---|---|---|---|---|---|---|
| Target Gene | Cas9 mRNA + sgRNA (ng/μl) | Injected embryos | Transfer red embryos (%) | Total newborns (%) | Live newborns * (%) | Founders † (%) |
| Foxn1 | 10 + 1 | 76 | 62 (82) | 45 (73) | 31 (50) | 12 (39) |
| | 10 + 10 | 104 | 90 (87) | 52 (58) | 58 (64) | 33 (57) |
| | 10 + 100 | 100 | 90 (90) | 62 (69) | 58 (64) | 54 (93) |
| | Total | 280 | 242 (86) | 159 (66) | 147 (61) | 99 (67) |
| Prkdc | 50 + 50 | 73 | 58 (79) | 35 (60) | 33 (57) | 11 (33) |
| | 50 + 100 | 79 | 59 (75) | 22 (37) | 21 (36) | 7 (33) |
| | 50 + 250 | 94 | 73 (78) | 37 (51) | 37 (51) | 21 (57) |
| | Total | 246 | 190 (77) | 94 (49) | 91 (48) | 39 (43) |

Figures 5B, 5C:
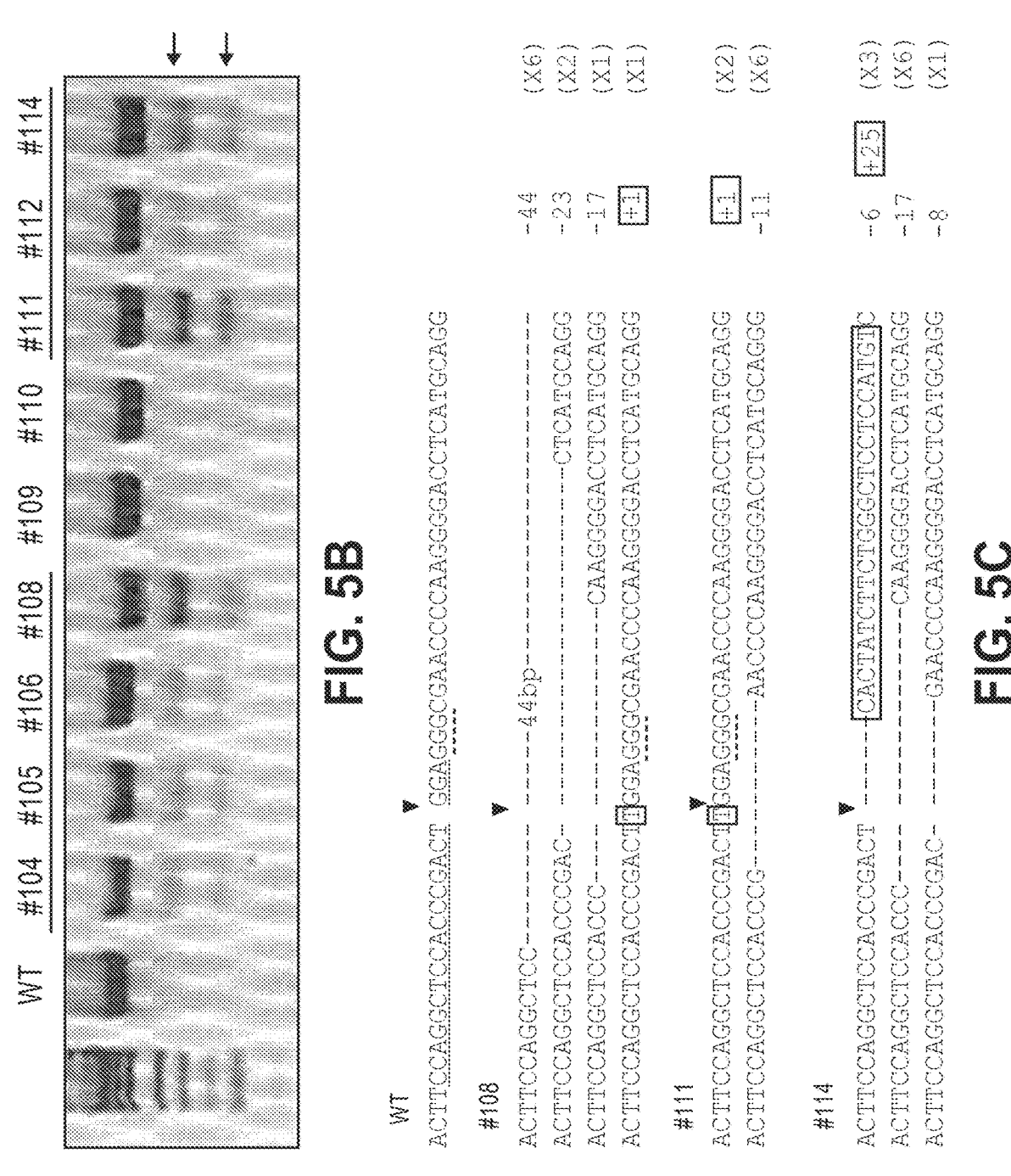

Out of 147 newborns, we obtained 99 mutant founder mice. Consistent with the results observed in cultivated embryos (FIG. 6b), mutant fractions were proportional to the doses of Foxn1-sgRNA, and reached up to 93% (100 ng/μl Foxn1-sgRNA) (Tables 6 and 7, FIG. 5b).

TABLE 7

DNA sequences of Foxn1 mutant alleles identified from a
subset of T7E1-positive mutant founders

```
ACTTCCAGGCTCCACCCGACTGGAGGGCGAACCCCAAGGGGA  del +          Founder
CCTCATGCAGG (SEQ ID NO: 134)                ins        #  mice ACTTCCAGGC------------------AACCCCAAGGGGA   Δ19        1  20
CCTCATGCAGG (SEQ ID NO: 297)

ACTTCCAGGC-----------------GAACCCCAAGGGGA   Δ18        1  115
CCTCATGCAGG (SEQ ID NO: 298)

ACTTCCAGGCTCC---------------------------    Δ60        1  19
----------- (SEQ ID NO: 299)

ACTTCCAGGCTCC---------------------------    Δ44        1  108
----------- (SEQ ID NO: 300)

ACTTCCAGGCTCC--------------------CAAGGGGA   Δ21        1  64
CCTCATGCAGG (SEQ ID NO: 301)

ACTTCCAGGCTCC-----------TTAGGAGGCGAACCCCA   Δ12 + 6    1  126
AGGGGACCTCA (SEQ ID NO: 302)

ACTTCCAGGCTCCACC------------------------    Δ28        1  5
--TCATGCAGG (SEQ ID NO: 303)
```

TABLE 7-continued

| DNA sequences of Foxn1 mutant alleles identified from a subset of T7E1-positive mutant founders | | | |
|---|---|---|---|

| ACTTCCAGGCTCCACCCGACTGGAGGGCGAACCCCAAGGGGA CCTCATGCAGG (SEQ ID NO: 134) | del + ins | # | Founder mice |
|---|---|---|---|
| ACTTCCAGGCTCCACCC--------------------CCAA GGGACCTCATG (SEQ ID NO: 304) | Δ21 + 4 | 1 | 61 |
| ACTTCCAGGCTCCACCC-----------------AAGGGGA CCTCATGCAGG (SEQ ID NO: 305) | Δ18 | 2 | 95, 29 |
| ACTTCCAGGCTCCACCC----------------CAAGGGGA CCTCATGCAGG (SEQ ID NO: 306) | Δ17 | 7 | 12, 14, 27, 66, 108, 114, 126 |
| ACTTCCAGGCTCCACCC--------------ACCCAAGGGG ACCTCATGCAG (SEQ ID NO: 307) | Δ15 + 1 | 1 | 32 |
| ACTTCCAGGCTCCACCC--------------CACCCAAGGG GACCTCATGCA (SEQ ID NO: 308) | Δ15 + 2 | 1 | 124 |
| ACTTCCAGGCTCCACCC------------ACCCCAAGGGGA CCTCATGCAGG (SEQ ID NO: 309) | Δ13 | 1 | 32 |
| ACTTCCAGGCTCCACCC-------GGCGAACCCCAAGGGGA CCTCATGCAGG (SEQ ID NO: 310) | Δ8 | 1 | 110 |
| ACTTCCAGGCTCCACCCT------------------GGGGA CCTCATGCAGG (SEQ ID NO: 311) | Δ20 + 1 | 1 | 29 |
| ACTTCCAGGCTCCACCCG-----------AACCCCAAGGGGA CCTCATGCAGG (SEQ ID NO: 312) | Δ11 | 1 | 111 |
| ACTTCCAGGCTCCACCCGA---------------------A CCTCATGCAGG (SEQ ID NO: 313) | Δ22 | 1 | 79 |
| ACTTCCAGGCTCCACCCGA------------------GGGGA CCTCATGCAGG (SEQ ID NO: 314) | Δ18 | 2 | 13, 127 |
| ACTTCCAGGCTCCACCCCA-----------------AGGGGA CCTCATGCAGG (SEQ ID NO: 315) | Δ17 | 1 | 24 |
| ACTTCCAGGCTCCACCCGA-----------ACCCCAAGGGGA CCTCATGCAGG (SEQ ID NO: 316) | Δ11 | 5 | 14, 53, 58, 69, 124 |
| ACTTCCAGGCTCCACCCGA----------GACCCCAAGGGGA CCTCATGCAGG (SEQ ID NO: 317) | Δ10 | 1 | 14 |
| ACTTCCAGGCTCCACCCGA-----GGGCGAACCCCAAGGGGA CCTCATGCAGG (SEQ ID NO: 318) | Δ5 | 3 | 53, 79, 115 |
| ACTTCCAGGCTCCACCCGAC--------------------- -CTCATGCAGG (SEQ ID NO: 319) | Δ23 | 1 | 108 |
| ACTTCCAGGCTCCACCCGAC-----------CCCCAAGGGGA CCTCATGCAGG (SEQ ID NO: 320) | Δ11 | 1 | 3 |
| ACTTCCAGGCTCCACCCGAC-----------GAAGGGCCCCA AGGGGACCTCA (SEQ ID NO: 321) | Δ11 + 6 | 1 | 66 |
| ACTTCCAGGCTCCACCCGAC--------GAACCCCAAGGGGA CCTCATGCAGG (SEQ ID NO: 322) | Δ8 | 2 | 3, 66 |
| ACTTCCAGGCTCCACCCGAC-----GGCGAACCCCAAGGGGA CCTCATGCAGG (SEQ ID NO: 323) | Δ5 | 1 | 27 |
| ACTTCCAGGCTCCACCCGAC--GTGCTTGAGGGCGAACCCCA AGGGGACCTCA (SEQ ID NO: 324) | Δ2 + 6 | 2 | 5 |
| ACTTCCAGGCTCCACCCGACT------CACTATCTTCTGGGC TCCTCCATGTC (SEQ ID NO: 325) | Δ6 + 25 | 2 | 21, 114 |
| ACTTCCAGGCTCCACCCGACT----TGGCGAACCCCAAGGGG ACCTCATGCAG (SEQ ID NO: 326) | Δ4 + 1 | 1 | 53 |
| ACTTCCAGGCTCCACCCGACT--TGCAGGGCGAACCCCAAGG GGACCTCATGC (SEQ ID NO: 327) | Δ2 + 3 | 1 | 126 |

TABLE 7-continued

DNA sequences of Foxn1 mutant alleles identified from a
subset of T7E1-positive mutant founders

| ACTTCCAGGCTCCACCCGACTGGAGGGCGAACCCCAAGGGGA<br>CCTCATGCAGG (SEQ ID NO: 134) | del +<br>ins | # | Founder<br>mice |
|---|---|---|---|
| ACTTCCAGGCTCCACCCGACTTGGAGGGCGAACCCCAAGGGG<br>ACCTCATGCAG (SEQ ID NO: 328) | +1 | 15 | 3, 5, 12,<br>19, 29,<br>55, 56,<br>61, 66,<br>68, 81,<br>108, 111,<br>124, 127 |
| ACTTCCAGGCTCCACCCGACTTTGGAGGGCGAACCCCAAGGG<br>GACCTCATGCA (SEQ ID NO: 329) | +2 | 2 | 79, 120 |
| ACTTCCAGGCTCCACCCGACTGTTGGAGGGCGAACCCCAAGG<br>GGACCTCATGC (SEQ ID NO: 330) | +3 | 1 | 55 |
| ACTTCCAGGCTCCACCCGACTGGAG(+455)GGCGAACCCCA<br>AGGGGACCTCC (SEQ ID NO: 331) | +455 | 1 | 13 |

To generate Prkdc-targeted mice, we applied a 5-fold higher concentration of Cas9 mRNA (50 ng/µl) with increasing doses of Prkdc-sgRNA (50, 100, and 250 ng/µl). Again, the birth rates were very high, ranging from 51% to 60%, enough to produce a sufficient number of newborns for the analysis (Table 6). The mutant fraction was 57% (21 mutant founders among 37 newborns) at the maximum dose of Prkdc-sgRNA. These birth rates obtained with RGENs were approximately 2- to 10-fold higher than those with TALENs reported in our previous study (Sung et al., 2013). These results demonstrate that RGENs are potent gene-targeting reagents with minimal toxicity.

To test the germ-line transmission of the mutant alleles, we crossed the Foxn1 mutant founder #108, a mosaic with four different alleles (FIG. 5c, and Table 8) with wild-type mice, and monitored the genotypes of F1 offspring.

TABLE 8

Genotypes of Foxn1 mutant mice

| Founder NO. | sgRNA<br>(ng/ml) | Genotyping Summary | Detected alleles |
|---|---|---|---|
| 58* | 1 | not determined | Δ11 |
| 19 | 100 | bi-allelic | Δ60/+1 |
| 20 | 100 | bi-allelic | Δ67/Δ19 |
| 13 | 100 | bi-allelic | Δ18/+455 |
| 32 | 10 | bi-allelic<br>(heterozygote) | Δ13/Δ15 + 1 |
| 115 | 10 | bi-allelic<br>(heterozygote) | Δ18/Δ5 |
| 111 | 10 | bi-allelic<br>(heterozygote) | Δ11/+1 |
| 110 | 10 | bi-allelic<br>(homozygote) | Δ8/Δ8 |
| 120 | 10 | bi-allelic<br>(homozygote) | +2/+2 |
| 81 | 100 | heterozygote | +1/WT |
| 69 | 100 | homozygote | Δ11/Δ11 |
| 55 | 1 | mosaic | Δ18/Δ17/+1/+3 |
| 56 | 1 | mosaic | Δ127/Δ41/Δ2/+1 |
| 127 | 1 | mosaic | Δ18/+1/WT |
| 53 | 1 | mosaic | Δ11/Δ5/Δ4 + 1/WT |
| 27 | 10 | mosaic | Δ17/Δ5/WT |
| 29 | 10 | mosaic | Δ18/Δ20 + 1/+1 |
| 95 | 10 | mosaic | Δ18/Δ14/Δ8/Δ4 |
| 108 | 10 | mosaic | +1/Δ17/Δ23/Δ44 |
| 114 | 10 | mosaic | Δ17/Δ8/Δ6 + 25 |

TABLE 8-continued

Genotypes of Foxn1 mutant mice

| Founder NO. | sgRNA<br>(ng/ml) | Genotyping Summary | Detected alleles |
|---|---|---|---|
| 124 | 10 | mosaic | Δ11/Δ15 + 2/+1 |
| 126 | 10 | mosaic | Δ17/Δ2 + 3/Δ12 + 6 |
| 12 | 100 | mosaic | Δ30/Δ28/Δ17/+1 |
| 5 | 100 | mosaic | Δ28/Δ11/Δ2 + 6/+1 |
| 14 | 100 | mosaic | Δ17/Δ11/Δ10 |
| 21 | 100 | mosaic | Δ127/Δ41/Δ2/Δ6 + 25 |
| 24 | 100 | mosaic | Δ17/+1/WT |
| 64 | 100 | mosaic | Δ31/Δ21/+1/WT |
| 68 | 100 | mosaic | Δ17/Δ11/+1/WT |
| 79 | 100 | mosaic | Δ22/Δ5/+2/WT |
| 61 | 100 | mosaic | Δ21 + 4/Δ6/+1/+9 |
| 66** | 100 | mosaic | Δ17/Δ8/Δ11 + 6/+1/WT |
| 3 | 100 | mosaic | Δ11/Δ8/+1 |

Underlined alleles were sequenced. Alleles in red, detected by sequencing, but not by fPCR.
*only one clone sequenced.
**Not determined by fPCR.

Figure 5D:
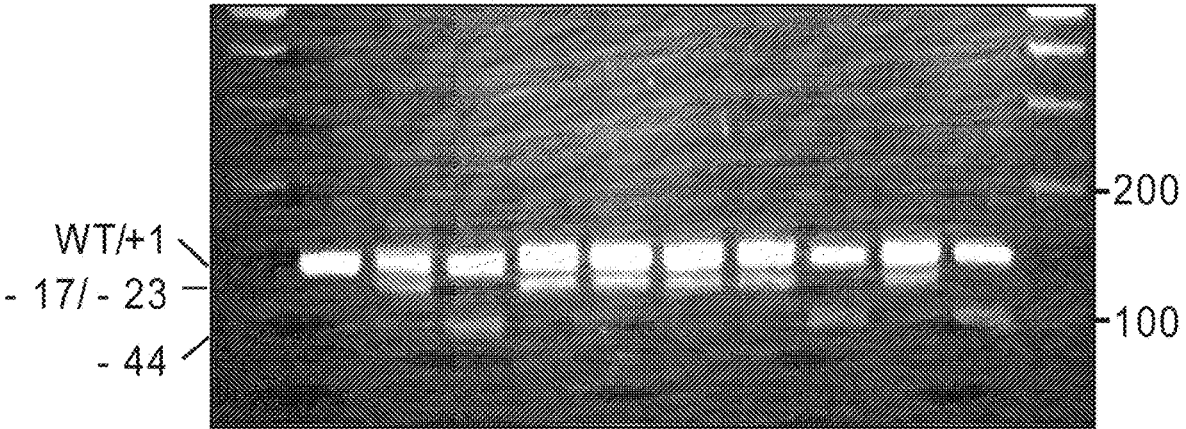
Figures 8A, 8B, 8C:
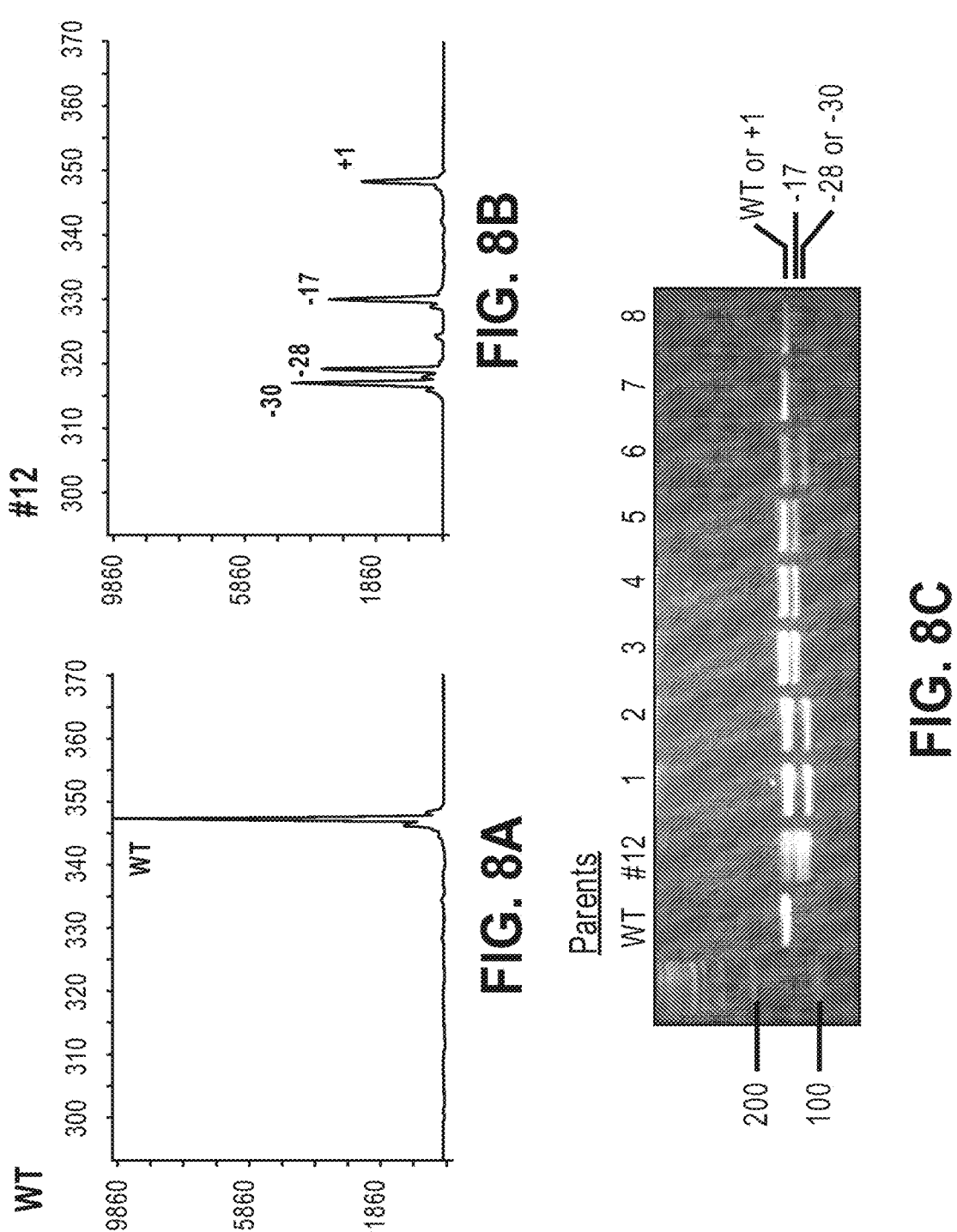
FIGS. 8A, 8B, and 8C show Germ-line transmission of the mutant alleles found in Foxn1 mutant founder #12.
Figures 9A, 9B:
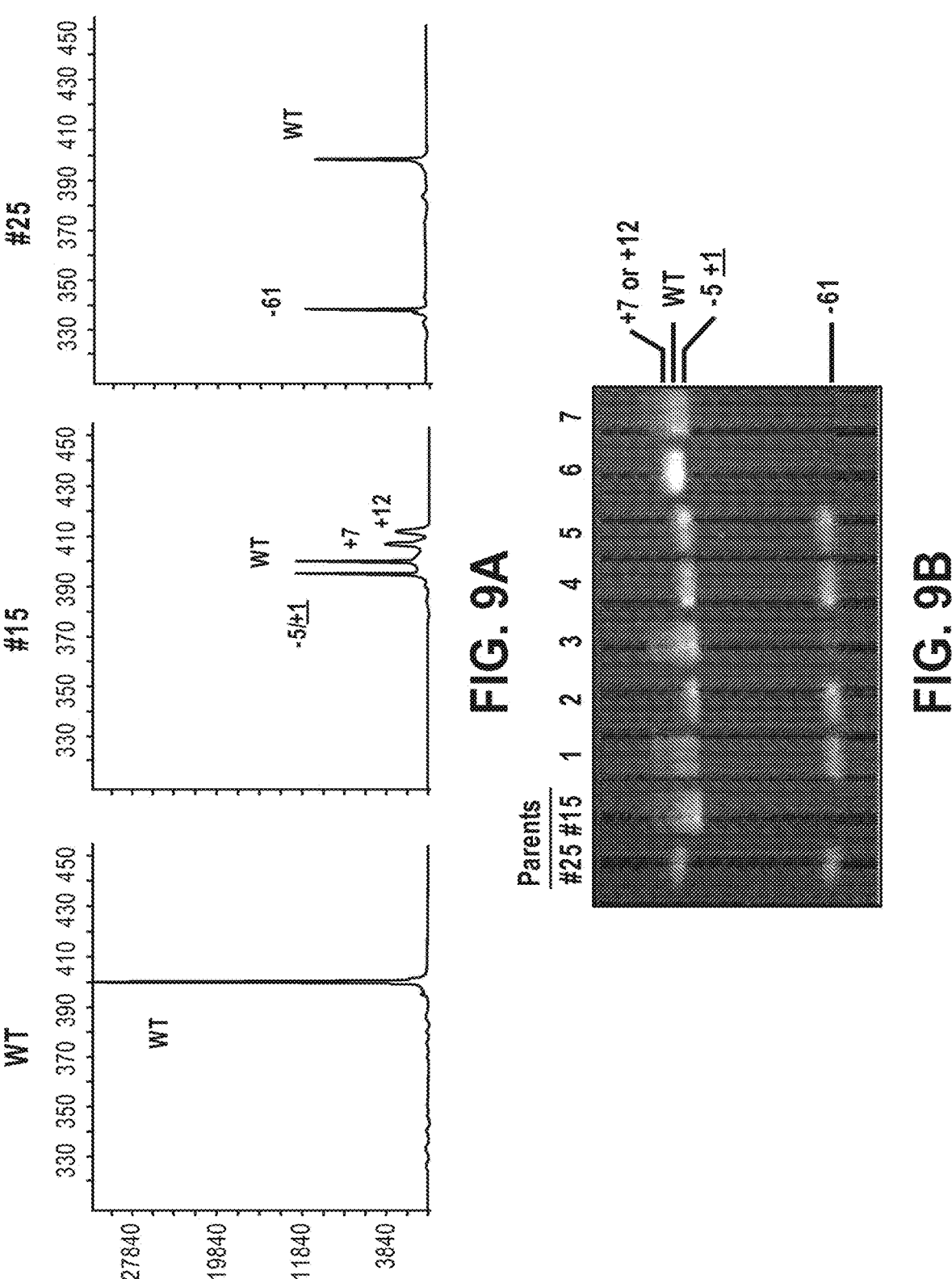
FIGS. 9A and 9B show Genotypes of embryos generated by crossing Prkdc mutant founders. Prkdc mutant founders ♂25 and ♀15 were crossed and E13.5 embryos were isolated.

As expected, all the progenies were heterozygous mutants possessing the wild-type allele and one of the mutant alleles (FIG. 5d). We also confirmed the germ-line transmission in independent founder mice of Foxn1 (FIG. 8) and Prkdc (FIG. 9). To the best of our knowledge, these results provide the first evidence that RGEN-induced mutant alleles are stably transmitted to F1 progenies in animals.

Example 4: RNA-Guided Genome Editing in Plants 4-1. Production of Cas9 Protein

The Cas9 coding sequence (4104 bps), derived from *Streptococcus pyogenes* strain M1 GAS (NC_002737.1), was cloned to pET28-b (+) plasmid. A nuclear targeting sequence (NLS) was included at the protein N terminus to ensure the localization of the protein to the nucleus. pET28-b (+) plasmid containing Cas9 ORF was transformed into BL21 (DE3). Cas9 was then induced using 0.2 mM IPTG for 16 hrs at 18° C. and purified using Ni-NTA agarose beads (Qiagen) following the manufacturer's instructions. Purified Cas9 protein was concentrated using Ultracel-100K (Millipore).

4-2. Production of Guide RNA

The genomic sequence of the *Arabidopsis* gene encoding the BRI1 was screened for the presence of a NGG motif, the so called protospacer adjacent motif (PAM), in an exon which is required for Cas9 targeting To disrupt the BRI1 gene in *Arabidopsis*, we identified two RGEN target sites in an exon that contain the NGG motif. sgRNAs were produced in vitro using template DNA. Each template DNA was generated by extension with two partially overlapped oligonucleotides (Macrogen, Table X1) and Phusion polymerase (Thermo Scientific) using the following conditions–98° C. 30 sec {98° C. 10 sec, 54° C. 20 sec, 72° C. 2 min}×20, 72° C. 5 min.

TABLE 9

Oligonucleotides for the production of the template DNA for in vitro transcription

| Oligonucleotides | Sequence (5'-3') | SEQ ID NO |
|---|---|---|
| BRI1 target 1 (Forward) | GAAATTAATACGACTCACTATAGGTTTGAAAGAT GGAAGCGCGGGTTTTAGAGCTAGAAATAGCAAGT TAAAATAAGGCTAGTCCG | 73 |
| BRI1 target 2 (Forward) | GAAATTAATACGACTCACTATAGGTGAAACTAAA CTGGTCCACAGTTTTAGAGCTAGAAATAGCAAGT TAAAATAAGGCTAGTCCG | 74 |
| Universal (Reverse) | AAAAAAGCACCGACTCGGTGCCACTTTTTCAAGT TGATAACGGACTAGCCTTATTTTAACTTGC | 75 |

The extended DNA was purified and used as a template for the in vitro production of the guide RNA's using the MEGAshortscript T7 kit (Life Technologies). Guide RNA were then purified by Phenol/Chloroform extraction and ethanol precipitation. To prepare Cas9/sgRNA complexes, 10 µl of purified Cas9 protein (12 µg/µl) and 4 µl each of two sgRNAs (11 µg/µl) were mixed in 20 µl NEB3 buffer (New England Biolabs) and incubated for 10 min at 37° C.

4-3. Transfection of Cas9/sgRNA Complex to Protoplast

The leaves of 4-week-old *Arabidopsis* seedlings grown aseptically in petri dishes were digested in enzyme solution (1% cellulose R10, 0.5% macerozyme R10, 450 mM mannitol, 20 mM MES pH 5.7 and CPW salt) for 8-16 hrs at 25° C. with 40 rpm shaking in the dark. Enzyme/protoplast solutions were filtered and centrifuged at 100×g for 3~5 min. Protoplasts were re-suspended in CPW solution after counting cells under the microscope (×100) using a hemacytometer. Finally, protoplasts were re-suspended at $1\times10^6$/ml in MMG solution (4 mM HEPES pH 5.7, 400 mM mannitol and 15 mM MgCl2). To transfect the protoplasts with Cas9/sgRNA complex, 200 µL (200,000 protoplasts) of the protoplast suspension were gently mixed with 3.3 or 10 µL of Cas9/sgRNA complex [Cas9 protein (6 µg/µL) and two sgRNAs (2.2 µg/µL each)] and 200 µL of 40% polyethylene glycol transfection buffer (40% PEG4000, 200 mM mannitol and 100 mM CaCl2) in 2 ml tubes. After 5~20 min incubation at room temperature, transfection was stopped by adding wash buffer with W5 solution (2 mM MES pH 5.7, 154 mM NaCl, 125 mM CaCl2 and 5 mM KCl). Protoplasts were then collected by centrifugation for 5 min at 100 X g, washed with 1 ml of W5 solution, centrifuged for another 5 min at 100 X g. The density of protoplasts was adjusted to $1\times10^5$/ml and they were cultured in modified KM 8p liquid medium with 400 mM glucose.

4-4. Detection of Mutations in *Arabidopsis* Protoplasts and Plants

Figure 11:
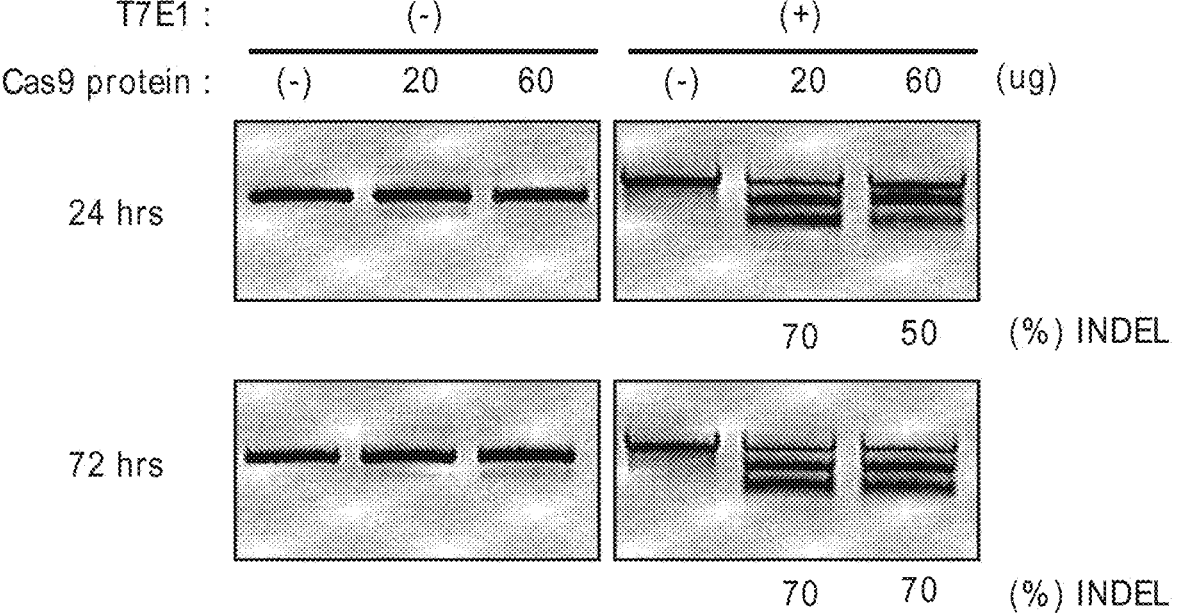
FIG. 11 shows recombinant Cas9 protein-induced mutations in Arabidopsis protoplasts.
Figure 12:
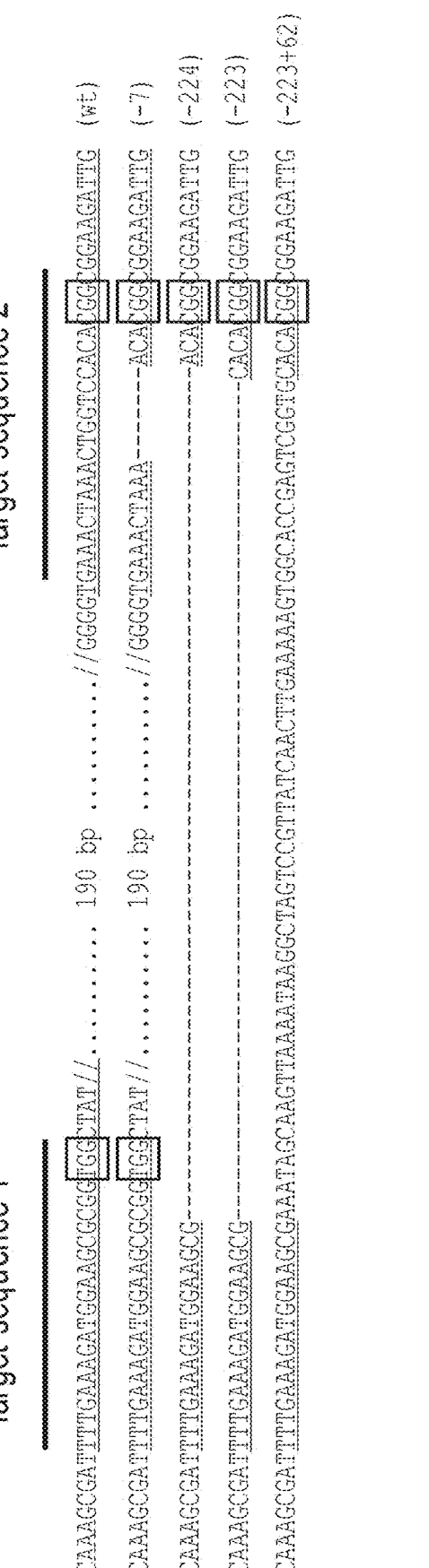
FIG. 12 shows wild type BRI1 sequence (SEQ ID NO: 177) and recombinant Cas9 protein-induced mutant sequences (SEQ ID NOs. 178-181) in the Arabidopsis BRI1 gene. The DNA sequences of the mutant sequences are: −7 (SEQ ID NO: 178), −224 (SEQ ID NO: 179), −223 (SEQ ID NO: 180), and −223, +62 (SEQ ID NO: 181).

After 24 hr or 72 hr post-transfection, protoplasts were collected and genomic DNA was isolated. The genomic DNA region spanning the two target sites was PCR-amplified and subjected to the T7E1 assay. As shown in FIG. 11, indels were induced by RGENs at high frequencies that ranged from 50% to 70%. Surprisingly, mutations were induced at 24 hr post-transfection. Apparently, Cas9 protein functions immediately after transfection. PCR products were purified and cloned into T-Blunt PCR Cloning Kit (Solgent). Plasmids were purified and subjected to Sanger sequencing with M13F primer. One mutant sequence had a 7-bp deletion at one site (FIG. 12). The other three mutant sequences had deletions of ~220-bp DNA segments between the two RGEN site.

Example 5: Cas9 Protein Transduction Using a Cell-Penetrating Peptide or Protein Transduction Domain 5-1. Construction of his-Cas9-Encoding Plasmid Cas9 with a cysteine at the C-terminal was prepared by PCR amplification using the previously described Cas9 plasmid {Cho, 2013 #166} as the template and cloned into pET28-(a) vector (Novagen, Merk Millipore, Germany) containing His-tag at the N-terminus.

5-2. Cell Culture 293T (Human embryonic kidney cell line), and HeLa (human ovarian cancer cell line) were grown in DMEM (GIBCO-BRL Rockville) supplemented with 10% FBS and 1% penicillin and streptomycin.

5-3. Expression and Purification of Cas9 Protein

To express the Cas9 protein, *E. coli* BL21 cells were transformed with the pET28-(a) vector encoding Cas9 and plated onto Luria-Bertani (LB) agar medium containing 50 µg/mL kanamycin (Amresco, Solon, OH). Next day, a single colony was picked and cultured in LB broth containing 50 µg/mL kanamycin at 37° C. overnight. Following day, this starter culture at 0.1 OD600 was inoculated into Luria broth containing 50 µg/mL kanamycin and incubated for 2 hrs at 37° C. until OD600 reached to 0.6-0.8. To induce Cas9 protein expression, the cells were cultured at 30° C. overnight after addition of isopropyl-B-D-thiogalactopyranoside (IPTG) (Promega, Madison, WI) to the final concentration of 0.5 mM.

The cells were collected by centrifugation at 4000 rpm for 15-20 mins, resuspended in a lysis buffer (20 mM Tris-Cl pH8.0, 300 mM NaCl, 20 mM imidazole, 1X protease inhibitor cocktail, 1 mg/ml lysozyme), and lysed by sonication (40% duty, 10 sec pulse, 30 sec rest, for 10 mins on ice). The soluble fraction was separated as the supernatant after centrifugation at 15,000 rpm for 20 mins at 4° C. Cas9 protein was purified at 4° C. using a column containing Ni-NTA agarose resin (QIAGEN) and AKTA prime instrument (AKTA prime, GE Healthcare, UK). During this chromatography step, soluble protein fractions were loaded onto Ni-NTA agarose resin column (GE Healthcare, UK) at the flow rate of 1 mL/min. The column was washed with a washing buffer (20 mM Tris-Cl pH8. 0, 300 mM NaCl, 20 mM imidazole, 1X protease inhibitor cocktail) and the bound protein was eluted at the flow rate of 0.5 ml/min with an elution buffer (20 mM Tris-Cl pH8.0, 300 mM NaCl, 250 mM imidazole, 1X protease inhibitor cocktail). The pooled eluted fraction was concentrated and dialyzed against storage buffer (50 mM Tris-HCl, pH8.0, 200 mM KCl, 0.1 mM EDTA, 1 mM DTT, 0.5 mM PMSF, 20% Glycerol). Protein concentration was quantitated by Bradford assay (Biorad, Hercules, CA) and purity was analyzed by SDS-PAGE using bovine serum albumin as the control.

5-4. Conjugation of Cas9 to 9R4L 1 mg Cas9 protein diluted in PBS at the concentration of 1 mg/mL and 50 μg of maleimide-9R4L peptide in 25 μL DW (Peptron, Korea) were gently mixed using a rotor at room temperature for 2 hrs and at 4° C. overnight. To remove unconjugated maleimide-9R4L, the samples were dialyzed using 50kDamolecular weight cutoff membrane against of DPBS (pH 7.4) at 4° C. for 24 hrs. Cas9-9R4L protein was collected from the dialysis membrane and the protein amount was determined using Bradford assay.

5-5. Preparation of sgRNA-9R4L sgRNA (1 μg) was gently added to various amounts of C9R4LC peptide (ranging from 1 to 40 weight ratio) in 100 μl of DPBS (pH 7.4). This mixture was incubated at room temperature for 30 mins and diluted to 10 folds using RNAse-free deionized water. The hydrodynamic diameter and z-potential of the formed nanoparticles were measured using dynamic light scattering (Zetasizer-nano analyzer ZS; Malvern instruments, Worcestershire, UK).

5-6. Cas9 Protein and sgRNA Treatments

Cas9-9R4L and sgRNA-C9R4LC were treated to the cells as follows: 1 μg of sgRNA and 15 μg of C9R4LC peptide were added to 250 mL of OPTIMEM medium and incubated at room temperature for 30 mins. At 24 hrs after seeding, cells were washed with OPTIMEM medium and treated with sgRNA-C9R4LC complex for 4 hrs at 37° C. Cells were washed again with OPTIMEM medium and treated with Cas9-9R4L for 2 hrs at 37° C. After treatment, culture media was replaced with serum-containing complete medium and incubated at 37° C. for 24 hrs before the next treatment. Same procedure was followed for multiple treatments of Cas9 and sgRNA for three consecutive days.

Figure 13:
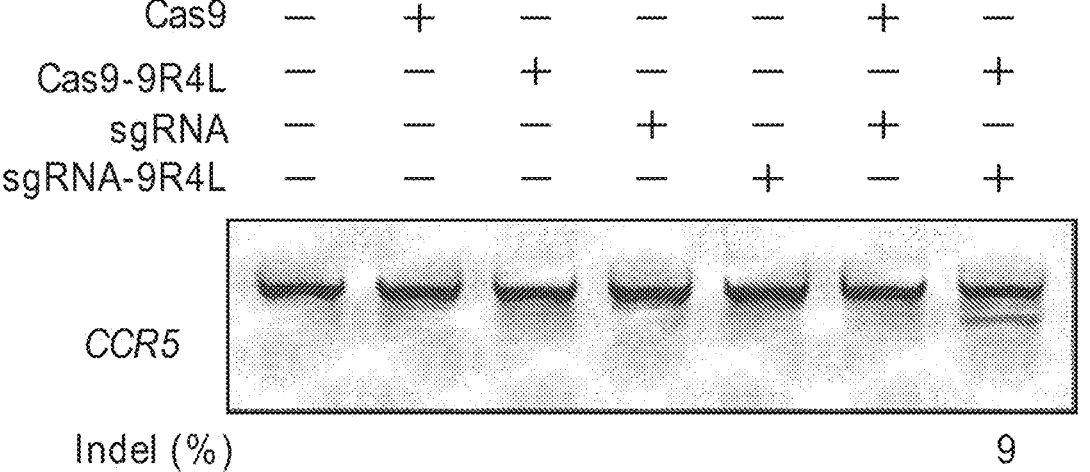
FIG. 13 shows T7E1 assay showing endogenous CCR5 gene disruption in 293 cells by treatment of Cas9-mal-9R4L and sgRNA/C9R4LC complex.

5-7. Cas9-9R4L and sgRNA-9R4L can Edit Endogenous Genes In Cultured Mammalian Cells without the Use of Additional Delivery Tools To determine whether Cas9-9R4L and sgRNA-9R4L can edit endogenous genes in cultured mammalian cells without the use of additional delivery tools, we treated 293 cells with Cas9-9R4L and sgRNA-9R4L targeting the CCR5 gene and analyzed the genomic DNA. T7E1 assay showed that 9% of CCR5 gene was disrupted in cells treated with both Cas9-9R4L and sgRNA-9R4L and that the CCR5 gene disruption was not observed in control cells including those untreated, treated with either Cas9-9R or sgRNA-9R4L, or treated with both unmodified Cas-9 and sgRNA (FIG. 13), suggesting that the treatment with Cas9-9R4L protein and sgRNA conjugated with 9R4L, but not unmodified Cas9 and sgRNA, can lead to efficient genome editing in mammalian cells.

Example 6: Control of Off-Target Mutation According to Guide RNA Structure

Figure 14A:
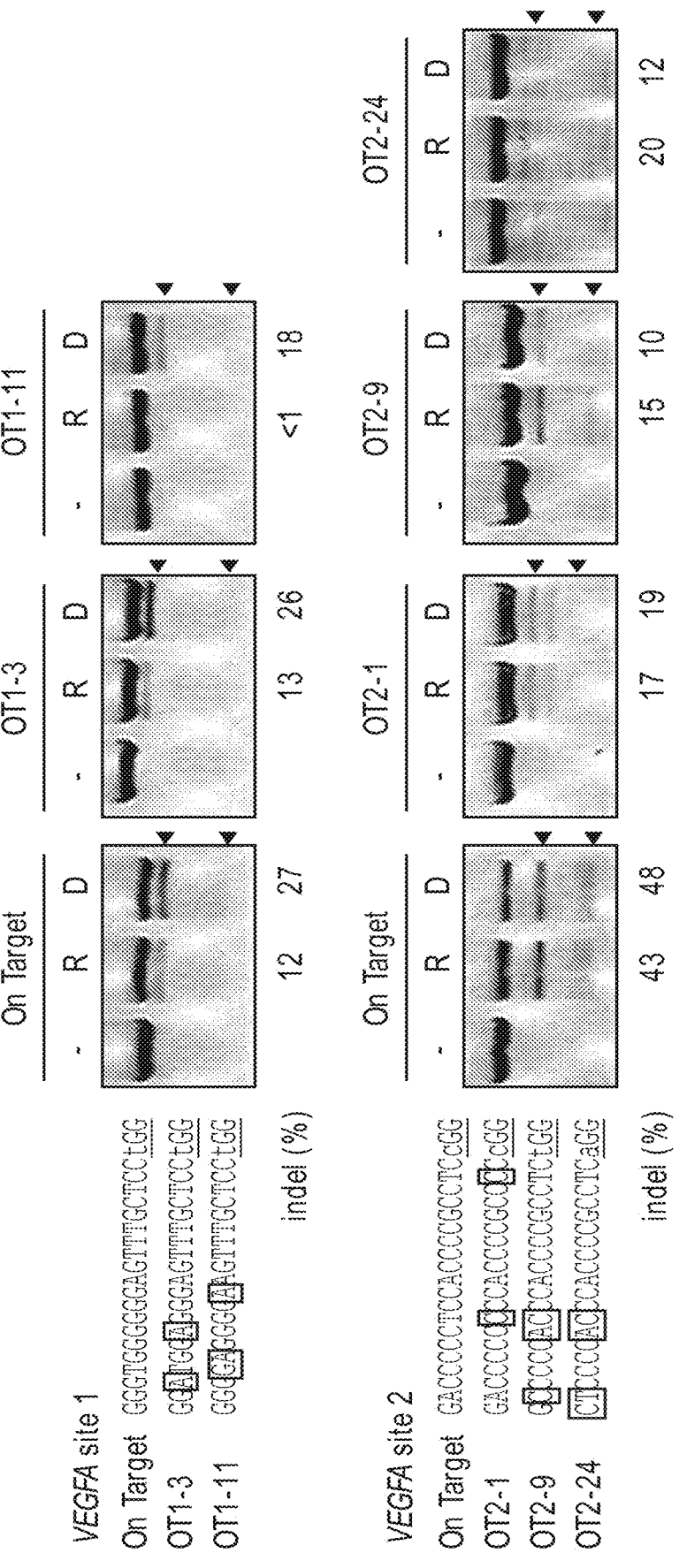
FIGS. 14A and 14B show mutation frequencies at on-target and off-target sites of RGENs reported in Fu et al. (2013). T7E1 assays analyzing genomic DNA from K562 cells (R) transfected serially with 20 μg of Cas9-encoding plasmid and with 60 μg and 120 μg of in vitro transcribed GX₁₉ crRNA and tracrRNA, respectively (1×10⁶ cells), or (D) co-transfected with 1 μg of Cas9-encoding plasmid and 1 μg of GX₁₉ SgRNA expression plasmid (2×10⁵ cells).
Figure 14B:
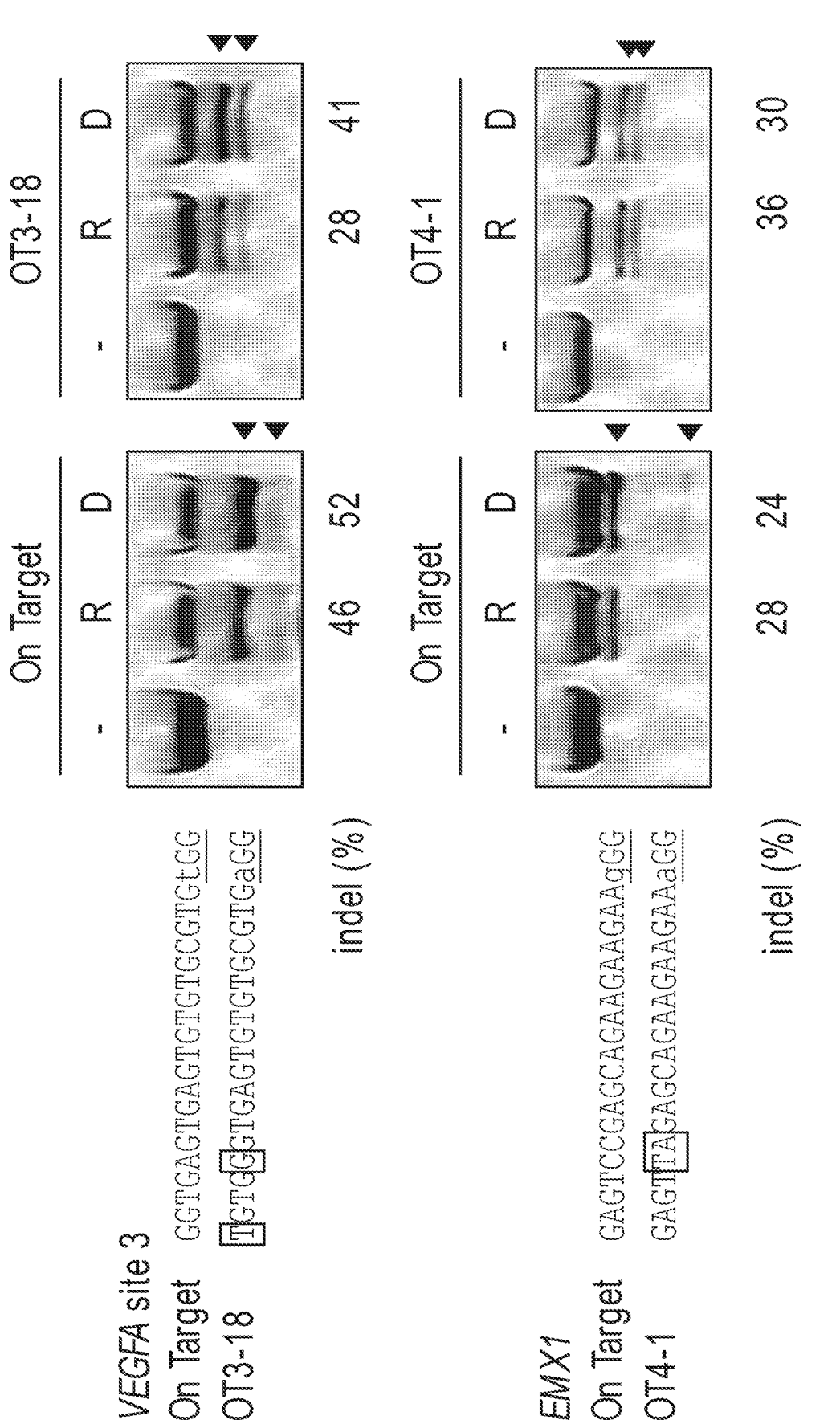

Recently, three groups reported that RGENs had off-target effects in human cells. To our surprise, RGENs induced mutations efficiently at off-target sites that differ by 3 to 5 nucleotides from on-target sites. We noticed, however, that there were several differences between our RGENs and those used by others. First, we used dualRNA, which is crRNA plus tracrRNA, rather than single-guide RNA (sgRNA) that is composed of essential portions of crRNA and tracrRNA. Second, we transfected K562 cells (but not Hela cells) with synthetic crRNA rather than plasmids encoding crRNA. Hela cells were transfected with crRNA-encoding plasmids. Other groups used sgRNA-encoding plasmids. Third, our guide RNA had two additional guanine nucleotides at the 5' end, which are required for efficient transcription by T7 polymerase in vitro. No such additional nucleotides were included in the sgRNA used by others. Thus, the RNA sequence of our guide RNA can be shown as 5'-GGX$_{20}$, whereas 5'-GX$_{19}$, in which X$_{20}$ or GX$_{19}$ corresponds to the 20-bp target sequence, represents the sequence used by others. The first guanine nucleotide is required for transcription by RNA polymerase in cells. To test whether off-target RGEN effects can be attributed to these differences, we chose four RGENs that induced off-target mutations in human cells at high frequencies (13). First, we compared our method of using in vitro transcribed dualRNA with the method of transfecting sgRNA-encoding plasmids in K562 cells and measured mutation frequencies at the on-target and off-target sites via the T7E1 assay. Three RGENs showed comparable mutation frequencies at on-target and off-target sites regardless of the composition of guide RNA. Interestingly, one RGEN (VEFGA site 1) did not induce indels at one validated off-target site, which differs by three nucleotides from the on-target site (termed OT1-11, FIG. 14), when synthetic dualRNA was used. But the synthetic dualRNA did not discriminate the other validated off-target site (OT1-3), which differs by two nucleotides from the on-target site.

Figure 15A:
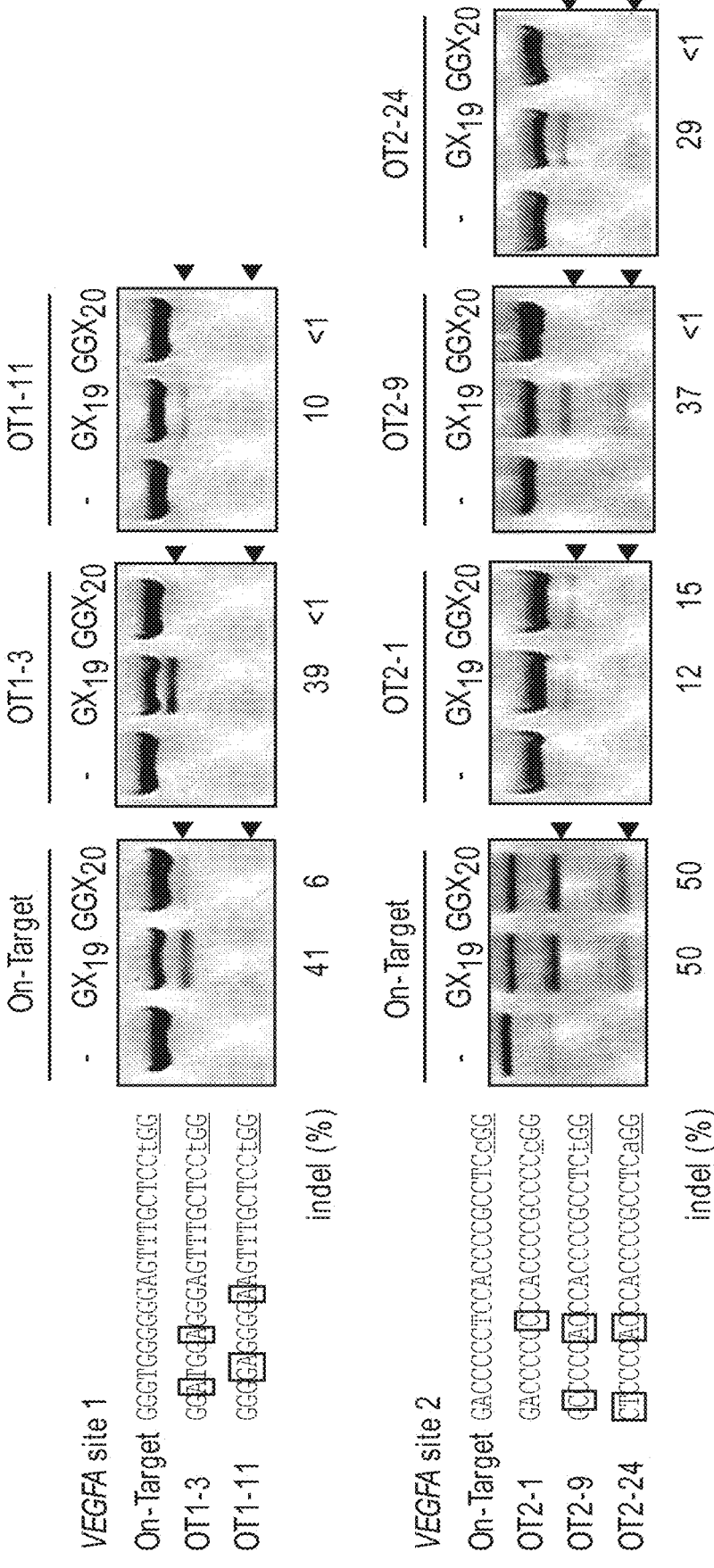
FIGS. 15A and 15B show comparison of guide RNA structure. Mutation frequencies of the RGENs reported in Fu et al. (2013) were measured at on-target and off-target sites using the T7E1 assay. K562 cells were co-transfected with the Cas9-encoding plasmid and the plasmid encoding GX₁₉ sgRNA or GGX₂₀ sgRNA. Off-target sites (OT1-3 etc.) are labeled as in Fu et al. (2013).
Figure 15B:
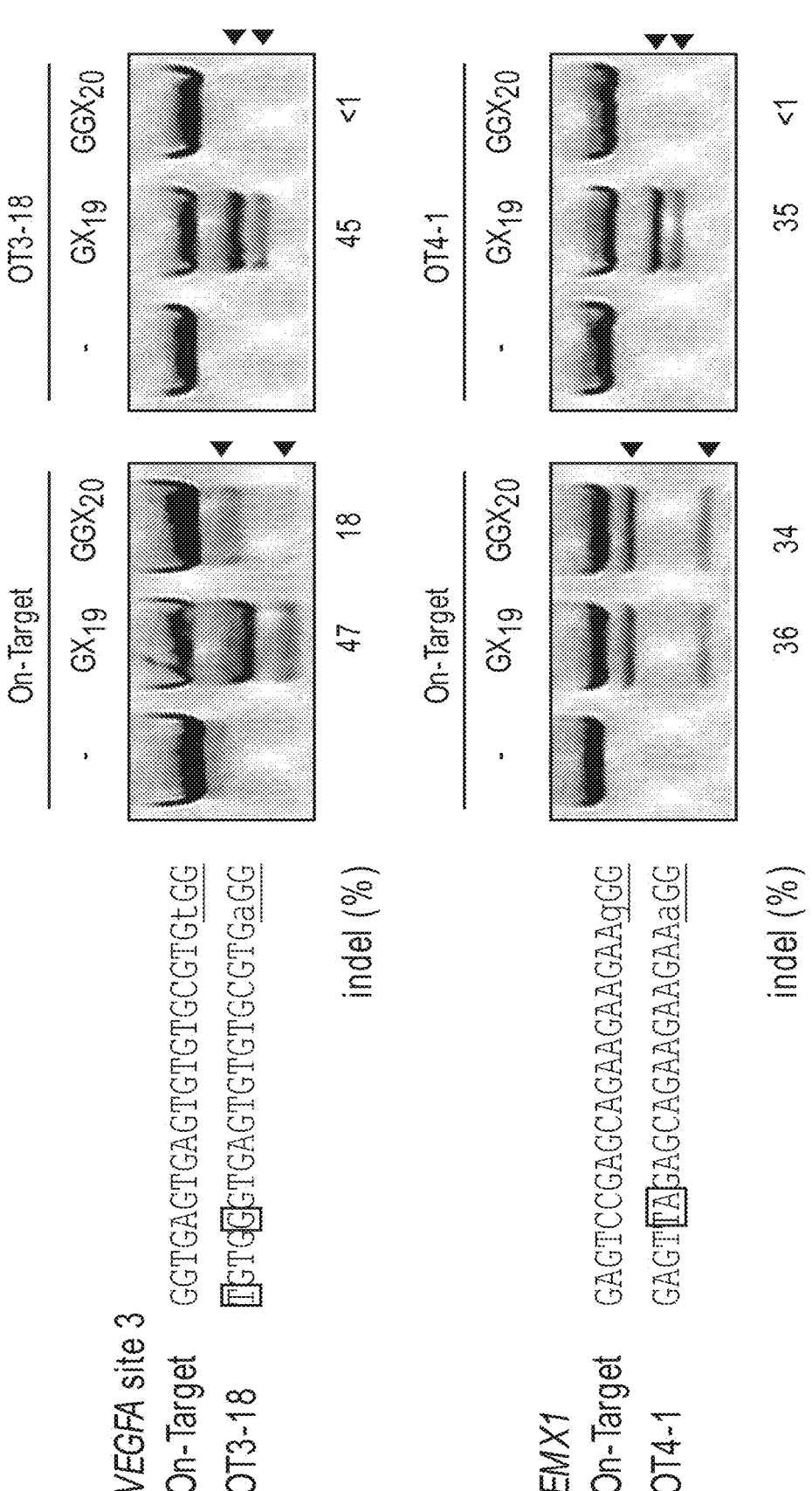

Next, we tested whether the addition of two guanine nucleotides at the 5' end of sgRNA could make RGENs more specific by comparing 5'-GGX$_{20}$ (or 5'-GGGX$_{19}$) sgRNA with 5'-GX$_{19}$ sgRNA. Four GX$_{19}$ sgRNAs complexed with Cas9 induced indels equally efficiently at on-target and off-target sites, tolerating up to four nucleotide mismatches. In sharp contrast, GGX$_{20}$ sgRNAs discriminated off-target sites effectively. In fact, the T7E1 assay barely detected RGEN-induced indels at six out of the seven validated off-target sites when we used the four GGX$_{20}$ sgRNAs (FIG. 15). We noticed, however, that two GGX$_{20}$ sgRNAs (VEGFA sites 1 and 3) were less active at on-target sites than were the corresponding GX$_{19}$ sgRNAs. These results show that the extra nucleotides at the 5' end can affect mutation frequencies at on-target and off-target sites, perhaps by altering guide RNA stability, concentration, or secondary structure.

These results suggest that three factors—the use of synthetic guide RNA rather than guide RNA-encoding plasmids, dualRNA rather than sgRNA, and GGX$_{20}$ sgRNA rather than GX$_{19}$ sgRNA-have cumulative effects on the discrimination of off-target sites.

Example 7: Paired Cas9 Nickases

Figures 16A, 16B:
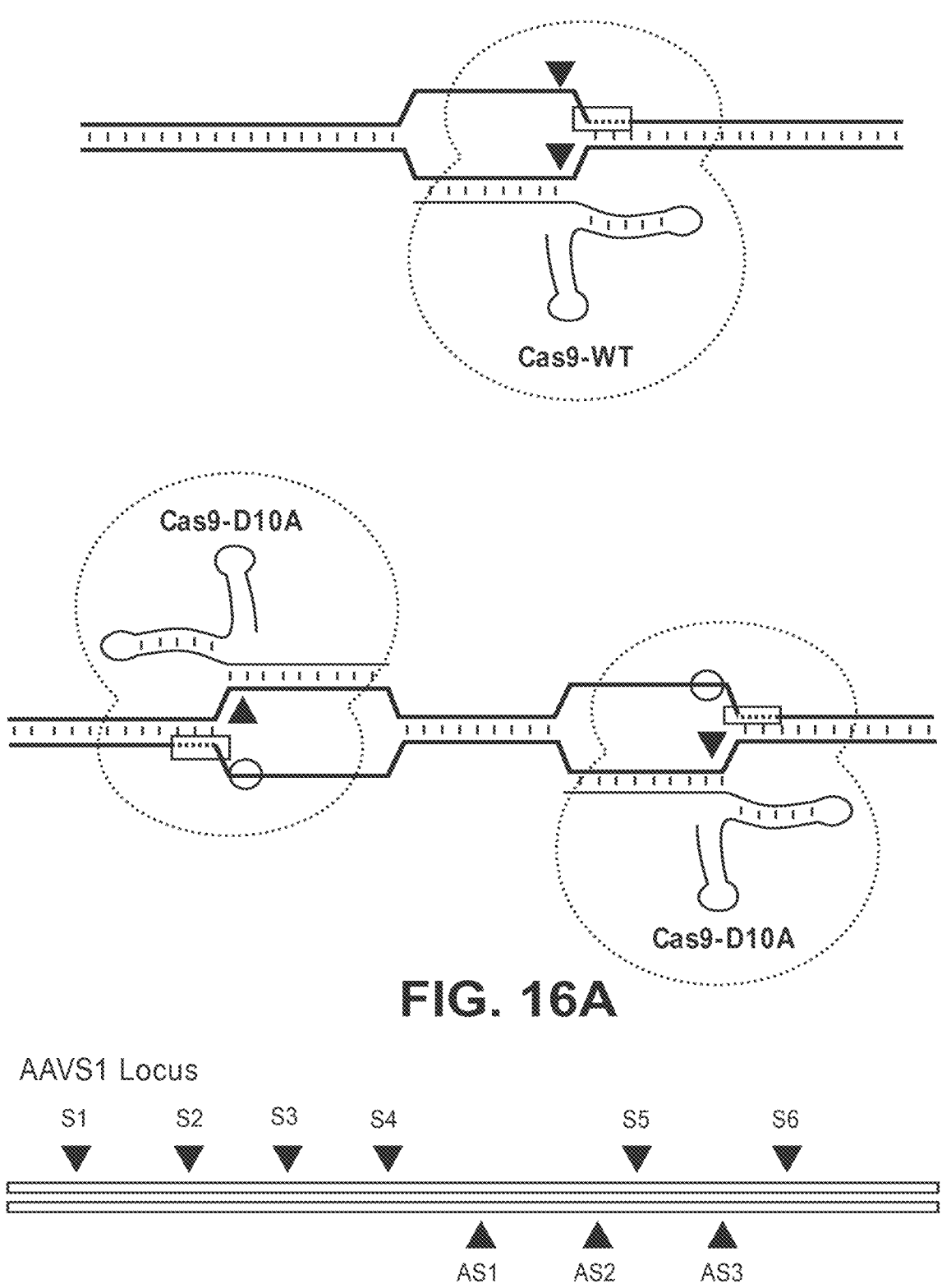
FIGS. 16A, 16B, 16C, and 16D show that in vitro DNA cleavage by Cas9 nickases.

In principle, single-strand breaks (SSBs) cannot be repaired by error-prone NHEJ but still trigger high fidelity homology-directed repair (HDR) or base excision repair. But nickase-induced targeted mutagenesis via HDR is much less efficient than is nuclease-induced mutagenesis. We reasoned that paired Cas9 nickases would produce composite DSBs, which trigger DNA repair via NHEJ or HDR, leading to efficient mutagenesis (FIG. 16A). Furthermore, paired nickases would double the specificity of Cas9-based genome editing.

Figure 16C:
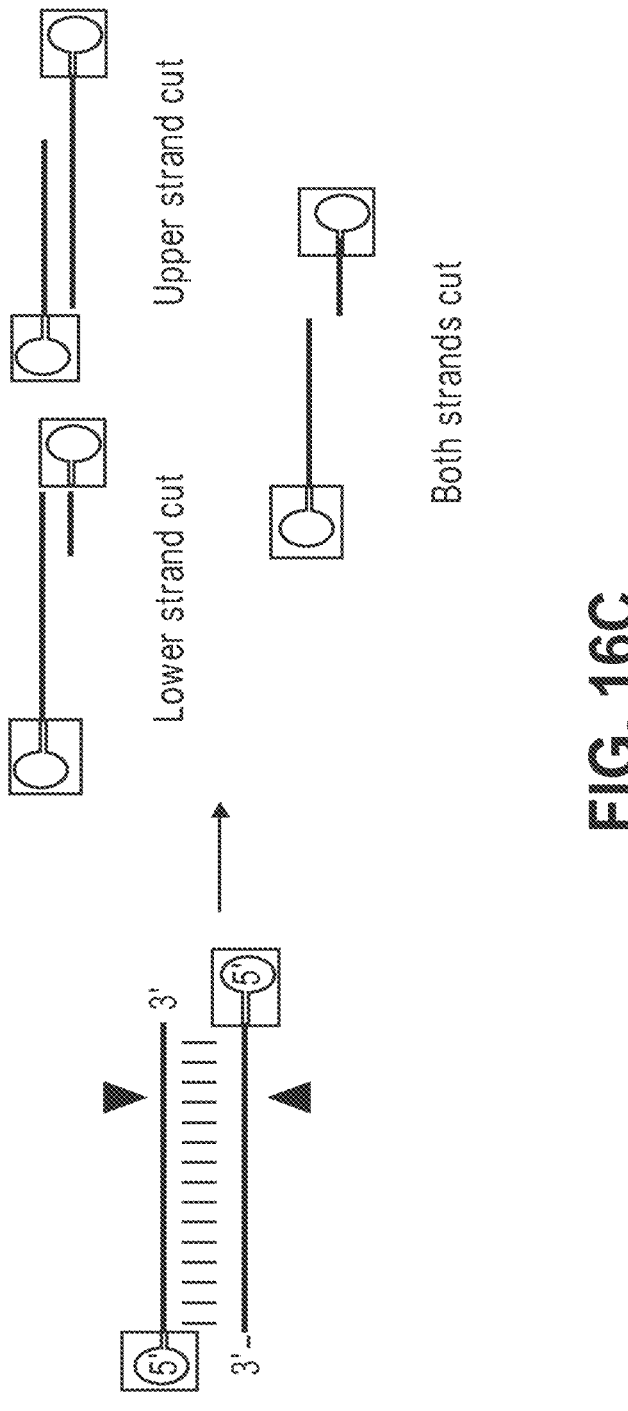
Figure 16D:
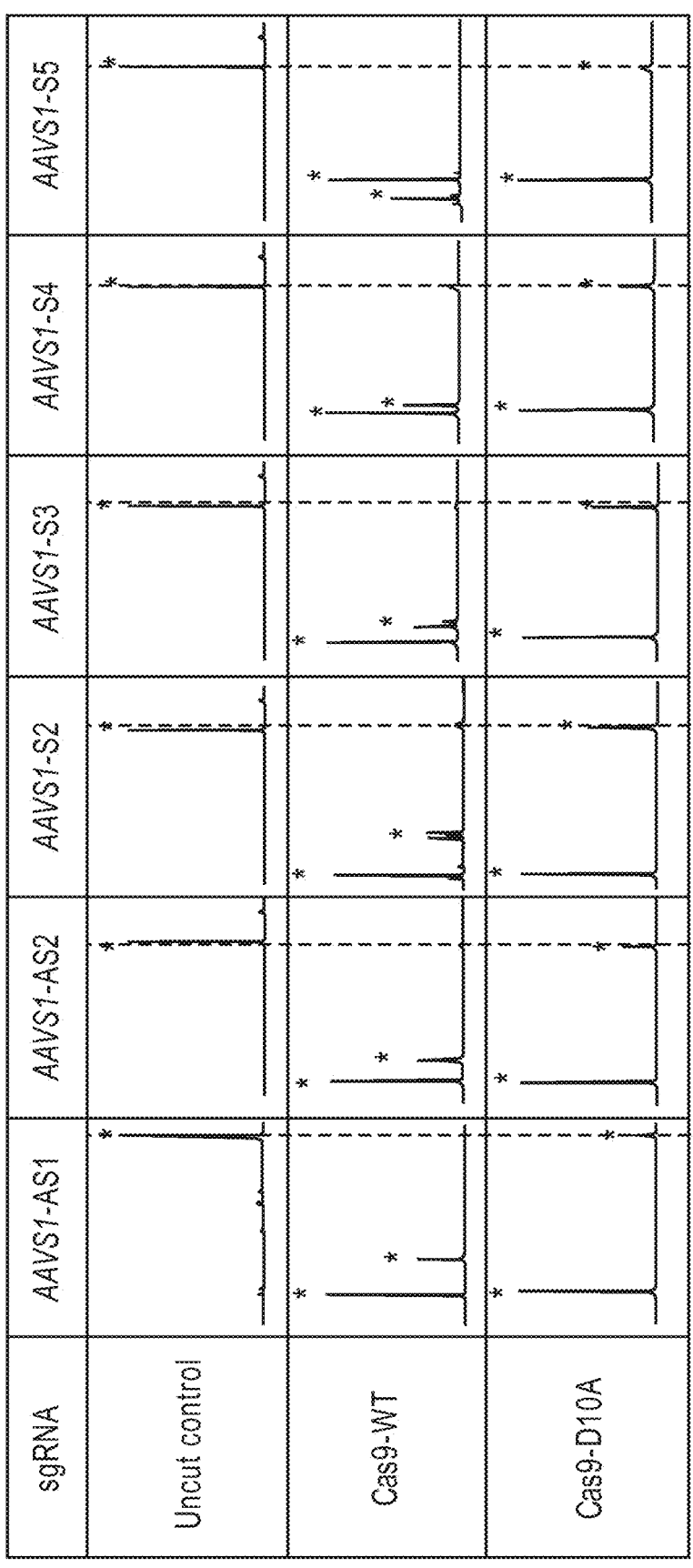
Figure 17A:
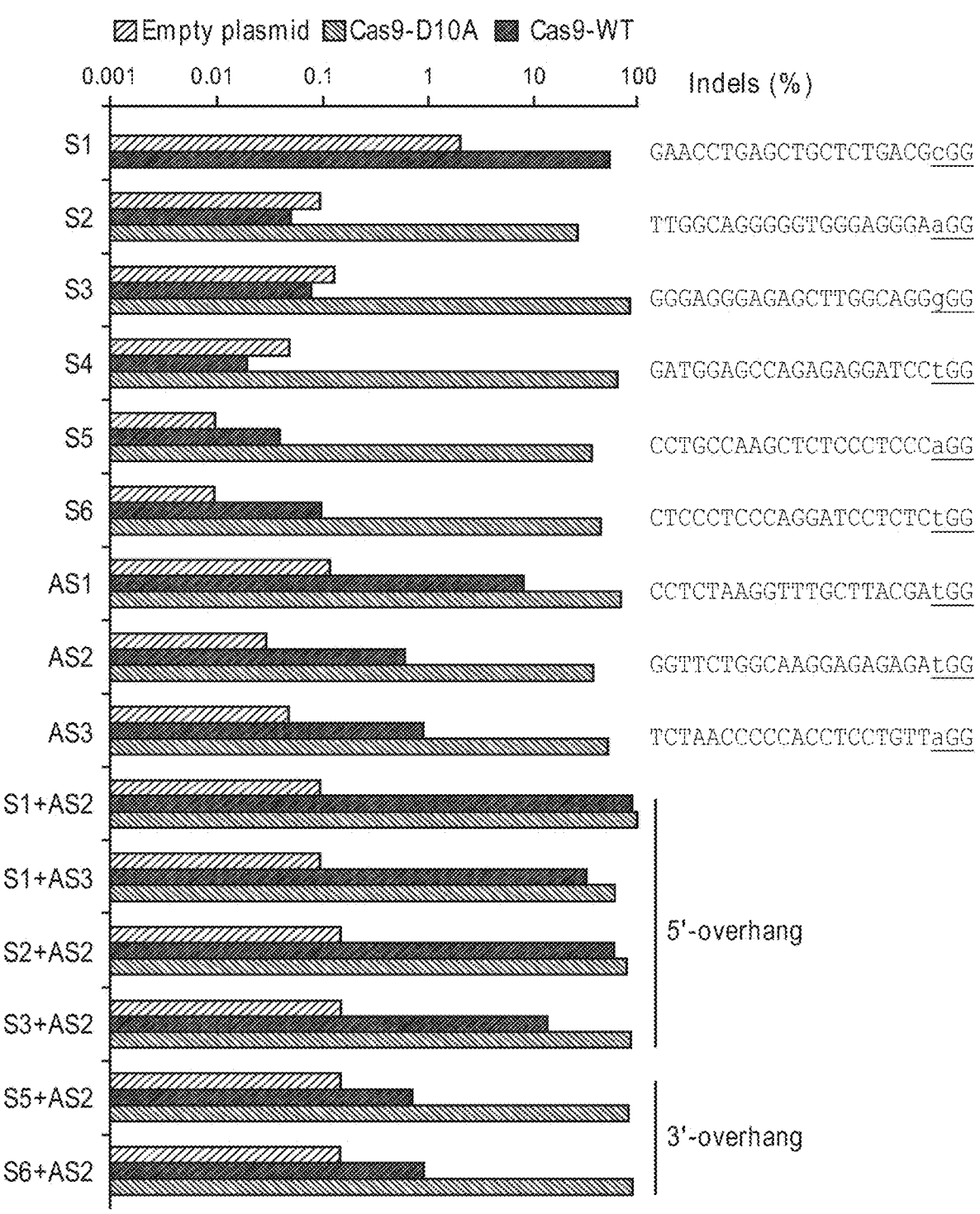
FIGS. 17A and 17B show comparison of Cas9 nuclease and nickase behavior.
Figure 18A:
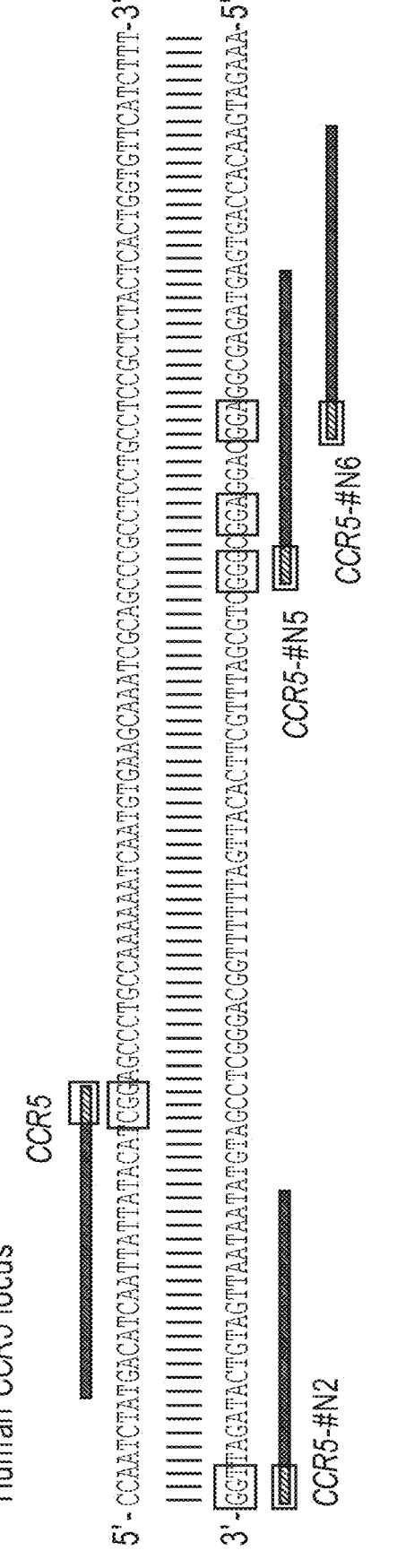
FIGS. 18A, 18B, 18C, and 18D show paired Cas9 nickases tested at other endogenous human loci. The sgRNA target sites at the human CCR5 locus (FIG. 18A; SEQ ID NO: 209) and the BRCA2 locus (FIG. 18C; SEQ ID NO: 210). PAM sequences are indicated in a box. Genome editing activities at CCR5 (FIG. 18B) and BRCA2 (FIG.
Figure 18B:
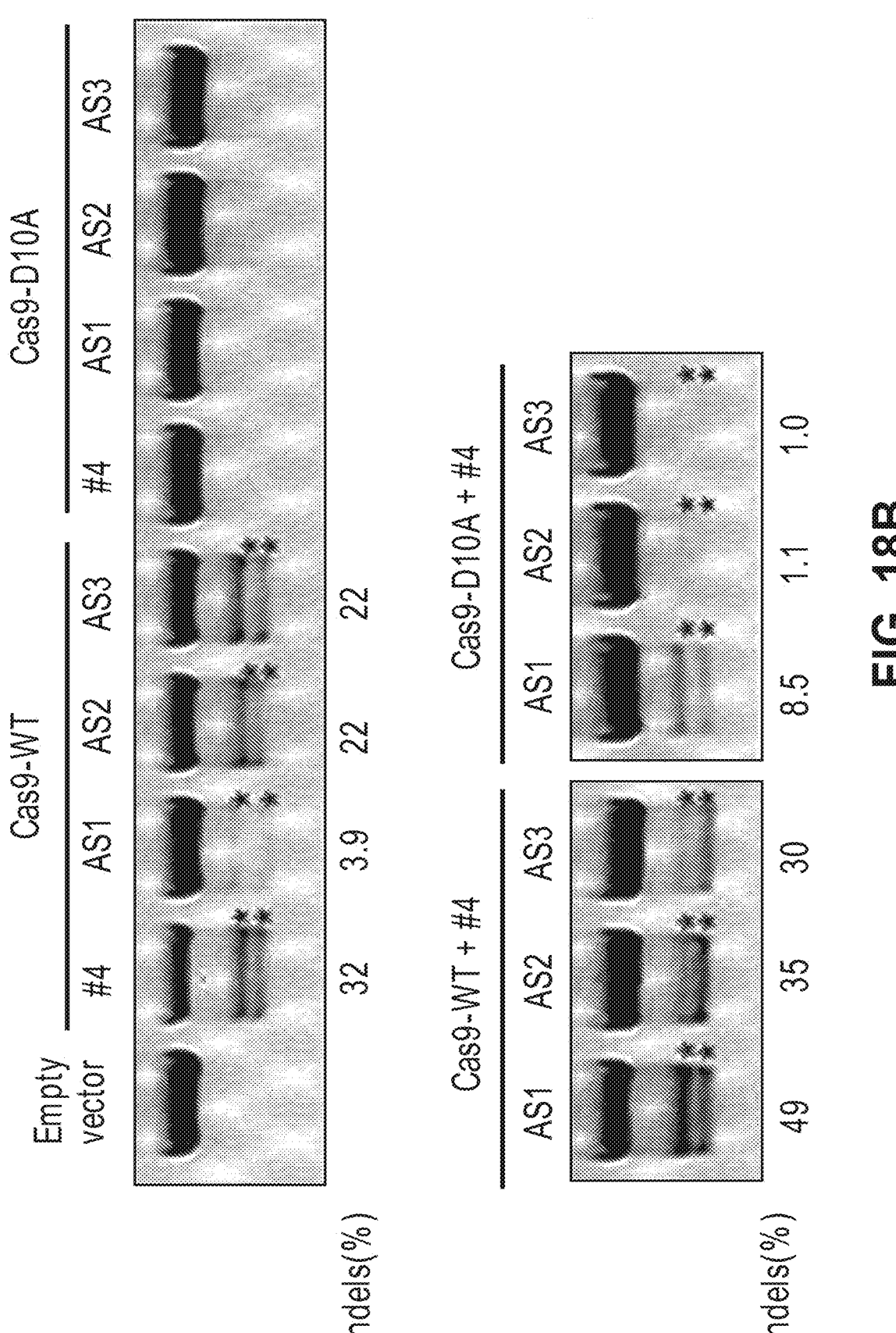
Figures 18C, 18D:
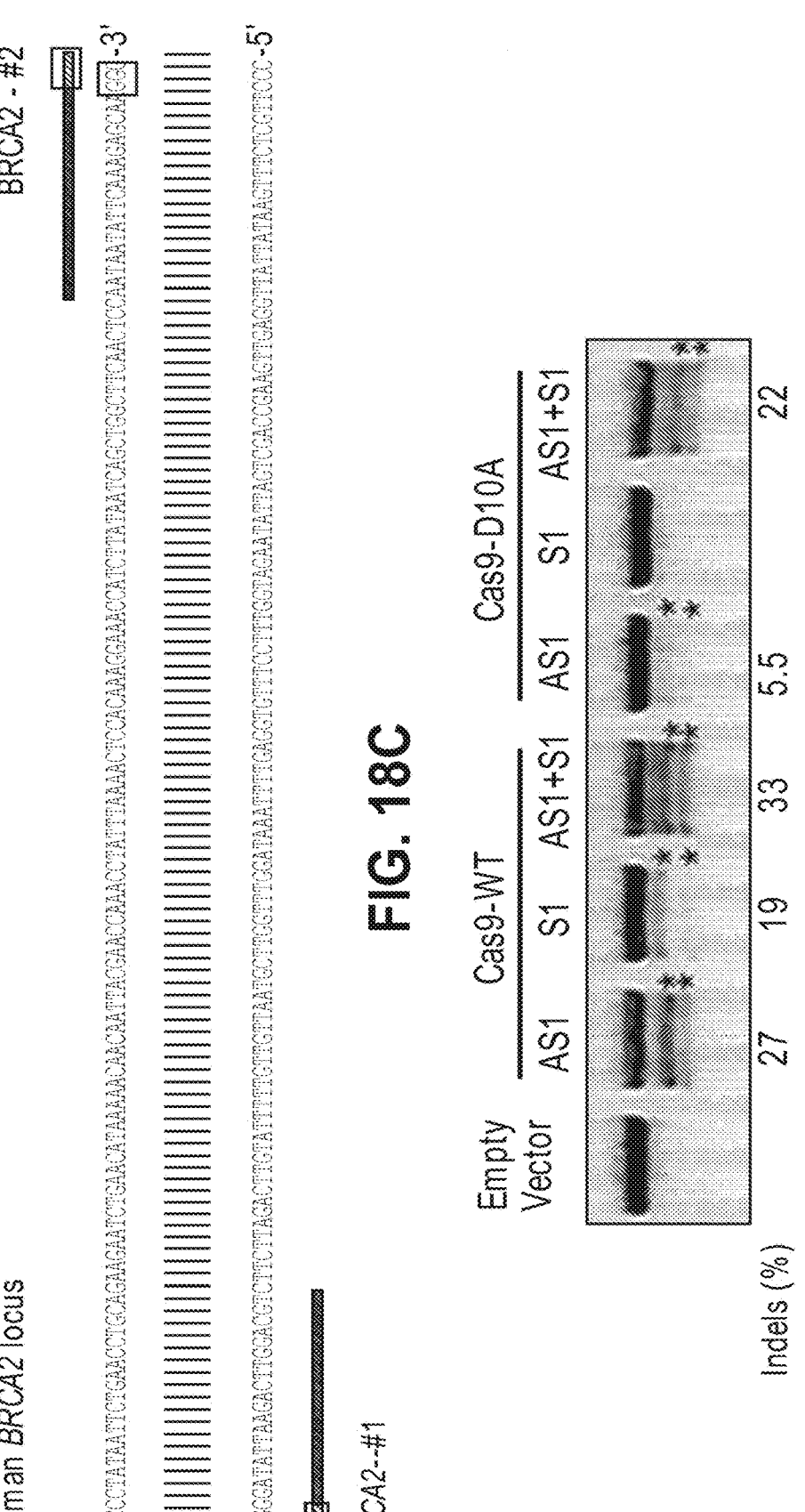

We first tested several Cas9 nucleases and nickases designed to target sites in the AAVS1 locus (FIG. 16B) in vitro via fluorescent capillary electrophoresis. Unlike Cas9 nucleases that cleaved both strands of DNA substrates, Cas9 nickases composed of guide RNA and a mutant form of Cas9 in which a catalytic aspartate residue is changed to an alanine (D10A Cas9) cleaved only one strand, producing site-specific nicks (FIG. 16C, D). Interestingly, however, some nickases (AS1, AS2, AS3, and S6 in FIG. 17A) induced indels at target sites in human cells, suggesting that nicks can be converted to DSBs, albeit inefficiently, in vivo. Paired Cas9 nickases producing two adjacent nicks on opposite DNA strands yielded indels at frequencies that ranged from 14% to 918, comparable to the effects of paired nucleases (FIG. 17A). The repair of two nicks that would produce 5' overhangs led to the formation of indels much more frequently than those producing 3' overhangs at three genomic loci (FIG. 17A and FIG. 18). In addition, paired nickases enabled targeted genome editing via homology-directed repair more efficiently than did single nickases (FIG. 19).

Figure 17B:
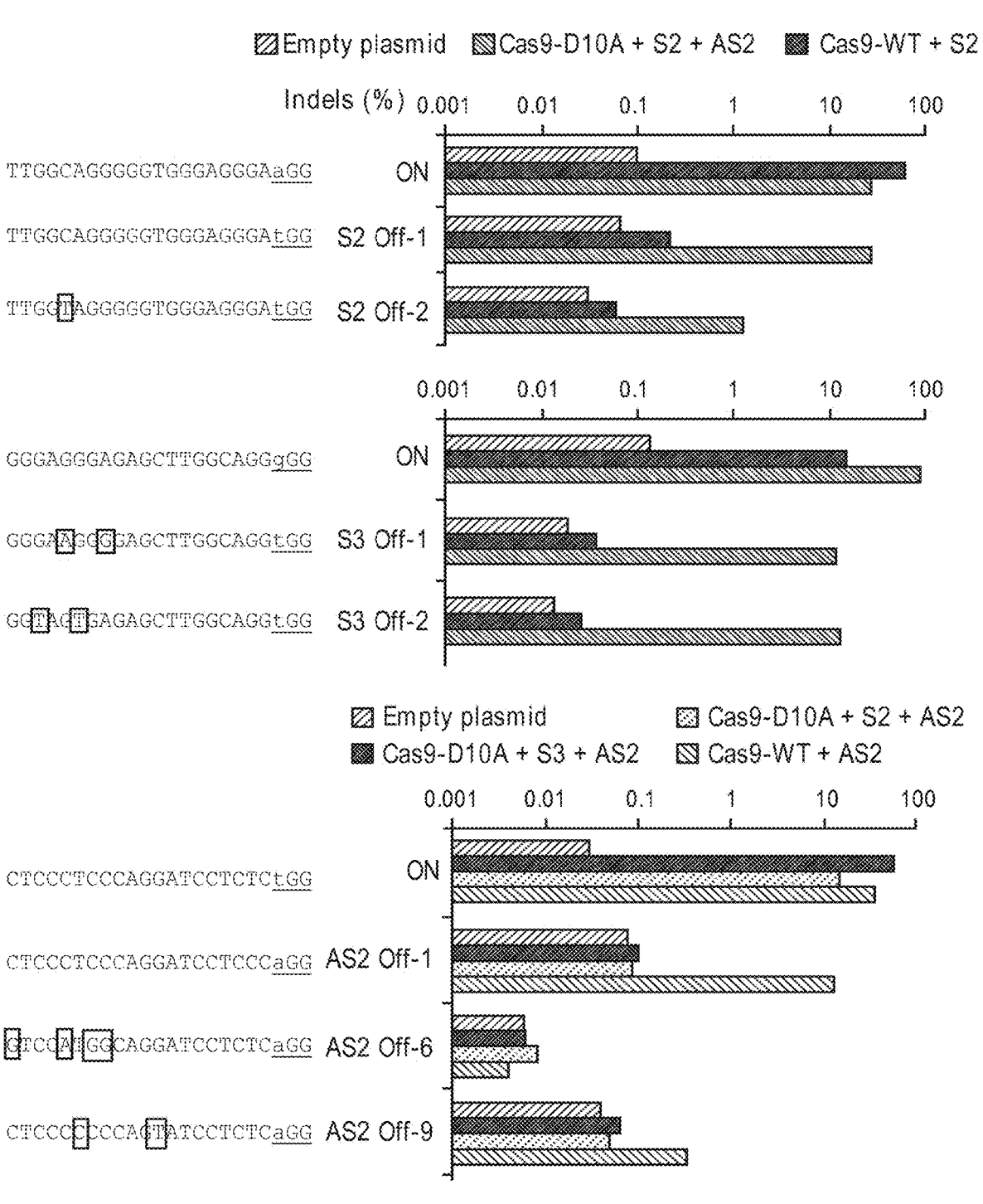

We next measured mutation frequencies of paired nickases and nucleases at off-target sites using deep sequencing. Cas9 nucleases complexed with three sgRNAs induced off-target mutations at six sites that differ by one or two nucleotides from their corresponding on-target sites with frequencies that ranged from 0.5% to 10% (FIG. 17B). In contrast, paired Cas9 nickases did not produce indels above the detection limit of 0.1% at any of the six off-target sites. The S2 Off-1 site that differs by a single nucleotide at the first position in the PAM (i.e., N in NGG) from its on-target site can be considered as another on-target site. As expected, the Cas9 nuclease complexed with the S2 sgRNA was equally efficient at this site and the on-target site. In sharp contrast, D10A Cas9 complexed with the S2 and AS2 sgRNAs discriminated this site from the on-target site by a factor of 270 fold. This paired nickase also discriminated the AS2 off-target sites (Off-1 and Off-9 in FIG. 17B) from the on-target site by factors of 160 fold and 990 fold, respectively.

Example 8: Chromosomal DNA Splicing Induced by Paired Cas9 Nickases

Two concurrent DSBs produced by engineered nucleases such as ZENs and TALENs can promote large deletions of the intervening chromosomal segments has been reported. We tested whether two SSBs induced by paired Cas9 nickases can also produce deletions in human cells. We used PCR to detect deletion events and found that seven paired nickases induced deletions of up to 1.1-kbp chromosomal segments as efficiently as paired Cas9 nucleases did (FIG. 20A, B). DNA sequences of the PCR products confirmed the deletion events (FIG. 20C). Interestingly, the sgRNA-matching sequence remained intact in two out of seven deletion-specific PCR amplicons (underlined in FIG. 20C). In contrast, Cas9 nuclease pairs did not produce sequences that contained intact target sites. This finding suggests that two distant nicks were not converted to two separate DSBs to promote deletions of the intervening chromosomal segment. In addition, it is unlikely that two nicks separated by more than a 100 bp can produce a composite DSB with large overhangs under physiological conditions because the melting temperature is very high.

We propose that two distant nicks are repaired by strand displacement in a head-to-head direction, resulting in the formation of a DSB in the middle, whose repair via NHEJ causes small deletions (FIG. 20D). Because the two target sites remain intact during this process, nickases can induce SSBs again, triggering the cycle repeatedly until the target sites are deleted. This mechanism explains why two offset nicks producing 5' overhangs but not those producing 3' overhangs induced indels efficiently at three loci.

We then investigated whether Cas9 nucleases and nickases can induce unwanted chromosomal translocations that result from NHEJ repair of on-target and off-target DNA cleavages (FIG. 21A). We were able to detect translocations induced by Cas9 nucleases using PCR (FIG. 21B, C). No such PCR products were amplified using genomic DNA isolated from cells transfected with the plasmids encoding the AS2+S3 Cas9 nickase pair. This result is in line with the fact that both AS2 and S3 nickases, unlike their corresponding nucleases, did not produce indels at off-target sites (FIG. 17B).

These results suggest that paired Cas9 nickases allow targeted mutagenesis and large deletions of up to 1-kbp chromosomal segments in human cells. Importantly, paired nickases did not induce indels at off-target sites at which their corresponding nucleases induce mutations. Furthermore, unlike nucleases, paired nickases did not promote unwanted translocations associated with off-target DNA cleavages. In principle, paired nickases double the specificity of Cas9-mediated mutagenesis and will broaden the utility of RNA-guided enzymes in applications that require precise genome editing such as gene and cell therapy. One caveat to this approach is that two highly active sgRNAs are needed to make an efficient nickase pair, limiting targetable sites. As shown in this and other studies, not all sgRNAs are equally active. When single clones rather than populations of cells are used for further studies or applications, the choice of guide RNAs that represent unique sequences in the genome and the use of optimized guide RNAs would suffice to avoid off-target mutations associated with Cas9 nucleases. We propose that both Cas9 nucleases and paired nickases are powerful options that will facilitate precision genome editing in cells and organisms.

Example 9: Genotyping with CRISPR/Cas-Derived RNA-Guided Endonucleases

Next, we reasoned that RGENs can be used in Restriction fragment length polymorphism (RFLP) analysis, replacing conventional restriction enzymes. Engineered nucleases including RGENs induce indels at target sites, when the DSBs caused by the nucleases are repaired by the error-prone non-homologous end-joining (NHEJ) system. RGENs that are designed to recognize the target sequences cannot cleave mutant sequences with indels but will cleave wild-type target sequences efficiently.

9-1. RGEN Components crRNA and tracrRNA were prepared by in vitro transcription using MEGAshortcript T7 kit (Ambion) according to the manufacturer's instruction. Transcribed RNAs were resolved on a 8% denaturing urea-PAGE gel. The gel slice containing RNA was cut out and transferred to elution buffer. RNA was recovered in nuclease-free water followed by phenol: chloroform extraction, chloroform extraction, and ethanol precipitation. Purified RNA was quantified by spectrometry. Templates for crRNA were prepared by annealing an oligonucleotide whose sequence is shown as 5'-GAAATTAATACGACTCACTATAGGX: 0GTTT-TAGAGCTATGCTGTTTTG-3' (SEQ ID NO: 76), in which Xco is the target sequence, and its complementary oligonucleotide. The template for tracrRNA was synthesized by extension of forward and reverse oligonucleotides (5'-GAAATTAATACGACTCACTATAGGAACCATT-CAAAACAGCATAGCAAGTTAAAATAAGGCTA GTCCG-3' (SEQ ID NO: 77) and 5'-AAAAAAAGCACCGACTCGGTGCCACTTTTT- CAAGTTGATAACGGACTAGCCTTATTTTAACT TGC-TATG-3' (SEQ ID NO: 78)) using Phusion polymerase (New England Biolabs).

9-2. Recombinant Cas9 Protein Purification

The Cas9 DNA construct used in our previous Example, which encodes Cas9 fused to the His6-tag at the C terminus, was inserted in the pET-28a expression vector. The recombinant Cas9 protein was expressed in *E. coli* strain BL21 (DE3) cultured in LB medium at 25° C. for 4 hours after induction with 1 mM IPTG. Cells were harvested and resuspended in buffer containing 20 mM Tris PH 8.0, 500 mM NaCl, 5 mM imidazole, and 1 mM PMSF. Cells were frozen in liquid nitrogen, thawed at 4° C., and sonicated. After centrifugation, the Cas9 protein in the lysate was bound to Ni-NTA agarose resin (Qiagen), washed with buffer containing 20 mM Tris pH 8.0, 500 mM NaCl, and 20 mM imidazole, and eluted with buffer containing 20 mM Tris pH 8.0, 500 mM NaCl, and 250 mM imidazole. Purified Cas9 protein was dialyzed against 20 mM HEPES (pH 7.5), 150 mM KCl, 1 mM DTT, and 10% glycerol and analyzed by SDS-PAGE.

9-3. T7 Endonuclease I Assay

The T7E1 assay was performed as following. In brief, PCR products amplified using genomic DNA were denatured at 95° C., reannealed at 16° C., and incubated with 5 units of T7 Endonuclease I (New England BioLabs) for 20 min at 37° C. The reaction products were resolved using 2 to 2.5% agarose gel electrophoresis.

9-4. RGEN-RFLP Assay

PCR products (100-150 ng) were incubated for 60 min at 37° C. with optimized concentrations (Table 10) of Cas9 protein, tracrRNA, crRNA in 10 µl NEB buffer 3 (1X). After the cleavage reaction, RNase A (4 µg) was added, and the reaction mixture was incubated for 30 min at 37° C. to remove RNA. Reactions were stopped with 6X stop solution buffer containing 30% glycerol, 1.2% SDS, and 100 mM EDTA. Products were resolved with 1-2.5% agarose gel electrophoresis and visualized with EtBr staining.

TABLE 10

Concentration of RGEN components in RFLP assays

| Target Name | Cas9 (ng/µl) | crRNA (ng/µl) | tracrRNA (ng/µl) |
|---|---|---|---|
| C4BPB | 100 | 25 | 60 |
| PIBF-NGG-RGEN | 100 | 25 | 60 |
| HLA-B | 1.2 | 0.3 | 0.7 |
| CCR5-ZFN | 100 | 25 | 60 |
| CTNNB1 Wild type specific | 30 | 10 | 20 |
| CTNNB1 mutant specific | 30 | 10 | 20 |
| CCR5 WT-specific | 100 | 25 | 60 |
| CCR5 Δ32-specific | 10 | 2.5 | 6 |
| KRAS WT specific (wt) | 30 | 10 | 20 |
| KRAS mutant specific (m8) | 30 | 10 | 20 |
| KRAS WT specific (m6) | 30 | 10 | 20 |
| KRAS mutant specific (m6,8) | 30 | 10 | 20 |
| PIK3CA WT specific (wt) | 100 | 25 | 60 |
| PIK3CA mutant specific (m4) | 30 | 10 | 20 |
| PIK3CA WT specific (m7) | 100 | 25 | 60 |
| PIK3CA mutant specific (m4,7) | 30 | 10 | 20 |
| BRAF WT-specific | 30 | 10 | 20 |
| BRAF mutant-specific | 100 | 25 | 60 |
| NRAS WT-specific | 100 | 25 | 60 |
| NRAS mutant-specific | 30 | 10 | 20 |
| IDH WT-specific | 30 | 10 | 20 |

TABLE 10-continued

Concentration of RGEN components in RFLP assays

| Target Name | Cas9 (ng/µl) | crRNA (ng/µl) | tracrRNA (ng/µl) |
|---|---|---|---|
| IDH mutant-specific | 30 | 10 | 20 |
| PIBF-NAG-RGEN | 30 | 10 | 60 |

TABLE 11

Primers

| Gene (site) | Direction | Sequence (5' to 3') | SEQ ID NO |
|---|---|---|---|
| CCR5 (RGEN) | F1 | CTCCATGGTGCTATAGAGCA | 79 |
| | F2 | GAGCCAAGCTCTCCATCTAGT | 80 |
| | R | GCCCTGTCAAGAGTTGACAC | 81 |
| CCR5 (ZFN) | F | GCACAGGGTGGAACAAGATGGA | 82 |
| | R | GCCAGGTACCTATCGATTGTCAGG | 83 |
| CCR5 (del32) | F | GAGCCAAGCTCTCCATCTAGT | 84 |
| | R | ACTCTGACTG GGTCACCAGC | 85 |
| C4BPB | F1 | TATTTGGCTGGTTGAAAGGG | 86 |
| | R1 | AAAGTCATGAAATAAACACACCCA | 87 |
| | F2 | CTGCATTGATATGGTAGTACCATG | 88 |
| | R2 | GCTGTTCATTGCAATGGAATG | 89 |
| CTNNB1 | F | ATGGAGTTGGACATGGCCATGG | 90 |
| | R | ACTCACTATCCACAGTTCAGCATTTACC | 91 |
| KRAS | F | TGGAGATAGCTGTCAGCAACTTT | 92 |
| | R | CAACAA AGCAAAGGTAAAGTTGGTAATAG | 93 |
| PIK3CA | F | GGTTTCAGGAGATGTGTTACAAGGC | 94 |
| | R | GATTGTGCAATTCCTATGCAATCGGTC | 95 |
| NRAS | F | CACTGGGTACTTAATCTGTAGCCTC | 96 |
| | R | GGTTCCAAGTCATTCCCAGTAGC | 97 |
| IDH1 | F | CATCACTGCAGTTGTAGGTTATAACTATCC | 98 |
| | R | TTGAAAACCACAGATCTGGTTGAACC | 99 |
| BRAF | F | GGAGTGCCAAGAGAATATCTGG | 100 |
| | R | CTGAAACTGGTTTCAAAATATTCGTTTTAAGG | 101 |
| PIBF | F | GCTCTGTATGCCCTGTAGTAGG | 102 |
| | R | TTTGCATCTGACCTTACCTTTG | 103 |

9-5. Plasmid Cleavage Assay

Restriction enzyme-treated linearized plasmid (100 ng) was incubated for 60 min at 37° C. with Cas9 protein (0.1 µg), tracrRNA (60 ng), and crRNA (25 ng) in 10 µl NEB 3 buffer (1X). Reactions were stopped with 6X stop solution containing 30% glycerol, 1.2% SDS, and100 mM EDTA. Products were resolved with 1% agarose gel electrophoresis and visualized with EtBr staining.

9-6. Strategy of RFLP

New RGENs with desired DNA specificities can be readily created by replacing crRNA; no de novo purification of custom proteins is required once recombinant Cas9 protein is available. Engineered nucleases, including RGENs, induce small insertions or deletions (indels) at target sites when the DSBs caused by the nucleases are repaired by error-prone non-homologous end-joining (NHEJ). RGENs that are designed to recognize the target sequences cleave wild-type sequences efficiently but cannot cleave mutant sequences with indels (FIG. 22).

We first tested whether RGENs can differentially cleave plasmids that contain wild-type or modified C4BPB target sequences that harbor 1- to 3-base indels at the cleavage site. None of the six plasmids with these indels were cleaved by a C4BPB-specific RGEN5 composed of target-specific crRNA, tracrRNA, and recombinant Cas9 protein (FIG. 23). In contrast, the plasmid with the intact target sequence was cleaved efficiently by this RGEN.

9-7. Detection of Mutations Induced by the Same RGENs Using RGEN-Mediated RFLP

Next, to test the feasibility of RGEN-mediated RFLP for detection of mutations induced by the same RGENs, we utilized gene-modified K562 human cancer cell clones established using an RGEN targeting C4BPB gene (Table 12).

TABLE 12

| Target sequence of RGENs used in this study | | |
| --- | --- | --- |
| Gene | Target sequence | SEQ ID NO |
| human C4BPB | AATGACCACTACATCCTCAAGGG | 104 |
| mouse Pibf1 | AGATGATGTCTCATCATCAGAGG | 105 |

C4BPB mutant clones used in this study have various mutations ranging from 94 bp deletion to 67 bp insertion (FIG. 24A). Importantly, all mutations occurred in mutant clones resulted in the loss of RGEN target site. Among 6 C4BPB clones analyzed, 4 clones have both wildtype and mutant alleles (+/−) and 2 clones have only mutant alleles (−/−).

The PCR products spanning the RGEN target site amplified from wildtype K562 genomic DNA were digested completely by the RGEN composed of target-specific crRNA, tracrRNA, and recombinant Cas9 protein expressed in and purified from *E. coli* (FIG. 24B/Lane 1). When the C4BPB mutant clones were subjected to RFLP analysis using the RGEN, PCR amplicons of +/− clones that contained both wildtype and mutant alleles were partially digested, and those of −/− cloned that did not contain the wildtype allele were not digested at all, yielding no cleavage products corresponding to the wildtype sequence (FIG. 24B). Even a single-base insertion at the target site blocked the digestion (#12 and #28 clones) of amplified mutant alleles by the C4BPB RGEN, showing the high specificity of RGEN-mediated RFLP. We subjected the PCR amplicons to the mismatch-sensitive T7E1 assay in parallel (FIG. 24B). Notably, the T7E1 assay was not able to distinguish −/− clones from +/− clones. To make it matters worse, the T7E1 assay cannot distinguish homozygous mutant clones that contain the same mutant sequence from wildtype clones, because annealing of the same mutant sequence will form a homoduplex. Thus, RGEN-mediated RFLP has a critical advantage over the conventional mismatch-sensitive nuclease assay in the analysis of mutant clones induced by engineered nucleases including ZENS, TALENS and RGENS.

9-8. Quantitative Assay for RGEN-RFLP Analysis

We also investigated whether RGEN-RFLP analysis is a quantitative method. Genomic DNA samples isolated from the C4BPB null clone and the wild-type cells were mixed at various ratios and used for PCR amplifications. The PCR products were subjected to RGEN genotyping and the T7E1 assay in parallel (FIG. 25b). As expected, DNA cleavage by the RGEN was proportional to the wild type to mutant ratio.

In contrast, results of the T7E1 assay correlated poorly with mutation frequencies inferred from the ratios and were inaccurate, especially at high mutant %, a situation in which complementary mutant sequences can hybridize with each other to form homoduplexes.

9-9. Analysis of Mutant Mouse Founders Using a RGEN-Mediated RFLP Genotyping

We also applied RGEN-mediated RFLP genotyping (RGEN genotyping in short) to the analysis of mutant mouse founders that had been established by injection of TALENs into mouse one-cell embryos (FIG. 26A). We designed and used an RGEN that recognized the TALEN target site in the Pibf1 gene (Table 10). Genomic DNA was isolated from a wildtype mouse and mutant mice and subjected to RGEN genotyping after PCR amplification. RGEN genotyping successfully detected various mutations, which ranged from one to 27-bp deletions (FIG. 26B). Unlike the T7E1 assay, RGEN genotyping enabled differential detection of +/− and −/− founder.

9-10. Detection of Mutations Induced in Human Cells by a CCR5-Specific ZFN Using RGENS In addition, we used RGENs to detect mutations induced in human cells by a CCR5-specific ZFN, representing yet another class of engineered nucleases (FIG. 27). These results show that RGENs can detect mutations induced by nucleases other than RGENs themselves. In fact, we expect that RGENs can be designed to detect mutations induced by most, if not all, engineered nucleases. The only limitation in the design of an RGEN genotyping assay is the requirement for the GG or AG (CC or CT on the complementary strand) dinucleotide in the PAM sequence recognized by the Cas9 protein, which occurs once per 4 bp on average. Indels induced anywhere within the seed region of several bases in crRNA and the PAM nucleotides are expected to disrupt RGEN-catalyzed DNA cleavage. Indeed, we identified at least one RGEN site in most (98%) of the ZEN and TALEN sites.

9-11. Detection of Polymorphisms or Variations Using RGEN

Next, we designed and tested a new RGEN that targets a highly polymorphic locus, HLA-B, that encodes Human Leukocyte Antigen B (a.k.a. MHC class I protein) (FIG. 28). HeLa cells were transfected with RGEN plasmids, and the genomic DNA was subjected to T7E1 and RGEN-RFLP analyses in parallel. T7E1 produced false positive bands that resulted from sequence polymorphisms near the target site (FIG. 25*c*). As expected, however, the same RGEN used for gene disruption cleaved PCR products from wild-type cells completely but those from RGEN-transfected cells partially, indicating the presence of RGEN-induced indels at the target site. This result shows that RGEN-RFLP analysis has a clear advantage over the T7E1 assay, especially when it is not known whether target genes have polymorphisms or variations in cells of interest.

9-12. Detection of Recurrent Mutations Found in Cancer and Naturally-Occurring Polymorphisms Through RGEN-RFLP Analysis RGEN-RFLP analysis has applications beyond genotyping of engineered nuclease-induced mutations. We sought to use RGEN genotyping to detect recurrent mutations found in cancer and naturally-occurring polymorphisms. We chose the human colorectal cancer cell line, HCT116, which carries a gain-of-function 3-bp deletion in the oncogenic CTNNB1 gene encoding beta-catenin. PCR products amplified from HCT116 genomic DNA were cleaved partially by both wild-type-specific and mutant-specific RGENs, in line with the heterozygous genotype in HCT116 cells (FIG. 29*a*). In sharp contrast, PCR products amplified from DNA from Hela cells harboring only wild-type alleles were digested completely by the wild-type-specific RGEN and were not cleaved at all by the mutation-specific RGEN.

We also noted that HEK293 cells harbor the 32-bp deletion (del32) in the CCR5 gene, which encodes an essential co-receptor of HIV infection: Homozygous del32 CCR5 carriers are immune to HIV infection. We designed one RGEN specific to the del32 allele and the other to the wild-type allele. As expected, the wild-type-specific RGEN cleaved the PCR products obtained from K562, SKBR3, or Hela cells (used as wild-type controls) completely but those from HEK293 cells partially (FIG. 30a), confirming the presence of the uncleavable del32 allele in HEK293 cells. Unexpectedly, however, the del32-specific RGEN cleaved the PCR products from wild-type cells as efficiently as those from HEK293 cells. Interestingly, this RGEN had an off-target site with a single-base mismatch immediately downstream of the on-target site (FIG. 30). These results suggest that RGENs can be used to detect naturally-occurring indels but cannot distinguish sequences with single nucleotide polymorphisms or point mutations due to their off-target effects.

To genotype oncogenic single-nucleotide variations using RGENs, we attenuated RGEN activity by employing a single-base mismatched guide RNA instead of a perfectly-matched RNA. RGENs that contained the perfectly-matched guide RNA specific to the wild-type sequence or mutant sequence cleaved both sequences (FIGS. 31a and 32a). In contrast, RGENS that contained a single-base mismatched guide RNA distinguished the two sequences, enabling genotyping of three recurrent oncogenic point mutations in the KRAS, PIK3CA, and IDH1 genes in human cancer cell lines (FIG. 29b and FIGS. 33a, b). In addition, we were able to detect point mutations in the BRAF and NRAS genes using RGENs that recognize the NAG PAM sequence (FIGS. 33c, d). We believe that we can use RGEN-RFLP to genotype almost any, if not all, mutations or polymorphisms in the human and other genomes.

The above data proposes RGENS as providing a platform to use simple and robust RFLP analysis for various sequence variations. With high flexibility in reprogramming target sequence, RGENs can be used to detect various genetic variations (single nucleotide variations, small insertion/deletions, structural variations) such as disease-related recurring mutations, genotypes related to drug-response by a patient and also mutations induced by engineered nucleases in cells. Here, we used RGEN genotyping to detect mutations induced by engineered nucleases in cells and animals. In principle, one could also use RGENs that will specifically detect and cleave naturally-occurring variations and mutations.

Based on the above description, it should be understood by those skilled in the art that various alternatives to the embodiments of the invention described herein may be employed in practicing the invention without departing from the technical idea or essential features of the invention as defined in the following claims. In this regard, the above-described examples are for illustrative purposes only, and the invention is not intended to be limited by these examples. The scope of the present invention should be understood to include all of the modifications or modified form derived from the meaning and scope of the following claims or its equivalent concepts.

REFERENCES

1. M. Jinek et al., Science 337, 816 (Aug. 17, 2012).
2. H. Kim, E. Um, S. R. Cho, C. Jung, J. S. Kim, Nat Methods 8, 941 (November 2011).
3. H. J. Kim, H. J. Lee, H. Kim, S. W. Cho, J. S. Kim, Genome Res 19, 1279 (July 2009).
4. E. E. Perez et al., Nat Biotechnol 26, 808 (July 2008).
5. J. C. Miller et al., Nat Biotechnol 29, 143 (February 2011).
6. C. Mussolino et al., Nucleic Acids Res 39, 9283 (November 2011).
7. J. Cohen, Science 332, 784 (May 13, 2011).
8. V. Pattanayak, C. L. Ramirez, J. K. Joung, D. R. Liu, Nat Methods 8, 765 (September 2011).
9. R. Gabriel et al., Nat Biotechnol 29, 816 (September 2011).
10. E. Kim et al., Genome Res, (Apr. 20, 2012).
11. H. J. Lee, J. Kweon, E. Kim, S. Kim, J. S. Kim, Genome Res 22, 539 (March 2012).
12. H. J. Lee, E. Kim, J. S. Kim, Genome Res 20,81 (January 2010).
13. Fu Y, Foden J A, Khayter C, Maeder M L, Reyon D, Joung J K, Sander J D. High-frequency off-target mutagenesis induced by CRISPR-Cas nucleases in human cells. Nat Biotech advance online publication (2013)

The invention claimed is:

1. A method of producing an engineered eukaryotic cell, the method comprising:

preparing a Cas9 protein, wherein the Cas9 protein comprises a nuclear localization signal (NLS);

preparing a single-guide RNA (sgRNA), wherein the sgRNA comprises a CRISPR RNA (crRNA) and a trans-activating crRNA (tracrRNA);

preparing a cell-free buffer disposing the Cas9 protein and the sgRNA in the cell-free buffer to provide for a transfection mixture comprising a Cas9/sgRNA complex; and introducing the transfection mixture into a eukaryotic cell via electroporation;

wherein the Cas9/sgRNA complex of the transfection mixture induces a modification of a target endogenous DNA sequence in the nucleus of the eukaryotic cell to provide for the engineered eukaryotic cell.

2. The method of claim 1, wherein the Cas9/sgRNA complex is formed in the cell-free buffer.

3. The method of claim 1, wherein the engineered eukaryotic cell is an engineered human cell.

4. The method of claim 1, wherein the engineered eukaryotic cell is an engineered plant cell.

* * * * *